United States Patent
Koizumi et al.

(10) Patent No.: US 10,731,159 B2
(45) Date of Patent: *Aug. 4, 2020

(54) CATIONIC LIPID

(71) Applicant: DAIICHI SANKYO COMPANY, LIMITED, Tokyo (JP)

(72) Inventors: Makoto Koizumi, Tokyo (JP); Yoshiyuki Onishi, Tokyo (JP); Takako Niwa, Tokyo (JP); Masakazu Tamura, Tokyo (JP); Yuji Kasuya, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/692,284

(22) Filed: Nov. 22, 2019

(65) Prior Publication Data
US 2020/0080086 A1  Mar. 12, 2020

Related U.S. Application Data

(63) Continuation of application No. 15/797,824, filed on Oct. 30, 2017, now Pat. No. 10,533,176, which is a continuation of application No. 14/903,711, filed as application No. PCT/JP2014/068002 on Jul. 7, 2014, now Pat. No. 9,803,199.

(30) Foreign Application Priority Data

Jul. 8, 2013 (JP) .................. 2013-142677

(51) Int. Cl.
| | |
|---|---|
| C12N 15/113 | (2010.01) |
| A61K 31/7088 | (2006.01) |
| A61K 31/713 | (2006.01) |
| C07C 219/16 | (2006.01) |
| C07D 211/22 | (2006.01) |
| C07D 211/46 | (2006.01) |
| A61K 9/127 | (2006.01) |
| C12N 15/11 | (2006.01) |
| A61K 47/54 | (2017.01) |
| A61K 9/10 | (2006.01) |
| A61K 47/18 | (2017.01) |
| A61K 47/22 | (2006.01) |
| A61K 47/28 | (2006.01) |
| A61K 47/44 | (2017.01) |
| A61K 48/00 | (2006.01) |

(52) U.S. Cl.
CPC .............. *C12N 15/113* (2013.01); *A61K 9/10* (2013.01); *A61K 9/127* (2013.01); *A61K 9/1271* (2013.01); *A61K 9/1272* (2013.01); *A61K 31/7088* (2013.01); *A61K 31/713* (2013.01); *A61K 47/18* (2013.01); *A61K 47/22* (2013.01); *A61K 47/28* (2013.01); *A61K 47/44* (2013.01); *A61K 47/543* (2017.08); *A61K 48/005* (2013.01); *A61K 48/0008* (2013.01); *C07C 219/16* (2013.01); *C07D 211/22* (2013.01); *C07D 211/46* (2013.01); *C12N 15/111* (2013.01); *C12N 2310/14* (2013.01); *C12N 2320/32* (2013.01)

(58) Field of Classification Search
CPC .................................................... C12N 15/113
See application file for complete search history.

(56) References Cited

U.S. PATENT DOCUMENTS

| | | | |
|---|---|---|---|
| 9,803,199 B2 | 10/2017 | Koizumi et al. | |
| 10,533,176 B2 | 1/2020 | Koizumi et al. | |
| 2011/0311582 A1 | 12/2011 | Manoharan et al. | |
| 2011/0311583 A1 | 12/2011 | Manoharan et al. | |

FOREIGN PATENT DOCUMENTS

| | | |
|---|---|---|
| JP | 2012-508263 A | 4/2012 |
| WO | WO 2010/054401 A1 | 5/2010 |
| WO | WO 2010/054405 A1 | 5/2010 |
| WO | WO 2012/054365 A2 | 4/2012 |
| WO | WO 2015/095346 A1 | 6/2015 |

OTHER PUBLICATIONS

Akita et al., "A Neutral Envelope-Type Nanoparticle Containing pH-Responsive and SS-Cleavable Lipid-Like Material as a Carrier for Plasmid DNA," *Adv. Healthcare Mater.*, (2013), 2:1120-1125.
Asai et al., "Cell-penetrating peptide-conjugated lipid nanoparticles for siRNA delivery," *Biochemical and Biophysical Research Communications*, (2014), 444:599-604.
Elbashir et al., "Duplexes of 21-nucleotide RNAs mediate RNA interference in cultured mammalian cells," *Nature*, (2001), 411:494-498.
Fire et al., "Potent and specific genetic interference by double-stranded RNA in *Caenorhabditis elegans*," *Nature*, (1998), 391:806-811.
Hamilton et al., "A Species of Small Antisense RNA in Post-transcriptional Gene Silencing in Plants," *Science*, (1999), 286:950-952.
Jayaraman et al., "Maximizing the Potency of siRNA Lipid Nanoparticles for Hepatic Gene Silencing In Vivo," *Angew. Chem. Int. Ed.*, (2012), 51:8529-8533.

(Continued)

*Primary Examiner* — David K O'Dell
(74) *Attorney, Agent, or Firm* — Dorsey & Whitney LLP

(57) ABSTRACT

The present invention provides a compound represented by the formula (Ia) as a novel cationic lipid that forms a lipid particle and also provides a lipid particle comprising the compound. The present invention further provides a nucleic acid lipid particle containing the lipid particle, and a pharmaceutical composition containing the nucleic acid lipid particle as an active ingredient.

19 Claims, 3 Drawing Sheets
Specification includes a Sequence Listing.

(56) References Cited

OTHER PUBLICATIONS

Judge et al., "Sequence-dependent stimulation of the mammalian innate immune response by synthetic siRNA," *Nature Biotechnology*, (2005), 23(4):457-462.
Maier et al., "Biodegradable Lipids Enabling Rapidly Eliminated Lipid Nanoparticles for Systemic Delivery of RNAi Therapeutics," *Molecular Therapy*, (2013), 21(8):1570-1578.
Patani et al., "Bioisosterism: A Rational Approach in Drug Design," *Chem. Rev.*, (1996), 96:3147-3176.
Rehman et al., "How cationic lipids transfer nucleic acids into cells and across cellular membranes: Recent advances," *Journal of Controlled Release*, (2013), 166:46-56.
Sato et al., "A pH-sensitive cationic lipid facilitates the delivery of liposomal siRNA and gene silencing activity in vitro and in vivo," *Journal of Controlled Release*, (2012), 163:267-276.
Semple et al., "Rational design of cationic lipids for siRNA delivery," *Nature Biotechnology*, (2010), 28(2):172-176 plus supplemental material (2 pages).
Stanton et al., "Medicinal Chemistry of siRNA Delivery," *J. Med. Chem.*, (2010), 53:7887-7901.
Tsui et al., "Stability of Endogenous and Added RNA in Blood Specimens, Serum, and Plasma," *Clinical Chemistry*, (2002), 48(10):1647-1653.
Wheeler et al., "Stabilized plasmid-lipid particles: construction and characterization," *Gene Therapy*, (1999), 6:271-281.
Wislicenus, "Adolph Strecker's Short Textbook of Organic Chemistry," (1881), Spottiswoode: London, pp. 38-39.
English translation of International Search Report dated Aug. 5, 2014, in PCT Application No. PCT/JP2014/068002, 3 pages.
English translation of Written Opinion of the International Searching Authority dated Aug. 5, 2014, in PCT Application No. PCT/JP2014/068002, 5 pages.
Supplementary Search Report dated Jan. 27, 2017, in European Application No. EP 14822439, 8 pages.

[Figure 1]
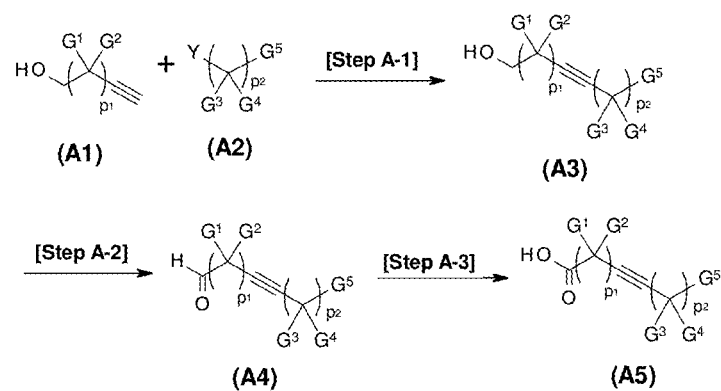
[Figure 2]
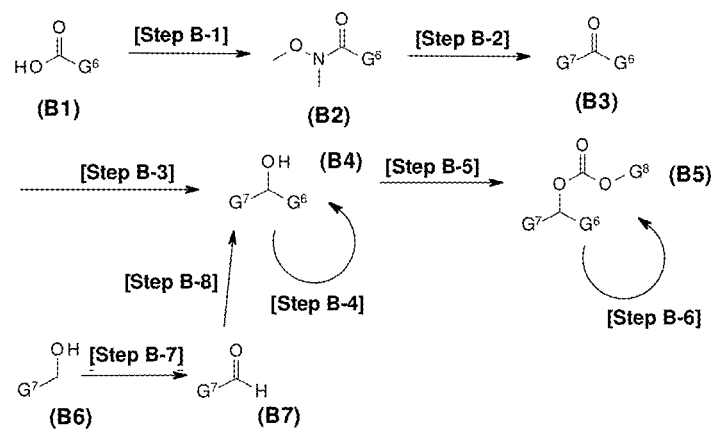

[Figure 3]
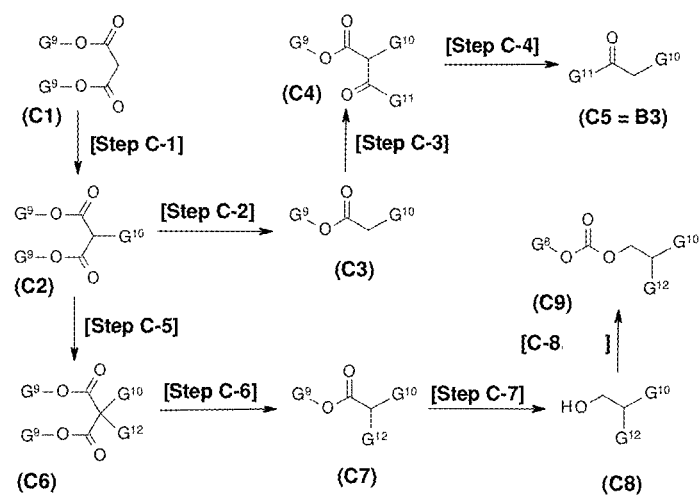
[Figure 4]
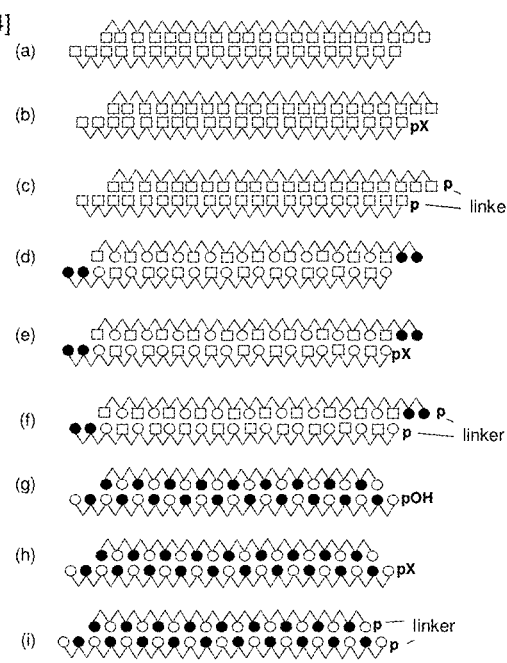

[Figure 5]
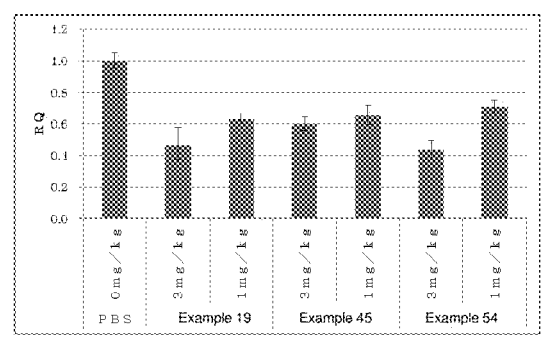
[Figure 6]
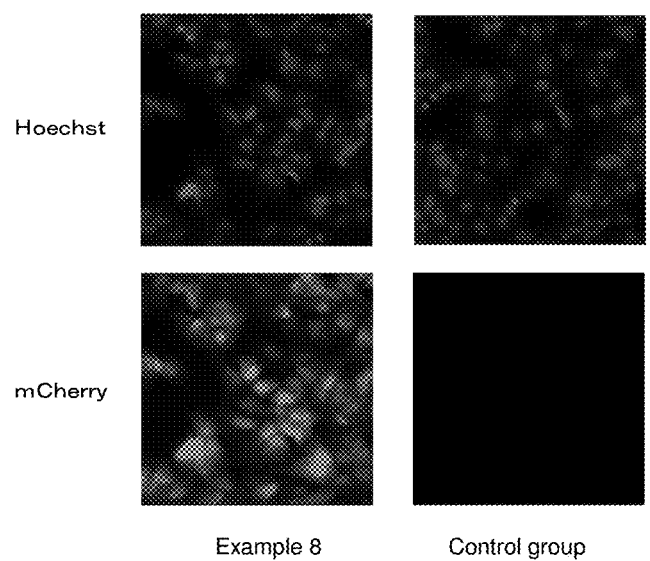

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: sense strand
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
```

```
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 1
gcacaagaau ggaucaca                                                 18

<210> SEQ ID NO 2
<211> LENGTH: 21
<212> TYPE: DNA
<213> ORGANISM: Artificial Sequence
<220> FEATURE:
<223> OTHER INFORMATION: antisense strand
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um
```

<400> SEQUENCE: 2
utgtgaucca utctugugct u                                    21

<210> SEQ ID NO 3
<211> LENGTH: 19
<212> TYPE: DNA
<213> ORGANISM: Artificial Sequence
<220> FEATURE:
<223> OTHER INFORMATION: sense strand
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 3
gcacaagaau ggaucacaa                                       19

<210> SEQ ID NO 4
<211> LENGTH: 20
<212> TYPE: DNA
<213> ORGANISM: Artificial Sequence
<220> FEATURE:
<223> OTHER INFORMATION: antisense strand
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)

```
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (20)..(20)
<223> OTHER INFORMATION: um

<400> SEQUENCE: 4
tgtgauccau tctugugctu                                              20

<210> SEQ ID NO 5
<211> LENGTH: 21
<212> TYPE: DNA
<213> ORGANISM: Artificial Sequence
<220> FEATURE:
<223> OTHER INFORMATION: antisense strand
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 5
```
utgtgaucca utctugugct u                                              21

<210> SEQ ID NO 6
<211> LENGTH: 21
<212> TYPE: DNA
<213> ORGANISM: Artificial Sequence
<220> FEATURE:
<223> OTHER INFORMATION: antisense strand
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 6
utgtgaucca utctugugct u                                              21

<210> SEQ ID NO 7
<211> LENGTH: 18
<212> TYPE: DNA
<213> ORGANISM: Artificial Sequence
<220> FEATURE:
<223> OTHER INFORMATION: sense strand region of CT-454
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:

```
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 7
gcacaagaau ggaucaca                                                    18

<210> SEQ ID NO 8
<211> LENGTH: 21
<212> TYPE: DNA
<213> ORGANISM: Artificial Sequence
<220> FEATURE:
<223> OTHER INFORMATION: antisense strand region of CT-454
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um
```

-continued

<400> SEQUENCE: 8
utgtgaucca utctugugct u                                          21

<210> SEQ ID NO 9
<211> LENGTH: 18
<212> TYPE: DNA
<213> ORGANISM: Artificial Sequence
<220> FEATURE:
<223> OTHER INFORMATION: sense strand region of HS-005
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 9
cgagacacau gggugcta                                              18

<210> SEQ ID NO 10
<211> LENGTH: 21
<212> TYPE: DNA
<213> ORGANISM: Artificial Sequence
<220> FEATURE:
<223> OTHER INFORMATION: antisense strand region of HS-005
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (9)..(9)

```
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 10
utagcaccca ugugucucgt u                                            21

<210> SEQ ID NO 11
<211> LENGTH: 18
<212> TYPE: DNA
<213> ORGANISM: Artificial Sequence
<220> FEATURE:
<223> OTHER INFORMATION: sense strand region of HS-006
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: um

<400> SEQUENCE: 11
cagacacatg ggtgcuau                                                18
```

```
<210> SEQ ID NO 12
<211> LENGTH: 21
<212> TYPE: DNA
<213> ORGANISM: Artificial Sequence
<220> FEATURE:
<223> OTHER INFORMATION: antisense strand region of HS-006
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 12
uauagcaccc atgtgtctgt u                                              21

<210> SEQ ID NO 13
<211> LENGTH: 18
<212> TYPE: DNA
<213> ORGANISM: Artificial Sequence
<220> FEATURE:
<223> OTHER INFORMATION: sense strand region of HS-005s
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (8)..(8)
<223> OTHER INFORMATION: cm
<220> FEATURE:
```

```
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (18)..(18)
<223> OTHER INFORMATION: 2'-O-methyladenosine

<400> SEQUENCE: 13
cgagacacau gggugcta                                                  18

<210> SEQ ID NO 14
<211> LENGTH: 21
<212> TYPE: DNA
<213> ORGANISM: Artificial Sequence
<220> FEATURE:
<223> OTHER INFORMATION: antisense strand region of HS-005s
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 14
utagcaccca ugugucucgt u                                              21
```

<210> SEQ ID NO 15
<211> LENGTH: 18
<212> TYPE: DNA
<213> ORGANISM: Artificial Sequence
<220> FEATURE:
<223> OTHER INFORMATION: sense strand region of HS-006s
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: um

<400> SEQUENCE: 15
cagacacatg ggtgcuau                                            18

<210> SEQ ID NO 16
<211> LENGTH: 21
<212> TYPE: DNA
<213> ORGANISM: Artificial Sequence
<220> FEATURE:
<223> OTHER INFORMATION: antisense strand region of HS-006s
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: gm

```
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (21)..(21)
<223> OTHER INFORMATION: um

<400> SEQUENCE: 16
uauagcaccc atgtgtctgt u                                          21
```

CATIONIC LIPID

This application is continuation of U.S. application Ser. No. 15/797,824, filed Oct. 30, 2017, entitled "Cationic Lipid," which is a continuation of U.S. application Ser. No. 14/903,711, filed Jan. 8, 2016, now U.S. Pat. No. 9,803,199, entitled "Cationic Lipid," which is a national stage application under 35 U.S.C. § 371 of International Application No. PCT/JP2014/068002, filed Jul. 7, 2014, entitled "Novel Lipid," which claims priority to Japanese Patent Application No. 2013-142677, filed Jul. 8, 2013.

TECHNICAL FIELD

The present invention relates to a novel cationic lipid, a novel cationic lipid that forms a lipid particle, a lipid particle comprising the cationic lipid, a nucleic acid lipid particle comprising the lipid particle together with a nucleic acid, a pharmaceutical composition containing the nucleic acid lipid particle as an active ingredient, and a treatment method using the pharmaceutical composition.

BACKGROUND ART

Methods for inhibiting the expression of a target gene in cells, tissues, or individuals include an approach in which double-stranded RNA is introduced into the cells, tissues, or individuals. By this introduction of double-stranded RNA, mRNA having homology to the sequence is degraded such that the expression of the target gene is inhibited. This effect is called "RNA interference" or "RNAi". RNA interference was originally reported in *C. elegans* (see e.g., Non Patent Reference 1) and then also reported in plants (see e.g., Non Patent Reference 2).

Double-stranded RNA consisting of 21-nucleotide sense and antisense strands having a 2-nucleotide overhang at the 3'-end (small interfering RNA:siRNA) has been reported to have an RNA interference effect in cultured cells of vertebrates (see e.g., Non Patent Reference 3). siRNA is considered to be useful for the identification of gene functions, screening of cell lines suitable for useful substance production, regulation of genes involved in disease, etc., but it is characteristically degraded easily by RNase (see e.g., Non Patent Reference 4).

Since a double-stranded polynucleotide such as siRNA or modified siRNA is a molecule having a molecular weight on the order of 13,000, water solubility, and electric charge, a delivery technique such as a transfection reagent is generally used for allowing the double-stranded polynucleotide to permeate a cell membrane (see e.g., Non Patent Reference 5). Particularly, liposomes are widely used in the delivery of nucleic acid molecules by encapsulating a nucleic acid molecule such as plasmid DNA into a liposome to form a nucleic acid lipid particle (see e.g., Non Patent Reference 6). Also, a liposome containing a cationic lipid has been reported to be able to deliver siRNA into cells by forming a nucleic acid lipid particle through mixing with the siRNA (see e.g., Patent Reference 1). The cationic lipid, however, is a non-biological component. In this respect, a cationic lipid that can be used at a low concentration has been demanded. A dimethylaminovaleric acid derivative (Patent Reference 1), a dimethylaminobutyric acid derivative (Patent Reference 2), a dimethylaminoethylcarbonate derivative (Patent Reference 3), or the like is known as the cationic lipid.

The present inventors have conducted diligent studies to obtain a lipid particle consisting of a cationic lipid that can encapsulate therein a nucleic acid such as a double-stranded polynucleotide (e.g., siRNA), DNA, or an antisense oligonucleotide and can be used at a low concentration. As a result, the present inventors have completed the present invention by finding a novel cationic lipid and further finding a nucleic acid lipid particle comprising the novel cationic lipid that can encapsulate therein a nucleic acid molecule, can be used at a low concentration, and permits a high level of delivery into cells.

CITATION LIST

Patent Reference
  Patent Reference 1: International Publication No. WO 2012/108397
  Patent Reference 2: International Publication No. WO 2012/054365
  Patent Reference 3: International Publication No. WO 2010/054405
Non Patent Reference
  Non Patent Reference 1: Nature, 1998, Vol. 391, p. 806-811
  Non Patent Reference 2: Science, 1999, Vol. 286, p. 950-952
  Non Patent Reference 3: Nature, 2001, Vol. 411, p. 494-498
  Non Patent Reference 4: Clinical Chemistry, 2002, Vol. 48, p. 1647-1653
  Non Patent Reference 5: Journal of Medicinal Chemistry, 2010, Vol. 57, p. 7887-7901
  Non Patent Reference 6: Gene Therapy 1999, Vol. 6, p. 271-281

SUMMARY OF INVENTION

Technical Problem

An object of the present invention is to provide a novel cationic lipid that forms a lipid particle.

Another object of the present invention is to provide a novel cationic lipid that forms a lipid particle in combination with an amphipathic lipid, a sterol, and a lipid reducing aggregation during lipid particle formation.

A further object of the present invention is to provide a lipid particle comprising the cationic lipid.

A further object of the present invention is to provide a nucleic acid lipid particle comprising the lipid particle and further a nucleic acid.

A further object of the present invention is to provide a pharmaceutical composition containing the nucleic acid lipid particle as an active ingredient.

A further object of the present invention is to provide a treatment method using the pharmaceutical composition.

Solution to Problem

Specifically, the present invention provides:
(1) A cationic lipid represented by the general formula (Ia) or a pharmacologically acceptable salt thereof:

[Formula 1]

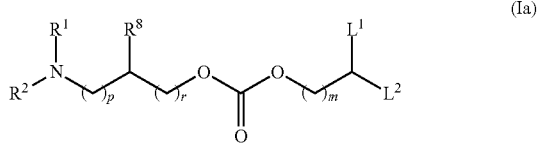

wherein

R$^1$ and R$^2$ each independently represent a hydrogen atom, a C$_1$-C$_6$ alkyl group optionally having one or more substituents selected from substituent group α, a C$_2$-C$_6$ alkenyl group optionally having one or more substituents selected from substituent group α, a C$_2$-C$_6$ alkynyl group optionally having one or more substituents selected from substituent group α, or a C$_3$-C$_7$ cycloalkyl group optionally having one or more substituents selected from substituent group α, or R$^1$ and R$^2$ form a 3- to 10-membered heterocyclic ring together with the nitrogen atom bonded thereto, wherein the heterocyclic ring optionally has one or more substituents selected from substituent group α and optionally contains one or more atoms selected from a nitrogen atom, an oxygen atom, and a sulfur atom, in addition to the nitrogen atom bonded to R$^1$ and R$^2$, as atoms constituting the heterocyclic ring;

R$^8$ represents a hydrogen atom or a C$_1$-C$_6$ alkyl group optionally having one or more substituents selected from substituent group α;

or R$^1$ and R$^8$ together represent a group —(CH$_2$)$_q$—;

substituent group α represents the group consisting of a halogen atom, an oxo group, a hydroxy group, a sulfanyl group, an amino group, a cyano group, a C$_1$-C$_6$ alkyl group, a C$_1$-C$_6$ halogenated alkyl group, a C$_1$-C$_6$ alkoxy group, a C$_1$-C$_6$ alkylsulfanyl group, a C$_1$-C$_6$ alkylamino group, and a C$_1$-C$_7$ alkanoyl group;

L$^1$ represents a C$_{10}$-C$_{24}$ alkyl group optionally having one or more substituents selected from substituent group β1, a C$_{10}$-C$_{24}$ alkenyl group optionally having one or more substituents selected from substituent group β1, a C$_3$-C$_{24}$ alkynyl group optionally having one or more substituents selected from substituent group β1, or a (C$_1$-C$_{10}$ alkyl)-(Q)$_k$-(C$_1$-C$_{10}$ alkyl) group optionally having one or more substituents selected from substituent group β1;

L$^2$ represents, independently of L$^1$, a C$_{10}$-C$_{24}$ alkyl group optionally having one or more substituents selected from substituent group β1, a C$_{10}$-C$_{24}$ alkenyl group optionally having one or more substituents selected from substituent group β1, a C$_3$-C$_{24}$ alkynyl group optionally having one or more substituents selected from substituent group β1, a (C$_1$-C$_{10}$ alkyl)-(Q)$_k$-(C$_1$-C$_{10}$ alkyl) group optionally having one or more substituents selected from substituent group β1, a (C$_{10}$-C$_{24}$ alkoxy)methyl group optionally having one or more substituents selected from substituent group β1, a (C$_{10}$-C$_{24}$ alkenyl)oxymethyl group optionally having one or more substituents selected from substituent group β1, a (C$_3$-C$_{24}$ alkynyl)oxymethyl group optionally having one or more substituents selected from substituent group β1, or a (C$_1$-C$_{10}$ alkyl)-(Q)$_k$-(C$_1$-C$_{10}$ alkoxy)methyl group optionally having one or more substituents selected from substituent group β1;

substituent group 1 represents the group consisting of a halogen atom, an oxo group, a cyano group, a C$_1$-C$_6$ alkyl group, a C$_1$-C$_6$ halogenated alkyl group, a C$_1$-C$_6$ alkoxy group, a C$_1$-C$_6$ alkylsulfanyl group, a C$_1$-C$_7$ alkanoyl group, a C$_1$-C$_7$ alkanoyloxy group, a C$_3$-C$_7$ alkoxyalkoxy group, a (C$_1$-C$_6$ alkoxy)carbonyl group, a (C$_1$-C$_6$ alkoxy)carboxyl group, a (C$_1$-C$_6$alkoxy)carbamoyl group, and a (C$_1$-C$_6$ alkylamino)carboxyl group;

Q represents a group represented by the following formula (II):

[Formula 2]

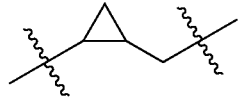

(II)

when L$^1$ and L$^2$ each have one or more substituents selected from substituent group β1 and substituent group β31 is a C$_1$-C$_6$ alkyl group, a C$_1$-C$_6$ alkoxy group, a C$_1$-C$_6$ alkylsulfanyl group, a C$_1$-C$_7$ alkanoyl group, or a C$_1$-C$_7$ alkanoyloxy group, the substituent(s) selected from substituent group β31 in L$^1$ and the substituent(s) selected from substituent group β31 in L$^2$ optionally bind to each other to form a cyclic structure;

k represents 1, 2, 3, 4, 5, 6, or 7;

m represents 0 or 1;

p represents 0, 1, or 2;

q represents 1, 2, 3, or 4; and r represents 0, 1, 2, or 3, provided that p+r is 2 or larger, or q+r is 2 or larger;

(2) The cationic lipid according to (1) or a pharmacologically acceptable salt thereof, wherein R$^1$ and R$^2$ are each independently a C$_1$-C$_6$ alkyl group optionally having one or more substituents selected from substituent group α;

(3) The cationic lipid according to (1) or a pharmacologically acceptable salt thereof, wherein R$^1$ and R$^2$ are each independently a C$_1$-C$_3$ alkyl group;

(4) The cationic lipid according to claim 2 (1) or a pharmacologically acceptable salt thereof, wherein both R$^1$ and R$^2$ are methyl groups;

(5) The cationic lipid according to (1) or a pharmacologically acceptable salt thereof, wherein R$^1$ and R$^2$ form azetidine, pyrrolidine, piperidine, azepane, dihydropyrrole, dihydropyridine, tetrahydropyridine, piperazine, morpholine, dihydrooxazole, or dihydrothiazole optionally having one or more substituents selected from substituent group α, together with the nitrogen atom bonded thereto;

(6) The cationic lipid according to (1) or a pharmacologically acceptable salt thereof, wherein R$^1$ and R$^2$ form azetidine, pyrrolidine, piperidine, or morpholine optionally having one or more substituents selected from substituent group α, together with the nitrogen atom bonded thereto;

(7) The cationic lipid according to (1) or a pharmacologically acceptable salt thereof, wherein R$^1$ and R$^2$ form azetidine, pyrrolidine, or morpholine together with the nitrogen atom bonded thereto;

(8) The cationic lipid according to (1) or a pharmacologically acceptable salt thereof, wherein R$^1$ and R$^8$ together represent a group —(CH$_2$)$_q$—; p+q is 2, 3, or 4; and R$^2$ is a C$_1$-C$_3$ alkyl group optionally having one or more substituents selected from substituent group (9) The cationic lipid according to (8) or a pharmacologically acceptable salt thereof, wherein R$^2$ is a C$_1$-C$_3$ alkyl group;

(10) The cationic lipid according to (8) or a pharmacologically acceptable salt thereof, wherein R$^2$ is a methyl group;

(11) The cationic lipid according to any one of (1) to (10) or a pharmacologically acceptable salt thereof, wherein L$^1$ is a C$_{17}$-C$_{19}$ alkyl group optionally having one or more substituents selected from substituent group β1, a C$_{17}$-C$_{19}$ alkenyl group optionally having one or more substituents selected from substituent group β1, or a (C$_1$-C$_4$ alkyl)-

(Q)$_k$-(C$_4$-C$_9$ alkyl) group optionally having one or more substituents selected from substituent group β1; and k is 1, 2, or 3;

(12) The cationic lipid according to any one of (1) to (10) or a pharmacologically acceptable salt thereof, wherein L$^1$ is a heptadecenyl group, an octadecenyl group, a nonadecenyl group, a heptadecadienyl group, an octadecadienyl group, a nonadecadienyl group, a heptadecatrienyl group, an octadecatrienyl group, or a nonadecatrienyl group optionally having one or more substituents selected from substituent group β1;

(13) The cationic lipid according to any one of (1) to (10) or a pharmacologically acceptable salt thereof, wherein L$^1$ is a (R)-11-acetyloxy-cis-8-heptadecenyl group, a (R)-11-(tetrahydro-2H-pyran-2-yloxy)-cis-8-heptadecenyl group, a cis-9-octadecenyl group (oleyl group), a cis-8,11-heptadecadienyl group, a cis-9,12-octadecadienyl group (linoleyl group), a cis-10,13-nonadecadienyl group, or a cis-6,9,12-octadecatrienyl group (linolenyl group);

(14) The cationic lipid according to any one of (1) to (13) or a pharmacologically acceptable salt thereof, wherein L$^2$ is a C$_{10}$-C$_{19}$ alkyl group optionally having one or more substituents selected from substituent group β1, a C$_{10}$-C$_{19}$ alkenyl group optionally having one or more substituents selected from substituent group β1, a (C$_1$-C$_4$ alkyl)-(Q)$_k$-(C$_4$-C$_9$ alkyl) group optionally having one or more substituents selected from substituent group β1, a (C$_{10}$-C$_{19}$ alkoxy)methyl group optionally having one or more substituents selected from substituent group β1, a (C$_{10}$-C$_{19}$ alkenyl)oxymethyl group optionally having one or more substituents selected from substituent group β1, or a (C$_1$-C$_{10}$ alkyl)-(Q)$_k$-(C$_1$-C$_{10}$ alkoxy)methyl group optionally having one or more substituents selected from substituent group β31; and k is 1, 2, or 3;

(15) The cationic lipid according to any one of (1) to (13) or a pharmacologically acceptable salt thereof, wherein L$^2$ is a decyl group, a decenyl group, an undecyl group, an undecenyl group, a dodecyl group, a dodecenyl group, a decadienyl group, an undecadienyl group, a dodecadienyl group, a heptadecadienyl group, an octadecadienyl group, a nonadecadienyl group, a heptadecatrienyl group, an octadecatrienyl group, a nonadecatrienyl group, a decyloxymethyl group, a decenyloxymethyl group, an undecyloxymethyl group, an undecenyloxymethyl group, a dodecyloxymethyl group, a dodecenyloxymethyl group, a decadienyloxymethyl group, an undecadienyloxymethyl group, a dodecadienyloxymethyl group, a heptadecadienyloxymethyl group, an octadecadienyloxymethyl group, a nonadecadienyloxymethyl group, a heptadecatrienyloxymethyl group, an octadecatrienyloxymethyl group, or a nonadecatrienyloxymethyl group optionally having one or more substituents selected from substituent group β1;

(16) The cationic lipid according to any one of (1) to (13) or a pharmacologically acceptable salt thereof, wherein L$^2$ is a decyl group, a cis-7-decenyl group, a (R)-11-acetyloxy-cis-8-heptadecenyl group, a (R)-11-(tetrahydro-2H-pyran-2-yloxy)-cis-8-heptadecenyl group, a cis-9-octadecenyl group (oleyl group), a cis-8,11-heptadecadienyl group, a cis-9,12-octadecadienyl group (linoleyl group), a cis-10,13-nonadecadienyl group, a cis-6,9,12-octadecatrienyl group (linolenyl group), a decyloxymethyl group, a cis-7-decenyloxymethyl group, a (R)-11-acetyloxy-cis-8-heptadecenyloxymethyl group, a (R)-11-(tetrahydro-2H-pyran-2-yloxy)-cis-8-heptadecenyloxymethyl group, a cis-9-octadecenyloxymethyl group (oleyloxymethyl group), a cis-8,11-heptadecadienyloxymethyl group, a cis-9,12-octadecadienyloxymethyl group (linoleyloxymethyl group), a cis-10,13-nonadecadienyloxymethyl group, or a cis-6,9,12-octadecatrienyloxymethyl group (linolenyloxymethyl group);

(17) The cationic lipid according to any one of (1) to (16) or a pharmacologically acceptable salt thereof, wherein m is 0;

(18) The cationic lipid according to (1) or a pharmacologically acceptable salt thereof, wherein both R$^1$ and R$^2$ are methyl groups; R$^8$ is a hydrogen atom; L$^1$ is a C$_{17}$-C$_{19}$ alkyl group optionally substituted by one acetyloxy group, or a C$_{17}$-C$_{19}$ alkenyl group optionally substituted by one acetyloxy group; L$^2$ is a C$_{10}$-C$_{19}$ alkyl group optionally substituted by one acetyloxy group, a C$_{10}$-C$_{19}$ alkenyl group optionally substituted by one acetyloxy group, a (C$_{10}$-C$_{19}$ alkoxy)methyl group optionally substituted by one acetyloxy group, or a (C$_{10}$-C$_{19}$ alkenyl)oxymethyl group optionally substituted by one acetyloxy group; p+r is 2; and m is 0;

(19) The cationic lipid according to (1) or a pharmacologically acceptable salt thereof, wherein R$^2$ is a methyl group; R$^1$ and R$^8$ together represent a group —(CH$_2$)$_q$—; L$^1$ is a C$_{17}$-C$_{19}$ alkyl group optionally substituted by one acetyloxy group, or a C$_{17}$-C$_{19}$ alkenyl group optionally substituted by one acetyloxy group; L$^2$ is a C$_{10}$-C$_{19}$ alkyl group optionally substituted by one acetyloxy group, a C$_{10}$-C$_{19}$ alkenyl group optionally substituted by one acetyloxy group, a (C$_{10}$-C$_{19}$ alkoxy)methyl group optionally substituted by one acetyloxy group, or a (C$_{10}$-C$_{19}$ alkenyl)oxymethyl group optionally substituted by one acetyloxy group; p is 2; q is 2; r is 0; and m is 0;

(20) The cationic lipid according to (1) or a pharmacologically acceptable salt thereof, wherein R$^2$ is a methyl group; R$^1$ and R$^8$ together represent a group —(CH$_2$)$_q$—; L$^1$ is a C$_{17}$-C$_{19}$ alkyl group optionally substituted by one acetyloxy group, or a C$_{17}$-C$_{19}$ alkenyl group optionally substituted by one acetyloxy group; L$^2$ is a C$_{10}$-C$_{19}$ alkyl group optionally substituted by one acetyloxy group, a C$_{10}$-C$_{19}$ alkenyl group optionally substituted by one acetyloxy group, a (C$_{10}$-C$_{19}$ alkoxy)methyl group optionally substituted by one acetyloxy group, or a (C$_{10}$-C$_{19}$ alkenyl)oxymethyl group optionally substituted by one acetyloxy group; p is 1; q is 2 or 3; r is 1; and m is 0;

(21) The cationic lipid according to (1) or a pharmacologically acceptable salt thereof, wherein R$^2$ is a methyl group; R$^1$ and R$^8$ together represent a group —(CH$_2$)$_q$—; L$^1$ is a C$_{17}$-C$_{19}$ alkyl group optionally substituted by one acetyloxy group, or a C$_{17}$-C$_{19}$ alkenyl group optionally substituted by one acetyloxy group; L$^2$ is a C$_{10}$-C$_{19}$ alkyl group optionally substituted by one acetyloxy group, a C$_{10}$-C$_{19}$ alkenyl group optionally substituted by one acetyloxy group, a (C$_{10}$-C$_{19}$ alkoxy)methyl group optionally substituted by one acetyloxy group, or a (C$_{10}$-C$_{19}$ alkenyl)oxymethyl group optionally substituted by one acetyloxy group; p is 0; q is 3 or 4; r is 2; and m is 0;

(22) The cationic lipid according to (1) or a pharmacologically acceptable salt thereof, wherein the cationic lipid is represented by the formula:

[Formula 3]

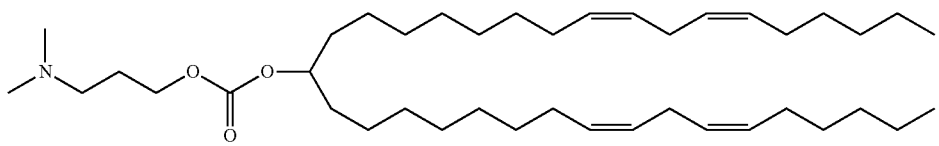

(23) The cationic lipid according to (1) or a pharmacologically acceptable salt thereof, wherein the cationic lipid is represented by the formula:

[Formula 4]

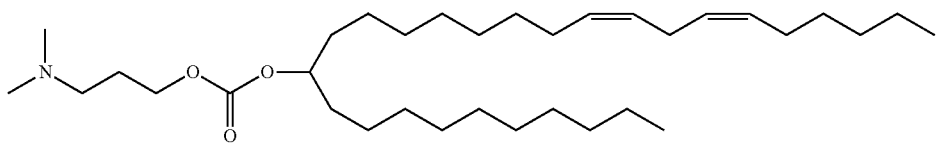

(24) The cationic lipid according to (1) or a pharmacologically acceptable salt thereof, wherein the cationic lipid is represented by the formula:

[Formula 5]

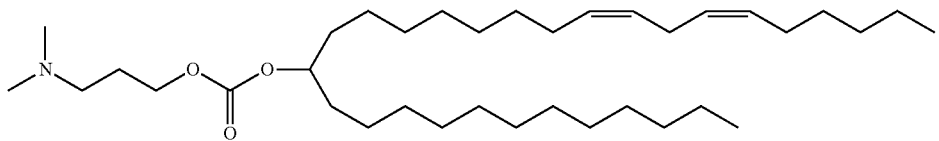

(25) The cationic lipid according to (1) or a pharmacologically acceptable salt thereof, wherein the cationic lipid is represented by the formula:

[Formula 6]

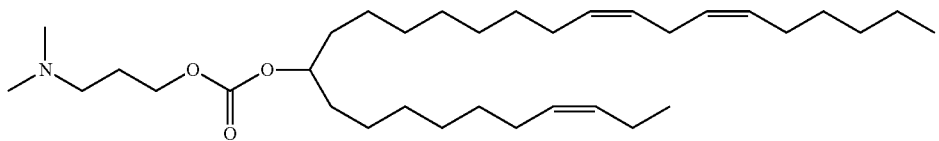

(26) The cationic lipid according to (1) or a pharmacologically acceptable salt thereof, wherein the cationic lipid is represented by the formula:

[Formula 7]

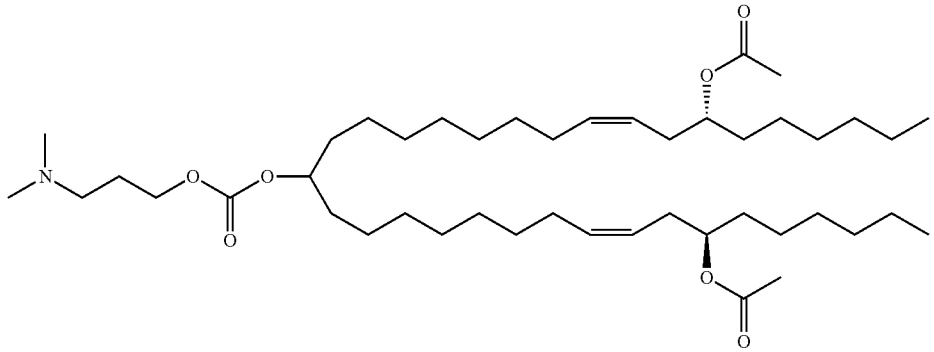

(27) The cationic lipid according to (1) or a pharmacologically acceptable salt thereof, wherein the cationic lipid is represented by the formula:

[Formula 8]

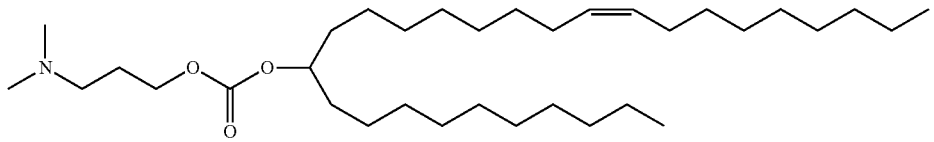

(28) The cationic lipid according to (1) or a pharmacologically acceptable salt thereof, wherein the cationic lipid is represented by the formula:

[Formula 9]

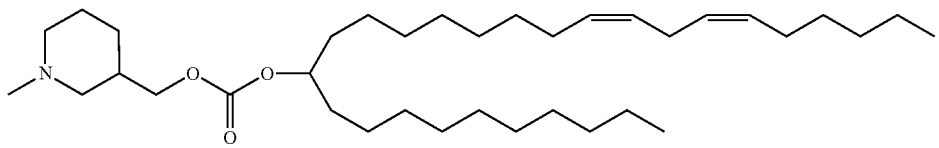

(29) The cationic lipid according to (1) or a pharmacologically acceptable salt thereof, wherein the cationic lipid is represented by the formula:

[Formula 10]

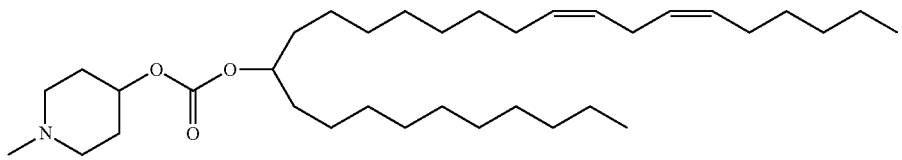

(30) The cationic lipid according to (1) or a pharmacologically acceptable salt thereof, wherein the cationic lipid is represented by the formula:

[Formula 11]

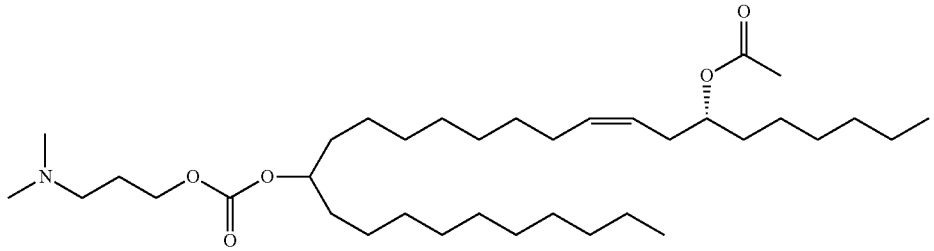

(31) The cationic lipid according to (1) or a pharmacologically acceptable salt thereof, wherein the cationic lipid is represented by the formula:

[Formula 12]

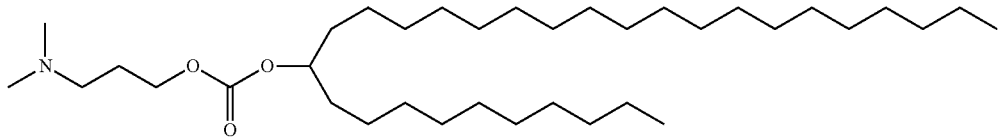

(32) The cationic lipid according to (1) or a pharmacologically acceptable salt thereof, wherein the cationic lipid is represented by the formula:

[Formula 13]

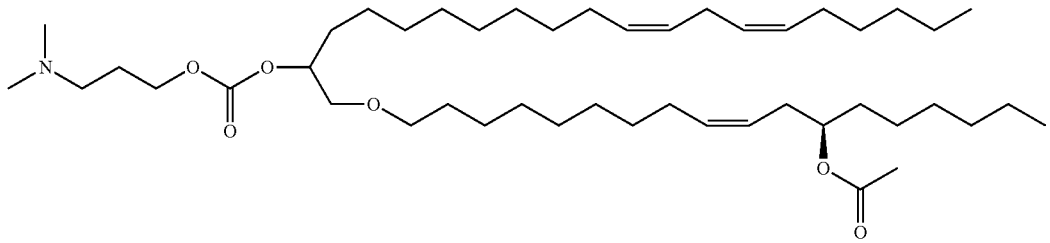

(33) A lipid particle comprising at least a cationic lipid according to any one of (1) to (32);
(34) The lipid particle according to (33), further comprising a lipid reducing aggregation during lipid particle formation;
(35) The lipid particle according to (34), wherein the lipid reducing aggregation during lipid particle formation is a PEG-lipid;
(36) The lipid particle according to (35), wherein the PEG-lipid is N-[methoxy poly(ethylene glycol)2000]carbamoyl]-1,2-dimyristyloxypropyl-3-amine (PEG-C-DMA), or 1,2-dimyristoyl-sn-glycerol methoxypolyethylene glycol;
(37) The lipid particle according to (35), wherein the PEG-lipid is N-[methoxy poly(ethylene glycol)2000]carbamoyl]-1,2-dimyristyloxypropyl-3-amine (PEG-C-DMA);
(38) The lipid particle according to (35), wherein the PEG-lipid is N-[methoxy poly(ethylene glycol)2000]carbamoyl]-1,2-dipalmityloxypropyl-3-amine (PEG-C-DPA), or 1,2-dipalmitoyl-sn-glycerol methoxypolyethylene glycol;
(39) The lipid particle according to (35), wherein the PEG-lipid is N-[methoxy poly(ethylene glycol)2000]carbamoyl]-1,2-dipalmityloxypropyl-3-amine (PEG-C-DPA);
(40) The lipid particle according to (35), wherein the PEG-lipid is N-[methoxy poly(ethylene glycol)2000]carbamoyl]-1,2-distearyloxypropyl-3-amine (PEG-C-DSA), or 1,2-distearoyl-sn-glycerol methoxypolyethylene glycol;
(41) The lipid particle according to (35), wherein the PEG-lipid is N-[methoxy poly(ethylene glycol)2000]carbamoyl]-1,2-distearyloxypropyl-3-amine (PEG-C-DSA);
(42) The lipid particle according to any one of (35) to (41), wherein the PEG has a molecular weight of 1,000 to 5,000;
(43) The lipid particle according to any one of (35) to (41), wherein the PEG has a molecular weight of 1,800 to 2,200;
(44) The lipid particle according to any one of (33) to (43), further comprising a sterol;
(45) The lipid particle according to (44), wherein the sterol is cholesterol;
(46) The lipid particle according to any one of claims (33) to (45), further comprising an amphipathic lipid;
(47) The lipid particle according to (46), wherein the amphipathic lipid is at least any one selected from distearoylphosphatidylcholine (DSPC), dipalmitoylphosphatidylcholine (DPPC), dimyristoylphosphatidylcholine (DMPC), 1-palmitoyl-2-oleoylphosphatidylcholine (POPC), dioleoylphosphatidylethanolamine (DOPE), and sphingomyelin (SM);

(48) The lipid particle according to (46), wherein the amphipathic lipid is distearoylphosphatidylcholine (DSPC) or dipalmitoylphosphatidylcholine (DPPC);

(49) The lipid particle according to any one of (46) to (48), wherein the lipid composition of the amphipathic lipid, the sterol, the cationic lipid, and the lipid reducing aggregation during lipid particle formation is 25% or less of the amphipathic lipid, 15% or more of the sterol, 20% to 70% of the cationic lipid, and 1% to 10% of the lipid reducing aggregation during lipid particle formation, in terms of molar quantity;

(50) The lipid particle according to any one of (46) to (48), wherein the lipid composition of the amphipathic lipid, the sterol, the cationic lipid, and the lipid reducing aggregation during lipid particle formation is 15% or less of the amphipathic lipid, 32% or more of the sterol, 45% to 65% of the cationic lipid, and 1.5% to 3% of the lipid reducing aggregation during lipid particle formation, in terms of molar quantity;

(51) A nucleic acid lipid particle comprising a lipid particle according to any one of (33) to (50) and a nucleic acid;

(52) The nucleic acid lipid particle according to (51), wherein the nucleic acid is any one selected from the group consisting of a single-stranded DNA, a single-stranded RNA, a single-stranded polynucleotide of a DNA and an RNA mixed with each other, a double-stranded DNA, a double-stranded RNA, a DNA-RNA hybrid polynucleotide, and two polynucleotides of a DNA and an RNA mixed with each other;

(53) The nucleic acid lipid particle according to (51), wherein the nucleic acid is a single-stranded or double-stranded polynucleotide having an RNA interference effect;

(54) The nucleic acid lipid particle according to (51), wherein the nucleic acid is a single-stranded RNA;

(55) The nucleic acid lipid particle according to any one of (51) to (54), wherein the ratio of the number of molecules of the cationic lipid (N) to the number of phosphorus atoms derived from the nucleic acid (P) is 2.0 to 9.0;

(56) The nucleic acid lipid particle according to any one of (51) to (54), wherein the ratio of the number of molecules of the cationic lipid (N) to the number of phosphorus atoms derived from the nucleic acid (P) is 3.0 to 9.0;

(57) The nucleic acid lipid particle according to any one of (51) to (56), wherein the average particle size is approximately 30 nm to approximately 300 nm;

(58) The nucleic acid lipid particle according to any one of (51) to (56), wherein the average particle size is approximately 30 nm to approximately 200 nm;

(59) The nucleic acid lipid particle according to any one of (51) to (56), wherein the average particle size is approximately 30 nm to approximately 100 nm;

(60) A pharmaceutical composition comprising a nucleic acid lipid particle according to any one of (51) to (59) as an active ingredient;

(61) The pharmaceutical composition according to (60), wherein the pharmaceutical composition is intended for the treatment or prevention of a disease derived from the expression of a target gene;

(62) The pharmaceutical composition according to (60), wherein the disease derived from the expression of a target gene is cancer, liver disease, gallbladder disease, fibrosis, anemia, or genetic disease;

(63) A method for inhibiting the expression of a target gene, comprising administering a nucleic acid lipid particle according to any one of (51) to (59) to a mammal;

(64) A method for treating or preventing a disease derived from the expression of a target gene, comprising administering a nucleic acid lipid particle according to any one of (51) to (59) to a mammal;

(65) The method according to (64), wherein the disease derived from the expression of a target gene is cancer; and

(66) A cationic lipid represented by the general formula (I):

[Formula 14]

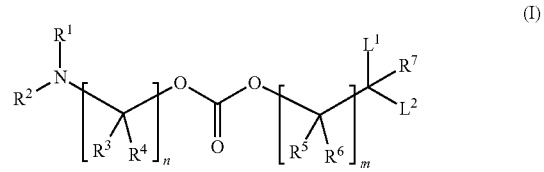

wherein $R^1$ and $R^2$ each independently represent a hydrogen atom, a $C_1$-$C_6$ alkyl group optionally having one or more substituents selected from substituent group α, a $C_2$-$C_6$ alkenyl group optionally having one or more substituents selected from substituent group α, a $C_2$-$C_6$ alkynyl group optionally having one or more substituents selected from substituent group α, or a $C_3$-$C_7$ cycloalkyl group optionally having one or more substituents selected from substituent group α, or $R^1$ and $R^2$ form a 3- to 10-membered heterocyclic ring together with the nitrogen atom bonded thereto, wherein the heterocyclic ring optionally has one or more substituents selected from substituent group α and optionally contains one or more atoms selected from a nitrogen atom, an oxygen atom, and a sulfur atom, in addition to the nitrogen atom bonded to $R^1$ and $R^2$, as atoms constituting the heterocyclic ring;

$R^3$ and $R^4$ each independently represent a hydrogen atom or a $C_1$-$C_6$ alkyl group optionally having one or more substituents selected from substituent group α, or $R^3$ and $R^4$ form a 3- to 10-membered hydrocarbon ring together with the carbon atom bonded thereto;

or $R^1$ forms a 3- to 10-membered heterocyclic ring together with the nitrogen atom bonded to $R^1$, $R^3$, and the carbon atom bonded to $R^3$, wherein the heterocyclic ring optionally has one or more substituents selected from substituent group α and optionally contains one or more atoms selected from a nitrogen atom, an oxygen atom, and a sulfur atom, in addition to the nitrogen atom bonded to $R^1$, as atoms constituting the heterocyclic ring;

$R^2$ and $R^4$ each independently represent a hydrogen atom, a $C_1$-$C_6$ alkyl group optionally having one or more substituents selected from substituent group α, a $C_2$-$C_6$ alkenyl group optionally having one or more substituents selected from substituent group α, or a $C_2$-$C_6$ alkynyl group optionally having one or more substituents selected from substituent group α;

$R^5$ and $R^6$ each independently represent a hydrogen atom or a $C_1$-$C_3$ alkyl group;

$R^7$ represents a hydrogen atom or a $C_1$-$C_6$ alkyl group optionally having one or more substituents selected from substituent group α;

substituent group α represents the group consisting of a halogen atom, an oxo group, a hydroxy group, a sulfanyl group, an amino group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_6$ alkylamino group, and a $C_1$-$C_7$ alkanoyl group;

$L^1$ and $L^2$ each independently represent a $C_{10}$-$C_{24}$ alkyl group optionally having one or more substituents selected from substituent group β, a $C_{10}$-$C_{24}$ alkenyl group optionally having one or more substituents selected from substituent group β, a $C_3$-$C_{24}$ alkynyl group optionally having one or more substituents selected from substituent group β, or a ($C_1$-$C_{10}$ alkyl)-(Q)$_k$-($C_1$-$C_{10}$ alkyl) group optionally having one or more substituents selected from substituent group β; substituent group β represents the group consisting of a halogen atom, an oxo group, a hydroxy group, a sulfanyl group, an amino group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_7$ alkanoyl group, a $C_1$-$C_7$ alkanoyloxy group, a $C_3$-$C_7$ alkoxyalkoxy group, a $C_1$-$C_6$ alkoxycarbonyl group, a $C_1$-$C_6$ alkoxycarboxyl group, a $C_1$-$C_6$ alkoxycarbamoyl group, and a $C_1$-$C_6$ alkylaminocarboxyl group;

Q represents a group represented by the following formula (II):

[Formula 15]

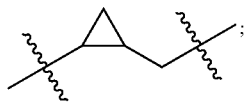

(II)

when $L^1$ and $L^2$ each have one or more substituents selected from substituent group β and substituent group β is a sulfanyl group, a $C_1$-$C_6$ alkyl group, a $C_1$-$C_6$ alkoxy group, a $C_1$-$C_6$ alkylsulfanyl group, a $C_1$-$C_7$ alkanoyl group, or a $C_1$-$C_7$ alkanoyloxy group, the substituent(s) selected from substituent group β in $L^1$ and the substituent(s) selected from substituent group β in $L^2$ optionally bind to each other to form a cyclic structure;

k represents an integer of 1 to 7;
m represents an integer of 0 or 1; and
n represents an integer of 3 to 6.

Advantageous Effects of Invention

The present invention may provide a novel cationic lipid that forms a lipid particle.

The present invention may also provide a novel cationic lipid that forms a lipid particle in combination with an amphipathic lipid, a sterol, and a lipid reducing aggregation during lipid particle formation.

The present invention may further provide a lipid particle comprising the cationic lipid.

The present invention may further provide a nucleic acid lipid particle comprising the lipid particle and further a nucleic acid.

The present invention may further provide a pharmaceutical composition containing the nucleic acid lipid particle as an active ingredient.

The present invention may further provide a method for treating a disease using the pharmaceutical composition.

BRIEF DESCRIPTION OF DRAWINGS

FIG. 1 is a diagram summarizing a method for producing an intermediate (A5) for use in the synthesis of a cationic lipid represented by the formula (I).

FIG. 2 is a diagram summarizing method B for use in the synthesis of the cationic lipid represented by the formula (I).

FIG. 3 is a diagram summarizing method C for use in the synthesis of the cationic lipid represented by the formula (I).

FIG. 4 is a diagram showing the structure of each nucleic acid having a double-stranded structure among nucleic acids constituting nucleic acid lipid particles. In the diagram, the upper sequences represent sense strands, and the lower sequences represent antisense strands. For symbols, the open square (□) represents an RNA, the filled circle (●) represents a DNA, and the open circle (○) represents a 2'-O-methyl RNA. The line between the symbols represents a phosphodiester bond between the nucleosides. In the diagram, p represents —P(=O)(OH)—. When p is bound, a hydrogen atom in the terminal hydroxy group of the polynucleotide is removed. When the end of the polynucleotide is unbound, the 3'-end or 5'-end of the RNA, the DNA, or the 2'-O-methyl RNA is an OH group. X represents a compound modifying the 5'-end of an antisense strand described in the paragraph "3-4-2. Modified double-stranded polynucleotide" in the specification. "linker" means a polynucleotide linker described in the paragraph "3-4-3. Modified single-stranded polynucleotide" in the specification.

FIG. 5 is a diagram showing PLK-1 expression inhibitory activity exhibited, in tumor, by a nucleic acid lipid particle having a compound of Example 19, 45, or 54 in Test Example 10.

FIG. 6 is a diagram showing that a nucleic acid lipid particle containing a compound of Example 8 in Test Example 11 promotes the expression of mRNA. The upper boxes depict images of nuclei stained with Hoechst, and the lower boxes depict images of mCherry.

DESCRIPTION OF EMBODIMENTS

Hereinafter, the embodiments of the present invention will be described in detail.

1. Cationic Lipid

The cationic lipid disclosed in the present specification can be used alone and can be used in combination with an additional substance. For example, the cationic lipid can be used as a component constituting a lipid particle and can be used as a component constituting a nucleic acid lipid particle.

1-1. Definition of Group

In the present invention, the "cationic lipid" is a lipid, some molecules of which have a net positive charge according to pKa of the lipid at a selected pH such as physiological pH. The cationic lipid of the present invention is a lipid that can be ionized (ionizable lipid) and differs from a cationic lipid having quaternary amine, which is a lipid, all molecules of which have a net positive charge at any pH (e.g., N,N-dioleyl-N,N-dimethylammonium chloride (DODAC)).

The "$C_1$-$C_6$ alkyl group" in the definitions of $R^1$, $R^2$, $R^3$, $R^4$, $R^7$, $R^8$, substituent group α, and substituent group β refers to a linear or branched alkyl group having 1 to 6 carbon atoms. Examples thereof can include a methyl group, an ethyl group, a n-propyl group, an isopropyl group, a n-butyl group, a sec-butyl group, a tert-butyl group, a n-pentyl group, an isopentyl group, a 2-methylbutyl group, a neopentyl group, a 1-ethylpropyl group, a n-hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group.

The $C_1$-$C_6$ alkyl group is preferably a $C_1$-$C_4$ alkyl group, more preferably a $C_1$-$C_3$ alkyl group.

The "$C_1$-$C_3$ alkyl group" in the definitions of $R^1$, $R^2$, $R^3$, $R^5$, and $R^6$ refers to a linear or branched alkyl group having 1 to 3 carbon atoms. Examples thereof can include a methyl group, an ethyl group, a propyl group, and an isopropyl group. The $C_1$-$C_3$ alkyl group is preferably a methyl group.

The "$C_2$-$C_6$ alkenyl group" in the definitions of $R^1$, $R^2$, and $R^4$ refers to a linear or branched alkenyl group having 2 to 6 carbon atoms. Examples thereof can include a vinyl group, a 1-propenyl group, a 2-propenyl group, an isopropenyl group, a 1-methyl-2-propenyl group, a 2-methyl-2-propenyl group, a 1-butenyl group, a 2-butenyl group, a 3-butenyl group, a 2-methyl-1-propenyl group, a 1-pentenyl group, a 4-pentenyl group, a 1-methyl-4-pentenyl group, and a 5-hexenyl group.

The "$C_2$-$C_6$ alkynyl group" in the definitions of $R^1$, $R^2$, and $R^4$ refers to a linear or branched alkynyl group having 2 to 6 carbon atoms. Examples thereof can include an ethynyl group, a 1-propynyl group, a 2-propynyl group, a 1-methyl-2-propynyl group, a 1-butynyl group, a 2-butynyl group, a 3-butynyl group, a 1-pentynyl group, a 4-pentynyl group, a 1-methyl-4-pentynyl group, and a 5-hexynyl group.

The "$C_3$-$C_7$ cycloalkyl group" in the definitions of $R^1$ and $R^2$ refers to a cycloalkyl group having 3 to 7 carbon atoms. Examples thereof can include a cyclopropyl group, a cyclobutyl group, a cyclopentyl group, a cyclohexyl group, and a cycloheptyl group.

The "3- to 10-membered heterocyclic ring" in the definitions of $R^1$, $R^2$, and $R^3$ refers to a saturated or partially unsaturated 3- to 10-membered monocyclic or bicyclic heterocyclic group containing at least one nitrogen atom and optionally further containing one or more atoms selected from the group consisting of a nitrogen atom, a sulfur atom, and an oxygen atom. Examples thereof can include azetidine, pyrrolidine, piperidine, azepane, dihydropyrrole, dihydropyridine, tetrahydropyridine, piperazine, morpholine, dihydrooxazole, and dihydrothiazole. The heterocyclic ring formed by $R^1$ and $R^2$ together with the nitrogen atom bonded thereto is preferably azetidine, pyrrolidine, or morpholine. The heterocyclic ring formed by $R^1$ together with the nitrogen atom bonded to $R^1$, $R^3$, and the carbon atom bonded to $R^3$ is preferably azetidine, pyrrolidine, piperidine, or morpholine.

The "3- to 10-membered hydrocarbon ring" in the definitions of $R^3$ and $R^4$ refers to a saturated hydrocarbon ring group having 3 to 10 carbon atoms. Examples thereof can include a cyclopropyl group, a cyclobutyl group, a cyclopentyl group, a cyclohexyl group, a cycloheptyl group, a cyclooctyl group, a cyclononyl group, and a cyclodecanyl group.

The "halogen atom" in the definitions of substituent group α and substituent group β is a fluorine atom, a chlorine atom, a bromine atom, or an iodine atom and is preferably a fluorine atom.

The "$C_1$-$C_6$ halogenated alkyl group" in the definitions of substituent group α and substituent group β refers to a group in which one or two hydrogen atoms in the "$C_1$-$C_6$ alkyl group" described above are replaced with the "halogen atom" described above. Examples thereof can include a fluoromethyl group, a chloromethyl group, a 1-fluoroethyl group, a 1-chloroethyl group, a 2-fluoroethyl group, and a 1,2-difluoropropyl group. The $C_1$-$C_6$ halogenated alkyl group is preferably a $C_1$-$C_4$ halogenated alkyl group, more preferably a $C_1$-$C_3$ halogenated alkyl group.

The "$C_1$-$C_6$ alkoxy group" in the definitions of substituent group α and substituent group β refers to a group in which the "$C_1$-$C_6$ alkyl group" described above is bonded to an oxygen atom. Examples thereof can include a methoxy group, an ethoxy group, a n-propoxy group, a n-butoxy group, a s-butoxy group, a tert-butoxy group, and a n-pentoxy group. The $C_1$-$C_6$ alkoxy group is preferably a $C_1$-$C_4$ alkoxy group, more preferably a $C_1$-$C_2$ alkoxy group.

The "$C_1$-$C_6$ alkylsulfanyl group" in the definitions of substituent group α and substituent group β refers to a group in which the "$C_1$-$C_6$ alkyl group" described above is bonded to a sulfur atom. Examples thereof can include a methylsulfanyl group, an ethylsulfanyl group, a n-propylsulfanyl group, a n-butylsulfanyl group, a s-butylsulfanyl group, a tert-butylsulfanyl group, and a n-pentylsulfanyl group. The $C_1$-$C_6$ alkylsulfanyl group is preferably a $C_1$-$C_4$ alkylsulfanyl group, more preferably a $C_1$-$C_2$ alkylsulfanyl group.

The "$C_1$-$C_6$ alkylamino group" in the definition of substituent group α refers to a group in which the "$C_1$-$C_6$ alkyl group" described above is bonded to a nitrogen atom. Examples thereof can include a methylamino group, an ethylamino group, a n-propylamino group, a n-butylamino group, a s-butylamino group, a tert-butylamino group, a n-pentylamino group, a n-hexylamino group, a N,N-dimethylamino group, a N,N-diethylamino group, a N,N-di-n-propylamino group, a N,N-diisopropylamino group, a N,N-di-n-butylamino group, a N,N-diisobutylamino group, a N,N-di-s-butylamino group, and a N,N-di-tert-butylamino group. The $C_1$-$C_6$ alkylamino group is preferably a $C_1$-$C_4$ alkylamino group, more preferably a $C_1$-$C_2$ alkylamino group.

The "$C_1$-$C_7$ alkanoyl group" in the definitions of substituent group α and substituent group β refers to an alkanoyl group having 1 to 7 carbon atoms. Examples thereof can include a formyl group, an acetyl group, a propionyl group, a butyryl group, an isobutyryl group, a pentanoyl group, a pivaloyl group, a valeryl group, an isovaleryl group, a hexanoyl group, and a heptanoyl group.

The "$C_1$-$C_7$ alkanoyloxy group" in the definition of substituent group β refers to a group in which the "$C_1$-$C_7$ alkanoyl group" described above is bonded to an oxygen atom. Examples thereof can include a formyloxy group, an acetyloxy group, a propionyloxy group, a butyryloxy group, an isobutyryloxy group, a pentanoyloxy group, a pivaloyloxy group, a valeryloxy group, an isovaleryloxy group, a hexanoyloxy group, and a heptanoyloxy group.

The "$C_3$-$C_7$ alkoxyalkoxy group" in the definition of substituent group β refers to a group in which one or two carbon atoms of a linear, branched, or cyclic alkane having 3 to 7 carbon atoms are replaced with an oxygen atom and the resulting group is further bonded to an oxygen atom (except for peroxide). Examples thereof can include a methoxymethoxy group, an ethoxymethoxy group, an ethoxyethoxy group, a 2-tetrahydrofuranyloxy group, and a 2-tetrahydropyranyloxy group.

The "($C_1$-$C_6$ alkoxy)carbonyl group" in the definition of substituent group β refers to a group in which the "$C_1$-$C_6$ alkoxy group" described above is bonded to a carbonyl group. Examples thereof can include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, and a hexyloxycarbonyl group.

The "($C_1$-$C_6$ alkoxy)carboxyl group" in the definition of substituent group β refers to a group in which the "$C_1$-$C_6$ alkoxy group" described above is bonded to a carboxyl group. Examples thereof can include a methoxycarboxyl group, an ethoxycarboxyl group, a propoxycarboxyl group, an isopropoxycarboxyl group, a butoxycarboxyl group, an isobutoxycarboxyl group, a sec-butoxycarboxyl group, a tert-butoxycarboxyl group, a pentyloxycarboxyl group, and a hexyloxycarboxyl group.

The "($C_1$-$C_6$ alkoxy)carbamoyl group" in the definition of substituent group β refers to a group in which the "$C_1$-$C_6$ alkoxy group" described above is bonded to a carbamoyl group. Examples thereof can include a methoxycarbamoyl group, an ethoxycarbamoyl group, a propoxycarbamoyl group, an isopropoxycarbamoyl group, a butoxycarbamoyl group, an isobutoxycarbamoyl group, a sec-butoxycarbamoyl group, a tert-butoxycarbamoyl group, a pentyloxycarbamoyl group, and a hexyloxycarbamoyl group.

The "($C_1$-$C_6$ alkylamino)carboxyl group" in the definition of substituent group β refers to a group in which the "$C_1$-$C_6$ alkylamino group" described above is bonded to a carboxyl group. Examples thereof can include a methylaminocarboxyl group, an ethylaminocarboxyl group, a n-propylaminocarboxyl group, a n-butylaminocarboxyl group, a s-butylaminocarboxyl group, a tert-butylaminocarboxyl group, a n-pentylaminocarboxyl group, a n-hexylaminocarboxyl group, a N,N-dimethylaminocarboxyl group, a N,N-diethylaminocarboxyl group, a N,N-di-n-propylaminocarboxyl group, a N,N-diisopropylaminocarboxyl group, a N,N-di-n-butylaminocarboxyl group, a N,N-diisobutylaminocarboxyl group, a N,N-di-s-butylaminocarboxyl group, and a N,N-di-tert-butylaminocarboxyl group.

The "$C_{10}$-$C_{24}$ alkyl group" in the definitions of $L^1$ and $L^2$ refer to a linear alkyl group having 10 to 24 carbon atoms. Examples thereof can include a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a tricosyl group, and a tetracosyl group. The "$C_{10}$-$C_{24}$ alkyl group" represented by $L^1$ is preferably a heptadecyl group, an octadecyl group, or a nonadecyl group. The "$C_{10}$-$C_{24}$ alkyl group" represented by $L^2$ is preferably a decyl group, an undecyl group, or a dodecyl group.

The "$C_{10}$-$C_{24}$ alkenyl group" in the definitions of $L^1$ and $L^2$ refers to a linear alkenyl group having 10 to 24 carbon atoms. The "$C_{10}$-$C_{24}$ alkenyl group" in the present application includes any of a $C_{10}$-$C_{24}$ alkadienyl group, a $C_{10}$-$C_{24}$ alkatrienyl group, and a $C_{10}$-$C_{24}$ alkatetraenyl group. Examples thereof can include a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, a henicosenyl group, a docosenyl group, a tricosenyl group, a tetracosenyl group, a decadienyl group, an undecadienyl group, a dodecadienyl group, a tridecadienyl group, a tetradecadienyl group, a pentadecadienyl group, a hexadecadienyl group, a heptadecadienyl group, an octadecadienyl group, a nonadecadienyl group, an icosadienyl group, a henicosadienyl group, a docosadienyl group, a tricosadienyl group, a tetracosadienyl group, a decatrienyl group, an undecatrienyl group, a dodecatrienyl group, a tridecatrienyl group, a tetradecatrienyl group, a pentadecatrienyl group, a hexadecatrienyl group, a heptadecatrienyl group, an octadecatrienyl group, a nonadecatrienyl group, an icosatrienyl group, a henicosatrienyl group, a docosatrienyl group, a tricosatrienyl group, and a tetracosatrienyl group. The "$C_{10}$-$C_{24}$ alkenyl group" represented by $L^1$ is preferably a heptadecenyl group, an octadecenyl group, a nonadecenyl group, a heptadecadienyl group, an octadecadienyl group, a nonadecadienyl group, a heptadecatrienyl group, an octadecatrienyl group, or a nonadecatrienyl group. $L^1$ is preferably a (R)-11-acetyloxy-cis-8-heptadecenyl group, a (R)-1-(tetrahydro-2H-pyran-2-yloxy)-cis-8-heptadecenyl group, a cis-9-octadecenyl group (oleyl group), a cis-8,11-heptadecadienyl group, a cis-9,12-octadecadienyl group (linoleyl group), a cis-10,13-nonadecadienyl group, or a cis-6,9,12-octadecatrienyl group (linolenyl group). The "$C_{10}$-$C_{24}$ alkenyl group" represented by $L^2$ is preferably a decenyl group, an undecenyl group, a dodecenyl group, a heptadecenyl group, an octadecenyl group, a decadienyl group, an undecadienyl group, a dodecadienyl group, a heptadecadienyl group, an octadecadienyl group, a nonadecadienyl group, a heptadecatrienyl group, an octadecatrienyl group, or a nonadecatrienyl group. $L^2$ is preferably a cis-7-decenyl group, a (R)-11-acetyloxy-cis-8-heptadecenyl group, a (R)-11-(tetrahydro-2H-pyran-2-yloxy)-cis-8-heptadecenyl group, a cis-9-octadecenyl group (oleyl group), a cis-8,11-heptadecadienyl group, a cis-9,12-octadecadienyl group (linoleyl group), a cis-10,13-nonadecadienyl group, or a cis-6,9,12-octadecatrienyl group (linolenyl group).

The "$C_3$-$C_{24}$ alkynyl group" in the definitions of $L^1$ and $L^2$ refers to a linear alkynyl group having 3 to 24 carbon atoms. The "$C_3$-$C_{24}$ alkynyl group" in the present application includes any of a $C_3$-$C_{24}$ alkadiynyl group, a $C_3$-$C_{24}$ alkatriynyl group, and a $C_3$-$C_{24}$ alkatetraynyl group. The $C_3$-$C_{24}$ alkynyl group is, for example, a propynyl group, a butynyl group, a pentynyl group, a hexynyl group, a heptynyl group, an octynyl group, a nonynyl group, a decynyl group, an undecynyl group, a dodecynyl group, a tridecynyl group, a tetradecynyl group, a pentadecynyl group, a hexadecynyl group, a heptadecynyl group, an octadecynyl group, a nonadecynyl group, an icosynyl group, a henicosynyl group, a docosynyl group, a tricosynyl group, or a tetracosynyl group and is preferably a decynyl group.

The "($C_1$-$C_{10}$ alkyl)-(Q)$_k$-($C_1$-$C_{10}$ alkyl) group" in the definitions of $L^1$ and $L^2$ is, for example, a group represented by any of the following structural formulas:

[Formula 16]

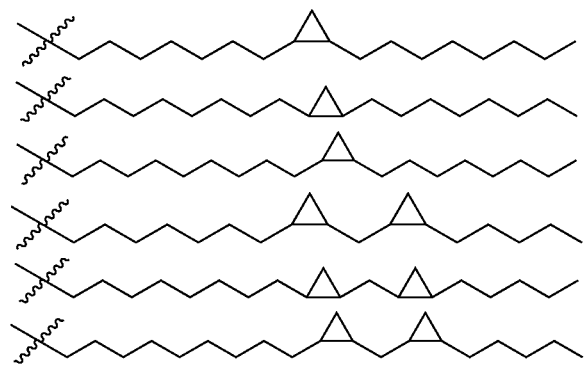

[Formula 17]

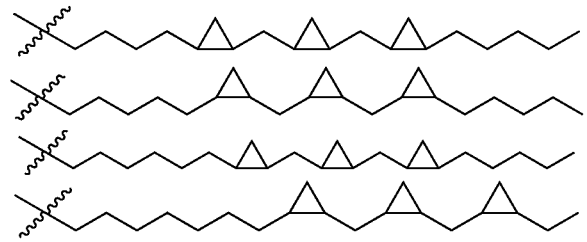

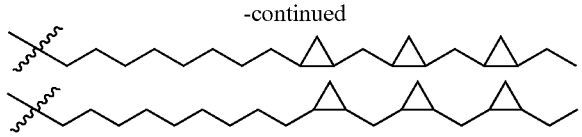

The "($C_{10}$-$C_{24}$ alkoxy)methyl group" in the definition of $L^2$ refers to a group in which the "$C_{10}$-$C_{24}$ alkyl group" described above is bonded to an oxygen atom which is further bonded to a methyl group. Examples thereof can include a decyloxymethyl group, an undecyloxymethyl group, a dodecyloxymethyl group, a tridecyloxymethyl group, a tetradecyloxymethyl group, a pentadecyloxymethyl group, a hexadecyloxymethyl group, a heptadecyloxymethyl group, an octadecyloxymethyl group, a nonadecyloxymethyl group, an icosyloxymethyl group, a henicosyloxymethyl group, a docosyloxymethyl group, a tricosyloxymethyl group, and a tetracosyloxymethyl group. The "($C_{10}$-$C_{24}$ alkoxy)methyl group" is preferably a decyloxymethyl group, an undecyloxymethyl group, or a dodecyloxymethyl group.

The "($C_{10}$-$C_{24}$ alkenyl)oxymethyl group" in the definition of $L^2$ refers to a group in which the "$C_{10}$-$C_{24}$ alkenyl group" described above is bonded to an oxygen atom which is further bonded to a methyl group. The "($C_{10}$-$C_{24}$ alkenyl)oxymethyl group" in the present application includes any of a ($C_{10}$-$C_{24}$ alkadienyl)oxymethyl group, a ($C_{10}$-$C_{24}$ alkatrienyl)oxymethyl group, and a ($C_{10}$-$C_{24}$ alkatetraenyl)oxymethyl group. Examples thereof can include a decenyloxymethyl group, an undecenyloxymethyl group, a dodecenyloxymethyl group, a tridecenyloxymethyl group, a tetradecenyloxymethyl group, a pentadecenyloxymethyl group, a hexadecenyloxymethyl group, a heptadecenyloxymethyl group, an octadecenyloxymethyl group, a nonadecenyloxymethyl group, an icosenyloxymethyl group, a henicosenyloxymethyl group, a docosenyloxymethyl group, a tricosenyloxymethyl group, a tetracosenyloxymethyl group, a decadienyloxymethyl group, an undecadienyloxymethyl group, a dodecadienyloxymethyl group, a tridecadienyloxymethyl group, a tetradecadienyloxymethyl group, a pentadecadienyloxymethyl group, a hexadecadienyloxymethyl group, a heptadecadienyloxymethyl group, an octadecadienyloxymethyl group, a nonadecadienyloxymethyl group, an icosadienyloxymethyl group, a henicosadienyloxymethyl group, a docosadienyloxymethyl group, a tricosadienyloxymethyl group, a tetracosadienyloxymethyl group, a decatrienyloxymethyl group, an undecatrienyloxymethyl group, a dodecatrienyloxymethyl group, a tridecatrienyloxymethyl group, a tetradecatrienyloxymethyl group, a pentadecatrienyloxymethyl group, a hexadecatrienyloxymethyl group, a heptadecatrienyloxymethyl group, an octadecatrienyloxymethyl group, a nonadecatrienyloxymethyl group, an icosatrienyloxymethyl group, a henicosatrienyloxymethyl group, a docosatrienyloxymethyl group, a tricosatrienyloxymethyl group, and a tetracosatrienyloxymethyl group. The "($C_{10}$-$C_{24}$ alkenyl)oxymethyl group" is preferably a decenyloxymethyl group, an undecenyloxymethyl group, a dodecenyloxymethyl group, a heptadecenyloxymethyl group, an octadecenyloxymethyl group, a decadienyloxymethyl group, an undecadienyloxymethyl group, a dodecadienyloxymethyl group, a heptadecadienyloxymethyl group, an octadecadienyloxymethyl group, a nonadecadienyloxymethyl group, a heptadecatrienyloxymethyl group, an octadecatrienyloxymethyl group, or a nonadecatrienyloxymethyl group, more preferably a cis-7-decenyloxymethyl group, a (R)-11-acetyloxy-cis-8-heptadecenyloxymethyl group, a (R)-11-(tetrahydro-2H-pyran-2-yloxy)-cis-8-heptadecenyloxymethyl group, a cis-9-octadecenyloxymethyl group (oleyloxymethyl group), a cis-8,11-heptadecadienyloxymethyl group, a cis-9,12-octadecadienyloxymethyl group (linoleyloxymethyl group), a cis-10,13-nonadecadienyloxymethyl group, or a cis-6,9,12-octadecatrienyloxymethyl group (linolenyloxymethyl group).

The "($C_3$-$C_{24}$ alkynyl)oxymethyl group" in the definition of $L^2$ refers to a group in which the "$C_3$-$C_{24}$ alkynyl group" described above is bonded to an oxygen atom which is further bonded to a methyl group. The "($C_3$-$C_{24}$ alkynyl)oxymethyl group" in the present application includes any of a ($C_3$-$C_{24}$ alkadiynyl)oxymethyl group, a ($C_3$-$C_{24}$ alkatriynyl)oxymethyl group, and a ($C_3$-$C_{24}$ alkatetraynyl)oxymethyl group. The "($C_3$-$C_{24}$ alkynyl)oxymethyl group" is, for example, a propynyloxymethyl group, a butynyloxymethyl group, a pentynyloxymethyl group, a hexynyloxymethyl group, a heptynyloxymethyl group, an octynyloxymethyl group, a nonynyloxymethyl group, a decynyloxymethyl group, an undecynyloxymethyl group, a dodecynyloxymethyl group, a tridecynyloxymethyl group, a tetradecynyloxymethyl group, a pentadecynyloxymethyl group, a hexadecynyloxymethyl group, a heptadecynyloxymethyl group, an octadecynyloxymethyl group, a nonadecynyloxymethyl group, an icosynyloxymethyl group, a henicosynyloxymethyl group, a docosynyloxymethyl group, a tricosynyloxymethyl group, or a tetracosynyloxymethyl group and is preferably a decynyloxymethyl group.

The "($C_1$-$C_{10}$ alkyl)-(Q)$_k$-($C_1$-$C_{10}$ alkyl)oxymethyl group" in the definition of $L^2$ refers to a group in which the "($C_1$-$C_{10}$ alkyl)-(Q)$_k$-($C_1$-$C_{10}$ alkyl) group" described above is bonded to an oxygen atom which is further bonded to a methyl group.

When $L^1$ and $L^2$ each have one or more substituents selected from substituent group β and the substituent(s) selected from substituent group β in $L^1$ and the substituent(s) selected from substituent group β in $L^2$ bind to each other to form a cyclic structure, substituent group β is preferably a $C_2$-$C_6$ alkanoyloxy group, more preferably a propionyloxy group. More specifically, the substituent(s) selected from substituent group β in $L^1$ and the substituent(s) selected from substituent group β in $L^2$ bind to each other to form a group —OCOCH$_2$CH$_2$COO—.

The substituent group β in the present application is preferably the group consisting of a halogen atom, an oxo group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_7$ alkanoyl group, a $C_1$-$C_7$ alkanoyloxy group, a $C_3$-$C_7$ alkoxyalkoxy group, a ($C_1$-$C_6$ alkoxy)carbonyl group, a ($C_1$-$C_6$ alkoxy)carboxyl group, a ($C_1$-$C_6$ alkoxy)carbamoyl group, and a ($C_1$-$C_6$ alkylamino)carboxyl group (substituent group β1), more preferably a $C_2$-$C_5$ alkanoyloxy group, further preferably an acetyloxy group or a propionyloxy group, particularly preferably an acetyloxy group.

The cationic lipid of the present invention can be converted to a "pharmacologically acceptable salt" by a standard method. Preferred examples of such a salt can include: metal salts including alkali metal salts such as a sodium salt, a potassium salt, and a lithium salt, alkaline earth metal salts such as a calcium salt and a magnesium salt, an aluminum salt, an iron salt, a zinc salt, a copper salt, a nickel salt, and a cobalt salt; amine salts including inorganic salts such as an ammonium salt and organic salts such as a t-octylamine salt, a dibenzylamine salt, a morpholine salt, a glucosamine salt, a phenylglycine alkyl ester salt, an ethylenediamine salt, a N-methylglucamine salt, a guanidine salt, a diethylamine salt, a triethylamine salt, a dicyclohexylamine salt, a N,N'-dibenzylethylenediamine salt, a chloroprocaine salt, a procaine salt, a diethanolamine salt, a N-benzyl-phenethylamine salt, a piperazine salt, a tetramethylammonium salt, and a tris(hydroxymethyl)aminomethane salt; inorganic acid salts such as a hydrohalide (e.g., a hydrofluoride, a hydrochloride, a hydrobromide, and a hydroiodide), a nitrate, a perchlorate, a sulfate, and a phosphate; organic acid salts such as lower alkanesulfonates (e.g., a methanesulfonate, a trifluoromethanesulfonate, and an ethanesulfonate), arylsulfonates (e.g., a benzenesulfonate and a p-toluenesulfonate), an acetate, a malate, a fumarate, a succinate, a citrate, a tartrate, an oxalate, and a maleate; and amino acid salts such as a glycine salt, a lysine salt, an arginine salt, an ornithine salt, a glutamate, and an aspartate.

The cationic lipid of the present invention can also exist as a hydrate or a solvate. The present invention encompasses even such a hydrate or solvate.

The cationic lipid of the present invention may have a stereoisomer, a geometric isomer, or an atropisomer. The present invention encompasses even these isomers and mixtures of arbitrary isomers at an arbitrary ratio, unless otherwise specified.

1-2. Specific Example of Cationic Lipid

Specific examples of the cationic lipid of the present invention can include compounds 1-1 to 1-481 described below in Table 1 and compounds 2-1 to 2-570 described below in Table 2. In Tables 1 and 2, "C17-1" represents a cis-8-heptadecenyl group; "C18-1" represents a cis-9-octadecenyl group (oleyl group); "C17-2" represents a cis,cis-8,11-heptadecadienyl group; "Lin" represents a cis,cis-9,12-octadecadienyl group (linoleyl group); "C19-2" represents a cis,cis-10,13-nonadecadienyl group; "C17-31" represents a cis,cis,cis-5,8,11-heptadecatrienyl group; "C17-32" represents a cis,cis,cis-8,11,14-heptadecatrienyl group; "C17-33" represents a 7-[2-({2-[(2-ethylcyclopropyl)methyl]cyclopropyl}methyl)cyclopropyl]heptyl group; "C17-A" represents a (R)-11-acetyloxy-cis-8-heptadecenyl group; "C17-H" represents a (R)-11-hexenyloxy-cis-8-heptadecenyl group; "C17-OH" represents a (R)-11-hydroxy-cis-8-heptadecenyl group; "C17-T" represents a (R)-11-(tetrahydro-2H-pyran-2-yloxy)-cis-8-heptadecenyl group; "C17-T2" represents a (R)-11-(tetrahydro-2H-furan-2-yloxy)-cis-8-heptadecenyl group; "Me" represents a methyl group; "Et" represents an ethyl group; "Pr" represents a propyl group; "C10" represents a decyl group; "C11" represents an undecyl group; "C12" represents a dodecyl group; "C13" represents a tridecyl group; "C14" represents a tetradecyl group; "C15" represents a pentadecyl group; "C16" represents a hexadecyl group; "C17" represents a heptadecyl group; "C18" represents an octadecyl group; "C19" represents a nonadecyl group; "C20" represents an icosyl group; "C21" represents a henicosyl group; "C22" represents a docosyl group; "C23" represents a tricosyl group; "C24" represents a tetracosyl group; "C10-1" represents a cis-7-decenyl group; "C10-2" represents a 7-decynyl group; "C17-O-Su-O—$C_{17}$" represents a group in which (R)-11-hydroxy-cis-8-heptadecenyl groups are cross-linked via succinic acid; and "-" represents a single bond.

TABLE 1

[Formula 18]

$$R^2\text{-}\underset{R^1}{N}\text{-}Z\text{-}O\text{-}\underset{O}{\overset{\parallel}{C}}\text{-}O\text{-}(CH_2)_m\text{-}\underset{L^2}{\overset{L^1}{C}}\text{-}R^3$$

| Compound | $R^1$ | $R^2$ | m | Z | $L^1$ | $L^2$ | $R^3$ |
|---|---|---|---|---|---|---|---|
| 1-1 | Me | Me | 0 | —(CH₂)₃— | C16 | C10 | H |
| 1-2 | Me | Me | 0 | —(CH₂)₃— | C16 | C11 | H |
| 1-3 | Me | Me | 0 | —(CH₂)₃— | C16 | C12 | H |
| 1-4 | Me | Me | 0 | —(CH₂)₃— | C16 | C13 | H |
| 1-5 | Me | Me | 0 | —(CH₂)₃— | C16 | C14 | H |
| 1-6 | Me | Me | 0 | —(CH₂)₃— | C16 | C15 | H |
| 1-7 | Me | Me | 0 | —(CH₂)₃— | C16 | C16 | H |
| 1-8 | Me | Me | 0 | —(CH₂)₃— | C17 | C10 | H |
| 1-9 | Me | Me | 0 | —(CH₂)₃— | C17 | C11 | H |
| 1-10 | Me | Me | 0 | —(CH₂)₃— | C17 | C12 | H |
| 1-11 | Me | Me | 0 | —(CH₂)₃— | C17 | C13 | H |
| 1-12 | Me | Me | 0 | —(CH₂)₃— | C17 | C14 | H |
| 1-13 | Me | Me | 0 | —(CH₂)₃— | C17 | C15 | H |
| 1-14 | Me | Me | 0 | —(CH₂)₃— | C17 | C16 | H |
| 1-15 | Me | Me | 0 | —(CH₂)₃— | C17 | C17 | H |
| 1-16 | Me | Me | 0 | —(CH₂)₃— | C17-1 | C10 | H |
| 1-17 | Me | Et | 0 | —(CH₂)₃— | C17-1 | C10 | H |
| 1-18 | Me | Pr | 0 | —(CH₂)₃— | C17-1 | C10 | H |
| 1-19 | Et | Et | 0 | —(CH₂)₃— | C17-1 | C10 | H |
| 1-20 | —(CH₂)₃— | | 0 | —(CH₂)₃— | C17-1 | C10 | H |
| 1-21 | —(CH₂)₄— | | 0 | —(CH₂)₃— | C17-1 | C10 | H |
| 1-22 | —(CH₂)₂O(CH₂)₂— | | 0 | —(CH₂)₃— | C17-1 | C10 | H |
| 1-23 | Me | Me | 0 | —CH₂CH(CH₃)CH₂— | C17-1 | C10 | H |
| 1-24 | Me | Me | 0 | —(CH₂)₄— | C17-1 | C10 | H |
| 1-25 | Me | Me | 0 | —(CH₂)₅— | C17-1 | C10 | H |
| 1-26 | Me | Me | 1 | —(CH₂)₃— | C17-1 | C10 | H |
| 1-27 | Me | Me | 1 | —(CH₂)₄— | C17-1 | C10 | H |
| 1-28 | Me | Me | 0 | —(CH₂)₃— | C17-1 | C10 | Me |
| 1-29 | Me | Et | 0 | —(CH₂)₃— | C17-1 | C10 | Me |
| 1-30 | Me | Me | 0 | —(CH₂)₃— | C17-1 | C10 | Et |
| 1-31 | Me | Me | 0 | —(CH₂)₃— | C17-1 | C10-1 | H |

TABLE 1-continued

[Formula 18]

$$\begin{array}{c} R^1 \\ | \\ R^2-N-Z-O-\overset{O}{\underset{\|}{C}}-O-(CH_2)_m-C(L^1)(L^2)R^3 \end{array}$$

| Compound | R¹ | R² | m | Z | L¹ | L² | R³ |
|---|---|---|---|---|---|---|---|
| 1-32 | Me | Et | 0 | —(CH₂)₃— | C17-1 | C10-1 | H |
| 1-33 | Me | Pr | 0 | —(CH₂)₃— | C17-1 | C10-1 | H |
| 1-34 | Et | Et | 0 | —(CH₂)₃— | C17-1 | C10-1 | H |
| 1-35 | —(CH₂)₃— | | 0 | —(CH₂)₃— | C17-1 | C10-1 | H |
| 1-36 | —(CH₂)₄— | | 0 | —(CH₂)₃— | C17-1 | C10-1 | H |
| 1-37 | —(CH₂)₂O(CH₂)₂— | | 0 | —(CH₂)₃— | C17-1 | C10-1 | H |
| 1-38 | Me | Me | 0 | —CH₂CH(CH₃)CH₂— | C17-1 | C10-1 | H |
| 1-39 | Me | Me | 0 | —(CH₂)₄— | C17-1 | C10-1 | H |
| 1-40 | Me | Me | 0 | —(CH₂)₅— | C17-1 | C10-1 | H |
| 1-41 | Me | Me | 1 | —(CH₂)₃— | C17-1 | C10-1 | H |
| 1-42 | Me | Me | 1 | —(CH₂)₄— | C17-1 | C10-1 | H |
| 1-43 | Me | Me | 0 | —(CH₂)₃— | C17-1 | C11 | H |
| 1-44 | Me | Me | 0 | —(CH₂)₃— | C17-1 | C12 | H |
| 1-45 | Me | Me | 0 | —(CH₂)₃— | C17-1 | C13 | H |
| 1-46 | Me | Me | 0 | —(CH₂)₃— | C17-1 | C14 | H |
| 1-47 | Me | Me | 0 | —(CH₂)₃— | C17-1 | C15 | H |
| 1-48 | Me | Me | 0 | —(CH₂)₃— | C17-1 | C16 | H |
| 1-49 | Me | Me | 0 | —(CH₂)₃— | C17-1 | C17 | H |
| 1-50 | Me | Me | 0 | —(CH₂)₃— | C17-1 | C17-1 | H |
| 1-51 | Me | Et | 0 | —(CH₂)₃— | C17-1 | C17-1 | H |
| 1-52 | Me | Pr | 0 | —(CH₂)₃— | C17-1 | C17-1 | H |
| 1-53 | Et | Et | 0 | —(CH₂)₃— | C17-1 | C17-1 | H |
| 1-54 | —(CH₂)₃— | | 0 | —(CH₂)₃— | C17-1 | C17-1 | H |
| 1-55 | —(CH₂)₄— | | 0 | —(CH₂)₃— | C17-1 | C17-1 | H |
| 1-56 | —(CH₂)₂O(CH₂)₂— | | 0 | —(CH₂)₃— | C17-1 | C17-1 | H |
| 1-57 | Me | Me | 0 | —CH₂CH(CH₃)CH₂— | C17-1 | C17-1 | H |
| 1-58 | Me | Me | 0 | —(CH₂)₄— | C17-1 | C17-1 | H |
| 1-59 | Me | Me | 0 | —(CH₂)₅— | C17-1 | C17-1 | H |
| 1-60 | Me | Me | 1 | —(CH₂)₃— | C17-1 | C17-1 | H |
| 1-61 | Me | Me | 1 | —(CH₂)₄— | C17-1 | C17-1 | H |
| 1-62 | Me | Me | 0 | —(CH₂)₃— | C17-1 | C17-1 | Me |
| 1-63 | Me | Et | 0 | —(CH₂)₃— | C17-1 | C17-1 | Me |
| 1-64 | Me | Me | 0 | —(CH₂)₃— | C17-1 | C17-1 | Et |
| 1-65 | Me | Me | 0 | —(CH₂)₃— | C17-1 | C18 | H |
| 1-66 | Me | Me | 0 | —(CH₂)₃— | C17-1 | C19 | H |
| 1-67 | Me | Me | 0 | —(CH₂)₃— | C17-1 | C20 | H |
| 1-68 | Me | Me | 0 | —(CH₂)₃— | C17-1 | C21 | H |
| 1-69 | Me | Me | 0 | —(CH₂)₃— | C17-1 | C22 | H |
| 1-70 | Me | Me | 0 | —(CH₂)₃— | C17-1 | C23 | H |
| 1-71 | Me | Me | 0 | —(CH₂)₃— | C17-1 | C24 | H |
| 1-72 | Me | Me | 0 | —(CH₂)₃— | C17-2 | C10 | H |
| 1-73 | Me | Et | 0 | —(CH₂)₃— | C17-2 | C10 | H |
| 1-74 | Me | Pr | 0 | —(CH₂)₃— | C17-2 | C10 | H |
| 1-75 | Et | Et | 0 | —(CH₂)₃— | C17-2 | C10 | H |
| 1-76 | —(CH₂)₃— | | 0 | —(CH₂)₃— | C17-2 | C10 | H |
| 1-77 | —(CH₂)₄— | | 0 | —(CH₂)₃— | C17-2 | C10 | H |
| 1-78 | —(CH₂)₂O(CH₂)₂— | | 0 | —(CH₂)₃— | C17-2 | C10 | H |
| 1-79 | Me | Me | 0 | —CH₂CH(CH₃)CH₂— | C17-2 | C10 | H |
| 1-80 | Me | Me | 0 | —(CH₂)₄— | C17-2 | C10 | H |
| 1-81 | Me | Me | 0 | —(CH₂)₅— | C17-2 | C10 | H |
| 1-82 | Me | Me | 1 | —(CH₂)₃— | C17-2 | C10 | H |
| 1-83 | Me | Me | 1 | —(CH₂)₄— | C17-2 | C10 | H |
| 1-84 | Me | Me | 0 | —(CH₂)₃— | C17-2 | C10 | Me |
| 1-85 | Me | Et | 0 | —(CH₂)₃— | C17-2 | C10 | Me |
| 1-86 | Me | Me | 0 | —(CH₂)₃— | C17-2 | C10 | Et |
| 1-87 | Me | Me | 0 | —(CH₂)₃— | C17-2 | C10-1 | H |
| 1-88 | Me | Et | 0 | —(CH₂)₃— | C17-2 | C10-1 | H |
| 1-89 | Me | Pr | 0 | —(CH₂)₃— | C17-2 | C10-1 | H |
| 1-90 | Et | Et | 0 | —(CH₂)₃— | C17-2 | C10-1 | H |
| 1-91 | —(CH₂)₃— | | 0 | —(CH₂)₃— | C17-2 | C10-1 | H |
| 1-92 | —(CH₂)₄— | | 0 | —(CH₂)₃— | C17-2 | C10-1 | H |
| 1-93 | —(CH₂)₂O(CH₂)₂— | | 0 | —(CH₂)₃— | C17-2 | C10-1 | H |
| 1-94 | Me | Me | 0 | —CH₂CH(CH₃)CH₂— | C17-2 | C10-1 | H |
| 1-95 | Me | Me | 0 | —(CH₂)₄— | C17-2 | C10-1 | H |
| 1-96 | Me | Me | 0 | —(CH₂)₅— | C17-2 | C10-1 | H |
| 1-97 | Me | Me | 1 | —(CH₂)₃— | C17-2 | C10-1 | H |
| 1-98 | Me | Me | 1 | —(CH₂)₄— | C17-2 | C10-1 | H |
| 1-99 | Me | Me | 0 | —(CH₂)₃— | C17-2 | C10-2 | H |
| 1-100 | Me | Et | 0 | —(CH₂)₃— | C17-2 | C10-2 | H |
| 1-101 | Me | Pr | 0 | —(CH₂)₃— | C17-2 | C10-2 | H |

TABLE 1-continued

[Formula 18]

| Compound | R$^1$ | R$^2$ | m | Z | L$^1$ | L$^2$ | R$^3$ |
|---|---|---|---|---|---|---|---|
| 1-102 | Et | Et | 0 | —(CH$_2$)$_3$— | C17-2 | C10-2 | H |
| 1-103 | —(CH$_2$)$_3$— | | 0 | —(CH$_2$)$_3$— | C17-2 | C10-2 | H |
| 1-104 | —(CH$_2$)$_4$— | | 0 | —(CH$_2$)$_3$— | C17-2 | C10-2 | H |
| 1-105 | —(CH$_2$)$_2$O(CH$_2$)$_2$— | | 0 | —(CH$_2$)$_3$— | C17-2 | C10-2 | H |
| 1-106 | Me | Me | 0 | —CH$_2$CH(CH$_3$)CH$_2$— | C17-2 | C10-2 | H |
| 1-107 | Me | Me | 0 | —(CH$_2$)$_4$— | C17-2 | C10-2 | H |
| 1-108 | Me | Me | 0 | —(CH$_2$)$_5$— | C17-2 | C10-2 | H |
| 1-109 | Me | Me | 1 | —(CH$_2$)$_3$— | C17-2 | C10-2 | H |
| 1-110 | Me | Me | 1 | —(CH$_2$)$_4$— | C17-2 | C10-2 | H |
| 1-111 | Me | Me | 0 | —(CH$_2$)$_3$— | C17-2 | C11 | H |
| 1-112 | Me | Me | 0 | —(CH$_2$)$_3$— | C17-2 | C12 | H |
| 1-113 | Me | Me | 0 | —(CH$_2$)$_3$— | C17-2 | C13 | H |
| 1-114 | Me | Me | 0 | —(CH$_2$)$_3$— | C17-2 | C14 | H |
| 1-115 | Me | Me | 0 | —(CH$_2$)$_3$— | C17-2 | C15 | H |
| 1-116 | Me | Me | 0 | —(CH$_2$)$_3$— | C17-2 | C16 | H |
| 1-117 | Me | Me | 0 | —(CH$_2$)$_3$— | C17-2 | C17 | H |
| 1-118 | Me | Me | 0 | —(CH$_2$)$_3$— | C17-2 | C17-2 | H |
| 1-119 | Me | Me | 0 | —(CH$_2$)$_3$— | C17-2 | C17-2 | H |
| 1-120 | Me | Me | 0 | —(CH$_2$)$_3$— | C17-2 | C17-2 | H |
| 1-121 | Me | Et | 0 | —(CH$_2$)$_3$— | C17-2 | C17-2 | H |
| 1-122 | Me | Et | 0 | —(CH$_2$)$_3$— | C17-2 | C17-2 | H |
| 1-123 | Me | Pr | 0 | —(CH$_2$)$_3$— | C17-2 | C17-2 | H |
| 1-124 | Et | Et | 0 | —(CH$_2$)$_3$— | C17-2 | C17-2 | H |
| 1-125 | —(CH$_2$)$_3$— | | 0 | —(CH$_2$)$_3$— | C17-2 | C17-2 | H |
| 1-126 | —(CH$_2$)$_4$— | | 0 | —(CH$_2$)$_3$— | C17-2 | C17-2 | H |
| 1-127 | —(CH$_2$)$_2$O(CH$_2$)$_2$— | | 0 | —(CH$_2$)$_3$— | C17-2 | C17-2 | H |
| 1-128 | Me | Me | 0 | —CH$_2$CH(CH$_3$)CH$_2$— | C17-2 | C17-2 | H |
| 1-129 | Me | Me | 0 | —(CH$_2$)$_4$— | C17-2 | C17-2 | H |
| 1-130 | Me | Me | 0 | —(CH$_2$)$_5$— | C17-2 | C17-2 | H |
| 1-131 | Me | Me | 1 | —(CH$_2$)$_3$— | C17-2 | C17-2 | H |
| 1-132 | Me | Me | 1 | —(CH$_2$)$_4$— | C17-2 | C17-2 | H |
| 1-133 | Me | Me | 0 | —(CH$_2$)$_3$— | C17-2 | C18 | H |
| 1-134 | Me | Me | 0 | —(CH$_2$)$_3$— | C17-2 | C19 | H |
| 1-135 | Me | Me | 0 | —(CH$_2$)$_3$— | C17-2 | C20 | H |
| 1-136 | Me | Me | 0 | —(CH$_2$)$_3$— | C17-2 | C21 | H |
| 1-137 | Me | Me | 0 | —(CH$_2$)$_3$— | C17-2 | C22 | H |
| 1-138 | Me | Me | 0 | —(CH$_2$)$_3$— | C17-2 | C23 | H |
| 1-139 | Me | Me | 0 | —(CH$_2$)$_3$— | C17-2 | C24 | H |
| 1-140 | Me | Me | 0 | —(CH$_2$)$_3$— | C17-31 | C10 | H |
| 1-141 | Me | Et | 0 | —(CH$_2$)$_3$— | C17-31 | C10 | H |
| 1-142 | Me | Pr | 0 | —(CH$_2$)$_3$— | C17-31 | C10 | H |
| 1-143 | Et | Et | 0 | —(CH$_2$)$_3$— | C17-31 | C10 | H |
| 1-144 | —(CH$_2$)$_3$— | | 0 | —(CH$_2$)$_3$— | C17-31 | C10 | H |
| 1-145 | —(CH$_2$)$_4$— | | 0 | —(CH$_2$)$_3$— | C17-31 | C10 | H |
| 1-146 | —(CH$_2$)$_2$O(CH$_2$)$_2$— | | 0 | —(CH$_2$)$_3$— | C17-31 | C10 | H |
| 1-147 | Me | Me | 0 | —CH$_2$CH(CH$_3$)CH$_2$— | C17-31 | C10 | H |
| 1-148 | Me | Me | 0 | —(CH$_2$)$_4$— | C17-31 | C10 | H |
| 1-149 | Me | Me | 0 | —(CH$_2$)$_5$— | C17-31 | C10 | H |
| 1-150 | Me | Me | 1 | —(CH$_2$)$_3$— | C17-31 | C10 | H |
| 1-151 | Me | Me | 1 | —(CH$_2$)$_4$— | C17-31 | C10 | H |
| 1-152 | Me | Me | 0 | —(CH$_2$)$_3$— | C17-31 | C17-31 | H |
| 1-153 | Me | Et | 0 | —(CH$_2$)$_3$— | C17-31 | C17-31 | H |
| 1-154 | Me | Pr | 0 | —(CH$_2$)$_3$— | C17-31 | C17-31 | H |
| 1-155 | Et | Et | 0 | —(CH$_2$)$_3$— | C17-31 | C17-31 | H |
| 1-156 | —(CH$_2$)$_3$— | | 0 | —(CH$_2$)$_3$— | C17-31 | C17-31 | H |
| 1-157 | —(CH$_2$)$_4$— | | 0 | —(CH$_2$)$_3$— | C17-31 | C17-31 | H |
| 1-158 | —(CH$_2$)$_2$O(CH$_2$)$_2$— | | 0 | —(CH$_2$)$_3$— | C17-31 | C17-31 | H |
| 1-159 | Me | Me | 0 | —CH$_2$CH(CH$_3$)CH$_2$— | C17-31 | C17-31 | H |
| 1-160 | Me | Me | 0 | —(CH$_2$)$_4$— | C17-31 | C17-31 | H |
| 1-161 | Me | Me | 0 | —(CH$_2$)$_5$— | C17-31 | C17-31 | H |
| 1-162 | Me | Me | 1 | —(CH$_2$)$_3$— | C17-31 | C17-31 | H |
| 1-163 | Me | Me | 1 | —(CH$_2$)$_4$— | C17-31 | C17-31 | H |
| 1-164 | Me | Me | 0 | —(CH$_2$)$_3$— | C17-32 | C10 | H |
| 1-165 | Me | Et | 0 | —(CH$_2$)$_3$— | C17-32 | C10 | H |
| 1-166 | Me | Pr | 0 | —(CH$_2$)$_3$— | C17-32 | C10 | H |
| 1-167 | Et | Et | 0 | —(CH$_2$)$_3$— | C17-32 | C10 | H |
| 1-168 | —(CH$_2$)$_3$— | | 0 | —(CH$_2$)$_3$— | C17-32 | C10 | H |
| 1-169 | —(CH$_2$)$_4$— | | 0 | —(CH$_2$)$_3$— | C17-32 | C10 | H |
| 1-170 | —(CH$_2$)$_2$O(CH$_2$)$_2$— | | 0 | —(CH$_2$)$_3$— | C17-32 | C10 | H |
| 1-171 | Me | Me | 0 | —CH$_2$CH(CH$_3$)CH$_2$— | C17-32 | C10 | H |

TABLE 1-continued

[Formula 18]

$$R^2\text{-}N(R^1)\text{-}Z\text{-}O\text{-}C(=O)\text{-}O\text{-}(CH)_m\text{-}C(L^1)(L^2)(R^3)$$

| Compound | $R^1$ | $R^2$ | m | Z | $L^1$ | $L^2$ | $R^3$ |
|---|---|---|---|---|---|---|---|
| 1-172 | Me | Me | 0 | —(CH$_2$)$_4$— | C17-32 | C10 | H |
| 1-173 | Me | Me | 0 | —(CH$_2$)$_5$— | C17-32 | C10 | H |
| 1-174 | Me | Me | 1 | —(CH$_2$)$_3$— | C17-32 | C10 | H |
| 1-175 | Me | Me | 1 | —(CH$_2$)$_4$— | C17-32 | C10 | H |
| 1-176 | Me | Me | 0 | —(CH$_2$)$_3$— | C17-32 | C17-32 | H |
| 1-177 | Me | Et | 0 | —(CH$_2$)$_3$— | C17-32 | C17-32 | H |
| 1-178 | Me | Pr | 0 | —(CH$_2$)$_3$— | C17-32 | C17-32 | H |
| 1-179 | Et | Et | 0 | —(CH$_2$)$_3$— | C17-32 | C17-32 | H |
| 1-180 | —(CH$_2$)$_3$— | | 0 | —(CH$_2$)$_3$— | C17-32 | C17-32 | H |
| 1-181 | —(CH$_2$)$_4$— | | 0 | —(CH$_2$)$_3$— | C17-32 | C17-32 | H |
| 1-182 | —(CH$_2$)$_2$O(CH$_2$)$_2$— | | 0 | —(CH$_2$)$_3$— | C17-32 | C17-32 | H |
| 1-183 | Me | Me | 0 | —CH$_2$CH(CH$_3$)CH$_2$— | C17-32 | C17-32 | H |
| 1-184 | Me | Me | 0 | —(CH$_2$)$_4$— | C17-32 | C17-32 | H |
| 1-185 | Me | Me | 0 | —(CH$_2$)$_5$— | C17-32 | C17-32 | H |
| 1-186 | Me | Me | 1 | —(CH$_2$)$_3$— | C17-32 | C17-32 | H |
| 1-187 | Me | Me | 1 | —(CH$_2$)$_4$— | C17-32 | C17-32 | H |
| 1-188 | Me | Me | 0 | —(CH$_2$)$_3$— | C17-33 | C10 | H |
| 1-189 | Me | Et | 0 | —(CH$_2$)$_3$— | C17-33 | C10 | H |
| 1-190 | Me | Pr | 0 | —(CH$_2$)$_3$— | C17-33 | C10 | H |
| 1-191 | Et | Et | 0 | —(CH$_2$)$_3$— | C17-33 | C10 | H |
| 1-192 | —(CH$_2$)$_3$— | | 0 | —(CH$_2$)$_3$— | C17-33 | C10 | H |
| 1-193 | —(CH$_2$)$_4$— | | 0 | —(CH$_2$)$_3$— | C17-33 | C10 | H |
| 1-194 | —(CH$_2$)$_2$O(CH$_2$)$_2$— | | 0 | —(CH$_2$)$_3$— | C17-33 | C10 | H |
| 1-195 | Me | Me | 0 | —CH$_2$CH(CH$_3$)CH$_2$— | C17-33 | C10 | H |
| 1-196 | Me | Me | 0 | —(CH$_2$)$_4$— | C17-33 | C10 | H |
| 1-197 | Me | Me | 0 | —(CH$_2$)$_5$— | C17-33 | C10 | H |
| 1-198 | Me | Me | 1 | —(CH$_2$)$_3$— | C17-33 | C10 | H |
| 1-199 | Me | Me | 1 | —(CH$_2$)$_4$— | C17-33 | C10 | H |
| 1-200 | Me | Me | 0 | —(CH$_2$)$_3$— | C17-33 | C17-33 | H |
| 1-201 | Me | Et | 0 | —(CH$_2$)$_3$— | C17-33 | C17-33 | H |
| 1-202 | Me | Pr | 0 | —(CH$_2$)$_3$— | C17-33 | C17-33 | H |
| 1-203 | Et | Et | 0 | —(CH$_2$)$_3$— | C17-33 | C17-33 | H |
| 1-204 | —(CH$_2$)$_3$— | | 0 | —(CH$_2$)$_3$— | C17-33 | C17-33 | H |
| 1-205 | —(CH$_2$)$_4$— | | 0 | —(CH$_2$)$_3$— | C17-33 | C17-33 | H |
| 1-206 | —(CH$_2$)$_2$O(CH$_2$)$_2$— | | 0 | —(CH$_2$)$_3$— | C17-33 | C17-33 | H |
| 1-207 | Me | Me | 0 | —CH$_2$CH(CH$_3$)CH$_2$— | C17-33 | C17-33 | H |
| 1-208 | Me | Me | 0 | —(CH$_2$)$_4$— | C17-33 | C17-33 | H |
| 1-209 | Me | Me | 0 | —(CH$_2$)$_5$— | C17-33 | C17-33 | H |
| 1-210 | Me | Me | 1 | —(CH$_2$)$_3$— | C17-33 | C17-33 | H |
| 1-211 | Me | Me | 1 | —(CH$_2$)$_4$— | C17-33 | C17-33 | H |
| 1-212 | Me | Me | 0 | —(CH$_2$)$_3$— | C17-A | C10 | H |
| 1-213 | Me | Et | 0 | —(CH$_2$)$_3$— | C17-A | C10 | H |
| 1-214 | Me | Pr | 0 | —(CH$_2$)$_3$— | C17-A | C10 | H |
| 1-215 | Et | Et | 0 | —(CH$_2$)$_3$— | C17-A | C10 | H |
| 1-216 | —(CH$_2$)$_3$— | | 0 | —(CH$_2$)$_3$— | C17-A | C10 | H |
| 1-217 | —(CH$_2$)$_4$— | | 0 | —(CH$_2$)$_3$— | C17-A | C10 | H |
| 1-218 | —(CH$_2$)$_2$O(CH$_2$)$_2$— | | 0 | —(CH$_2$)$_3$— | C17-A | C10 | H |
| 1-219 | Me | Me | 0 | —CH$_2$CH(CH$_3$)CH$_2$— | C17-A | C10 | H |
| 1-220 | Me | Me | 0 | —(CH$_2$)$_4$— | C17-A | C10 | H |
| 1-221 | Me | Me | 0 | —(CH$_2$)$_5$— | C17-A | C10 | H |
| 1-222 | Me | Me | 1 | —(CH$_2$)$_3$— | C17-A | C10 | H |
| 1-223 | Me | Me | 1 | —(CH$_2$)$_4$— | C17-A | C10 | H |
| 1-224 | Me | Me | 0 | —(CH$_2$)$_3$— | C17-A | C11 | H |
| 1-225 | Me | Me | 0 | —(CH$_2$)$_3$— | C17-A | C12 | H |
| 1-226 | Me | Me | 0 | —(CH$_2$)$_3$— | C17-A | C13 | H |
| 1-227 | Me | Me | 0 | —(CH$_2$)$_3$— | C17-A | C14 | H |
| 1-228 | Me | Me | 0 | —(CH$_2$)$_3$— | C17-A | C15 | H |
| 1-229 | Me | Me | 0 | —(CH$_2$)$_3$— | C17-A | C16 | H |
| 1-230 | Me | Me | 0 | —(CH$_2$)$_3$— | C17-A | C17 | H |
| 1-231 | Me | Me | 0 | —(CH$_2$)$_3$— | C17-A | C17-1 | H |
| 1-232 | Me | Me | 0 | —(CH$_2$)$_3$— | C17-A | C17-2 | H |
| 1-233 | Me | Me | 0 | —(CH$_2$)$_3$— | C17-A | C17-A | H |
| 1-234 | Me | Et | 0 | —(CH$_2$)$_3$— | C17-A | C17-A | H |
| 1-235 | Me | Pr | 0 | —(CH$_2$)$_3$— | C17-A | C17-A | H |
| 1-236 | Et | Et | 0 | —(CH$_2$)$_3$— | C17-A | C17-A | H |
| 1-237 | —(CH$_2$)$_3$— | | 0 | —(CH$_2$)$_3$— | C17-A | C17-A | H |
| 1-238 | —(CH$_2$)$_4$— | | 0 | —(CH$_2$)$_3$— | C17-A | C17-A | H |
| 1-239 | —(CH$_2$)$_2$O(CH$_2$)$_2$— | | 0 | —(CH$_2$)$_3$— | C17-A | C17-A | H |
| 1-240 | Me | Me | 0 | —CH$_2$CH(CH$_3$)CH$_2$— | C17-A | C17-A | H |
| 1-241 | Me | Me | 0 | —(CH$_2$)$_4$— | C17-A | C17-A | H |

TABLE 1-continued

[Formula 18]

$$R^2\text{-}N(R^1)\text{-}Z\text{-}O\text{-}C(=O)\text{-}O\text{-}(CH_2)_m\text{-}C(L^1)(L^2)R^3$$

| Compound | $R^1$ | $R^2$ | m | Z | $L^1$ | $L^2$ | $R^3$ |
|---|---|---|---|---|---|---|---|
| 1-242 | Me | Me | 0 | —(CH$_2$)$_5$— | C17-A | C17-A | H |
| 1-243 | Me | Me | 1 | —(CH$_2$)$_3$— | C17-A | C17-A | H |
| 1-244 | Me | Me | 1 | —(CH$_2$)$_4$— | C17-A | C17-A | H |
| 1-245 | Me | Me | 0 | —(CH$_2$)$_3$— | C17-A | C18 | H |
| 1-246 | Me | Me | 0 | —(CH$_2$)$_3$— | C17-A | C18-1 | H |
| 1-247 | Me | Me | 0 | —(CH$_2$)$_3$— | C17-A | C19 | H |
| 1-248 | Me | Me | 0 | —(CH$_2$)$_3$— | C17-A | C19-2 | H |
| 1-249 | Me | Me | 0 | —(CH$_2$)$_3$— | C17-A | C20 | H |
| 1-250 | Me | Me | 0 | —(CH$_2$)$_3$— | C17-A | C21 | H |
| 1-251 | Me | Me | 0 | —(CH$_2$)$_3$— | C17-A | C22 | H |
| 1-252 | Me | Me | 0 | —(CH$_2$)$_3$— | C17-A | C23 | H |
| 1-253 | Me | Me | 0 | —(CH$_2$)$_3$— | C17-A | C24 | H |
| 1-254 | Me | Me | 0 | —(CH$_2$)$_3$— | C17-A | Lin | H |
| 1-255 | Me | Me | 0 | —(CH$_2$)$_3$— | C17-H | C10 | H |
| 1-256 | Me | Et | 0 | —(CH$_2$)$_3$— | C17-H | C10 | H |
| 1-257 | Me | Pr | 0 | —(CH$_2$)$_3$— | C17-H | C10 | H |
| 1-258 | Et | Et | 0 | —(CH$_2$)$_3$— | C17-H | C10 | H |
| 1-259 | —(CH$_2$)$_3$— | | 0 | —(CH$_2$)$_3$— | C17-H | C10 | H |
| 1-260 | —(CH$_2$)$_4$— | | 0 | —(CH$_2$)$_3$— | C17-H | C10 | H |
| 1-261 | —(CH$_2$)$_2$O(CH$_2$)$_2$— | | 0 | —(CH$_2$)$_3$— | C17-H | C10 | H |
| 1-262 | Me | Me | 0 | —CH$_2$CH(CH$_3$)CH$_2$— | C17-H | C10 | H |
| 1-263 | Me | Me | 0 | —(CH$_2$)$_4$— | C17-H | C10 | H |
| 1-264 | Me | Me | 0 | —(CH$_2$)$_5$— | C17-H | C10 | H |
| 1-265 | Me | Me | 1 | —(CH$_2$)$_3$— | C17-H | C10 | H |
| 1-266 | Me | Me | 1 | —(CH$_2$)$_4$— | C17-H | C10 | H |
| 1-267 | Me | Me | 0 | —(CH$_2$)$_3$— | C17-H | C11 | H |
| 1-268 | Me | Me | 0 | —(CH$_2$)$_3$— | C17-H | C12 | H |
| 1-269 | Me | Me | 0 | —(CH$_2$)$_3$— | C17-H | C13 | H |
| 1-270 | Me | Me | 0 | —(CH$_2$)$_3$— | C17-H | C14 | H |
| 1-271 | Me | Me | 0 | —(CH$_2$)$_3$— | C17-H | C15 | H |
| 1-272 | Me | Me | 0 | —(CH$_2$)$_3$— | C17-H | C16 | H |
| 1-273 | Me | Me | 0 | —(CH$_2$)$_3$— | C17-H | C17 | H |
| 1-274 | Me | Me | 0 | —(CH$_2$)$_3$— | C17-H | C17-1 | H |
| 1-275 | Me | Me | 0 | —(CH$_2$)$_3$— | C17-H | C17-2 | H |
| 1-276 | Me | Me | 0 | —(CH$_2$)$_3$— | C17-H | C17-H | H |
| 1-277 | Me | Et | 0 | —(CH$_2$)$_3$— | C17-H | C17-H | H |
| 1-278 | Me | Pr | 0 | —(CH$_2$)$_3$— | C17-H | C17-H | H |
| 1-279 | Et | Et | 0 | —(CH$_2$)$_3$— | C17-H | C17-H | H |
| 1-280 | —(CH$_2$)$_3$— | | 0 | —(CH$_2$)$_3$— | C17-H | C17-H | H |
| 1-281 | —(CH$_2$)$_4$— | | 0 | —(CH$_2$)$_3$— | C17-H | C17-H | H |
| 1-282 | —(CH$_2$)$_2$O(CH$_2$)$_2$— | | 0 | —(CH$_2$)$_3$— | C17-H | C17-H | H |
| 1-283 | Me | Me | 0 | —CH$_2$CH(CH$_3$)CH$_2$— | C17-H | C17-H | H |
| 1-284 | Me | Me | 0 | —(CH$_2$)$_4$— | C17-H | C17-H | H |
| 1-285 | Me | Me | 0 | —(CH$_2$)$_5$— | C17-H | C17-H | H |
| 1-286 | Me | Me | 1 | —(CH$_2$)$_3$— | C17-H | C17-H | H |
| 1-287 | Me | Me | 1 | —(CH$_2$)$_4$— | C17-H | C17-H | H |
| 1-288 | Me | Me | 0 | —(CH$_2$)$_3$— | C17-H | C18 | H |
| 1-289 | Me | Me | 0 | —(CH$_2$)$_3$— | C17-H | C18-1 | H |
| 1-290 | Me | Me | 0 | —(CH$_2$)$_3$— | C17-H | C19 | H |
| 1-291 | Me | Me | 0 | —(CH$_2$)$_3$— | C17-H | C19-2 | H |
| 1-292 | Me | Me | 0 | —(CH$_2$)$_3$— | C17-H | C20 | H |
| 1-293 | Me | Me | 0 | —(CH$_2$)$_3$— | C17-H | C21 | H |
| 1-294 | Me | Me | 0 | —(CH$_2$)$_3$— | C17-H | C22 | H |
| 1-295 | Me | Me | 0 | —(CH$_2$)$_3$— | C17-H | C23 | H |
| 1-296 | Me | Me | 0 | —(CH$_2$)$_3$— | C17-H | C24 | H |
| 1-297 | Me | Me | 0 | —(CH$_2$)$_3$— | C17-H | Lin | H |
| 1-298 | Me | Me | 0 | —(CH$_2$)$_3$— | C17—OH | C10 | H |
| 1-299 | Me | Me | 0 | —(CH$_2$)$_3$— | C17—OH | C11 | H |
| 1-300 | Me | Me | 0 | —(CH$_2$)$_3$— | C17—OH | C12 | H |
| 1-301 | Me | Me | 0 | —(CH$_2$)$_3$— | C17—OH | C13 | H |
| 1-302 | Me | Me | 0 | —(CH$_2$)$_3$— | C17—OH | C14 | H |
| 1-303 | Me | Me | 0 | —(CH$_2$)$_3$— | C17—OH | C15 | H |
| 1-304 | Me | Me | 0 | —(CH$_2$)$_3$— | C17—OH | C16 | H |
| 1-305 | Me | Me | 0 | —(CH$_2$)$_3$— | C17—OH | C17 | H |
| 1-306 | Me | Me | 0 | —(CH$_2$)$_3$— | C17—OH | C17-1 | H |
| 1-307 | Me | Me | 0 | —(CH$_2$)$_3$— | C17—OH | C17-2 | H |
| 1-308 | Me | Me | 0 | —(CH$_2$)$_3$— | C17—OH | C17—OH | H |
| 1-309 | Me | Me | 0 | —(CH$_2$)$_3$— | C17—OH | C18 | H |
| 1-310 | Me | Me | 0 | —(CH$_2$)$_3$— | C17—OH | C18-1 | H |
| 1-311 | Me | Me | 0 | —(CH$_2$)$_3$— | C17—OH | C19 | H |

TABLE 1-continued

[Formula 18]

$$\underset{R^2}{\overset{R^1}{N}}-Z-O-\underset{\underset{O}{\|}}{C}-O-(\phantom{)}_m\underset{L^2}{\overset{L^1}{C}}R^3$$

| Compound | R¹ | R² | m | Z | L¹ | L² | R³ |
|---|---|---|---|---|---|---|---|
| 1-312 | Me | Me | 0 | —(CH₂)₃— | C17—OH | C19-2 | H |
| 1-313 | Me | Me | 0 | —(CH₂)₃— | C17—OH | C20 | H |
| 1-314 | Me | Me | 0 | —(CH₂)₃— | C17—OH | C21 | H |
| 1-315 | Me | Me | 0 | —(CH₂)₃— | C17—OH | C22 | H |
| 1-316 | Me | Me | 0 | —(CH₂)₃— | C17—OH | C23 | H |
| 1-317 | Me | Me | 0 | —(CH₂)₃— | C17—OH | C24 | H |
| 1-318 | Me | Me | 0 | —(CH₂)₃— | C17—OH | Lin | H |
| 1-319 | Me | Me | 0 | —(CH₂)₃— | C17—O—Su—O—C17 | | H |
| 1-320 | Me | Me | 0 | —(CH₂)₃— | C17—O—Su—O—C17 | | H |
| 1-321 | Me | Me | 0 | —(CH₂)₃— | C17—O—Su—O—C17 | | H |
| 1-322 | Me | Et | 0 | —(CH₂)₃— | C17—O—Su—O—C17 | | H |
| 1-323 | Me | Et | 0 | —(CH₂)₃— | C17—O—Su—O—C17 | | H |
| 1-324 | Me | Pr | 0 | —(CH₂)₃— | C17—O—Su—O—C17 | | H |
| 1-325 | Et | Et | 0 | —(CH₂)₃— | C17—O—Su—O—C17 | | H |
| 1-326 | —(CH₂)₃— | | 0 | —(CH₂)₃— | C17—O—Su—O—C17 | | H |
| 1-327 | —(CH₂)₄— | | 0 | —(CH₂)₃— | C17—O—Su—O—C17 | | H |
| 1-328 | —(CH₂)₂O(CH₂)₂— | | 0 | —(CH₂)₃— | C17—O—Su—O—C17 | | H |
| 1-329 | Me | Me | 0 | —CH₂CH(CH₃)CH₂— | C17—O—Su—O—C17 | | H |
| 1-330 | Me | Me | 0 | —(CH₂)₄— | C17—O—Su—O—C17 | | H |
| 1-331 | Me | Me | 0 | —(CH₂)₅— | C17—O—Su—O—C17 | | H |
| 1-332 | Me | Me | 1 | —(CH₂)₃— | C17—O—Su—O—C17 | | H |
| 1-333 | Me | Me | 1 | —(CH₂)₄— | C17—O—Su—O—C17 | | H |
| 1-334 | Me | Me | 0 | —(CH₂)₃— | C17-T | C10 | H |
| 1-335 | Me | Et | 0 | —(CH₂)₃— | C17-T | C10 | H |
| 1-336 | Me | Pr | 0 | —(CH₂)₃— | C17-T | C10 | H |
| 1-337 | Et | Et | 0 | —(CH₂)₃— | C17-T | C10 | H |
| 1-338 | —(CH₂)₃— | | 0 | —(CH₂)₃— | C17-T | C10 | H |
| 1-339 | —(CH₂)₄— | | 0 | —(CH₂)₃— | C17-T | C10 | H |
| 1-340 | —(CH₂)₂O(CH₂)₂— | | 0 | —(CH₂)₃— | C17-T | C10 | H |
| 1-341 | Me | Me | 0 | —CH₂CH(CH₃)CH₂— | C17-T | C10 | H |
| 1-342 | Me | Me | 0 | —(CH₂)₄— | C17-T | C10 | H |
| 1-343 | Me | Me | 0 | —(CH₂)₅— | C17-T | C10 | H |
| 1-344 | Me | Me | 1 | —(CH₂)₃— | C17-T | C10 | H |
| 1-345 | Me | Me | 1 | —(CH₂)₄— | C17-T | C10 | H |
| 1-346 | Me | Me | 0 | —(CH₂)₃— | C17-T | C11 | H |
| 1-347 | Me | Me | 0 | —(CH₂)₃— | C17-T | C12 | H |
| 1-348 | Me | Me | 0 | —(CH₂)₃— | C17-T | C13 | H |
| 1-349 | Me | Me | 0 | —(CH₂)₃— | C17-T | C14 | H |
| 1-350 | Me | Me | 0 | —(CH₂)₃— | C17-T | C15 | H |
| 1-351 | Me | Me | 0 | —(CH₂)₃— | C17-T | C16 | H |
| 1-352 | Me | Me | 0 | —(CH₂)₃— | C17-T | C17 | H |
| 1-353 | Me | Me | 0 | —(CH₂)₃— | C17-T | C17-1 H | H |
| 1-354 | Me | Me | 0 | —(CH₂)₃— | C17-T | C17-2 H | H |
| 1-355 | Me | Me | 0 | —(CH₂)₃— | C17-T | C17-T H | H |
| 1-356 | Me | Et | 0 | —(CH₂)₃— | C17-T | C17-T H | H |
| 1-357 | Me | Pr | 0 | —(CH₂)₃— | C17-T | C17-T H | H |
| 1-358 | Et | Et | 0 | —(CH₂)₃— | C17-T | C17-T H | H |
| 1-359 | —(CH₂)₃— | | 0 | —(CH₂)₃— | C17-T | C17-T H | H |
| 1-360 | —(CH₂)₄— | | 0 | —(CH₂)₃— | C17-T | C17-T H | H |
| 1-361 | —(CH₂)₂O(CH₂)₂— | | 0 | —(CH₂)₃— | C17-T | C17-T H | H |
| 1-362 | Me | Me | 0 | —CH₂CH(CH₃)CH₂— | C17-T | C17-T H | H |
| 1-363 | Me | Me | 0 | —(CH₂)₄— | C17-T | C17-T H | H |
| 1-364 | Me | Me | 0 | —(CH₂)₅— | C17-T | C17-T H | H |
| 1-365 | Me | Me | 1 | —(CH₂)₃— | C17-T | C17-T H | H |
| 1-366 | Me | Me | 1 | —(CH₂)₄— | C17-T | C17-T H | H |
| 1-367 | Me | Me | 0 | —(CH₂)₃— | C17-T | C18 | H |
| 1-368 | Me | Me | 0 | —(CH₂)₃— | C17-T | C18-1 | H |
| 1-369 | Me | Me | 0 | —(CH₂)₃— | C17-T | C19 | H |
| 1-370 | Me | Me | 0 | —(CH₂)₃— | C17-T | C19-2 | H |
| 1-371 | Me | Me | 0 | —(CH₂)₃— | C17-T | C20 | H |
| 1-372 | Me | Me | 0 | —(CH₂)₃— | C17-T | C21 | H |
| 1-373 | Me | Me | 0 | —(CH₂)₃— | C17-T | C22 | H |
| 1-374 | Me | Me | 0 | —(CH₂)₃— | C17-T | C23 | H |
| 1-375 | Me | Me | 0 | —(CH₂)₃— | C17-T | C24 | H |
| 1-376 | Me | Me | 0 | —(CH₂)₃— | C17-T | Lin | H |
| 1-377 | Me | Me | 0 | —(CH₂)₃— | C17-T2 | C10 | H |
| 1-378 | Me | Et | 0 | —(CH₂)₃— | C17-T2 | C10 | H |
| 1-379 | Me | Pr | 0 | —(CH₂)₃— | C17-T2 | C10 | H |
| 1-380 | Et | Et | 0 | —(CH₂)₃— | C17-T2 | C10 | H |
| 1-381 | —(CH₂)₃— | | 0 | —(CH₂)₃— | C17-T2 | C10 | H |

TABLE 1-continued

[Formula 18]

$$R^2\text{-}N(R^1)\text{-}Z\text{-}O\text{-}C(=O)\text{-}O\text{-}(CH_2)_m\text{-}C(L^1)(L^2)R^3$$

| Compound | $R^1$ | $R^2$ | m | Z | $L^1$ | $L^2$ | $R^3$ |
| --- | --- | --- | --- | --- | --- | --- | --- |
| 1-382 | —(CH$_2$)$_4$— | | 0 | —(CH$_2$)$_3$— | C17-T2 | C10 | H |
| 1-383 | —(CH$_2$)$_2$O(CH$_2$)$_2$— | | 0 | —(CH$_2$)$_3$— | C17-T2 | C10 | H |
| 1-384 | Me | Me | 0 | —CH$_2$CH(CH$_3$)CH$_2$— | C17-T2 | C10 | H |
| 1-385 | Me | Me | 0 | —(CH$_2$)$_4$— | C17-T2 | C10 | H |
| 1-386 | Me | Me | 0 | —(CH$_2$)$_5$— | C17-T2 | C10 | H |
| 1-387 | Me | Me | 1 | —(CH$_2$)$_3$— | C17-T2 | C10 | H |
| 1-388 | Me | Me | 1 | —(CH$_2$)$_4$— | C17-T2 | C10 | H |
| 1-389 | Me | Me | 0 | —(CH$_2$)$_3$— | C17-T2 | C11 | H |
| 1-390 | Me | Me | 0 | —(CH$_2$)$_3$— | C17-T2 | C12 | H |
| 1-391 | Me | Me | 0 | —(CH$_2$)$_3$— | C17-T2 | C13 | H |
| 1-392 | Me | Me | 0 | —(CH$_2$)$_3$— | C17-T2 | C14 | H |
| 1-393 | Me | Me | 0 | —(CH$_2$)$_3$— | C17-T2 | C15 | H |
| 1-394 | Me | Me | 0 | —(CH$_2$)$_3$— | C17-T2 | C16 | H |
| 1-395 | Me | Me | 0 | —(CH$_2$)$_3$— | C17-T2 | C17 | H |
| 1-396 | Me | Me | 0 | —(CH$_2$)$_3$— | C17-T2 | C17-1 | H |
| 1-397 | Me | Me | 0 | —(CH$_2$)$_3$— | C17-T2 | C17-2 | H |
| 1-398 | Me | Me | 0 | —(CH$_2$)$_3$— | C17-T2 | C17-T2 | H |
| 1-399 | Me | Et | 0 | —(CH$_2$)$_3$— | C17-T2 | C17-T2 | H |
| 1-400 | Me | Pr | 0 | —(CH$_2$)$_3$— | C17-T2 | C17-T2 | H |
| 1-401 | Et | Et | 0 | —(CH$_2$)$_3$— | C17-T2 | C17-T2 | H |
| 1-402 | —(CH$_2$)$_3$— | | 0 | —(CH$_2$)$_3$— | C17-T2 | C17-T2 | H |
| 1-403 | —(CH$_2$)$_4$— | | 0 | —(CH$_2$)$_3$— | C17-T2 | C17-T2 | H |
| 1-404 | —(CH$_2$)$_2$O(CH$_2$)$_2$— | | 0 | —(CH$_2$)$_3$— | C17-T2 | C17-T2 | H |
| 1-405 | Me | Me | 0 | —CH$_2$CH(CH$_3$)CH$_2$— | C17-T2 | C17-T2 | H |
| 1-406 | Me | Me | 0 | —(CH$_2$)$_4$— | C17-T2 | C17-T2 | H |
| 1-407 | Me | Me | 0 | —(CH$_2$)$_5$— | C17-T2 | C17-T2 | H |
| 1-408 | Me | Me | 1 | —(CH$_2$)$_3$— | C17-T2 | C17-T2 | H |
| 1-409 | Me | Me | 1 | —(CH$_2$)$_4$— | C17-T2 | C17-T2 | H |
| 1-410 | Me | Me | 0 | —(CH$_2$)$_3$— | C17-T2 | C18 | H |
| 1-411 | Me | Me | 0 | —(CH$_2$)$_3$— | C17-T2 | C18-1 | H |
| 1-412 | Me | Me | 0 | —(CH$_2$)$_3$— | C17-T2 | C19 | H |
| 1-413 | Me | Me | 0 | —(CH$_2$)$_3$— | C17-T2 | C19-2 | H |
| 1-414 | Me | Me | 0 | —(CH$_2$)$_3$— | C17-T2 | C20 | H |
| 1-415 | Me | Me | 0 | —(CH$_2$)$_3$— | C17-T2 | C21 | H |
| 1-416 | Me | Me | 0 | —(CH$_2$)$_3$— | C17-T2 | C22 | H |
| 1-417 | Me | Me | 0 | —(CH$_2$)$_3$— | C17-T2 | C23 | H |
| 1-418 | Me | Me | 0 | —(CH$_2$)$_3$— | C17-T2 | C24 | H |
| 1-419 | Me | Me | 0 | —(CH$_2$)$_3$— | C17-T2 | Lin | H |
| 1-420 | Me | Me | 0 | —(CH$_2$)$_3$— | C18 | C10 | H |
| 1-421 | Me | Me | 0 | —(CH$_2$)$_3$— | C18 | C11 | H |
| 1-422 | Me | Me | 0 | —(CH$_2$)$_3$— | C18 | C12 | H |
| 1-423 | Me | Me | 0 | —(CH$_2$)$_3$— | C18 | C13 | H |
| 1-424 | Me | Me | 0 | —(CH$_2$)$_3$— | C18 | C14 | H |
| 1-425 | Me | Me | 0 | —(CH$_2$)$_3$— | C18 | C15 | H |
| 1-426 | Me | Me | 0 | —(CH$_2$)$_3$— | C18 | C16 | H |
| 1-427 | Me | Me | 0 | —(CH$_2$)$_3$— | C18 | C17 | H |
| 1-428 | Me | Me | 0 | —(CH$_2$)$_3$— | C18 | C18 | H |
| 1-429 | Me | Me | 0 | —(CH$_2$)$_3$— | C18-1 | C18-1 | H |
| 1-430 | Me | Et | 0 | —(CH$_2$)$_3$— | C18-1 | C18-1 | H |
| 1-431 | Me | Pr | 0 | —(CH$_2$)$_3$— | C18-1 | C18-1 | H |
| 1-432 | Et | Et | 0 | —(CH$_2$)$_3$— | C18-1 | C18-1 | H |
| 1-433 | —(CH$_2$)$_3$— | | 0 | —(CH$_2$)$_3$— | C18-1 | C18-1 | H |
| 1-434 | —(CH$_2$)$_4$— | | 0 | —(CH$_2$)$_3$— | C18-1 | C18-1 | H |
| 1-435 | —(CH$_2$)$_2$O(CH$_2$)$_2$— | | 0 | —(CH$_2$)$_3$— | C18-1 | C18-1 | H |
| 1-436 | Me | Me | 0 | —CH$_2$CH(CH$_3$)CH$_2$— | C18-1 | C18-1 | H |
| 1-437 | Me | Me | 0 | —(CH$_2$)$_4$— | C18-1 | C18-1 | H |
| 1-438 | Me | Me | 0 | —(CH$_2$)$_5$— | C18-1 | C18-1 | H |
| 1-439 | Me | Me | 1 | —(CH$_2$)$_3$— | C18-1 | C18-1 | H |
| 1-440 | Me | Me | 1 | —(CH$_2$)$_4$— | C18-1 | C18-1 | H |
| 1-441 | Me | Me | 0 | —(CH$_2$)$_3$— | C18-1 | C18-1 | Me |
| 1-442 | Me | Et | 0 | —(CH$_2$)$_3$— | C18-1 | C18-1 | Me |
| 1-443 | Me | Me | 0 | —(CH$_2$)$_3$— | C18-1 | C18-1 | Et |
| 1-444 | Me | Me | 0 | —(CH$_2$)$_3$— | C19-2 | C10 | H |
| 1-445 | Me | Et | 0 | —(CH$_2$)$_3$— | C19-2 | C10 | H |
| 1-446 | Me | Pr | 0 | —(CH$_2$)$_3$— | C19-2 | C10 | H |
| 1-447 | Et | Et | 0 | —(CH$_2$)$_3$— | C19-2 | C10 | H |
| 1-448 | —(CH$_2$)$_3$— | | 0 | —(CH$_2$)$_3$— | C19-2 | C10 | H |
| 1-449 | —(CH$_2$)$_4$— | | 0 | —(CH$_2$)$_3$— | C19-2 | C10 | H |
| 1-450 | —(CH$_2$)$_2$O(CH$_2$)$_2$— | | 0 | —(CH$_2$)$_3$— | C19-2 | C10 | H |
| 1-451 | Me | Me | 0 | —CH$_2$CH(CH$_3$)CH$_2$— | C19-2 | C10 | H |

TABLE 1-continued

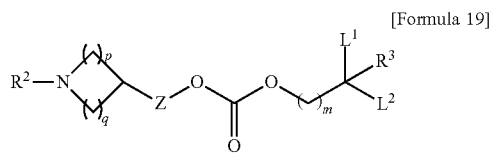

[Formula 18]

| Compound | R¹ | R² | m | Z | L¹ | L² | R³ |
|---|---|---|---|---|---|---|---|
| 1-452 | Me | Me | 0 | —(CH$_2$)$_4$— | C19-2 | C10 | H |
| 1-453 | Me | Me | 0 | —(CH$_2$)$_5$— | C19-2 | C10 | H |
| 1-454 | Me | Me | 1 | —(CH$_2$)$_3$— | C19-2 | C10 | H |
| 1-455 | Me | Me | 1 | —(CH$_2$)$_4$— | C19-2 | C10 | H |
| 1-456 | Me | Me | 0 | —(CH$_2$)$_3$— | C19-2 | C10 | Me |
| 1-457 | Me | Et | 0 | —(CH$_2$)$_3$— | C19-2 | C10 | Me |
| 1-458 | Me | Me | 0 | —(CH$_2$)$_3$— | C19-2 | C10 | Et |
| 1-459 | Me | Me | 1 | —(CH$_2$)$_3$— | Lin | C10 | H |
| 1-460 | Me | Et | 1 | —(CH$_2$)$_3$— | Lin | C10 | H |
| 1-461 | Me | Pr | 1 | —(CH$_2$)$_3$— | Lin | C10 | H |
| 1-462 | Et | Et | 1 | —(CH$_2$)$_3$— | Lin | C10 | H |
| 1-463 | —(CH$_2$)$_3$— | | 1 | —(CH$_2$)$_3$— | Lin | C10 | H |
| 1-464 | —(CH$_2$)$_4$— | | 1 | —(CH$_2$)$_3$— | Lin | C10 | H |
| 1-465 | —(CH$_2$)$_2$O(CH$_2$)$_2$— | | 1 | —(CH$_2$)$_3$— | Lin | C10 | H |
| 1-466 | Me | Me | 1 | —(CH$_2$)$_4$— | Lin | C10 | H |
| 1-467 | Me | Me | 0 | —(CH$_2$)$_3$— | Lin | Lin | H |
| 1-468 | Me | Et | 0 | —(CH$_2$)$_3$— | Lin | Lin | H |
| 1-469 | Me | Pr | 0 | —(CH$_2$)$_3$— | Lin | Lin | H |
| 1-470 | Et | Et | 0 | —(CH$_2$)$_3$— | Lin | Lin | H |
| 1-471 | —(CH$_2$)$_3$— | | 0 | —(CH$_2$)$_3$— | Lin | Lin | H |
| 1-472 | —(CH$_2$)$_4$— | | 0 | —(CH$_2$)$_3$— | Lin | Lin | H |
| 1-473 | —(CH$_2$)$_2$O(CH$_2$)$_2$— | | 0 | —(CH$_2$)$_3$— | Lin | Lin | H |
| 1-474 | Me | Me | 0 | —CH$_2$CH(CH$_3$)CH$_2$— | Lin | Lin | H |
| 1-475 | Me | Me | 0 | —(CH$_2$)$_4$— | Lin | Lin | H |
| 1-476 | Me | Me | 0 | —(CH$_2$)$_5$— | Lin | Lin | H |
| 1-477 | Me | Me | 1 | —(CH$_2$)$_3$— | Lin | Lin | H |
| 1-478 | Me | Me | 1 | —(CH$_2$)$_4$— | Lin | Lin | H |
| 1-479 | Me | Me | 0 | —(CH$_2$)$_3$— | Lin | Lin | Me |
| 1-480 | Me | Et | 0 | —(CH$_2$)$_3$— | Lin | Lin | Me |
| 1-481 | Me | Me | 0 | —(CH$_2$)$_3$— | Lin | Lin | Et |

TABLE 2

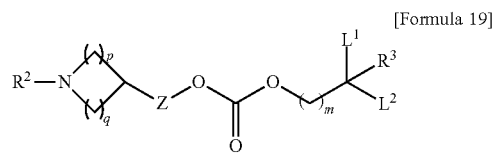

[Formula 19]

| Compound | R² | p | q | m | Z | L¹ | L² | R³ |
|---|---|---|---|---|---|---|---|---|
| 2-1 | Me | 0 | 2 | 0 | — | C17-1 | C10 | H |
| 2-2 | Me | 0 | 3 | 0 | — | C17-1 | C10 | H |
| 2-3 | Me | 0 | 4 | 0 | — | C17-1 | C10 | H |
| 2-4 | Me | 1 | 2 | 0 | — | C17-1 | C10 | H |
| 2-5 | Me | 1 | 3 | 0 | — | C17-1 | C10 | H |
| 2-6 | Me | 2 | 2 | 0 | — | C17-1 | C10 | H |
| 2-7 | Me | 0 | 2 | 0 | —CH$_2$— | C17-1 | C10 | H |
| 2-8 | Me | 0 | 3 | 0 | —CH$_2$— | C17-1 | C10 | H |
| 2-9 | Me | 0 | 4 | 0 | —CH$_2$— | C17-1 | C10 | H |
| 2-10 | Me | 1 | 1 | 0 | —CH$_2$— | C17-1 | C10 | H |
| 2-11 | Me | 1 | 2 | 0 | —CH$_2$— | C17-1 | C10 | H |
| 2-12 | Me | 1 | 3 | 0 | —CH$_2$— | C17-1 | C10 | H |
| 2-13 | Me | 2 | 2 | 0 | —CH$_2$— | C17-1 | C10 | H |
| 2-14 | Me | 0 | 2 | 0 | —(CH$_2$)$_2$— | C17-1 | C10 | H |
| 2-15 | Me | 0 | 3 | 0 | —(CH$_2$)$_2$— | C17-1 | C10 | H |
| 2-16 | Me | 0 | 4 | 0 | —(CH$_2$)$_2$— | C17-1 | C10 | H |
| 2-17 | Me | 1 | 1 | 0 | —(CH$_2$)$_2$— | C17-1 | C10 | H |
| 2-18 | Me | 1 | 2 | 0 | —(CH$_2$)$_2$— | C17-1 | C10 | H |
| 2-19 | Me | 1 | 3 | 0 | —(CH$_2$)$_2$— | C17-1 | C10 | H |
| 2-20 | Me | 2 | 2 | 0 | —(CH$_2$)$_2$— | C17-1 | C10 | H |
| 2-21 | Me | 0 | 2 | 0 | —(CH$_2$)$_3$— | C17-1 | C10 | H |
| 2-22 | Me | 0 | 3 | 0 | —(CH$_2$)$_3$— | C17-1 | C10 | H |
| 2-23 | Me | 0 | 4 | 0 | —(CH$_2$)$_3$— | C17-1 | C10 | H |
| 2-24 | Me | 1 | 1 | 0 | —(CH$_2$)$_3$— | C17-1 | C10 | H |
| 2-25 | Me | 1 | 2 | 0 | —(CH$_2$)$_3$— | C17-1 | C10 | H |
| 2-26 | Me | 1 | 3 | 0 | —(CH$_2$)$_3$— | C17-1 | C10 | H |
| 2-27 | Me | 2 | 2 | 0 | —(CH$_2$)$_3$— | C17-1 | C10 | H |
| 2-28 | Me | 1 | 3 | 0 | — | C17-1 | C10 | Me |
| 2-29 | Me | 2 | 2 | 0 | — | C17-1 | C10 | Me |
| 2-30 | Me | 1 | 3 | 0 | —CH$_2$— | C17-1 | C10 | Me |
| 2-31 | Me | 0 | 2 | 0 | — | C17-1 | C17-1 | H |
| 2-32 | Me | 0 | 3 | 0 | — | C17-1 | C17-1 | H |
| 2-33 | Me | 0 | 4 | 0 | — | C17-1 | C17-1 | H |
| 2-34 | Me | 1 | 2 | 0 | — | C17-1 | C17-1 | H |
| 2-35 | Me | 1 | 3 | 0 | — | C17-1 | C17-1 | H |
| 2-36 | Me | 2 | 2 | 0 | — | C17-1 | C17-1 | H |
| 2-37 | Me | 0 | 2 | 0 | —CH$_2$— | C17-1 | C17-1 | H |
| 2-38 | Me | 0 | 3 | 0 | —CH$_2$— | C17-1 | C17-1 | H |
| 2-39 | Me | 0 | 4 | 0 | —CH$_2$— | C17-1 | C17-1 | H |
| 2-40 | Me | 1 | 1 | 0 | —CH$_2$— | C17-1 | C17-1 | H |
| 2-41 | Me | 1 | 2 | 0 | —CH$_2$— | C17-1 | C17-1 | H |
| 2-42 | Me | 1 | 3 | 0 | —CH$_2$— | C17-1 | C17-1 | H |
| 2-43 | Me | 2 | 2 | 0 | —CH$_2$— | C17-1 | C17-1 | H |
| 2-44 | Me | 0 | 2 | 0 | —(CH$_2$)$_2$— | C17-1 | C17-1 | H |
| 2-45 | Me | 0 | 3 | 0 | —(CH$_2$)$_2$— | C17-1 | C17-1 | H |
| 2-46 | Me | 0 | 4 | 0 | —(CH$_2$)$_2$— | C17-1 | C17-1 | H |
| 2-47 | Me | 1 | 1 | 0 | —(CH$_2$)$_2$— | C17-1 | C17-1 | H |
| 2-48 | Me | 1 | 2 | 0 | —(CH$_2$)$_2$— | C17-1 | C17-1 | H |

TABLE 2-continued

[Formula 19]

$$R^2-N\underset{q}{\overset{p}{\diamond}}Z-O-\underset{O}{\overset{\parallel}{C}}-O-(\phantom{i})_m\underset{L^2}{\overset{L^1}{\diamond}}R^3$$

| Compound | $R^2$ | p | q | m | Z | $L^1$ | $L^2$ | $R^3$ |
|---|---|---|---|---|---|---|---|---|
| 2-49 | Me | 1 | 3 | 0 | —(CH$_2$)$_2$— | C17-1 | C17-1 | H |
| 2-50 | Me | 2 | 2 | 0 | —(CH$_2$)$_2$— | C17-1 | C17-1 | H |
| 2-51 | Me | 0 | 2 | 0 | —(CH$_2$)$_3$— | C17-1 | C17-1 | H |
| 2-52 | Me | 0 | 3 | 0 | —(CH$_2$)$_3$— | C17-1 | C17-1 | H |
| 2-53 | Me | 0 | 4 | 0 | —(CH$_2$)$_3$— | C17-1 | C17-1 | H |
| 2-54 | Me | 1 | 1 | 0 | —(CH$_2$)$_3$— | C17-1 | C17-1 | H |
| 2-55 | Me | 1 | 2 | 0 | —(CH$_2$)$_3$— | C17-1 | C17-1 | H |
| 2-56 | Me | 1 | 3 | 0 | —(CH$_2$)$_3$— | C17-1 | C17-1 | H |
| 2-57 | Me | 2 | 2 | 0 | —(CH$_2$)$_3$— | C17-1 | C17-1 | H |
| 2-58 | Me | 1 | 3 | 0 | — | C17-1 | C17-1 | Me |
| 2-59 | Me | 2 | 2 | 0 | — | C17-1 | C17-1 | Me |
| 2-60 | Me | 1 | 3 | 0 | —CH$_2$— | C17-1 | C17-1 | Me |
| 2-61 | Me | 0 | 2 | 0 | — | C17-2 | C10 | H |
| 2-62 | Me | 0 | 3 | 0 | — | C17-2 | C10 | H |
| 2-63 | Me | 0 | 4 | 0 | — | C17-2 | C10 | H |
| 2-64 | Me | 1 | 1 | 0 | — | C17-2 | C10 | H |
| 2-65 | Me | 1 | 3 | 0 | — | C17-2 | C10 | H |
| 2-66 | Me | 2 | 2 | 0 | — | C17-2 | C10 | H |
| 2-67 | Me | 0 | 2 | 0 | —CH$_2$— | C17-2 | C10 | H |
| 2-68 | Me | 0 | 3 | 0 | —CH$_2$— | C17-2 | C10 | H |
| 2-69 | Me | 0 | 4 | 0 | —CH$_2$— | C17-2 | C10 | H |
| 2-70 | Me | 1 | 1 | 0 | —CH$_2$— | C17-2 | C10 | H |
| 2-71 | Me | 1 | 2 | 0 | —CH$_2$— | C17-2 | C10 | H |
| 2-72 | Me | 1 | 3 | 0 | —CH$_2$— | C17-2 | C10 | H |
| 2-73 | Me | 2 | 2 | 0 | —CH$_2$— | C17-2 | C10 | H |
| 2-74 | Me | 0 | 2 | 0 | —(CH$_2$)$_2$— | C17-2 | C10 | H |
| 2-75 | Me | 0 | 3 | 0 | —(CH$_2$)$_2$— | C17-2 | C10 | H |
| 2-76 | Me | 0 | 4 | 0 | —(CH$_2$)$_2$— | C17-2 | C10 | H |
| 2-77 | Me | 1 | 1 | 0 | —(CH$_2$)$_2$— | C17-2 | C10 | H |
| 2-78 | Me | 1 | 2 | 0 | —(CH$_2$)$_2$— | C17-2 | C10 | H |
| 2-79 | Me | 1 | 3 | 0 | —(CH$_2$)$_2$— | C17-2 | C10 | H |
| 2-80 | Me | 2 | 2 | 0 | —(CH$_2$)$_2$— | C17-2 | C10 | H |
| 2-81 | Me | 0 | 2 | 0 | —(CH$_2$)$_3$— | C17-2 | C10 | H |
| 2-82 | Me | 0 | 3 | 0 | —(CH$_2$)$_3$— | C17-2 | C10 | H |
| 2-83 | Me | 0 | 4 | 0 | —(CH$_2$)$_3$— | C17-2 | C10 | H |
| 2-84 | Me | 1 | 1 | 0 | —(CH$_2$)$_3$— | C17-2 | C10 | H |
| 2-85 | Me | 1 | 2 | 0 | —(CH$_2$)$_3$— | C17-2 | C10 | H |
| 2-86 | Me | 1 | 3 | 0 | —(CH$_2$)$_3$— | C17-2 | C10 | H |
| 2-87 | Me | 2 | 2 | 0 | —(CH$_2$)$_3$— | C17-2 | C10 | H |
| 2-88 | Me | 1 | 3 | 0 | — | C17-2 | C10 | Me |
| 2-89 | Me | 2 | 2 | 0 | — | C17-2 | C10 | Me |
| 2-90 | Me | 1 | 3 | 0 | —CH$_2$— | C17-2 | C10 | Me |
| 2-91 | Me | 0 | 2 | 0 | — | C17-2 | C17-2 | H |
| 2-92 | Me | 0 | 3 | 0 | — | C17-2 | C17-2 | H |
| 2-93 | Me | 0 | 4 | 0 | — | C17-2 | C17-2 | H |
| 2-94 | Me | 1 | 2 | 0 | — | C17-2 | C17-2 | H |
| 2-95 | Me | 1 | 3 | 0 | — | C17-2 | C17-2 | H |
| 2-96 | Me | 2 | 2 | 0 | — | C17-2 | C17-2 | H |
| 2-97 | Me | 0 | 2 | 0 | —CH$_2$— | C17-2 | C17-2 | H |
| 2-98 | Me | 0 | 3 | 0 | —CH$_2$— | C17-2 | C17-2 | H |
| 2-99 | Me | 0 | 4 | 0 | —CH$_2$— | C17-2 | C17-2 | H |
| 2-100 | Me | 1 | 1 | 0 | —CH$_2$— | C17-2 | C17-2 | H |
| 2-101 | Me | 1 | 2 | 0 | —CH$_2$— | C17-2 | C17-2 | H |
| 2-102 | Me | 1 | 3 | 0 | —CH$_2$— | C17-2 | C17-2 | H |
| 2-103 | Me | 2 | 2 | 0 | —CH$_2$— | C17-2 | C17-2 | H |
| 2-104 | Me | 0 | 2 | 0 | —(CH$_2$)$_2$— | C17-2 | C17-2 | H |
| 2-105 | Me | 0 | 3 | 0 | —(CH$_2$)$_2$— | C17-2 | C17-2 | H |
| 2-106 | Me | 0 | 4 | 0 | —(CH$_2$)$_2$— | C17-2 | C17-2 | H |
| 2-107 | Me | 1 | 1 | 0 | —(CH$_2$)$_2$— | C17-2 | C17-2 | H |
| 2-108 | Me | 1 | 2 | 0 | —(CH$_2$)$_2$— | C17-2 | C17-2 | H |
| 2-109 | Me | 1 | 3 | 0 | —(CH$_2$)$_2$— | C17-2 | C17-2 | H |
| 2-110 | Me | 2 | 2 | 0 | —(CH$_2$)$_2$— | C17-2 | C17-2 | H |
| 2-111 | Me | 0 | 2 | 0 | —(CH$_2$)$_3$— | C17-2 | C17-2 | H |
| 2-112 | Me | 0 | 3 | 0 | —(CH$_2$)$_3$— | C17-2 | C17-2 | H |
| 2-113 | Me | 0 | 4 | 0 | —(CH$_2$)$_3$— | C17-2 | C17-2 | H |
| 2-114 | Me | 1 | 1 | 0 | —(CH$_2$)$_3$— | C17-2 | C17-2 | H |
| 2-115 | Me | 1 | 2 | 0 | —(CH$_2$)$_3$— | C17-2 | C17-2 | H |
| 2-116 | Me | 1 | 3 | 0 | —(CH$_2$)$_3$— | C17-2 | C17-2 | H |
| 2-117 | Me | 2 | 2 | 0 | —(CH$_2$)$_3$— | C17-2 | C17-2 | H |
| 2-118 | Me | 1 | 3 | 0 | — | C17-2 | C17-2 | Me |
| 2-119 | Me | 2 | 2 | 0 | — | C17-2 | C17-2 | Me |
| 2-120 | Me | 1 | 3 | 0 | —CH$_2$— | C17-2 | C17-2 | Me |
| 2-121 | Me | 0 | 2 | 0 | — | C17-A | C10 | H |
| 2-122 | Me | 0 | 3 | 0 | — | C17-A | C10 | H |
| 2-123 | Me | 0 | 4 | 0 | — | C17-A | C10 | H |
| 2-124 | Me | 1 | 2 | 0 | — | C17-A | C10 | H |
| 2-125 | Me | 1 | 3 | 0 | — | C17-A | C10 | H |
| 2-126 | Me | 2 | 2 | 0 | — | C17-A | C10 | H |
| 2-127 | Me | 0 | 2 | 0 | —CH$_2$— | C17-A | C10 | H |
| 2-128 | Me | 0 | 3 | 0 | —CH$_2$— | C17-A | C10 | H |
| 2-129 | Me | 0 | 4 | 0 | —CH$_2$— | C17-A | C10 | H |
| 2-130 | Me | 1 | 1 | 0 | —CH$_2$— | C17-A | C10 | H |
| 2-131 | Me | 1 | 2 | 0 | —CH$_2$— | C17-A | C10 | H |
| 2-132 | Me | 1 | 3 | 0 | —CH$_2$— | C17-A | C10 | H |
| 2-133 | Me | 2 | 2 | 0 | —CH$_2$— | C17-A | C10 | H |
| 2-134 | Me | 0 | 2 | 0 | —(CH$_2$)$_2$— | C17-A | C10 | H |
| 2-135 | Me | 0 | 3 | 0 | —(CH$_2$)$_2$— | C17-A | C10 | H |
| 2-136 | Me | 0 | 4 | 0 | —(CH$_2$)$_2$— | C17-A | C10 | H |
| 2-137 | Me | 1 | 1 | 0 | —(CH$_2$)$_2$— | C17-A | C10 | H |
| 2-138 | Me | 1 | 2 | 0 | —(CH$_2$)$_2$— | C17-A | C10 | H |
| 2-139 | Me | 1 | 3 | 0 | —(CH$_2$)$_2$— | C17-A | C10 | H |
| 2-140 | Me | 2 | 2 | 0 | —(CH$_2$)$_2$— | C17-A | C10 | H |
| 2-141 | Me | 0 | 2 | 0 | —(CH$_2$)$_3$— | C17-A | C10 | H |
| 2-142 | Me | 0 | 3 | 0 | —(CH$_2$)$_3$— | C17-A | C10 | H |
| 2-143 | Me | 0 | 4 | 0 | —(CH$_2$)$_3$— | C17-A | C10 | H |
| 2-144 | Me | 1 | 1 | 0 | —(CH$_2$)$_3$— | C17-A | C10 | H |
| 2-145 | Me | 1 | 2 | 0 | —(CH$_2$)$_3$— | C17-A | C10 | H |
| 2-146 | Me | 1 | 3 | 0 | —(CH$_2$)$_3$— | C17-A | C10 | H |
| 2-147 | Me | 2 | 2 | 0 | —(CH$_2$)$_3$— | C17-A | C10 | H |
| 2-148 | Me | 1 | 3 | 0 | — | C17-A | C10 | Me |
| 2-149 | Me | 2 | 2 | 0 | — | C17-A | C10 | Me |
| 2-150 | Me | 1 | 3 | 0 | —CH$_2$— | C17-A | C10 | Me |
| 2-151 | Me | 0 | 2 | 0 | — | C17-A | C17-A | H |
| 2-152 | Me | 0 | 3 | 0 | — | C17-A | C17-A | H |
| 2-153 | Me | 0 | 4 | 0 | — | C17-A | C17-A | H |
| 2-154 | Me | 1 | 2 | 0 | — | C17-A | C17-A | H |
| 2-155 | Me | 1 | 3 | 0 | — | C17-A | C17-A | H |
| 2-156 | Me | 2 | 2 | 0 | — | C17-A | C17-A | H |
| 2-157 | Me | 0 | 2 | 0 | —CH$_2$— | C17-A | C17-A | H |
| 2-158 | Me | 0 | 3 | 0 | —CH$_2$— | C17-A | C17-A | H |
| 2-159 | Me | 0 | 4 | 0 | —CH$_2$— | C17-A | C17-A | H |
| 2-160 | Me | 1 | 1 | 0 | —CH$_2$— | C17-A | C17-A | H |
| 2-161 | Me | 1 | 2 | 0 | —CH$_2$— | C17-A | C17-A | H |
| 2-162 | Me | 1 | 3 | 0 | —CH$_2$— | C17-A | C17-A | H |
| 2-163 | Me | 2 | 2 | 0 | —CH$_2$— | C17-A | C17-A | H |
| 2-164 | Me | 0 | 2 | 0 | —(CH$_2$)$_2$— | C17-A | C17-A | H |
| 2-165 | Me | 0 | 3 | 0 | —(CH$_2$)$_2$— | C17-A | C17-A | H |
| 2-166 | Me | 0 | 4 | 0 | —(CH$_2$)$_2$— | C17-A | C17-A | H |
| 2-167 | Me | 1 | 1 | 0 | —(CH$_2$)$_2$— | C17-A | C17-A | H |
| 2-168 | Me | 1 | 2 | 0 | —(CH$_2$)$_2$— | C17-A | C17-A | H |
| 2-169 | Me | 1 | 3 | 0 | —(CH$_2$)$_2$— | C17-A | C17-A | H |
| 2-170 | Me | 2 | 2 | 0 | —(CH$_2$)$_2$— | C17-A | C17-A | H |
| 2-171 | Me | 0 | 2 | 0 | —(CH$_2$)$_3$— | C17-A | C17-A | H |
| 2-172 | Me | 0 | 3 | 0 | —(CH$_2$)$_3$— | C17-A | C17-A | H |
| 2-173 | Me | 0 | 4 | 0 | —(CH$_2$)$_3$— | C17-A | C17-A | H |
| 2-174 | Me | 1 | 1 | 0 | —(CH$_2$)$_3$— | C17-A | C17-A | H |
| 2-175 | Me | 1 | 2 | 0 | —(CH$_2$)$_3$— | C17-A | C17-A | H |
| 2-176 | Me | 1 | 3 | 0 | —(CH$_2$)$_3$— | C17-A | C17-A | H |
| 2-177 | Me | 2 | 2 | 0 | —(CH$_2$)$_3$— | C17-A | C17-A | H |
| 2-178 | Me | 1 | 3 | 0 | — | C17-A | C17-A | Me |
| 2-179 | Me | 2 | 2 | 0 | — | C17-A | C17-A | Me |
| 2-180 | Me | 1 | 3 | 0 | —CH$_2$— | C17-A | C17-A | Me |
| 2-181 | Me | 0 | 2 | 0 | — | C17-H | C10 | H |
| 2-182 | Me | 0 | 3 | 0 | — | C17-H | C10 | H |
| 2-183 | Me | 0 | 4 | 0 | — | C17-H | C10 | H |
| 2-184 | Me | 1 | 1 | 0 | — | C17-H | C10 | H |
| 2-185 | Me | 1 | 3 | 0 | — | C17-H | C10 | H |
| 2-186 | Me | 2 | 2 | 0 | — | C17-H | C10 | H |
| 2-187 | Me | 0 | 2 | 0 | —CH$_2$— | C17-H | C10 | H |
| 2-188 | Me | 0 | 3 | 0 | —CH$_2$— | C17-H | C10 | H |

TABLE 2-continued

[Formula 19]

$$R^2-N\underset{q}{\overset{p}{\langle\ \ \rangle}}Z-O-\underset{O}{\overset{\|}{C}}-O-(CH_2)_m-\underset{L^2}{\overset{L^1}{\underset{|}{C}}}-R^3$$

| Compound | R² | p | q | m | Z | L¹ | L² | R³ |
|---|---|---|---|---|---|---|---|---|
| 2-189 | Me | 0 | 4 | 0 | —CH₂— | C17-H | C10 | H |
| 2-190 | Me | 1 | 1 | 0 | —CH₂— | C17-H | C10 | H |
| 2-191 | Me | 1 | 2 | 0 | —CH₂— | C17-H | C10 | H |
| 2-192 | Me | 1 | 3 | 0 | —CH₂— | C17-H | C10 | H |
| 2-193 | Me | 2 | 2 | 0 | —CH₂— | C17-H | C10 | H |
| 2-194 | Me | 0 | 2 | 0 | —(CH₂)₂— | C17-H | C10 | H |
| 2-195 | Me | 0 | 3 | 0 | —(CH₂)₂— | C17-H | C10 | H |
| 2-196 | Me | 0 | 4 | 0 | —(CH₂)₂— | C17-H | C10 | H |
| 2-197 | Me | 1 | 1 | 0 | —(CH₂)₂— | C17-H | C10 | H |
| 2-198 | Me | 1 | 2 | 0 | —(CH₂)₂— | C17-H | C10 | H |
| 2-199 | Me | 1 | 3 | 0 | —(CH₂)₂— | C17-H | C10 | H |
| 2-200 | Me | 2 | 2 | 0 | —(CH₂)₂— | C17-H | C10 | H |
| 2-201 | Me | 0 | 2 | 0 | —(CH₂)₃— | C17-H | C10 | H |
| 2-202 | Me | 0 | 3 | 0 | —(CH₂)₃— | C17-H | C10 | H |
| 2-203 | Me | 0 | 4 | 0 | —(CH₂)₃— | C17-H | C10 | H |
| 2-204 | Me | 1 | 1 | 0 | —(CH₂)₃— | C17-H | C10 | H |
| 2-205 | Me | 1 | 2 | 0 | —(CH₂)₃— | C17-H | C10 | H |
| 2-206 | Me | 1 | 3 | 0 | —(CH₂)₃— | C17-H | C10 | H |
| 2-207 | Me | 2 | 2 | 0 | —(CH₂)₃— | C17-H | C10 | H |
| 2-208 | Me | 1 | 3 | 0 | — | C17-H | C10 | Me |
| 2-209 | Me | 2 | 2 | 0 | — | C17-H | C10 | Me |
| 2-210 | Me | 1 | 3 | 0 | —CH₂— | C17-H | C10 | Me |
| 2-211 | Me | 0 | 2 | 0 | — | C17-H | C17-H | H |
| 2-212 | Me | 0 | 3 | 0 | — | C17-H | C17-H | H |
| 2-213 | Me | 0 | 4 | 0 | — | C17-H | C17-H | H |
| 2-214 | Me | 1 | 2 | 0 | — | C17-H | C17-H | H |
| 2-215 | Me | 1 | 3 | 0 | — | C17-H | C17-H | H |
| 2-216 | Me | 2 | 2 | 0 | — | C17-H | C17-H | H |
| 2-217 | Me | 0 | 2 | 0 | —CH₂— | C17-H | C17-H | H |
| 2-218 | Me | 0 | 3 | 0 | —CH₂— | C17-H | C17-H | H |
| 2-219 | Me | 0 | 4 | 0 | —CH₂— | C17-H | C17-H | H |
| 2-220 | Me | 1 | 1 | 0 | —CH₂— | C17-H | C17-H | H |
| 2-221 | Me | 1 | 2 | 0 | —CH₂— | C17-H | C17-H | H |
| 2-222 | Me | 1 | 3 | 0 | —CH₂— | C17-H | C17-H | H |
| 2-223 | Me | 2 | 2 | 0 | —CH₂— | C17-H | C17-H | H |
| 2-224 | Me | 0 | 2 | 0 | —(CH₂)₂— | C17-H | C17-H | H |
| 2-225 | Me | 0 | 3 | 0 | —(CH₂)₂— | C17-H | C17-H | H |
| 2-226 | Me | 0 | 4 | 0 | —(CH₂)₂— | C17-H | C17-H | H |
| 2-227 | Me | 1 | 1 | 0 | —(CH₂)₂— | C17-H | C17-H | H |
| 2-228 | Me | 1 | 2 | 0 | —(CH₂)₂— | C17-H | C17-H | H |
| 2-229 | Me | 1 | 3 | 0 | —(CH₂)₂— | C17-H | C17-H | H |
| 2-230 | Me | 2 | 2 | 0 | —(CH₂)₂— | C17-H | C17-H | H |
| 2-231 | Me | 0 | 2 | 0 | —(CH₂)₃— | C17-H | C17-H | H |
| 2-232 | Me | 0 | 3 | 0 | —(CH₂)₃— | C17-H | C17-H | H |
| 2-233 | Me | 0 | 4 | 0 | —(CH₂)₃— | C17-H | C17-H | H |
| 2-234 | Me | 1 | 1 | 0 | —(CH₂)₃— | C17-H | C17-H | H |
| 2-235 | Me | 1 | 2 | 0 | —(CH₂)₃— | C17-H | C17-H | H |
| 2-236 | Me | 1 | 3 | 0 | —(CH₂)₃— | C17-H | C17-H | H |
| 2-237 | Me | 2 | 2 | 0 | —(CH₂)₃— | C17-H | C17-H | H |
| 2-238 | Me | 1 | 3 | 0 | — | C17-H | C17-H | Me |
| 2-239 | Me | 2 | 2 | 0 | — | C17-H | C17-H | Me |
| 2-240 | Me | 1 | 3 | 0 | —CH₂— | C17-H | C17-H | Me |
| 2-241 | Me | 0 | 2 | 0 | — | C17-T | C10 | H |
| 2-242 | Me | 0 | 3 | 0 | — | C17-T | C10 | H |
| 2-243 | Me | 0 | 4 | 0 | — | C17-T | C10 | H |
| 2-244 | Me | 1 | 2 | 0 | — | C17-T | C10 | H |
| 2-245 | Me | 1 | 3 | 0 | — | C17-T | C10 | H |
| 2-246 | Me | 2 | 2 | 0 | — | C17-T | C10 | H |
| 2-247 | Me | 0 | 2 | 0 | —CH₂— | C17-T | C10 | H |
| 2-248 | Me | 0 | 3 | 0 | —CH₂— | C17-T | C10 | H |
| 2-249 | Me | 0 | 4 | 0 | —CH₂— | C17-T | C10 | H |
| 2-250 | Me | 1 | 1 | 0 | —CH₂— | C17-T | C10 | H |
| 2-251 | Me | 1 | 2 | 0 | —CH₂— | C17-T | C10 | H |
| 2-252 | Me | 1 | 3 | 0 | —CH₂— | C17-T | C10 | H |
| 2-253 | Me | 2 | 2 | 0 | —CH₂— | C17-T | C10 | H |
| 2-254 | Me | 0 | 2 | 0 | —(CH₂)₂— | C17-T | C10 | H |
| 2-255 | Me | 0 | 3 | 0 | —(CH₂)₂— | C17-T | C10 | H |
| 2-256 | Me | 0 | 4 | 0 | —(CH₂)₂— | C17-T | C10 | H |
| 2-257 | Me | 1 | 1 | 0 | —(CH₂)₂— | C17-T | C10 | H |
| 2-258 | Me | 1 | 2 | 0 | —(CH₂)₂— | C17-T | C10 | H |
| 2-259 | Me | 1 | 3 | 0 | —(CH₂)₂— | C17-T | C10 | H |
| 2-260 | Me | 2 | 2 | 0 | —(CH₂)₂— | C17-T | C10 | H |
| 2-261 | Me | 0 | 2 | 0 | —(CH₂)₃— | C17-T | C10 | H |
| 2-262 | Me | 0 | 3 | 0 | —(CH₂)₃— | C17-T | C10 | H |
| 2-263 | Me | 0 | 4 | 0 | —(CH₂)₃— | C17-T | C10 | H |
| 2-264 | Me | 1 | 1 | 0 | —(CH₂)₃— | C17-T | C10 | H |
| 2-265 | Me | 1 | 2 | 0 | —(CH₂)₃— | C17-T | C10 | H |
| 2-266 | Me | 1 | 3 | 0 | —(CH₂)₃— | C17-T | C10 | H |
| 2-267 | Me | 2 | 2 | 0 | —(CH₂)₃— | C17-T | C10 | H |
| 2-268 | Me | 1 | 3 | 0 | — | C17-T | C10 | Me |
| 2-269 | Me | 2 | 2 | 0 | — | C17-T | C10 | Me |
| 2-270 | Me | 1 | 3 | 0 | —CH₂— | C17-T | C10 | Me |
| 2-271 | Me | 0 | 2 | 0 | — | C17-T | C17-T | H |
| 2-272 | Me | 0 | 3 | 0 | — | C17-T | C17-T | H |
| 2-273 | Me | 0 | 4 | 0 | — | C17-T | C17-T | H |
| 2-274 | Me | 1 | 2 | 0 | — | C17-T | C17-T | H |
| 2-275 | Me | 1 | 3 | 0 | — | C17-T | C17-T | H |
| 2-276 | Me | 2 | 2 | 0 | — | C17-T | C17-T | H |
| 2-277 | Me | 0 | 2 | 0 | —CH₂— | C17-T | C17-T | H |
| 2-278 | Me | 0 | 3 | 0 | —CH₂— | C17-T | C17-T | H |
| 2-279 | Me | 0 | 4 | 0 | —CH₂— | C17-T | C17-T | H |
| 2-280 | Me | 1 | 1 | 0 | —CH₂— | C17-T | C17-T | H |
| 2-281 | Me | 1 | 2 | 0 | —CH₂— | C17-T | C17-T | H |
| 2-282 | Me | 1 | 3 | 0 | —CH₂— | C17-T | C17-T | H |
| 2-283 | Me | 2 | 2 | 0 | —CH₂— | C17-T | C17-T | H |
| 2-284 | Me | 0 | 2 | 0 | —(CH₂)₂— | C17-T | C17-T | H |
| 2-285 | Me | 0 | 3 | 0 | —(CH₂)₂— | C17-T | C17-T | H |
| 2-286 | Me | 0 | 4 | 0 | —(CH₂)₂— | C17-T | C17-T | H |
| 2-287 | Me | 1 | 1 | 0 | —(CH₂)₂— | C17-T | C17-T | H |
| 2-288 | Me | 1 | 2 | 0 | —(CH₂)₂— | C17-T | C17-T | H |
| 2-289 | Me | 1 | 3 | 0 | —(CH₂)₂— | C17-T | C17-T | H |
| 2-290 | Me | 2 | 2 | 0 | —(CH₂)₂— | C17-T | C17-T | H |
| 2-291 | Me | 0 | 2 | 0 | —(CH₂)₃— | C17-T | C17-T | H |
| 2-292 | Me | 0 | 3 | 0 | —(CH₂)₃— | C17-T | C17-T | H |
| 2-293 | Me | 0 | 4 | 0 | —(CH₂)₃— | C17-T | C17-T | H |
| 2-294 | Me | 1 | 1 | 0 | —(CH₂)₃— | C17-T | C17-T | H |
| 2-295 | Me | 1 | 2 | 0 | —(CH₂)₃— | C17-T | C17-T | H |
| 2-296 | Me | 1 | 3 | 0 | —(CH₂)₃— | C17-T | C17-T | H |
| 2-297 | Me | 2 | 2 | 0 | —(CH₂)₃— | C17-T | C17-T | H |
| 2-298 | Me | 1 | 3 | 0 | — | C17-T | C17-T | Me |
| 2-299 | Me | 2 | 2 | 0 | — | C17-T | C17-T | Me |
| 2-300 | Me | 1 | 3 | 0 | —CH₂— | C17-T | C17-T | Me |
| 2-301 | Me | 0 | 2 | 0 | — | C17-T2 | C10 | H |
| 2-302 | Me | 0 | 3 | 0 | — | C17-T2 | C10 | H |
| 2-303 | Me | 0 | 4 | 0 | — | C17-T2 | C10 | H |
| 2-304 | Me | 1 | 2 | 0 | — | C17-T2 | C10 | H |
| 2-305 | Me | 1 | 3 | 0 | — | C17-T2 | C10 | H |
| 2-306 | Me | 2 | 2 | 0 | — | C17-T2 | C10 | H |
| 2-307 | Me | 0 | 2 | 0 | —CH₂— | C17-T2 | C10 | H |
| 2-308 | Me | 0 | 3 | 0 | —CH₂— | C17-T2 | C10 | H |
| 2-309 | Me | 0 | 4 | 0 | —CH₂— | C17-T2 | C10 | H |
| 2-310 | Me | 1 | 1 | 0 | —CH₂— | C17-T2 | C10 | H |
| 2-311 | Me | 1 | 2 | 0 | —CH₂— | C17-T2 | C10 | H |
| 2-312 | Me | 1 | 3 | 0 | —CH₂— | C17-T2 | C10 | H |
| 2-313 | Me | 2 | 2 | 0 | —CH₂— | C17-T2 | C10 | H |
| 2-314 | Me | 0 | 2 | 0 | —(CH₂)₂— | C17-T2 | C10 | H |
| 2-315 | Me | 0 | 3 | 0 | —(CH₂)₂— | C17-T2 | C10 | H |
| 2-316 | Me | 0 | 4 | 0 | —(CH₂)₂— | C17-T2 | C10 | H |
| 2-317 | Me | 1 | 1 | 0 | —(CH₂)₂— | C17-T2 | C10 | H |
| 2-318 | Me | 1 | 2 | 0 | —(CH₂)₂— | C17-T2 | C10 | H |
| 2-319 | Me | 1 | 3 | 0 | —(CH₂)₂— | C17-T2 | C10 | H |
| 2-320 | Me | 2 | 2 | 0 | —(CH₂)₂— | C17-T2 | C10 | H |
| 2-321 | Me | 0 | 2 | 0 | —(CH₂)₃— | C17-T2 | C10 | H |
| 2-322 | Me | 0 | 3 | 0 | —(CH₂)₃— | C17-T2 | C10 | H |
| 2-323 | Me | 0 | 4 | 0 | —(CH₂)₃— | C17-T2 | C10 | H |
| 2-324 | Me | 1 | 1 | 0 | —(CH₂)₃— | C17-T2 | C10 | H |
| 2-325 | Me | 1 | 2 | 0 | —(CH₂)₃— | C17-T2 | C10 | H |
| 2-326 | Me | 1 | 3 | 0 | —(CH₂)₃— | C17-T2 | C10 | H |
| 2-327 | Me | 2 | 2 | 0 | —(CH₂)₃— | C17-T2 | C10 | H |
| 2-328 | Me | 1 | 3 | 0 | — | C17-T2 | C10 | Me |

TABLE 2-continued

[Formula 19]

$$R^2-N\underset{q}{\overset{p}{\diamond}}-Z-O-\underset{O}{\overset{\|}{C}}-O-(CH_2)_m-C(R^3)(L^1)(L^2)$$

| Compound | R² | p | q | m | Z | L¹ | L² | R³ |
|---|---|---|---|---|---|---|---|---|
| 2-329 | Me | 2 | 2 | 0 | — | C17-T2 | C10 | Me |
| 2-330 | Me | 1 | 3 | 0 | —CH₂— | C17-T2 | C10 | Me |
| 2-331 | Me | 0 | 2 | 0 | — | C17-T2 | C17-T2 | H |
| 2-332 | Me | 0 | 3 | 0 | — | C17-T2 | C17-T2 | H |
| 2-333 | Me | 0 | 4 | 0 | — | C17-T2 | C17-T2 | H |
| 2-334 | Me | 1 | 2 | 0 | — | C17-T2 | C17-T2 | H |
| 2-335 | Me | 1 | 3 | 0 | — | C17-T2 | C17-T2 | H |
| 2-336 | Me | 2 | 2 | 0 | — | C17-T2 | C17-T2 | H |
| 2-337 | Me | 0 | 2 | 0 | —CH₂— | C17-T2 | C17-T2 | H |
| 2-338 | Me | 0 | 3 | 0 | —CH₂— | C17-T2 | C17-T2 | H |
| 2-339 | Me | 0 | 4 | 0 | —CH₂— | C17-T2 | C17-T2 | H |
| 2-340 | Me | 1 | 1 | 0 | —CH₂— | C17-T2 | C17-T2 | H |
| 2-341 | Me | 1 | 2 | 0 | —CH₂— | C17-T2 | C17-T2 | H |
| 2-342 | Me | 1 | 3 | 0 | —CH₂— | C17-T2 | C17-T2 | H |
| 2-343 | Me | 2 | 2 | 0 | —CH₂— | C17-T2 | C17-T2 | H |
| 2-344 | Me | 0 | 2 | 0 | —(CH₂)₂— | C17-T2 | C17-T2 | H |
| 2-345 | Me | 0 | 3 | 0 | —(CH₂)₂— | C17-T2 | C17-T2 | H |
| 2-346 | Me | 0 | 4 | 0 | —(CH₂)₂— | C17-T2 | C17-T2 | H |
| 2-347 | Me | 1 | 1 | 0 | —(CH₂)₂— | C17-T2 | C17-T2 | H |
| 2-348 | Me | 1 | 2 | 0 | —(CH₂)₂— | C17-T2 | C17-T2 | H |
| 2-349 | Me | 1 | 3 | 0 | —(CH₂)₂— | C17-T2 | C17-T2 | H |
| 2-350 | Me | 2 | 2 | 0 | —(CH₂)₂— | C17-T2 | C17-T2 | H |
| 2-351 | Me | 0 | 2 | 0 | —(CH₂)₃— | C17-T2 | C17-T2 | H |
| 2-352 | Me | 0 | 3 | 0 | —(CH₂)₃— | C17-T2 | C17-T2 | H |
| 2-353 | Me | 0 | 4 | 0 | —(CH₂)₃— | C17-T2 | C17-T2 | H |
| 2-354 | Me | 1 | 1 | 0 | —(CH₂)₃— | C17-T2 | C17-T2 | H |
| 2-355 | Me | 1 | 2 | 0 | —(CH₂)₃— | C17-T2 | C17-T2 | H |
| 2-356 | Me | 1 | 3 | 0 | —(CH₂)₃— | C17-T2 | C17-T2 | H |
| 2-357 | Me | 2 | 2 | 0 | —(CH₂)₃— | C17-T2 | C17-T2 | H |
| 2-358 | Me | 1 | 3 | 0 | — | C17-T2 | C17-T2 | Me |
| 2-359 | Me | 2 | 2 | 0 | — | C17-T2 | C17-T2 | Me |
| 2-360 | Me | 1 | 3 | 0 | —CH₂— | C17-T2 | C17-T2 | Me |
| 2-361 | Me | 0 | 2 | 0 | — | Lin | Lin | H |
| 2-362 | Me | 0 | 3 | 0 | — | Lin | Lin | H |
| 2-363 | Me | 0 | 4 | 0 | — | Lin | Lin | H |
| 2-364 | Me | 1 | 2 | 0 | — | Lin | Lin | H |
| 2-365 | Me | 1 | 3 | 0 | — | Lin | Lin | H |
| 2-366 | Me | 2 | 2 | 0 | — | Lin | Lin | H |
| 2-367 | Me | 0 | 2 | 0 | —CH₂— | Lin | Lin | H |
| 2-368 | Me | 0 | 3 | 0 | —CH₂— | Lin | Lin | H |
| 2-369 | Me | 0 | 4 | 0 | —CH₂— | Lin | Lin | H |
| 2-370 | Me | 1 | 1 | 0 | —CH₂— | Lin | Lin | H |
| 2-371 | Me | 1 | 2 | 0 | —CH₂— | Lin | Lin | H |
| 2-372 | Me | 1 | 3 | 0 | —CH₂— | Lin | Lin | H |
| 2-373 | Me | 2 | 2 | 0 | —CH₂— | Lin | Lin | H |
| 2-374 | Me | 0 | 2 | 0 | —(CH₂)₂— | Lin | Lin | H |
| 2-375 | Me | 0 | 3 | 0 | —(CH₂)₂— | Lin | Lin | H |
| 2-376 | Me | 0 | 4 | 0 | —(CH₂)₂— | Lin | Lin | H |
| 2-377 | Me | 1 | 1 | 0 | —(CH₂)₂— | Lin | Lin | H |
| 2-378 | Me | 1 | 2 | 0 | —(CH₂)₂— | Lin | Lin | H |
| 2-379 | Me | 1 | 3 | 0 | —(CH₂)₂— | Lin | Lin | H |
| 2-380 | Me | 2 | 2 | 0 | —(CH₂)₂— | Lin | Lin | H |
| 2-381 | Me | 0 | 2 | 0 | —(CH₂)₃— | Lin | Lin | H |
| 2-382 | Me | 0 | 3 | 0 | —(CH₂)₃— | Lin | Lin | H |
| 2-383 | Me | 0 | 4 | 0 | —(CH₂)₃— | Lin | Lin | H |
| 2-384 | Me | 1 | 1 | 0 | —(CH₂)₃— | Lin | Lin | H |
| 2-385 | Me | 1 | 2 | 0 | —(CH₂)₃— | Lin | Lin | H |
| 2-386 | Me | 1 | 3 | 0 | —(CH₂)₃— | Lin | Lin | H |
| 2-387 | Me | 2 | 2 | 0 | —(CH₂)₃— | Lin | Lin | H |
| 2-388 | Me | 1 | 3 | 0 | — | Lin | Lin | Me |
| 2-389 | Me | 2 | 2 | 0 | — | Lin | Lin | Me |
| 2-390 | Me | 1 | 3 | 0 | —CH₂— | Lin | Lin | Me |
| 2-391 | Me | 0 | 2 | 0 | — | C16 | C10 | H |
| 2-392 | Me | 0 | 3 | 0 | — | C16 | C10 | H |
| 2-393 | Me | 0 | 4 | 0 | — | C16 | C10 | H |
| 2-394 | Me | 1 | 2 | 0 | — | C16 | C10 | H |
| 2-395 | Me | 1 | 3 | 0 | — | C16 | C10 | H |
| 2-396 | Me | 2 | 2 | 0 | — | C16 | C10 | H |
| 2-397 | Me | 0 | 2 | 0 | —CH₂— | C16 | C10 | H |
| 2-398 | Me | 0 | 3 | 0 | —CH₂— | C16 | C10 | H |
| 2-399 | Me | 0 | 4 | 0 | —CH₂— | C16 | C10 | H |
| 2-400 | Me | 1 | 1 | 0 | —CH₂— | C16 | C10 | H |
| 2-401 | Me | 1 | 2 | 0 | —CH₂— | C16 | C10 | H |
| 2-402 | Me | 1 | 3 | 0 | —CH₂— | C16 | C10 | H |
| 2-403 | Me | 2 | 2 | 0 | —CH₂— | C16 | C10 | H |
| 2-404 | Me | 0 | 2 | 0 | —(CH₂)₂— | C16 | C10 | H |
| 2-405 | Me | 0 | 3 | 0 | —(CH₂)₂— | C16 | C10 | H |
| 2-406 | Me | 0 | 4 | 0 | —(CH₂)₂— | C16 | C10 | H |
| 2-407 | Me | 1 | 1 | 0 | —(CH₂)₂— | C16 | C10 | H |
| 2-408 | Me | 1 | 2 | 0 | —(CH₂)₂— | C16 | C10 | H |
| 2-409 | Me | 1 | 3 | 0 | —(CH₂)₂— | C16 | C10 | H |
| 2-410 | Me | 2 | 2 | 0 | —(CH₂)₂— | C16 | C10 | H |
| 2-411 | Me | 0 | 2 | 0 | —(CH₂)₃— | C16 | C10 | H |
| 2-412 | Me | 0 | 3 | 0 | —(CH₂)₃— | C16 | C10 | H |
| 2-413 | Me | 0 | 4 | 0 | —(CH₂)₃— | C16 | C10 | H |
| 2-414 | Me | 1 | 1 | 0 | —(CH₂)₃— | C16 | C10 | H |
| 2-415 | Me | 1 | 2 | 0 | —(CH₂)₃— | C16 | C10 | H |
| 2-416 | Me | 1 | 3 | 0 | —(CH₂)₃— | C16 | C10 | H |
| 2-417 | Me | 2 | 2 | 0 | —(CH₂)₃— | C16 | C10 | H |
| 2-418 | Me | 1 | 3 | 0 | — | C16 | C10 | Me |
| 2-419 | Me | 2 | 2 | 0 | — | C16 | C10 | Me |
| 2-420 | Me | 1 | 3 | 0 | —CH₂— | C16 | C10 | Me |
| 2-421 | Me | 0 | 2 | 0 | — | C16 | C16 | H |
| 2-422 | Me | 0 | 3 | 0 | — | C16 | C16 | H |
| 2-423 | Me | 0 | 4 | 0 | — | C16 | C16 | H |
| 2-424 | Me | 1 | 2 | 0 | — | C16 | C16 | H |
| 2-425 | Me | 1 | 3 | 0 | — | C16 | C16 | H |
| 2-426 | Me | 2 | 2 | 0 | — | C16 | C16 | H |
| 2-427 | Me | 0 | 2 | 0 | —CH₂— | C16 | C16 | H |
| 2-428 | Me | 0 | 3 | 0 | —CH₂— | C16 | C16 | H |
| 2-429 | Me | 0 | 4 | 0 | —CH₂— | C16 | C16 | H |
| 2-430 | Me | 1 | 1 | 0 | —CH₂— | C16 | C16 | H |
| 2-431 | Me | 1 | 2 | 0 | —CH₂— | C16 | C16 | H |
| 2-432 | Me | 1 | 3 | 0 | —CH₂— | C16 | C16 | H |
| 2-433 | Me | 2 | 2 | 0 | —CH₂— | C16 | C16 | H |
| 2-434 | Me | 0 | 2 | 0 | —(CH₂)₂— | C16 | C16 | H |
| 2-435 | Me | 0 | 3 | 0 | —(CH₂)₂— | C16 | C16 | H |
| 2-436 | Me | 0 | 4 | 0 | —(CH₂)₂— | C16 | C16 | H |
| 2-437 | Me | 1 | 1 | 0 | —(CH₂)₂— | C16 | C16 | H |
| 2-438 | Me | 1 | 2 | 0 | —(CH₂)₂— | C16 | C16 | H |
| 2-439 | Me | 1 | 3 | 0 | —(CH₂)₂— | C16 | C16 | H |
| 2-440 | Me | 2 | 2 | 0 | —(CH₂)₂— | C16 | C16 | H |
| 2-441 | Me | 0 | 2 | 0 | —(CH₂)₃— | C16 | C16 | H |
| 2-442 | Me | 0 | 3 | 0 | —(CH₂)₃— | C16 | C16 | H |
| 2-443 | Me | 0 | 4 | 0 | —(CH₂)₃— | C16 | C16 | H |
| 2-444 | Me | 1 | 1 | 0 | —(CH₂)₃— | C16 | C16 | H |
| 2-445 | Me | 1 | 2 | 0 | —(CH₂)₃— | C16 | C16 | H |
| 2-446 | Me | 1 | 3 | 0 | —(CH₂)₃— | C16 | C16 | H |
| 2-447 | Me | 2 | 2 | 0 | —(CH₂)₃— | C16 | C16 | H |
| 2-448 | Me | 1 | 3 | 0 | — | C16 | C16 | Me |
| 2-449 | Me | 2 | 2 | 0 | — | C16 | C16 | Me |
| 2-450 | Me | 1 | 3 | 0 | —CH₂— | C16 | C16 | Me |
| 2-451 | Me | 0 | 2 | 0 | — | C17 | C10 | H |
| 2-452 | Me | 0 | 3 | 0 | — | C17 | C10 | H |
| 2-453 | Me | 0 | 4 | 0 | — | C17 | C10 | H |
| 2-454 | Me | 1 | 2 | 0 | — | C17 | C10 | H |
| 2-455 | Me | 1 | 3 | 0 | — | C17 | C10 | H |
| 2-456 | Me | 2 | 2 | 0 | — | C17 | C10 | H |
| 2-457 | Me | 0 | 2 | 0 | —CH₂— | C17 | C10 | H |
| 2-458 | Me | 0 | 3 | 0 | —CH₂— | C17 | C10 | H |
| 2-459 | Me | 0 | 4 | 0 | —CH₂— | C17 | C10 | H |
| 2-460 | Me | 1 | 1 | 0 | —CH₂— | C17 | C10 | H |
| 2-461 | Me | 1 | 2 | 0 | —CH₂— | C17 | C10 | H |
| 2-462 | Me | 1 | 3 | 0 | —CH₂— | C17 | C10 | H |
| 2-463 | Me | 2 | 2 | 0 | —CH₂— | C17 | C10 | H |
| 2-464 | Me | 0 | 2 | 0 | —(CH₂)₂— | C17 | C10 | H |
| 2-465 | Me | 0 | 3 | 0 | —(CH₂)₂— | C17 | C10 | H |
| 2-466 | Me | 0 | 4 | 0 | —(CH₂)₂— | C17 | C10 | H |
| 2-467 | Me | 1 | 1 | 0 | —(CH₂)₂— | C17 | C10 | H |
| 2-468 | Me | 1 | 2 | 0 | —(CH₂)₂— | C17 | C10 | H |

TABLE 2-continued

[Formula 19]

$$R^2-N\underset{(\phantom{X})_q}{\overset{(\phantom{X})_p}{\diagup}}Z-O-\underset{O}{\overset{\phantom{|}}{C}}-O-(CH_2)_m-C\underset{L^2}{\overset{R^3}{\diagdown}}L^1$$

| Compound | R² | p | q | m | Z | L¹ | L² | R³ |
|---|---|---|---|---|---|---|---|---|
| 2-469 | Me | 1 | 3 | 0 | —(CH₂)₂— | C17 | C10 | H |
| 2-470 | Me | 2 | 2 | 0 | —(CH₂)₂— | C17 | C10 | H |
| 2-471 | Me | 0 | 2 | 0 | —(CH₂)₃— | C17 | C10 | H |
| 2-472 | Me | 0 | 3 | 0 | —(CH₂)₃— | C17 | C10 | H |
| 2-473 | Me | 0 | 4 | 0 | —(CH₂)₃— | C17 | C10 | H |
| 2-474 | Me | 1 | 1 | 0 | —(CH₂)₃— | C17 | C10 | H |
| 2-475 | Me | 1 | 2 | 0 | —(CH₂)₃— | C17 | C10 | H |
| 2-476 | Me | 1 | 3 | 0 | —(CH₂)₃— | C17 | C10 | H |
| 2-477 | Me | 2 | 2 | 0 | —(CH₂)₃— | C17 | C10 | H |
| 2-478 | Me | 1 | 3 | 0 | — | C17 | C10 | Me |
| 2-479 | Me | 2 | 2 | 0 | — | C17 | C10 | Me |
| 2-480 | Me | 1 | 3 | 0 | —CH₂— | C17 | C10 | Me |
| 2-481 | Me | 0 | 2 | 0 | — | C17 | C17 | H |
| 2-482 | Me | 0 | 3 | 0 | — | C17 | C17 | H |
| 2-483 | Me | 0 | 4 | 0 | — | C17 | C17 | H |
| 2-484 | Me | 1 | 2 | 0 | — | C17 | C17 | H |
| 2-485 | Me | 1 | 3 | 0 | — | C17 | C17 | H |
| 2-486 | Me | 2 | 2 | 0 | — | C17 | C17 | H |
| 2-487 | Me | 0 | 2 | 0 | —CH₂— | C17 | C17 | H |
| 2-488 | Me | 0 | 3 | 0 | —CH₂— | C17 | C17 | H |
| 2-489 | Me | 0 | 4 | 0 | —CH₂— | C17 | C17 | H |
| 2-490 | Me | 1 | 1 | 0 | —CH₂— | C17 | C17 | H |
| 2-491 | Me | 1 | 2 | 0 | —CH₂— | C17 | C17 | H |
| 2-492 | Me | 1 | 3 | 0 | —CH₂— | C17 | C17 | H |
| 2-493 | Me | 2 | 2 | 0 | —CH₂— | C17 | C17 | H |
| 2-494 | Me | 0 | 2 | 0 | —(CH₂)₂— | C17 | C17 | H |
| 2-495 | Me | 0 | 3 | 0 | —(CH₂)₂— | C17 | C17 | H |
| 2-496 | Me | 0 | 4 | 0 | —(CH₂)₂— | C17 | C17 | H |
| 2-497 | Me | 1 | 1 | 0 | —(CH₂)₂— | C17 | C17 | H |
| 2-498 | Me | 1 | 2 | 0 | —(CH₂)₂— | C17 | C17 | H |
| 2-499 | Me | 1 | 3 | 0 | —(CH₂)₂— | C17 | C17 | H |
| 2-500 | Me | 2 | 2 | 0 | —(CH₂)₂— | C17 | C17 | H |
| 2-501 | Me | 0 | 2 | 0 | —(CH₂)₃— | C17 | C17 | H |
| 2-502 | Me | 0 | 3 | 0 | —(CH₂)₃— | C17 | C17 | H |
| 2-503 | Me | 0 | 4 | 0 | —(CH₂)₃— | C17 | C17 | H |
| 2-504 | Me | 1 | 1 | 0 | —(CH₂)₃— | C17 | C17 | H |
| 2-505 | Me | 1 | 2 | 0 | —(CH₂)₃— | C17 | C17 | H |
| 2-506 | Me | 1 | 3 | 0 | —(CH₂)₃— | C17 | C17 | H |
| 2-507 | Me | 2 | 2 | 0 | —(CH₂)₃— | C17 | C17 | H |
| 2-508 | Me | 1 | 3 | 0 | — | C17 | C17 | Me |
| 2-509 | Me | 2 | 2 | 0 | — | C17 | C17 | Me |
| 2-510 | Me | 1 | 3 | 0 | —CH₂— | C17 | C17 | Me |
| 2-511 | Me | 0 | 2 | 0 | — | C18 | C10 | H |
| 2-512 | Me | 0 | 3 | 0 | — | C18 | C10 | H |
| 2-513 | Me | 0 | 4 | 0 | — | C18 | C10 | H |
| 2-514 | Me | 1 | 2 | 0 | — | C18 | C10 | H |
| 2-515 | Me | 1 | 3 | 0 | — | C18 | C10 | H |
| 2-516 | Me | 2 | 2 | 0 | — | C18 | C10 | H |
| 2-517 | Me | 0 | 2 | 0 | —CH₂— | C18 | C10 | H |
| 2-518 | Me | 0 | 3 | 0 | —CH₂— | C18 | C10 | H |
| 2-519 | Me | 0 | 4 | 0 | —CH₂— | C18 | C10 | H |
| 2-520 | Me | 1 | 1 | 0 | —CH₂— | C18 | C10 | H |
| 2-521 | Me | 1 | 2 | 0 | —CH₂— | C18 | C10 | H |
| 2-522 | Me | 1 | 3 | 0 | —CH₂— | C18 | C10 | H |
| 2-523 | Me | 2 | 2 | 0 | —CH₂— | C18 | C10 | H |
| 2-524 | Me | 0 | 2 | 0 | —(CH₂)₂— | C18 | C10 | H |
| 2-525 | Me | 0 | 3 | 0 | —(CH₂)₂— | C18 | C10 | H |
| 2-526 | Me | 0 | 4 | 0 | —(CH₂)₂— | C18 | C10 | H |
| 2-527 | Me | 1 | 1 | 0 | —(CH₂)₂— | C18 | C10 | H |
| 2-528 | Me | 1 | 2 | 0 | —(CH₂)₂— | C18 | C10 | H |
| 2-529 | Me | 1 | 3 | 0 | —(CH₂)₂— | C18 | C10 | H |
| 2-530 | Me | 2 | 2 | 0 | —(CH₂)₂— | C18 | C10 | H |
| 2-531 | Me | 0 | 2 | 0 | —(CH₂)₃— | C18 | C10 | H |
| 2-532 | Me | 0 | 3 | 0 | —(CH₂)₃— | C18 | C10 | H |
| 2-533 | Me | 0 | 4 | 0 | —(CH₂)₃— | C18 | C10 | H |
| 2-534 | Me | 1 | 1 | 0 | —(CH₂)₃— | C18 | C10 | H |
| 2-535 | Me | 1 | 2 | 0 | —(CH₂)₃— | C18 | C10 | H |
| 2-536 | Me | 1 | 3 | 0 | —(CH₂)₃— | C18 | C10 | H |
| 2-537 | Me | 2 | 2 | 0 | —(CH₂)₃— | C18 | C10 | H |
| 2-538 | Me | 1 | 3 | 0 | — | C18 | C10 | Me |
| 2-539 | Me | 2 | 2 | 0 | — | C18 | C10 | Me |
| 2-540 | Me | 1 | 3 | 0 | —CH₂— | C18 | C10 | Me |
| 2-541 | Me | 0 | 2 | 0 | — | C18 | C18 | H |
| 2-542 | Me | 0 | 3 | 0 | — | C18 | C18 | H |
| 2-543 | Me | 0 | 4 | 0 | — | C18 | C18 | H |
| 2-544 | Me | 1 | 2 | 0 | — | C18 | C18 | H |
| 2-545 | Me | 1 | 3 | 0 | — | C18 | C18 | H |
| 2-546 | Me | 2 | 2 | 0 | — | C18 | C18 | H |
| 2-547 | Me | 0 | 2 | 0 | —CH₂— | C18 | C18 | H |
| 2-548 | Me | 0 | 3 | 0 | —CH₂— | C18 | C18 | H |
| 2-549 | Me | 0 | 4 | 0 | —CH₂— | C18 | C18 | H |
| 2-550 | Me | 1 | 1 | 0 | —CH₂— | C18 | C18 | H |
| 2-551 | Me | 1 | 2 | 0 | —CH₂— | C18 | C18 | H |
| 2-552 | Me | 1 | 3 | 0 | —CH₂— | C18 | C18 | H |
| 2-553 | Me | 2 | 2 | 0 | —CH₂— | C18 | C18 | H |
| 2-554 | Me | 0 | 2 | 0 | —(CH₂)₂— | C18 | C18 | H |
| 2-555 | Me | 0 | 3 | 0 | —(CH₂)₂— | C18 | C18 | H |
| 2-556 | Me | 0 | 4 | 0 | —(CH₂)₂— | C18 | C18 | H |
| 2-557 | Me | 1 | 1 | 0 | —(CH₂)₂— | C18 | C18 | H |
| 2-558 | Me | 1 | 2 | 0 | —(CH₂)₂— | C18 | C18 | H |
| 2-559 | Me | 1 | 3 | 0 | —(CH₂)₂— | C18 | C18 | H |
| 2-560 | Me | 2 | 2 | 0 | —(CH₂)₂— | C18 | C18 | H |
| 2-561 | Me | 0 | 2 | 0 | —(CH₂)₃— | C18 | C18 | H |
| 2-562 | Me | 0 | 3 | 0 | —(CH₂)₃— | C18 | C18 | H |
| 2-563 | Me | 0 | 4 | 0 | —(CH₂)₃— | C18 | C18 | H |
| 2-564 | Me | 1 | 1 | 0 | —(CH₂)₃— | C18 | C18 | H |
| 2-565 | Me | 1 | 2 | 0 | —(CH₂)₃— | C18 | C18 | H |
| 2-566 | Me | 1 | 3 | 0 | —(CH₂)₃— | C18 | C18 | H |
| 2-567 | Me | 2 | 2 | 0 | —(CH₂)₃— | C18 | C18 | H |
| 2-568 | Me | 1 | 3 | 0 | — | C18 | C18 | Me |
| 2-569 | Me | 2 | 2 | 0 | — | C18 | C18 | Me |
| 2-570 | Me | 1 | 3 | 0 | —CH₂— | C18 | C18 | Me |

1-3. Method for Producing Cationic Lipid

The cationic lipid of the present invention can be produced by the application of various synthesis methods known in the art. The synthesis methods known in the art include those described in "Comprehensive Organic Transformations (2nd ed.)", Wiley-VCH, 1999, "Comprehensive Organic Synthesis", Pergamon Press, 1991, etc. Depending on the type of the functional group used, the protection of a starting material or an intermediate with a suitable protective group, or reaction after replacement with a functional group that can be easily converted to the functional group of interest may be effective for the production. Such a functional group includes a hydroxy group, a carboxyl group, an amino group, multiple bonds, and the like. The protection and deprotection of the functional group or derivatization to the functional group can be carried out by a method known in the art. The method known in the art includes "Protective Groups in Organic Synthesis (4th ed.)", Wiley-Interscience, 2006, etc.

The method for producing the cationic lipid (I) of the present invention, which is summarized in FIGS. 1 to 3, will be shown below. However, the production method is not limited to the methods described below.

In the formulas, $G^1$, $G^2$, $G^3$, $G^4$, and $G^5$ each independently represent a hydrogen atom, a substituent selected from substituent group β, or a substituent that can serve as a synthetic-chemically acceptable protected form or precursor for inducing any substituent of substituent group β.

$p^1$ and $p^2$ each independently represent an integer of 0 to 21.

$G^6$, $G^7$, $G^{10}$, $G^{11}$, and $G^{12}$ each independently represent a $C_{10}$-$C_{24}$ alkyl group optionally having one or more substituents selected from substituent group β, a $C_{10}$-$C_{24}$ alkenyl group optionally having one or more substituents selected from substituent group β, a $C_3$-$C_{24}$ alkynyl group optionally having one or more substituents selected from substituent group β, a $(C_1$-$C_{10}$ alkyl$)$-$(Q)_k$-$(C_1$-$C_{10}$ alkyl$)$ group optionally having one or more substituents selected from substituent group β, or a substituent that can serve as a synthetic-chemically acceptable protected form or precursor for inducing any of these substituents.

$G^8$ represents a substituent represented by the following structural formula, or a substituent that can serve as a synthetic-chemically acceptable protected form or precursor for inducing the substituent:

[Formula 20]

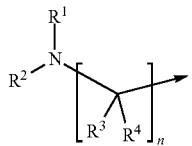

$G^9$ is not particularly limited as long as it can be generally used as a protective group for a carboxyl group. Examples thereof include a methyl group, an ethyl group, a propyl group, an isopropyl group, a butyl group, an isobutyl group, a sec-butyl group, a tert-butyl group, a benzyl group, a p-nitrobenzyl group, an o-nitrobenzyl group, and a p-methoxybenzyl group.

1-3-1. Method A

Method A is summarized in FIG. 1.

1-3-1-1. Step A-1

Step A-1 is the step of producing an internal alkyne compound (A3) having a hydroxy group from a terminal alkyne compound (A1) having a hydroxy group and an alkyl compound (A2) having a leaving substituent.

The solvent used is not particularly limited as long as the solvent does not inhibit the reaction and can dissolve starting materials to some extent. Examples thereof include aromatic, ether, ester, amide, nitrile, sulfoxide, and halogenated hydrocarbon solvents. Aprotic polar solvents such as amide and sulfoxide solvents are preferred, and N,N-dimethylformamide (DMF) is more preferred.

Examples of the reagent used include transition metal compounds. Copper compounds are preferred, and copper(I) iodide is more preferred.

Two or more of inorganic salts, inorganic bases, alkali metal alkoxides, alkaline earth metal alkoxides, organic bases, and the like are used as additives. Inorganic salts and inorganic bases are preferred, and sodium iodide and potassium carbonate are more preferred.

The reaction temperature differs depending on the types of the starting materials, the solvent, the reagent, and the like and is usually 0° C. to 100° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-1-2. Step A-2

Step A-2 is the step of producing an internal alkyne compound (A4) having a formyl group from the internal alkyne compound (A3) having a hydroxy group.

The solvent used is not particularly limited as long as the solvent does not inhibit the reaction and can dissolve starting materials to some extent. Examples thereof include sulfoxide solvents. Dimethyl sulfoxide (DMSO) is preferred.

Examples of the reagent used include sulfur trioxide-pyridine complexes and oxalic acid chloride.

Inorganic bases and organic bases are used as additives. Organic bases are preferred, and triethylamine is more preferred.

The reaction temperature differs depending on the types of the starting materials, the solvent, the reagent, and the like and is usually 0° C. to 100° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-1-3. Step A-3

Step A-3 is the step of producing an internal alkyne compound (A5) having a carboxyl group from the internal alkyne compound (A4) having a formyl group.

The solvent used is not particularly limited as long as the solvent does not inhibit the reaction and can dissolve starting materials to some extent. Examples thereof include alcohol, amine, and aqueous solvents. Alcohol solvents are preferred, and tert-butyl alcohol is more preferred.

Examples of the reagent used include inorganic oxidizing agents such as sodium chlorite.

Inorganic salts, inorganic bases, alkali metal alkoxides, and alkaline earth metal alkoxides are used as additives. Phosphates are preferred, and sodium dihydrogen phosphates are more preferred.

The additive further used is, for example, 2-methyl-2-butene.

The reaction temperature differs depending on the types of the starting materials, the solvent, the reagent, and the like and is usually 0° C. to 100° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-2. Method B

Method B is summarized in FIG. 2.

1-3-2-1. Step B-1

Step B-1 is the step of producing a N-methoxy carboxylic acid amide (B2) from a carboxylic acid (B1).

The solvent used is not particularly limited as long as the solvent does not inhibit the reaction and can dissolve starting materials to some extent. Examples thereof include aromatic, ether, ester, amide, nitrile, sulfoxide, and halogenated hydrocarbon solvents. Halogenated hydrocarbon solvents are preferred, and dichloromethane is more preferred.

Examples of the secondary material used include N,O-dimethylhydroxylamine hydrochloride.

Examples of the reagent used include dehydrative condensation agents such as carbodiimides. 1-Ethyl-3-(3'-dimethylaminopropyl)carbodiimide hydrochloride is preferred.

Inorganic bases, alkali metal alkoxides, alkaline earth metal alkoxides, and organic bases are used as additives. Organic bases are preferred, and triethylamine is more preferred. The additive further used is a N-hydroxy heterocyclic compound as a dehydrative condensation activator. 1-Hydroxybenzimidazole hydrate is preferred.

The reaction temperature differs depending on the types of the starting materials, the solvent, the reagent, and the like and is usually −78° C. to 100° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-2-2. Step B-2

Step B-2 is the step of producing a ketone (B3) from the N-methoxy carboxylic acid amide (B2).

The solvent used is not particularly limited as long as the solvent does not inhibit the reaction and can dissolve starting materials to some extent. Examples thereof include aromatic, ether, ester, amide, nitrile, and sulfoxide solvents. Ether solvents such as diethyl ether and tetrahydrofuran are preferred.

Examples of the reagent used include Grignard reagents, alkyllithium reagents, and alkylzinc reagents. Grignard reagents and alkyllithium reagents are preferred.

The reaction temperature differs depending on the types of the starting materials, the solvent, the reagent, and the like and is usually −78° C. to 100° C., preferably −30° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-2-3. Step B-3

Step B-3 is the step of producing an alcohol (B4) from the ketone (B3).

The solvent used is not particularly limited as long as the solvent does not inhibit the reaction and can dissolve starting materials to some extent. Examples thereof include ether, ester, amide, nitrile, sulfoxide, alcohol, amine, and aqueous solvents. Protonic solvents such as alcohol and aqueous solvents are preferred, and an aqueous solution of methanol or ethanol is more preferred.

Examples of the reagent used include boron reagents and aluminum reagents generally used as reducing agents. Sodium borohydride is preferred.

The reaction temperature differs depending on the types of the starting materials, the solvent, the reagent, and the like and is usually 0° C. to 100° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-2-4. Step B-4

Step B-4 is the step of producing an alcohol (B4') having a double bond in the molecule from the alcohol (B4) having a triple bond in the molecule.

The solvent used is not particularly limited as long as the solvent does not inhibit the reaction and can dissolve starting materials to some extent. Examples thereof include aromatic, ether, ester, amide, alcohol, amine, and aqueous solvents. Protonic solvents such as alcohol and aqueous solvents are preferred, and methanol or ethanol is more preferred.

Examples of the secondary material used include reducing agents as hydrogen gas or hydrogen donors. Hydrogen, sodium borohydride, and the like are preferred. These secondary materials are used alone or in combination of two or more thereof.

Examples of the catalyst used include transition metal compounds. Supported palladium metals, nickel compounds, and cobalt compounds are preferred, and polyethyleneimine-supported palladium and nickel(II) acetate tetrahydrate are more preferred.

In the case of using a nickel compound, a cobalt compound, or the like as the catalyst, organic bases are used as additives. Ethylenediamine is preferred.

The reaction temperature differs depending on the types of the starting materials, the solvent, the reagent, and the like and is usually −78° C. to 80° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-2-5. Step B-5

Step B-5 is the step of producing a carbonate (B5) from the alcohol (B4).

The solvent used is not particularly limited as long as the solvent does not inhibit the reaction and can dissolve starting materials to some extent. Examples thereof include aromatic, ether, ester, amide, nitrile, sulfoxide, halogenated hydrocarbon, and amine solvents. Low polar solvents such as aromatic and halogenated hydrocarbon solvents are preferred, and toluene and dichloromethane are more preferred.

Examples of the secondary material used include alcohols and active carbonates such as p-nitrophenyl-substituted carbonate.

In the case of using an alcohol as the secondary material, examples of the reagent used include phosgene equivalents. Diphosgene and triphosgene are preferred.

The reaction temperature differs depending on the types of the starting materials, the solvent, the reagent, and the like and is usually −78° C. to 100° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-2-6. Step B-6

Step B-6 is the step of producing a carbonate (B5') having a double bond in the molecule from the carbonate (B5) having a triple bond in the molecule.

This step can be carried out in the same way as in step B-4.

1-3-2-7. Step B-7

Step B-7 is the step of producing an aldehyde (B7) from the alcohol (B6).

Various general oxidation reactions may be used. In the case of using a sulfoxide as an oxidizing agent, the solvent used is preferably dimethyl sulfoxide.

Examples of the reagent used include oxalyl chloride, trifluoroacetic acid, dicyclohexylcarbodiimide, and sulfur trioxide-pyridine complexes.

The reaction temperature differs depending on the types of the starting materials, the solvent, the reagent, and the like and is usually −78° C. to 80° C., preferably 0° C. to 60° C.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-2-8. Step B-8

Step B-8 is the step of producing an alcohol (B4) from the aldehyde (B7).

The solvent used is not particularly limited as long as the solvent does not inhibit the reaction and can dissolve starting materials to some extent. Examples thereof include aromatic, ether, ester, amide, nitrile, and sulfoxide solvents. Ether solvents such as diethyl ether and tetrahydrofuran are preferred.

Examples of the reagent used include Grignard reagents, alkyllithium reagents, and alkylzinc reagents. Grignard reagents and alkyllithium reagents are preferred.

The reaction temperature differs depending on the types of the starting materials, the solvent, the reagent, and the like and is usually −78° C. to 100° C., preferably −30° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-3. Method C

Method C is summarized in FIG. 3.

1-3-3-1. Step C-1

Step C-1 is the step of producing a monosubstituted malonate (C2) from an unsubstituted malonate (C1).

The solvent used is not particularly limited as long as the solvent does not inhibit the reaction and can dissolve starting materials to some extent. Examples thereof include aromatic, ether, ester, amide, nitrile, sulfoxide, and alcohol solvents. Aromatic solvents such as toluene and xylene are preferred.

Examples of the secondary material used include alkyl halides and alkyl sulfonates.

Examples of the reagent used include inorganic bases, alkali metal alkoxides, alkaline earth metal alkoxides, and organic bases. Sodium hydride and sodium methoxide are preferred.

The reaction temperature differs depending on the types of the starting materials, the solvent, the reagent, and the like and is usually 0° C. to 200° C., preferably 50° C. to 150° C.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-3-2. Step C-2

Step C-2 is the step of producing an ester (C3) from the monosubstituted malonate (C2).

The solvent used is not particularly limited as long as the solvent does not inhibit the reaction and can dissolve starting materials to some extent. Examples thereof include aromatic, ester, amide, nitrile, sulfoxide, and aqueous solvents. Aprotic polar solvents such as amide and sulfoxide solvents are preferred, and dimethyl sulfoxide (DMSO) is more preferred.

Examples of the reagent used include inorganic salts and inorganic bases. Lithium chloride and sodium cyanide are preferred.

Examples of the additive used include water.

The reaction temperature differs depending on the types of the starting materials, the solvent, the reagent, and the like and is usually 80° C. to 200° C., preferably 120° C. to 180° C.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-3-3. Step C-3

Step C-3 is the step of producing a ketoester (C4) from the ester (C3).

The solvent used is not particularly limited as long as the solvent does not inhibit the reaction and can dissolve starting materials to some extent. Examples thereof include aromatic, ether, ester, amide, nitrile, and sulfoxide solvents. Aromatic solvents are preferred, and xylenes are more preferred.

Examples of the secondary material used include various organic acid esters having a structure condensed with the same alcohol as the starting material.

Examples of the reagent used include inorganic bases, alkali metal alkoxides, alkaline earth metal alkoxides, and organic bases. Sodium hydride is preferred.

The reaction temperature differs depending on the types of the starting materials, the solvent, the reagent, and the like and is usually 50° C. to 200° C., preferably 120° C. to 180° C.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-3-4. Step C-4

Step C-4 is the step of producing a ketone (C5; compound corresponding to B3) from the ketoester (C4).

The solvent used is not particularly limited as long as the solvent does not inhibit the reaction and can dissolve starting materials to some extent. Examples thereof include ether, ester, amide, nitrile, sulfoxide, alcohol, and aqueous solvents. Protonic solvents such as alcohol and aqueous solvents are preferred, and an aqueous solution of methanol or ethanol is more preferred.

Examples of the reagent used include inorganic bases, alkali metal alkoxides, and alkaline earth metal alkoxides. Sodium hydroxide and lithium hydroxide are preferred.

The reaction temperature differs depending on the types of the starting materials, the solvent, the reagent, and the like and is usually 0° C. to 120° C., preferably 50° C. to 100° C.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-3-5. Step C-5

Step C-5 is the step of producing a disubstituted malonate (C6) from the monosubstituted malonate (C2).

This step can be carried out in the same way as in step C-1.

1-3-3-6. Step C-6

Step C-6 is the step of producing an ester (C7) from the disubstituted malonate (C6).

This step can be carried out in the same way as in step C-2.

1-3-3-7. Step C-7

Step C-7 is the step of producing a 2-substituted alcohol (C8) from the ester (C7).

The solvent used is not particularly limited as long as the solvent does not inhibit the reaction and can dissolve starting materials to some extent. Examples thereof include aromatic and ether solvents. Tetrahydrofuran is preferred.

Examples of the reagent used include general reducing agents such as lithium aluminum hydride.

The reaction temperature differs depending on the types of the starting materials, the solvent, the reagent, and the like and is usually −78° C. to 80° C., preferably 0° C. to room temperature.

After completion of the reaction, the compound of interest of this reaction is collected from the reaction mixture according to a standard method. The compound of interest is obtained, for example, by: appropriately neutralizing the reaction mixture, or removing insoluble matter, if any, by filtration; then adding water and a water-immiscible organic solvent such as hexane or ethyl acetate; after washing with water, separating the organic layer containing the compound of interest; drying the organic layer over anhydrous magnesium sulfate, anhydrous sodium sulfate, anhydrous sodium bicarbonate, or the like; and then distilling off the solvent. The obtained compound of interest is further purified, if necessary, by a standard method, for example, recrystallization, reprecipitation, or chromatography.

1-3-3-8. Step C-8

Step C-8 is the step of producing a carbonate (C9) from the 2-substituted alcohol (C8).

This step can be carried out in the same way as in step B-5.

2. Lipid Particle

The lipid particle in the present specification includes a composition having any structure selected from a liposome, a lipid aggregate in which lipids are aggregated, and a micelle. The structure of the lipid particle is not limited to them as long as the lipid particle is a composition containing a lipid. The liposome has a lipid bilayer structure and has an aqueous phase in the inside. The liposome is classified as a multilamellar liposome, which has a multilayered structure of lipid bilayers, or as a unilamellar liposome, which has one bilayer. The liposome of the present invention includes both such liposomes.

The "lipid particle" of the present invention includes any composition selected from the following (a) to (c):

(a) a composition comprising a cationic lipid and a lipid reducing aggregation during lipid particle formation, (b) a composition comprising a cationic lipid, a lipid reducing aggregation during lipid particle formation, and a sterol, and (c) a composition comprising a cationic lipid, a lipid reducing aggregation during lipid particle formation, a sterol, and an amphipathic lipid.

In this context, the cationic lipid is one or two or more of various cationic lipids described in the preceding paragraph "1. Cationic lipid". Specific examples thereof can include one or two or more of the compounds described in Table 1 or 2.

Examples of the amphipathic lipid can include one or two or more of those described below in the paragraph "2-1. Amphipathic lipid".

Examples of the sterol can include one or two or more of those described below in the paragraph "2-2. Sterol".

Examples of the lipid reducing aggregation during lipid particle formation can include one or two or more of those described below in the paragraph "2-3. Lipid reducing aggregation during lipid particle formation".

2-1. Amphipathic Lipid

In the present specification, the "amphipathic lipid" refers to a lipid having affinity for both polar and nonpolar solvents.

Examples of the amphipathic lipid can include lipids described in "Liposomes: from physics to applications", Chapter 1. Chemistry of lipids and liposomes (published by Elsevier B.V. in 1993, author: D. D. Lasic), etc. The amphipathic lipid includes, for example, phospholipids, glycolipids, aminolipids, sphingolipids, glycols, and saturated or unsaturated fatty acids, though the amphipathic lipid of the present invention is not limited to them. Specific examples thereof are described in the paragraphs 2-1-1 to 2-1-3.

2-1-1. Phospholipids

The phospholipids are broadly divided into glycerophospholipids and sphingophospholipids. Typical examples of the glycerophospholipids include phosphatidyl cholines (PC), phosphatidyl serines (PS), phosphatidyl inositols (PI), phosphatidyl glycerols (PG), phosphatidyl ethanolamines (PE), and phosphatidic acids (PA). On the other hand, typical examples of the sphingophospholipids include sphingomyelin (SM). For example, lipids described in the following (a) to (g) can be listed.

(a) Phosphatidylcholines

Specific examples of the phosphatidylcholines can include dipalmitoylphosphatidylcholine (DPPC), distearoylphosphatidylcholine (DSPC), dimyristoylphosphatidylcholine (DMPC), dioleoylphosphatidylcholine (DOPC), dilauroylphosphatidylcholine (DLPC), didecanoylphosphatidylcholine (DDPC), dioctanoylphosphatidylcholine (DOPC), dihexanoylphosphatidylcholine (DHPC), dibutyrylphosphatidylcholine (DBPC), dielaidoylphosphatidylcholine (DEPC), dilinoleoylphosphatidylcholine, diarachidonoylphosphatidylcholine, diicosenoylphosphatidylcholine, diheptanoylphosphatidylcholine, dicaproylphosphatidylcholine, diheptadecanoylphosphatidylcholine, dibehenoylphosphatidylcholine, eleostearoylphosphatidylcholine, hydrogenated egg phosphatidylcholine (HEPC), hydrogenated soybean phosphatidylcholine (HSPC), 1-palmitoyl-2-arachidonoylphosphatidylcholine, 1-palmitoyl-2-oleoylphosphatidylcholine (POPC), 1-palmitoyl-2-linoleoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, 1,2-dimyristoylamido-1,2-deoxyphosphatidylcholine, 1-myristoyl-2-palmitoylphosphatidylcholine, 1-myristoyl-2-stearoylphosphatidylcholine, di-O-hexadecylphosphatidylcholine, trans-dielaidoylphosphatidylcholine, dipalmitelaidoyl-phosphatidylcholine, n-octadecyl-2-methylphosphatidylcholine, n-octadecylphosphatidylcholine, 1-laurylpropanediol-3-phosphocholine, erythro-N-lignoceroylsphingophosphatidylcholine, and palmitoyl-(9-cis-octadecenoyl)-3-sn-phosphatidylcholine. Preferred examples thereof can include DSPC, DPPC, and DMPC.

(b) Phosphatidylserines

Specific examples of the phosphatidylserines include distearoylphosphatidylserine (DSPS), dimyristoylphosphatidylserine (DMPS), dilauroylphosphatidylserine (DLPS), dipalmitoylphosphatidylserine (DPPS), dioleoylphosphatidylserine (DOPS), lysophosphatidylserine, eleostearoylphosphatidylserine, and 1,2-di-(9-cis-octadecenoyl)-3-sn-phosphatidylserine.

(c) Phosphatidylinositols

Specific examples of the phosphatidylinositols include dipalmitoylphosphatidylinositol (DPPI), distearoylphosphatidylinositol (DSPI), and dilauroylphosphatidylinositol (DLPI).

(d) Phosphatidylglycerols

Specific examples of the phosphatidylglycerols include dipalmitoylphosphatidylglycerol (DPPG), distearoylphosphatidylglycerol (DSPG), dioleoylphosphatidylglycerol (DOPG), dilauroylphosphatidylglycerol (DLPG), dimyristoylphosphatidylglycerol (DMPG), lysophosphatidylglycerol, hydrogenated soybean phosphatidylglycerol (HSPG), hydrogenated egg phosphatidylglycerol (HEPG), and cardiolipin (diphosphatidylglycerol).

(e) Phosphatidylethanolamines

Specific examples of the phosphatidylethanolamines include dipalmitoylphosphatidylethanolamine (DPPE), distearoylphosphatidylethanolamine (DSPE), dioleoylphosphatidylethanolamine (DOPE), dilauroylphosphatidylethanolamine (DLPE), dimyristoylphosphatidylethanolamine (DMPE), didecanoylphosphatidylethanolamine (DDPE), N-glutarylphosphatidylethanolamine (NGPE), lysophosphatidylethanolamine, N-(7-nitro-2,1,3-benzoxadiazol-4-yl)-1,2-dioleoyl-sn-phosphatidylethanolamine, eleostearoylphosphatidylethanolamine, N-succinyldioleoylphosphatidylethanolamine, and 1-hexadecyl-2-palmitoylglycerophosphatidylethanolamine. Preferred examples thereof can include DOPE.

(f) Phosphatidic Acids

Specific examples of the phosphatidic acids include dipalmitoylphosphatidic acid (DPPA), distearoylphosphatidic acid (DSPA), dimyristoylphosphatidic acid (DMPA), and dioleylphosphatidic acid (DOPA).

(g) Sphingophospholipids

Specific examples of the sphingophospholipids include sphingomyelin (SM), dipalmitoylsphingomyelin, distearoylsphingomyelin, ceramide ciliatine, ceramide phosphoryletanolamine, and ceramide phosphorylglycerol. Preferred examples thereof can include SM.

2-1-2. Glycolipids

The glycolipids are broadly divided into glyceroglycolipids and sphingoglycolipids. For example, lipids described in the following (a) or (b) can be listed.

(a) Glyceroglycolipids

Specific examples of the glyceroglycolipids include diglycosyl diglyceride, glycosyl diglyceride, digalactosyl diglyceride, galactosyl diglyceride, sulfoxyribosyl diglyceride, (1,3)-D-mannosyl (1,3)diglyceride, digalactosyl glyceride, digalactosyl dilauroyl glyceride, digalactosyl dimyristoyl glyceride, digalactosyl dipalmitoyl glyceride, digalactosyl distearoyl glyceride, galactosyl glyceride, galactosyl dilauroyl glyceride, galactosyl dimyristoyl glyceride, galactosyl dipalmitoyl glyceride, galactosyl distearoyl glyceride, and digalactosyl diacyl glycerol.

(b) Sphingoglycolipids

Specific examples of the sphingoglycolipids can include ceramide (cerebroside), galactosyl ceramide, lactosyl ceramide, digalactosyl ceramide, ganglioside GM1, ganglioside GM2, ganglioside GM3, sulfatide, ceramide oligohexoside, and globoside.

2-1-3. Saturated or Unsaturated Fatty Acids

Specific examples of the saturated fatty acids and the unsaturated fatty acids used include saturated or unsaturated fatty acids each having 5 to 30 carbon atoms, such as caprylic acid, pelargonic acid, capric acid, undecylenic acid, lauric acid, tridecylenic acid, myristic acid, pentadecylenic acid, palmitic acid, margaric acid, stearic acid, nonadecylenic acid, arachidic acid, dodecenoic acid, tetradecenoic acid, oleic acid, linoleic acid, linolenic acid, eicosenoic acid, erucic acid, and docosapentaenoic acid.

2-2. Sterol

Specific examples of the sterol can include cholesterol, cholesterol succinic acid, dihydrocholesterol, lanosterol, dihydrolanosterol, desmosterol, stigmasterol, sitosterol, campesterol, brassicasterol, zymosterol, ergosterol, fucosterol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, epicholesterol, dehydroergosterol, cholesterol sulfate, cholesterol hemisuccinate, cholesterol phthalate, cholesterol phosphate, cholesterol valerate, 3β-[N—(N',N'-dimethylaminoethane)-carbamoyl]-cholesterol, cholesterol acetate, cholesteryl oleate, cholesteryl linoleate, cholesteryl myristate, cholesteryl palmitate, cholesteryl arachidate, coprostanol, cholesterol ester, cholesteryl phosphorylcholine, and 3,6,9-trioxaoctan-1-ol-cholesteryl-3e-ol. Preferred examples thereof can include cholesterol and cholesterol hemisuccinate, more preferably cholesterol.

2-3. Lipid Reducing Aggregation During Lipid Particle Formation

A lipid bound with a nonionic water-soluble polymer can be used as the lipid reducing aggregation during lipid particle formation.

The nonionic water-soluble polymer refers to a polymer having no dissociable group at a site other than the end in an aqueous medium such as water or a buffer solution, or a polymer derived from the polymer such that its end is alkoxy. Examples of such a nonionic water-soluble polymer can include:

(1) a nonionic vinyl polymer having, as a constituent, a monomer unit such as vinyl alcohol, methyl vinyl ether, vinylpyrrolidone, vinyl oxazolidone, vinyl methyl oxazolidone, 2-vinylpyridine, 4-vinylpyridine, N-vinylsuccinimide, N-vinylformamide, N-vinyl-N-methylformamide, N-vinylacetamide, N-vinyl-N-methylacetamide, 2-hydroxyethyl methacrylate, acrylamide, methacrylamide, N,N-dimethylacrylamide, N-isopropylacrylamide, diacetoneacrylamide, methylolacrylamide, acryloylmorpholine, acryloylpyrrolidine, acryloylpiperidine, styrene, chloromethylstyrene, bromomethylstyrene, vinyl acetate, methyl methacrylate, butyl acrylate, methyl cyanoacrylate, ethyl cyanoacrylate, n-propyl cyanoacrylate, isopropyl cyanoacrylate, n-butyl cyanoacrylate, isobutyl cyanoacrylate, tert-butyl cyanoacrylate, glycidyl methacrylate, ethyl vinyl ether, n-propyl vinyl ether, isopropyl vinyl ether, n-butyl vinyl ether, isobutyl vinyl ether, or tert-butyl vinyl ether, or a polymer derived from the polymer by the alkoxylation of its end;

(2) a nonionic polyamino acid having, as a constituent, any one monomer unit selected from amino acids such as glycine, alanine, valine, leucine, isoleucine, proline, phenylalanine, serine, threonine, asparagine, and glutamine, or a polymer derived from the polymer by the alkoxylation of its end;

(3) a nonionic synthetic polypeptide having, as a constituent, two or more monomer units selected from amino acids such as glycine, alanine, valine, leucine, isoleucine, proline, phenylalanine, serine, threonine, asparagine, and glutamine, or a polymer derived from the polymer by the alkoxylation of its end;

(4) a nonionic polyester having, as a constituent, a monomer unit selected from glycolic acid and lactic acid, or a polymer derived from the polymer by the alkoxylation of its end;

(5) a nonionic polyether having, as a constituent, a monomer unit selected from glycols such as methylene glycol, ethylene glycol, n-propylene glycol, isopropylene glycol, and hydroxypropylene glycol, or a polymer derived from the polymer by the alkoxylation of its end;

(6) a nonionic natural polymer including sugars such as dextran, pectin, and pullulan, or a polymer derived from the polymer by the alkoxylation of its end;

(7) a nonionic modified natural polymer including celluloses such as methylcellulose and hydroxypropylcellulose, or a polymer derived from the polymer by the alkoxylation of its end; and (8) a block polymer or a graft copolymer having two or more different polymers selected from the polymers (1) to (7) as constituent units, or a copolymer derived from the copolymer by the alkoxylation of its end.

Of these nonionic water-soluble polymers, a nonionic polyether, a nonionic polyester, a nonionic polyamino acid, or a nonionic synthetic polypeptide, or a polymer derived from any of these polymers by the alkoxylation of the end is preferred. A nonionic polyether or a nonionic polyester, or a polymer derived from any of these polymers by the alkoxylation of the end is more preferred. A nonionic polyether or a nonionic monoalkoxy polyether is further preferred. Polyethylene glycol or monomethoxypolyethylene glycol is particularly preferred. Monomethoxypolyethylene glycol is most preferred.

The average molecular weight of the nonionic water-soluble polymer is not particularly limited and is preferably 1000 to 12000, more preferably 1000 to 5000, further preferably 1800 to 2200.

For example, any of the lipids listed in the paragraphs "2-1. Amphipathic lipid" and "2-2. Sterol" can be used in the lipid moiety.

Specific examples of the lipid bound with the nonionic water-soluble polymer can include, but are not limited to, diacylglycerol-bound monomethoxypolyethylene glycol, phosphatidyl ethanolamine-bound monomethoxypolyethylene glycol, and ceramide-bound monomethoxypolyethylene glycol (U.S. Pat. No. 5,885,613).

More specific examples thereof can include 1,2-dilauroyl-sn-glycerol methoxypolyethylene glycol represented by the following formula:

[Formula 21]

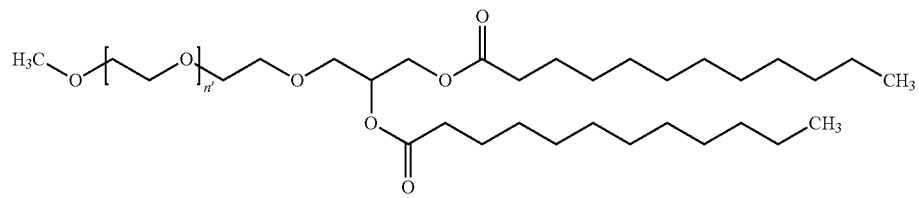

1,2-dimyristoyl-sn-glycerol methoxypolyethylene glycol represented by the following formula:

[Formula 22]

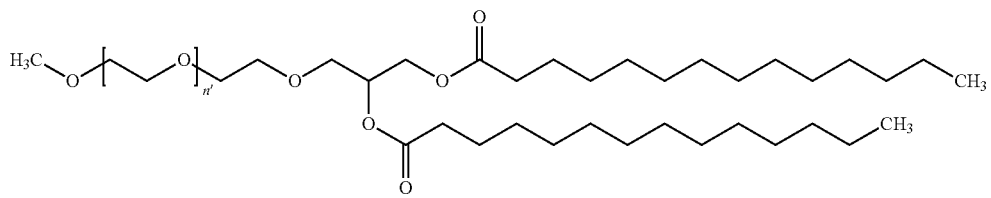

1,2-dipalmitoyl-sn-glycerol methoxypolyethylene glycol represented by the following formula:

[Formula 23]

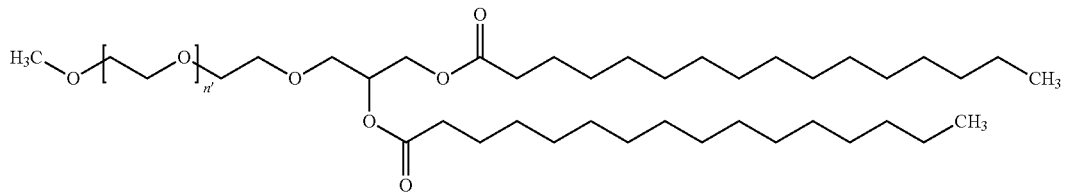

1,2-distearoyl-sn-glycerol methoxypolyethylene glycol represented by the following formula:

[Formula 24]

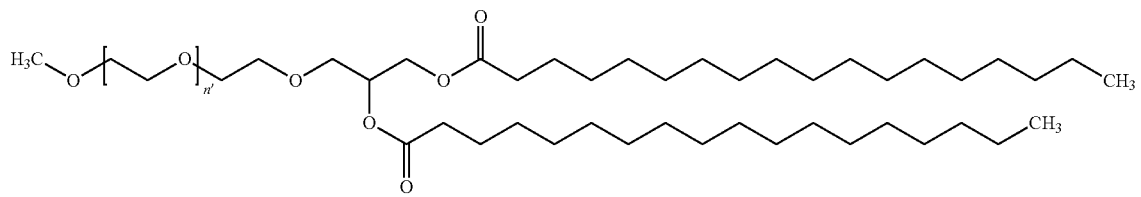

N-[methoxy poly(ethylene glycol)2000]carbamoyl]-1,2-dimyristyloxypropyl-3-amine (PEG-C-DMA; J. Controlled Release (2006) 112, p. 280-290) represented by the following formula:

[Formula 25]

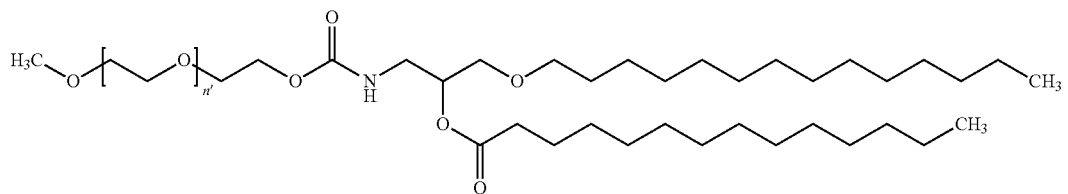

N-[methoxy poly(ethylene glycol)2000]carbamoyl]-1,2-dipalmityloxypropyl-3-amine (PEG-C-DPA; J. Controlled Release (2006) 112, p. 280-290) represented by the following formula:

[Formula 26]

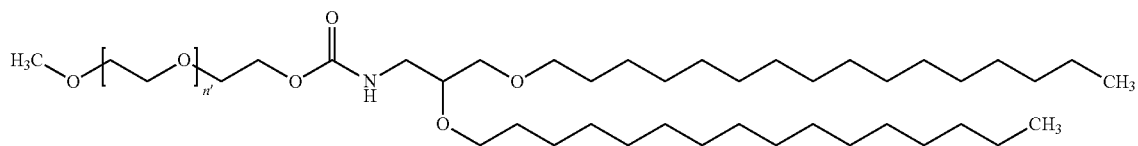

N-[methoxy poly(ethylene glycol)2000]carbamoyl]-1,2-distearyloxypropyl-3-amine (PEG-C-DSA; J. Controlled Release (2006) 112, p. 280-290) represented by the following formula:

[Formula 27]

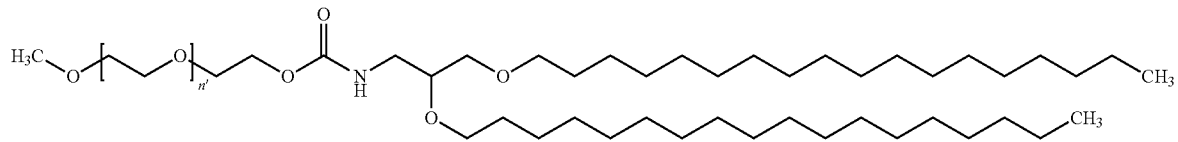

mPEG2000-1,2-di-O-myristyl-sn3-carbomoylglyceride (PEG-DMG; described in Example 21 of WO2009/132131) represented by the following formula:

[Formula 28]

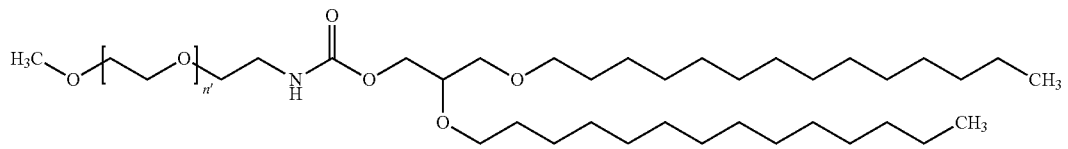

mPEG2000-1,2-di-O-palmityl-sn3-carbomoylglyceride (PEG-DPG; described in Example 21 of WO2009/132131) represented by the following formula:

[Formula 29]

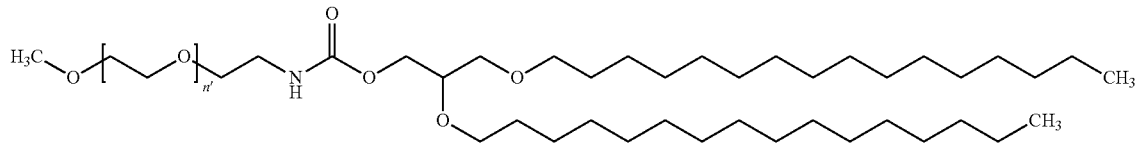

and
mPEG2000-1,2-di-O-stearyl-sn3-carbomoylglyceride (PEG-DSG; described in Example 21 of WO2009/132131) represented by the following formula:

[Formula 30]

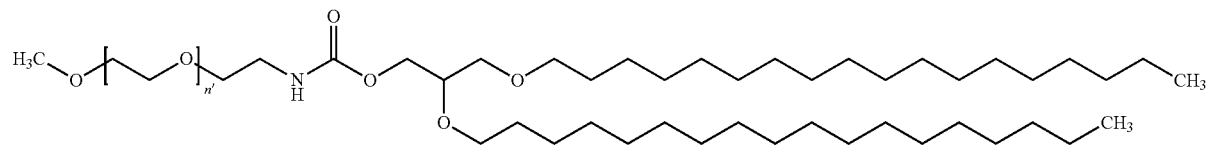

all of which have PEG having a molecular weight of approximately 2000.

Preferred examples thereof can include N-[methoxy poly(ethylene glycol)2000]carbamoyl]-1,2-dimyristyloxypropyl-3-amine (PEG-C-DMA) and 1,2-dimyristoyl-sn-glycerol methoxypolyethylene glycol. More preferred examples thereof can include N-[methoxy poly(ethylene glycol)2000]carbamoyl]-1,2-dimyristyloxypropyl-3-amine (PEG-C-DMA).

$CH_3O(CH_2CH_2O)_nCH_2CH_2O-$ in the structural formulas described above represents the nonionic water-soluble polymer. Its average molecular weight is not particularly limited and is preferably 1000 to 12000, more preferably 1000 to 5000, further preferably 1800 to 2200. n' represents a numeric value estimated from the average molecular weight of the nonionic water-soluble polymer, and the number is not particularly limited and is preferably 20 to 280, more preferably 20 to 120, further preferably 35 to 50.

Normal PEG can also be used instead of or at the same time with the PEG-lipid described above as long as the PEG can prevent the aggregation of lipid particles. The PEG may be removed by dialysis before administration if the lipid particle is stable after its production.

2-4. Other Constituents of the Lipid Particle

The lipid particle of the present invention can contain an additional substance as long as the lipid particle maintains its structure. One example of such a lipid particle can include a lipid particle containing one or two or more substances selected from a polyamide oligomer (see U.S. Pat. No. 6,320,017), a peptide, a protein, and a detergent.

A constituent in the lipid particle of the present invention may be bound with a ligand having directivity to a target molecule.

Examples of the ligand can include: (1) a hormone, a growth factor, a suitable oligopeptide fragment thereof, or a low-molecular compound, which is bound with a particular cell receptor dominantly expressed by a cell desired to be delivered; and (2) a polyclonal or monoclonal antibody, or a suitable fragment thereof (e.g., Fab or F(ab')2), which specifically binds to an antigenic epitope dominantly found on a target cell.

2-5. Compositional Ratio of Lipid Particle

The cationic lipid in the lipid particle according to the present invention is contained at approximately 20% to approximately 80%, preferably approximately 20% to approximately 70%, more preferably approximately 45% to approximately 65%, in terms of molar quantity with respect to all lipids present in the lipid particle. As for the molar quantity of the cationic lipid used in the present invention, the lower limit is preferably 20%, more preferably 45%, with respect to all lipids present in the lipid particle, and the upper limit is preferably 80%, more preferably 70%, further preferably 65%, with respect to all lipids present in the lipid particle. The amphipathic lipid is contained at approximately 0% to approximately 35%, preferably approximately 0% to approximately 20%, more preferably approximately 5% to approximately 15%, in terms of molar quantity with respect to all lipids present in the lipid particle. As for the molar quantity of the amphipathic lipid used in the present invention, the lower limit is preferably 5% with respect to all lipids present in the lipid particle, and the upper limit is preferably 35%, more preferably 20%, further preferably 15%, with respect to all lipids present in the lipid particle. The sterol is contained at approximately 0% to approximately 70%, preferably approximately 15% to approximately 70%, more preferably approximately 15% to approximately 35%, in terms of molar quantity with respect to all lipids present in the lipid particle. As for the molar quantity of the sterol used in the present invention, the lower limit is preferably 15% with respect to all lipids present in the lipid particle, and the upper limit is preferably 70%, more preferably 35%, with respect to all lipids present in the lipid particle. The lipid reducing aggregation during lipid particle formation is contained at approximately 0.5% to approximately 10%, preferably approximately 1% to approximately 10%, more preferably approximately 1.5% to approximately 10%, particularly preferably approximately 1.5% to approximately 3%, in terms of molar quantity with respect to all lipids present in the lipid particle. As for the molar quantity of the lipid reducing aggregation during lipid particle formation of the present invention, the lower limit is preferably 0.5%, more preferably 1%, further preferably 1.1%, still further preferably 1.2%, still further preferably 1.3%, particularly preferably 1.4%, most preferably 1.5%, with respect to all lipids present in the lipid particle, and the upper limit is preferably 10%, more preferably 5%, further preferably 3%, with respect to all lipids present in the lipid particle.

When the amphipathic lipid, the sterol, the cationic lipid, and the lipid reducing aggregation during lipid particle formation are used in the lipid particle of the present invention, the lipid composition is preferably 20% or less of the amphipathic lipid, 15% to 70% of the sterol, 20% to 70% of the cationic lipid, and 1% to 10% of the lipid reducing aggregation during lipid particle formation, more preferably 5% to 15% or less of the amphipathic lipid, 15% to 40% or more of the sterol, 45% to 65% of the cationic lipid, and 1.5% to 3% of the lipid reducing aggregation during lipid particle formation, in terms of molar quantity.

Preferred examples of the lipid particle of the present invention can include a lipid particle having any ratio selected from molar ratios of amphipathic lipid:sterol:cationic lipid:lipid reducing aggregation during lipid particle formation of 10:48:40:2, 10:38:50:2, 10:33:55:2, 10:28:60:2, 15:33:50:2, 10:48.5:40:1.5, and 10:47.5:40:2.5. More preferred examples thereof can include a lipid particle having any ratio selected from molar ratios of amphipathic lipid:sterol:cationic lipid:lipid reducing aggregation during lipid particle formation of 10:38:50:2, 10:33:55:2, 10:28:60:2, and 15:33:50:2.

3. Nucleic Acid Lipid Particle

The present invention provides a nucleic acid lipid particle comprising the lipid particle described in the preceding paragraph "2. Lipid particle" and further a nucleic acid. The term "nucleic acid lipid particle" means a complex of the lipid particle and a nucleic acid. One example of the nucleic acid lipid particle in which the lipid particle is complexed with the nucleic acid can include a nucleic acid lipid particle having a structure where a nucleic acid is buried in the bilayer of a lipid. One example of the nucleic acid lipid particle of the present invention can include a composition comprising the nucleic acid, the cationic lipid, the amphipathic lipid, the sterol, and the lipid reducing aggregation during lipid particle formation.

The ratio (N/P) of the number of molecules of the cationic lipid (N) to the number of phosphorus atoms derived from the nucleic acid (P) in the nucleic acid lipid particle of the present invention is preferably approximately 2.0 to 15.0, more preferably approximately 2.0 to 12.0, further preferably 2.0 to 9.0, still further preferably 3.0 to 9.0. The lower limit of the N/P ratio is preferably 2.0, more preferably 2.5, further preferably 3.0, and the upper limit thereof is preferably 15.0, more preferably 12.0, further preferably 9.0.

The nucleic acid lipid particle of the present invention has an average particle size of preferably approximately 30 nm to approximately 300 nm, more preferably approximately 30 nm to approximately 200 nm, further preferably approximately 30 nm to approximately 100 nm. The average particle size refers to a volume-average particle size measured on the basis of the principle of a dynamic light scattering method or the like using an apparatus such as Zeta Potential/Particle Sizer NICOMP™ 380ZLS (Particle Sizing Systems, LLC).

A nucleic acid that is degraded by nuclease under usual conditions is resistant to degradation by nuclease in an aqueous solution, when present in the nucleic acid lipid particle of the present invention.

The nucleic acid lipid particle and a preparation method thereof are disclosed in U.S. Pat. Nos. 5,753,613, 5,785,992, 5,705,385, 5,976,567, 5,981,501, 6,110,745, and 6,320,017, and International Publication Nos. WO 96/40964 and WO 07/012191.

In the present specification, the term "nucleic acid", "oligonucleotide", or "polynucleotide" refers to a polymer containing at least two deoxyribonucleotides or ribonucleotides in any form of a single strand, a double strand, and a triple strand.

A specific nucleic acid sequence also encompasses, implicitly, conservatively modified variants (e.g., degenerate codon substitutes), alleles, orthologs, SNPs, and complementary sequences thereof, and explicitly specified sequences, unless otherwise specified.

DNA may be in the form of an antisense, a plasmid DNA, a portion of the plasmid DNA, a DNA concentrated beforehand, a polymerase chain reaction (PCR) product, a vector (P1, PAC, BAC, YAC, or artificial chromosome), an expression cassette, a chimeric sequence, a chromosomal DNA, or a derivative of these groups.

In the present specification, the term "nucleic acid" is used for all of a gene, a plasmid, a cDNA, a messenger RNA (mRNA), and an interference RNA molecule (e.g., synthetic siRNA or siRNA expressed from a plasmid).

3-1. Nucleic Acid that Forms Nucleic Acid Lipid Particle

The nucleic acid that forms the nucleic acid lipid particle of the present invention can include any form known to those skilled in the art. Specific examples of such a form of the nucleic acid can include a single-stranded DNA, a single-stranded RNA, and a single-stranded polynucleotide of a DNA and an RNA mixed with each other. Specific examples of other forms of the nucleic acid can include a double-stranded polynucleotide consisting of a double-stranded DNA, a double-stranded RNA, a DNA-RNA hybrid polynucleotide, or two polynucleotides of a DNA and an RNA mixed with each other.

3-2. Nucleoside or Nucleotide

Each nucleoside or nucleotide constituting the nucleic acid contained in the nucleic acid lipid particle of the present invention includes natural one as well as a modified nucleoside or a modified nucleotide prepared by chemical modification. Examples of the modified nucleoside or nucleotide include a sugar-modified nucleoside or nucleotide, a nucleobase-modified nucleoside or nucleotide, a backbone-modified nucleoside or nucleotide, and combinations thereof (see e.g., Nucleic Acid Research, 1997, Vol. 25, No. 22, 4429-4443).

In the present specification, the "natural nucleoside" refers to a 2'-deoxynucleoside such as 2'-deoxyadenosine, 2'-deoxyguanosine, 2'-deoxycytidine, 2'-deoxy-5-methylcytidine, and thymidine or a ribonucleoside such as adenosine, guanosine, cytidine, 5-methylcytidine, and uridine. Moreover, the "oligonucleotide" refers to an oligonucleotide composed of a compound in which the sugar moiety of the nucleoside forms an ester with phosphoric acid. In the present specification, the terms "oligonucleotide" and "polynucleotide" are used interchangeably.

In the present specification, 2'-deoxyadenosine may be referred to as $A^r$; 2'-deoxyguanosine may be referred to as $G^r$; 2'-deoxycytidine may be referred to as $C^r$; 2'-deoxy-5-methylcytidine may be referred to as $5meC^r$; thymidine may be referred to as $T^r$; 2'-deoxyuridine may be referred to as $U^r$; adenosine may be referred to as $A^{rt}$; guanosine may be referred to as $G^{rt}$; cytidine may be referred to as $C^{rt}$; 5-methylcytidine may be referred to as $5meC^{rt}$; and uridine may be referred to as $U^{rt}$. Moreover, in the present specification, a 2'-deoxyadenosine nucleotide may be referred to as AP; a 2'-deoxyguanosine nucleotide may be referred to as GP; a 2'-deoxycytidine nucleotide may be referred to as $C^P$; a 2'-deoxy-5-methylcytidine nucleotide may be referred to as 5meCP; a thymidine nucleotide may be referred to as $T^P$; a 2'-deoxyuridine nucleotide may be referred to as UP; an adenosine nucleotide may be referred to as $A^{rP}$; a guanosine nucleotide may be referred to as $G^{rp}$; a cytidine nucleotide may be referred to as $C^{rp}$; a 5-methylcytidine nucleotide may be referred to as $5meC^{rp}$; and a uracil nucleotide may be referred to as $U^{rp}$.

In the present specification, where there are phosphorothioate ester forms instead of phosphoester forms of a nucleotide, a counterpart of $A^p$ may be referred to as $A^s$; a counterpart of $G^p$ may be referred to as $G^s$; a counterpart of $C^p$ may be referred to as $C^s$; a counterpart of $5meC^p$ may be referred to as $5meC^s$; a counterpart of $T^p$ may be referred to as $T^s$; a counterpart of $U^p$ may be referred to as $U^s$; a counterpart of $A^{rp}$ may be referred to as $A^{rs}$; a counterpart of $G^{rp}$ may be referred to as $G^{rs}$; a counterpart of $C^{rp}$ may be referred to as $C^{rs}$; a counterpart of $5meC^{rp}$ may be referred to as $5meC^{rs}$; and a counterpart of $U^{rp}$ may be referred to as $U^{rs}$.

In the present specification, the term "sugar-modified nucleoside" refers to a nucleoside modified at its sugar moiety. Examples of the sugar-modified nucleoside include 2'-O-methyl nucleoside, 2'-O,4'-C-ethylene nucleoside (ENA), and 2'-O,4'-C-methylene nucleotide (BNA/LNA).

In particular, examples of 2'-O-methyl modification include 2'-O-methyl nucleoside and 2'-O-methyl nucleotide: a counterpart of $A^{rt}$ may be referred to as $A^{m1t}$; a counterpart of $G^{rt}$ may be referred to as $G^{m1t}$; a counterpart of $C^{rt}$ may be referred to as $C^{m1t}$; a counterpart of $5meC^{rt}$ may be referred to as $5meC^{m1t}$; a counterpart of $U^{rt}$ may be referred to as $U^{m1t}$; a counterpart of $A^{rp}$ may be referred to as $A^{m1p}$; a counterpart of $G^{rp}$ may be referred to as $G^{m1p}$; a counterpart of $C^{rp}$ may be referred to as $C^{m1p}$; a counterpart of $5meC^{rp}$ may be referred to as $5meC^{m1p}$; a counterpart of $U^{rp}$ may be referred to as $U^{m1p}$; a counterpart of $A^{rs}$ may be referred to as $A^{m1s}$; a counterpart of $G^{rs}$ may be referred to as $G^{m1s}$; a counterpart of $C^{rs}$ may be referred to as $C^{m1s}$; a counterpart of $5meC^{rs}$ may be referred to as $5meC^{m1s}$; and a counterpart of $U^{rs}$ may be referred to as $U^{m1s}$.

In the Sequence Listing attached to the present specification, "cm" in the item <223> of each sequence represents 2'-O-methylcytidine; "um" represents 2'-O-methyluridine; and "gm" represents 2'-O-methylguanosine.

In the present specification, the 2'-O,4'-C-ethylene nucleotide unit and the "ENA unit" refer to those nucleosides and nucleotides having an ENA and also refer to nucleosides and nucleotides having an ENA unit: a counterpart of $A^t$ may be referred to as $A^{2t}$; a counterpart of $A^p$ may be referred to as $A^{e2p}$; a counterpart of $A^s$ may be referred to as $A^{e2s}$; a counterpart of $G^t$ may be referred to as $G^{2t}$; a counterpart of $G^p$ may be referred to as $G^{e2}p$; a counterpart of $G^s$ may be referred to as $G^{e2s}$; a counterpart of $5meC^t$ may be referred to as $C^{2t}$; a counterpart of $5meC^p$ may be referred to as $C^{e2p}$; a counterpart of $5meC^s$ may be referred to as $C^{e2s}$; a counterpart of $T^t$ may be referred to as $T^{2t}$; a counterpart of $T^p$ may be referred to as $T^{e2p}$; and a counterpart of $T^s$ may be referred to as $T^{e2s}$.

In the present specification, the 2'-O,4'-C-methylene nucleotide unit and the "2',4'-BNA/LNA unit" refer to those nucleosides and nucleotides having a 2',4'-BNA/LNA and also refer to nucleosides and nucleotides having a 2',4'-BNA/LNA unit: a counterpart of $A^t$ may be referred to as $A^{1t}$; a counterpart of $A^p$ may be referred to as $A^{e1p}$; a counterpart of $A^s$ may be referred to as $A^{e1s}$; a counterpart of $G^t$ may be referred to as $G^{1t}$; a counterpart of $G^p$ may be referred to as $G^{e1p}$; a counterpart of $G^s$ may be referred to as $G^{e1s}$; a counterpart of $5meC^t$ may be referred to as $C^{1t}$; a counterpart of $5meC^p$ may be referred to as $C^{e1p}$; a counterpart of $5meC^s$ may be referred to as $C^{e1s}$; a counterpart of $T^t$ may be referred to as $T^{1t}$; a counterpart of $T^p$ may be referred to as $T^{e1p}$; and a counterpart of $T^s$ may be referred to as $T^{e1s}$.

Hereinafter, the structural formula of each nucleotide is shown.

[Formula 31]

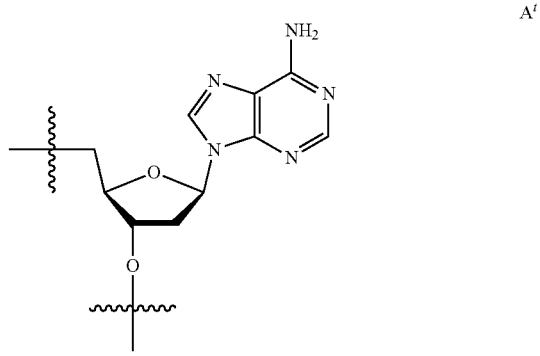

$A^t$

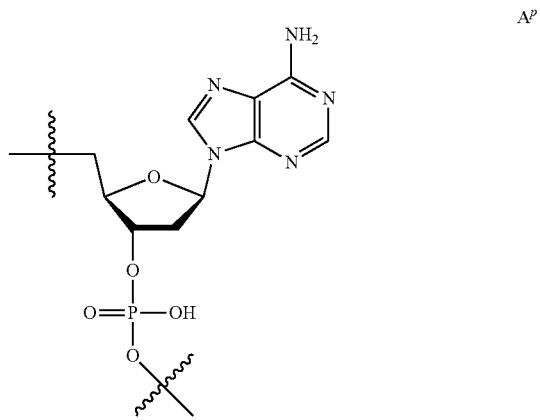

$A^p$

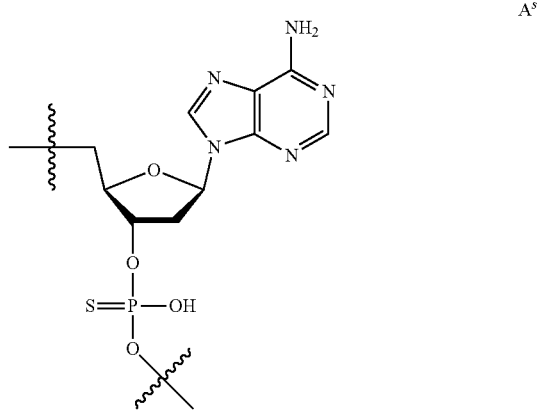

$A^s$

69
-continued
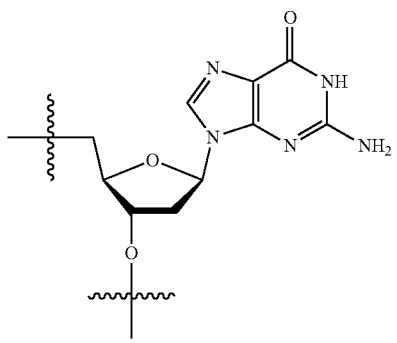
G^t
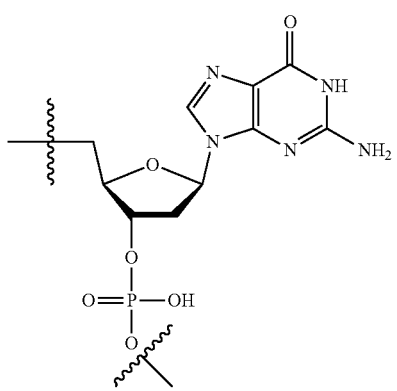
G^p
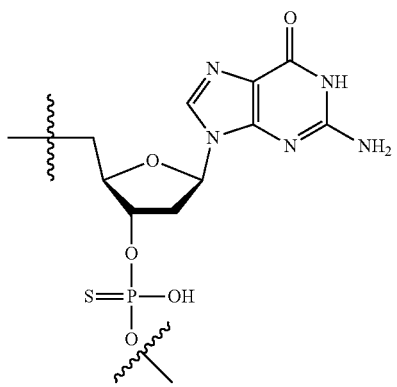
G^s
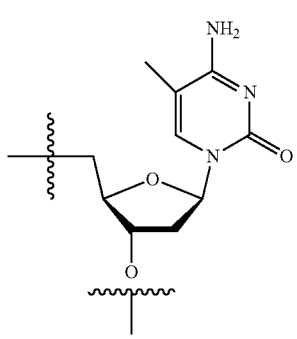
5meC^t
70
-continued
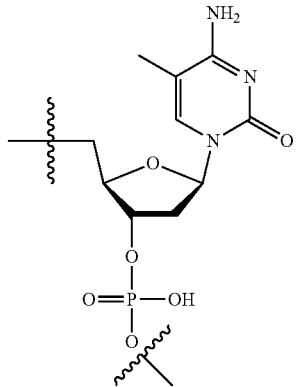
5meC^p
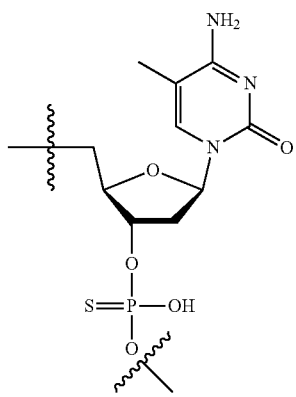
5meC^s
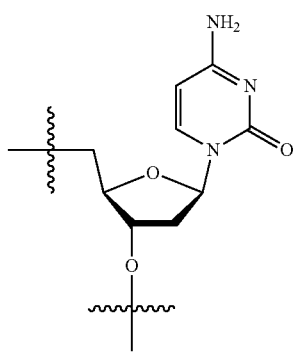
C^t
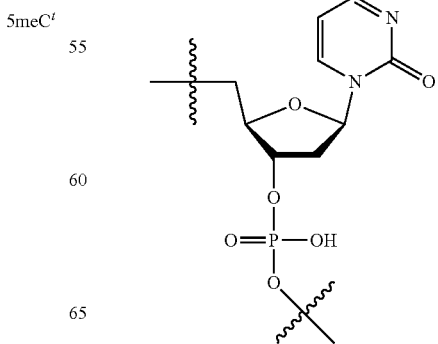
C^p

71
-continued
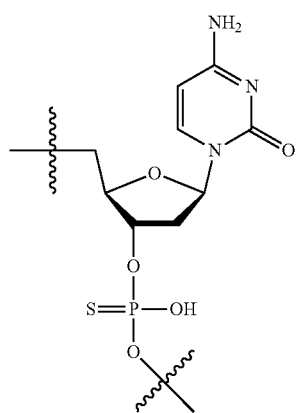
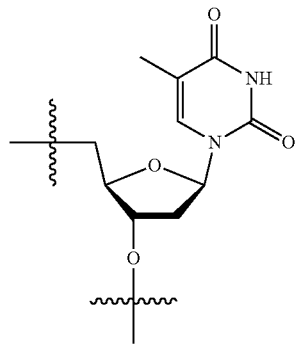 Tᵗ
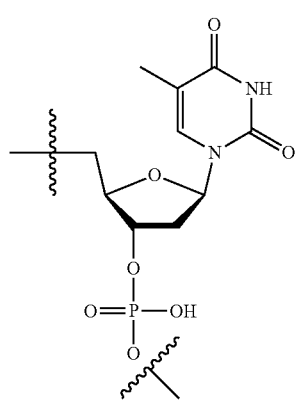 Tᵖ
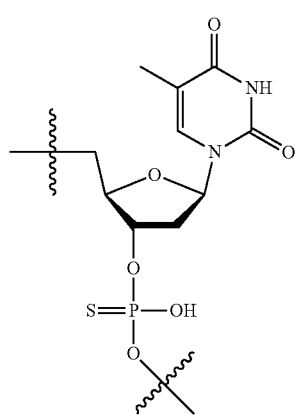 Tˢ
72
-continued
Cˢ
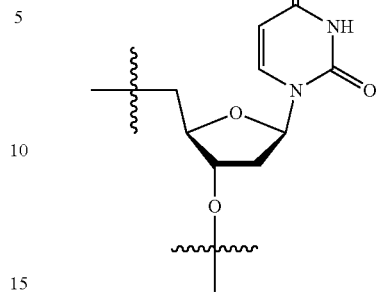
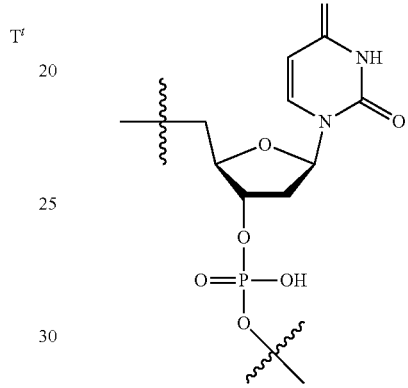
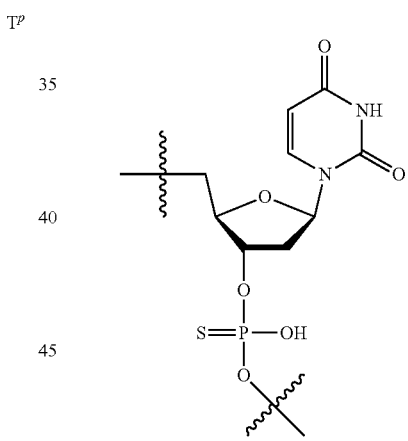
[Formula 32]
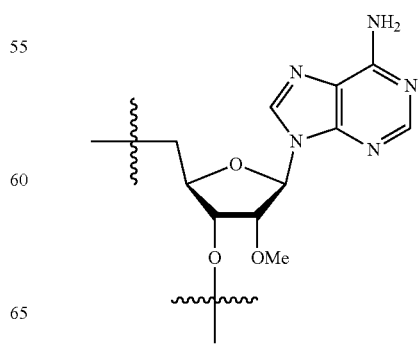
Uᵗ
Uᵖ
Uˢ
Aᵐ¹ᵗ

-continued
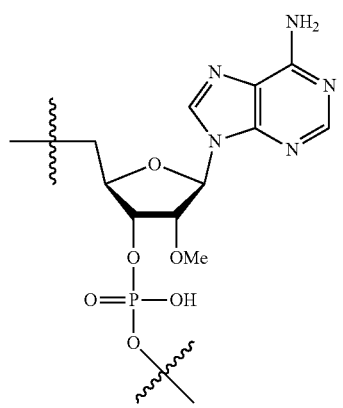
A^{m1p}
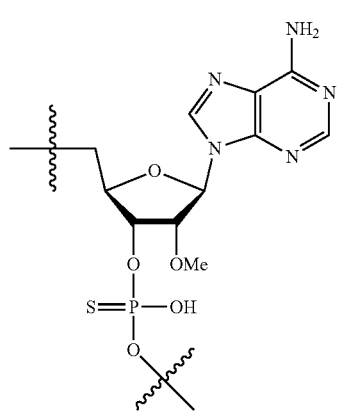
A^{m1s}
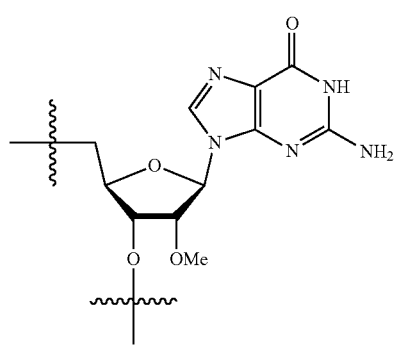
G^{m1t}
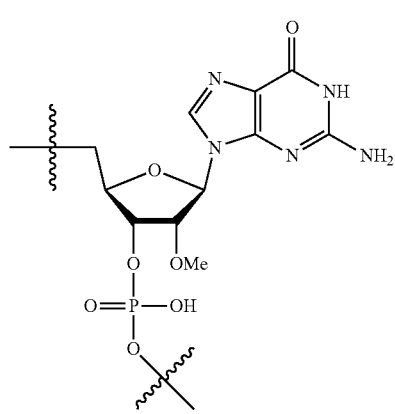
G^{m1p}
-continued
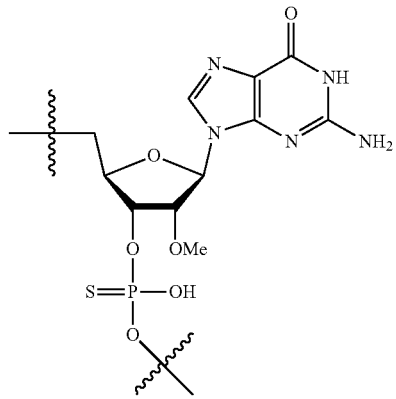
G^{m1s}
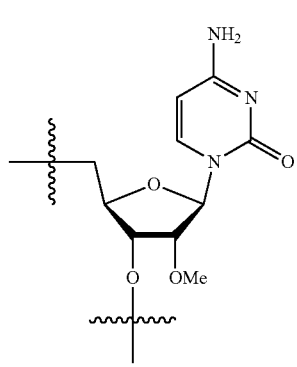
C^{m1t}
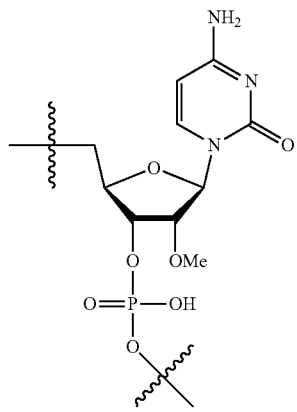
C^{m1p}
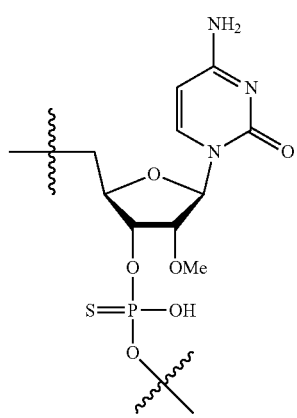
C^{m1s}

75
-continued
5meC^{m1t}
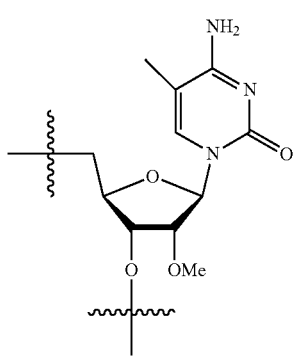
5meC^{m1p}
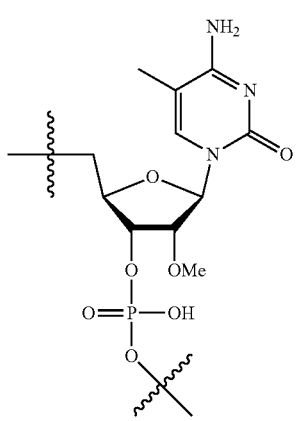
5meC^{m1s}
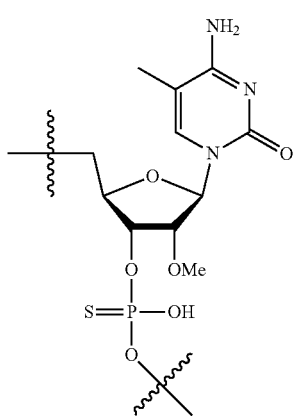
U^{m1t}
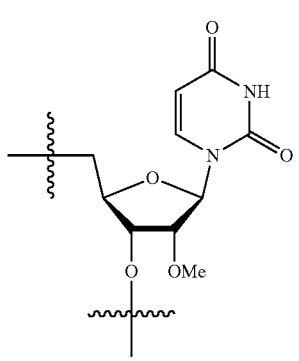
76
-continued
U^{m1p}
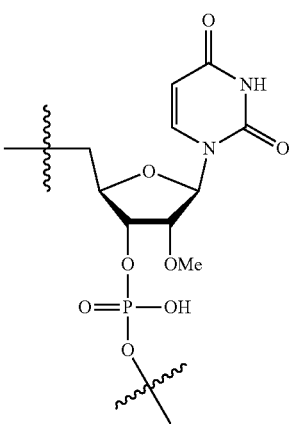
U^{m1s}
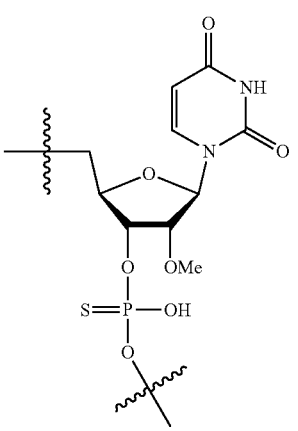
[Formula 33]
A^{2t}
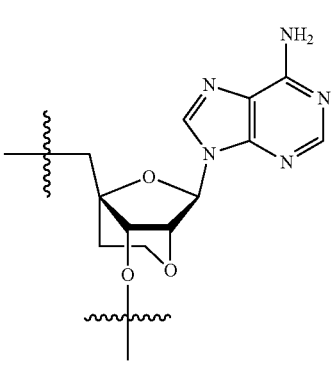
A^{e2p}
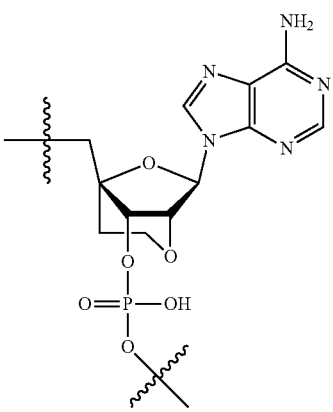

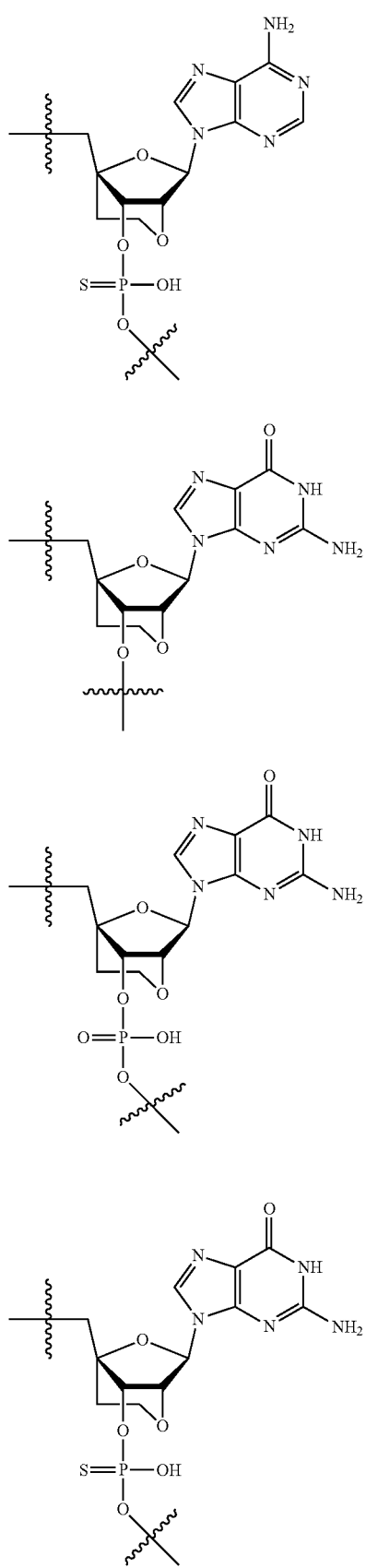
A^{e2s}
G^{2t}
G^{e2p}
G^{e2s}
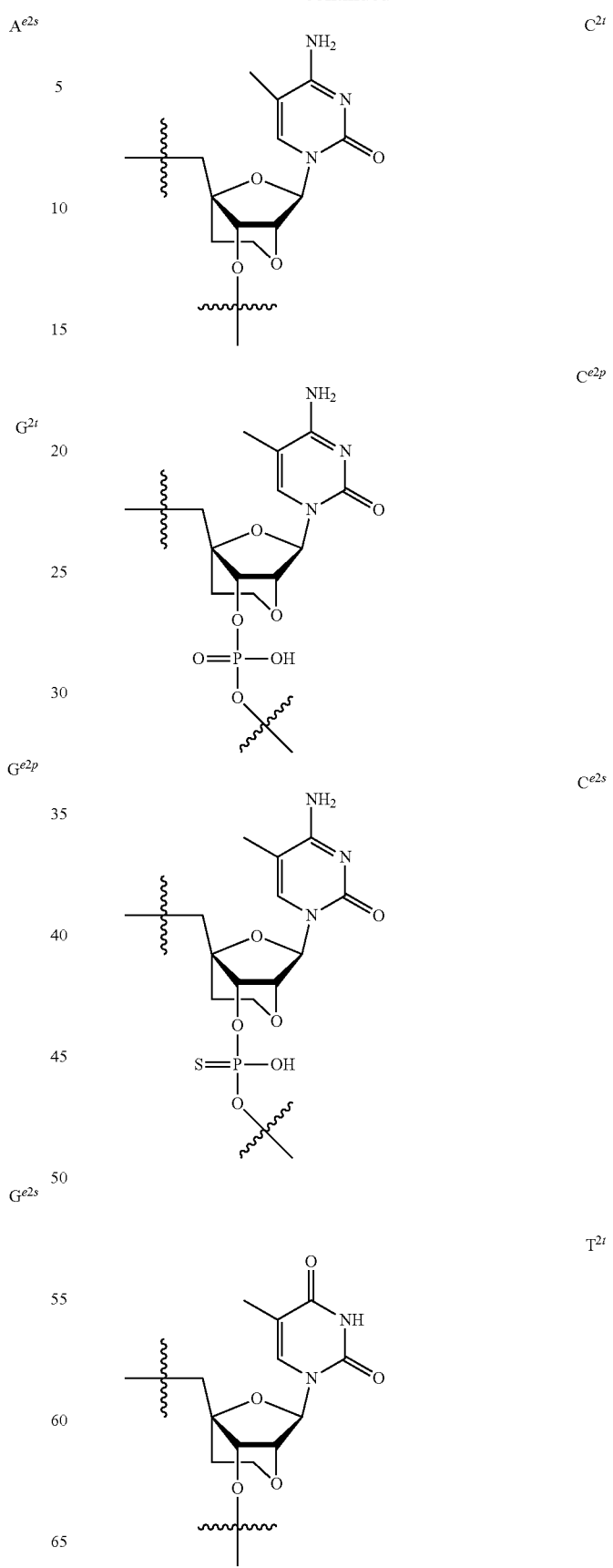
C^{2t}
C^{e2p}
C^{e2s}
T^{2t}

79
-continued
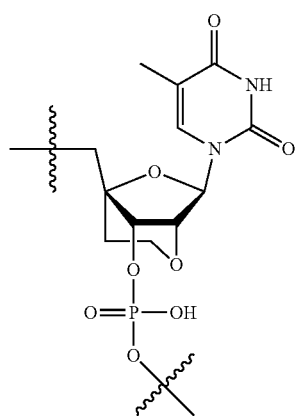
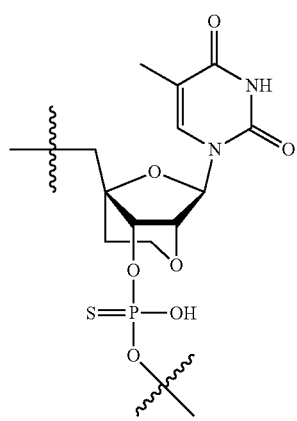
[Formula 34]
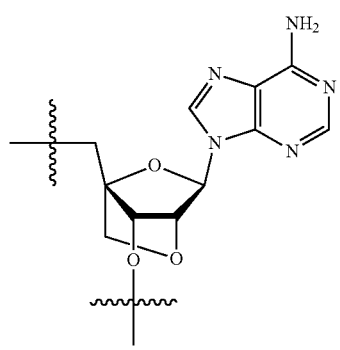
A$^{lt}$
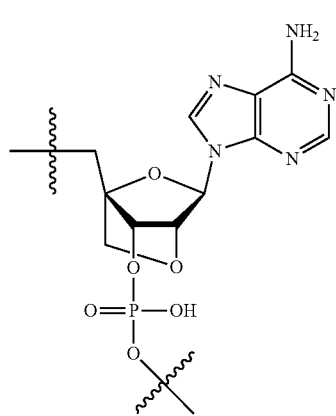
A$^{e1p}$
80
-continued
T$^{e2p}$
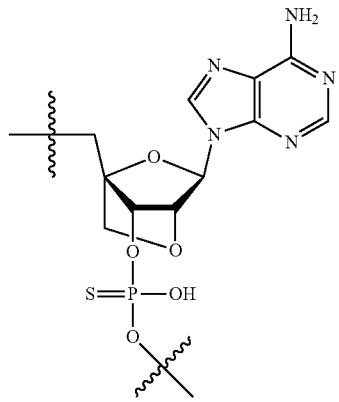
A$^{e1s}$
T$^{e2s}$
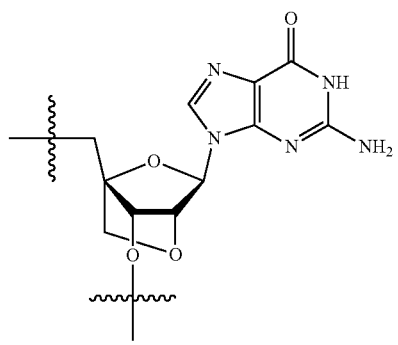
G$^{lt}$
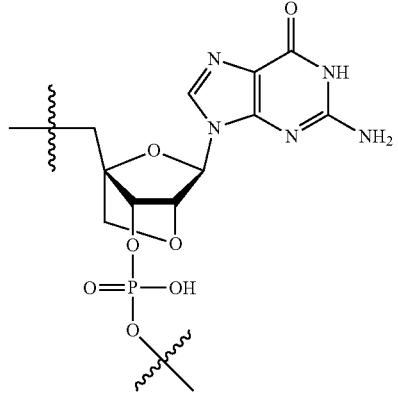
G$^{e1p}$
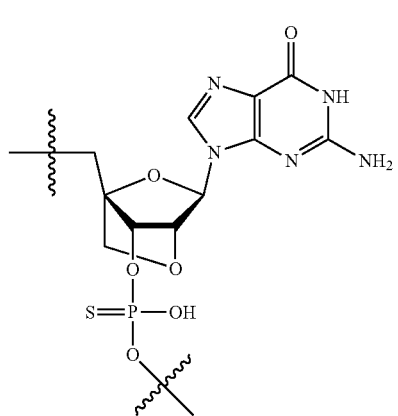
G$^{e1s}$ -continued
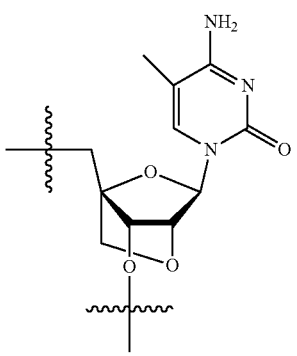
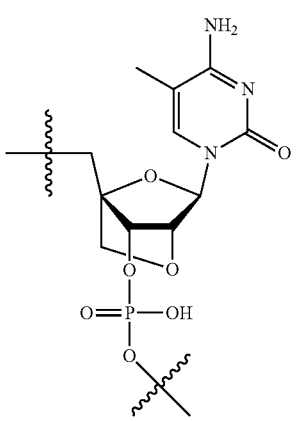
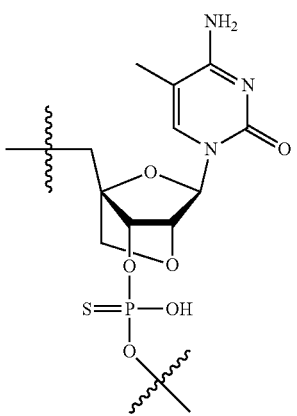
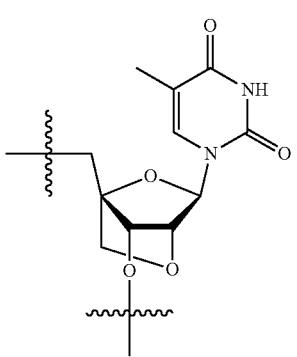
-continued
C$^{lt}$
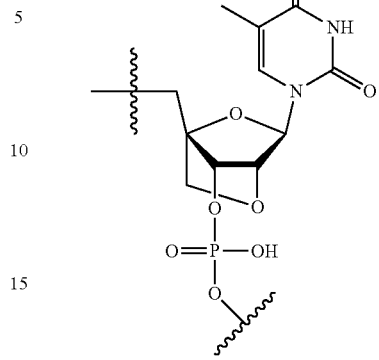
C$^{elp}$
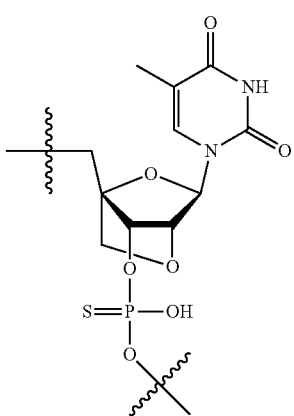
C$^{els}$
T$^{lt}$
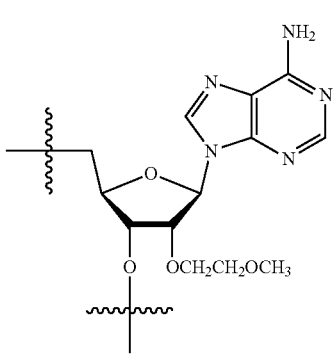
T$^{elp}$
T$^{els}$
[Formula 35]
A$^{m2t}$
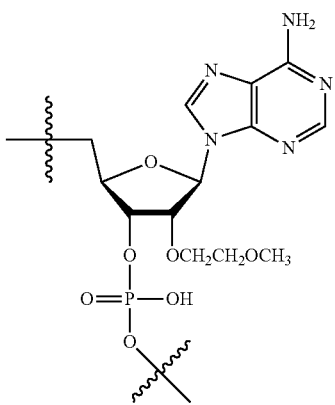
A$^{m2p}$ -continued
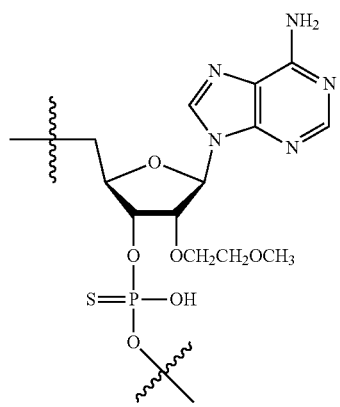
A^{m2s}
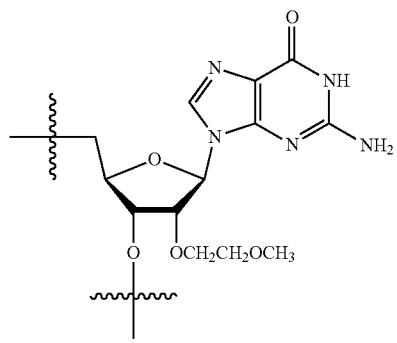
G^{m2t}
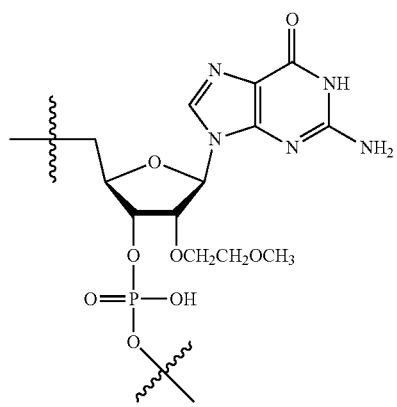
G^{m2p}
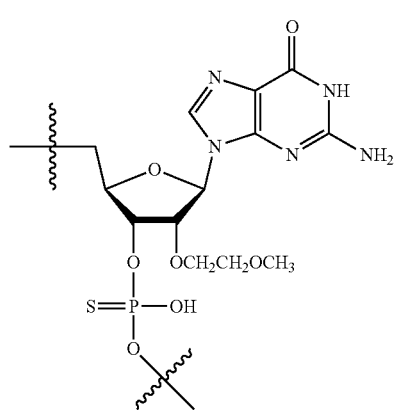
G^{m2s}
-continued
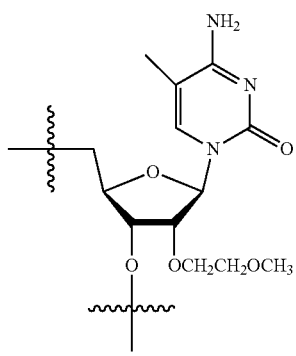
5meC^{m2t}
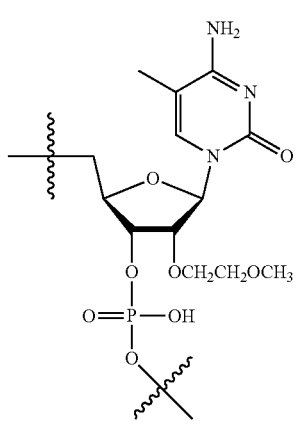
5meC^{m2p}
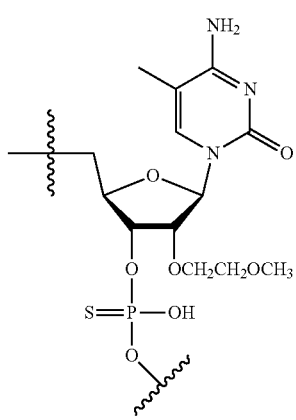
5meC^{m2s}
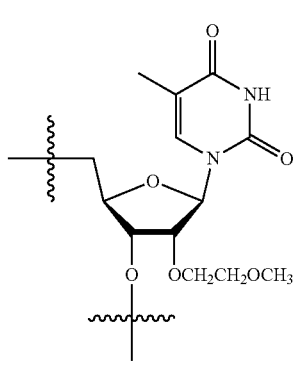
T^{m2t}

$T^{m2p}$
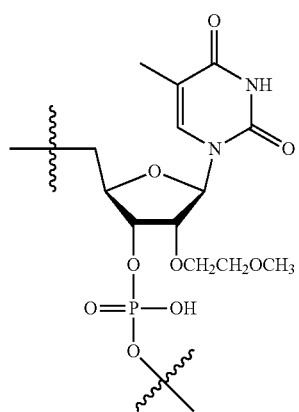
$T^{m2s}$
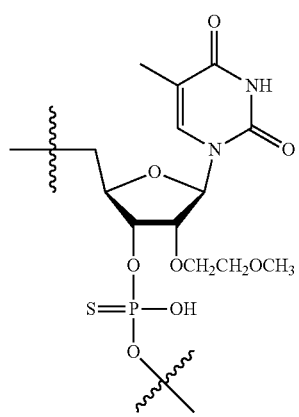
[Formula 36]
$A^{rt}$
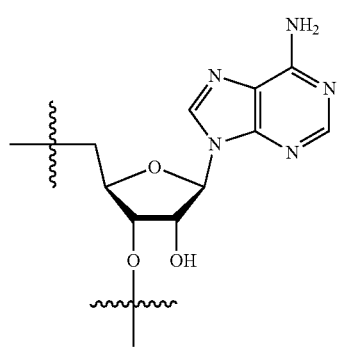
$A^{rp}$
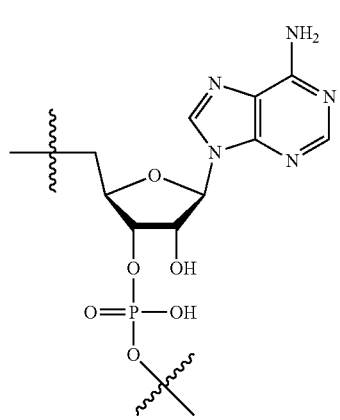
$A^{rs}$
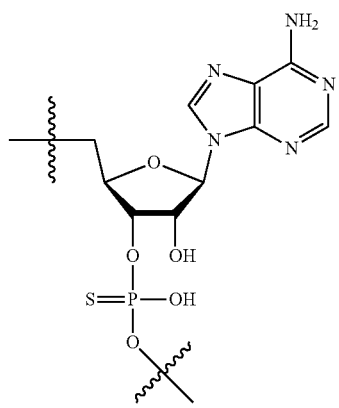
$G^{rt}$
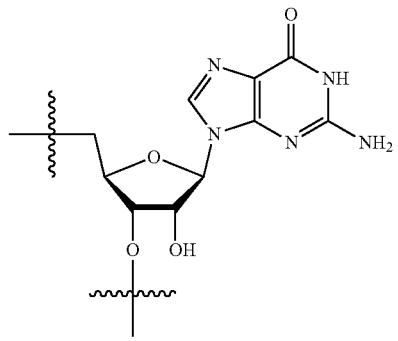
$G^{rp}$
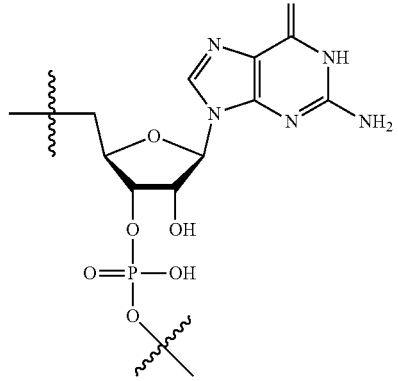
$G^{rs}$
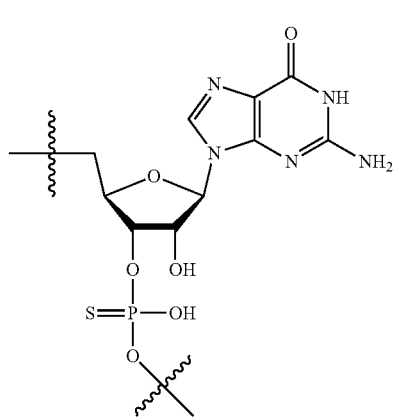

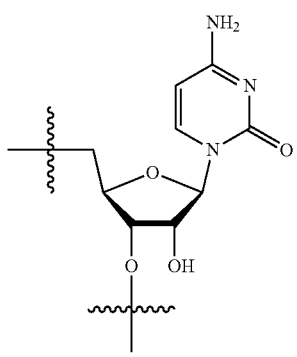
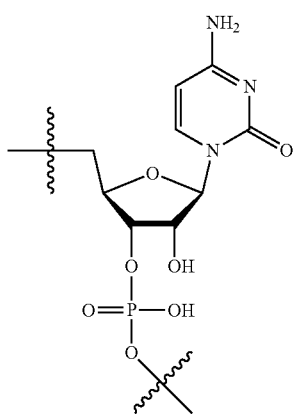
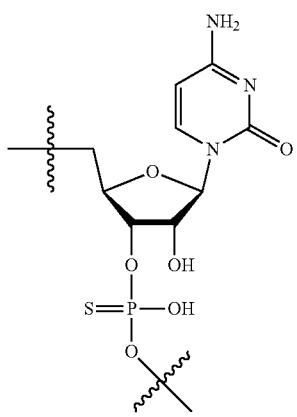
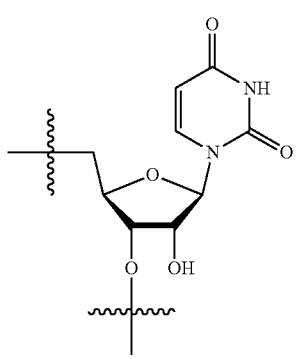
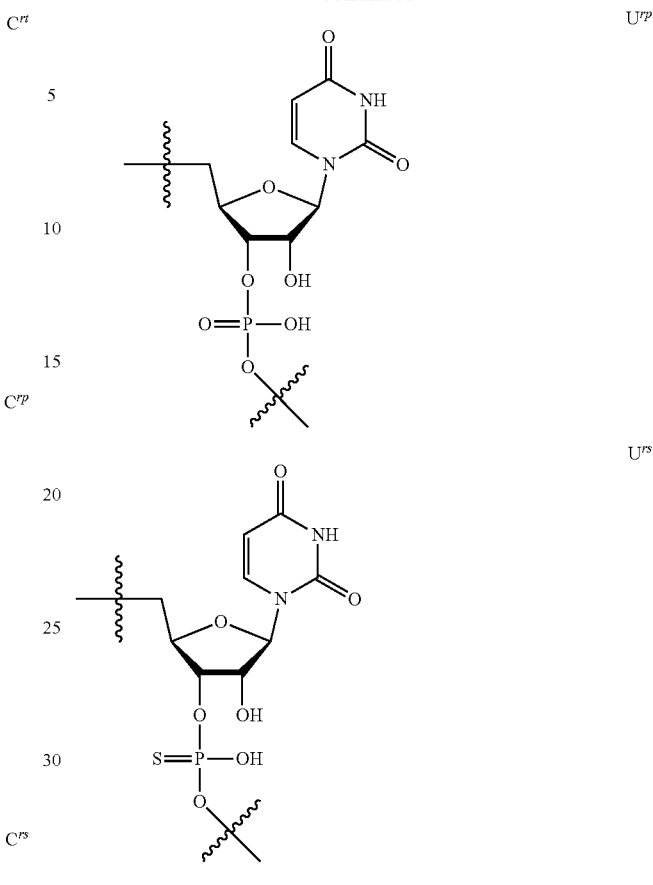

3-3. Target Gene

In the present specification, the "target gene" is not particularly limited as long as it is RNA in cells, tissues, or individuals to which or to whom this gene is introduced (hereinafter, they may be referred to as "recipients"). The target gene may be mRNA that is translated into a protein or may be non-coding RNA that is not translated into a protein. Examples of the non-coding RNA include functional RNA, for example, an untranslated region of mRNA, tRNA, rRNA, mRNA-like non-coding RNA (mRNA-like ncRNA), long non-coding RNA (long ncRNA), small nuclear RNA (snRNA), small nucleolar RNA (snoRNA), and microRNA (miRNA). Specifically, the target gene may be endogenous to the recipients for introduction or may be exogenous and introduced thereto by an approach such as gene transfer. It may also be a gene present on a chromosome or on an extrachromosomal gene. Examples of the exogenous gene include, but are not limited to, those derived from viruses, bacteria, fungi, and protozoans, which can infect the recipients. The function of the gene may be known or unknown.

Examples of such a target gene can include genes whose expression is specifically increased and/or which are specifically mutated in patients having a particular disease. Examples of the disease can include central nervous system disease (e.g., Alzheimer's disease, dementia, and eating disorders), inflammatory disease (e.g., allergy, rheumatism, osteoarthritis, and lupus erythematosus), cardiovascular disease (e.g., hypertension, cardiomegaly, angina pectoris, arteriosclerosis, and hypercholesterolemia), cancer (e.g., non-small cell lung cancer, ovarian cancer, prostatic cancer, gastric cancer, bladder cancer, breast cancer, uterine cervix cancer, colon cancer, rectal cancer, liver cancer, kidney cancer, pancreatic cancer, and malignant melanoma), respiratory disease (e.g., pneumonia, bronchitis, asthma, chronic obstructive pulmonary disease, and lung fibrosis), diabetes mellitus, diabetic retinopathy, diabetic nephropathy, anemia (e.g., anemia associated with chronic disease and iron-refractory iron deficiency anemia), age-related macular degeneration, immunological disease (e.g., Crohn's disease, atopic dermatitis, autoimmune disease, immunodeficiency, and leukemia), liver/gallbladder disease (e.g., non-alcoholic steatohepatitis, liver cirrhosis, hepatitis, liver failure, cholestasis, and calculus), gastrointestinal disease (e.g., ulcer, enteritis, and malabsorption), infection, adiposity, and fibrosis (e.g., lung fibrosis, liver fibrosis, renal fibrosis, and myelofibrosis). Examples of causative genes of these diseases can include, but are not limited to, kinesin spindle protein (KSP), vascular endothelial growth factor (VEGF), transthyretin (TTR), proprotein convertase subtilisin/kexin type 9 (PCSK9), polo-like kinase 1 (PLK-1), ApoB-100, ribonucleotide reductase M2 subunit (RRM2), clusterin, heat shock protein 27 (Hsp27), survivin, eukaryotic initiation factor-4E (eIF-4E), intercellular adhesion molecule 1 (ICAM-1), the alpha subunit of the interleukin 4 receptor (IL-4R-alpha), Factor XI, Factor VII, N-ras, H-ras, K-ras, bcl-2, bcl-xL, Her-1, Her-2, Her-3, Her-4, MDR-1, human β-catenin gene, DDX3 (DEAD (Asp-Glu-Ala-Asp) box polypeptide 3, X-linked), Myeloid Cell Leukemia Sequence 1 (MCL1) gene, PKR (Eif2ak2), Hsp47 (Serpinhl), Hepcidin, active protein c (APC), signal transducer and activator of transcription (STAT3), and Collagen, type I, alpha 1 (Col1A1).

3-4. Double-Stranded Polynucleotide

When the nucleic acid contained in the nucleic acid lipid particle of the present invention is a nucleic acid having an RNA interference effect on a target gene, the nucleic acid is not limited by its structure and chemical modification as long as it has an RNA interference effect. Examples thereof can include siRNA (see e.g., WO2002/044321 and Current Opinion in Chemical Biology 570-579), AtuRNAi consisting of a polynucleotide containing alternately bound RNAs and 2'-OMeRNAs (see e.g., WO2004/015107), a double-stranded polynucleotide in which sense and antisense strands of polynucleotides containing alternately bound DNAs and 2'-OMeRNAs form a double strand by Watson-Crick base pairing between different types of nucleic acids (see e.g., WO2010/001909), which is described below in the paragraph 3-4-1, a nucleic acid consisting of a terminally modified polynucleotide (see e.g., WO2010/052715), which is described below in the paragraph 3-4-2, and a single-stranded polynucleotide in which the 5'-end of an antisense strand polynucleotide and the 3'-end of a sense strand polynucleotide are bound to each other via a linker to form a single strand, which further intramolecularly forms a double-stranded structure by Watson-Crick base pairing (see e.g., WO2012/074038), which is described below in the paragraph 3-4-3.

The structures of these polynucleotides are shown in FIG. 4.

In the present specification, the phrase "having a nucleotide sequence identical to a target gene" refers to having a sequence identical to at least a partial nucleotide sequence of the target gene. It includes a completely identical sequence and also includes a substantially identical sequence as long as the resulting polynucleotide has an RNA interference effect and/or a gene expression inhibitory effect on the target gene. The phrase "having a nucleotide sequence complementary to the target gene" refers to having a sequence complementary to at least a partial nucleotide sequence of the target gene. It includes a completely complementary sequence and also includes a substantially identical sequence as long as the resulting polynucleotide has an RNA interference effect and/or a gene expression inhibitory effect on the target gene. When the target gene is known to have SNPs or the like, a sequence having these variations is also included as an identical nucleotide sequence. In the present specification, a polynucleotide that comprises a nucleotide sequence complementary to a target gene and has an RNA interference effect and/or a gene expression inhibitory effect on the target gene is referred to as a polynucleotide against the target gene.

The nucleotide sequence of the nucleic acid contained in the nucleic acid particle of the present invention is not particularly limited as long as it has an RNA interference effect and/or a gene expression inhibitory effect on the target gene. For example, the nucleotide sequence can be determined by determining the sequences of sense and antisense strands on the basis of a sequence predicted to have RNA interference effect on the target gene using computer software (e.g., GENETYX(R): manufactured by GENETYX CORPORATION), and can also be determined by further confirming the RNA interference effect and/or gene expression inhibitory effect of a polynucleotide prepared on the basis of the selected sequence.

The respective chain lengths of the sense and antisense strands of the double-stranded polynucleotide having an RNA interference effect may be any length from 10 nucleotides to the full length of the open reading frame (ORF) of the target gene as long as the resulting polynucleotide has an RNA interference effect and/or a gene expression inhibitory effect. The respective chain lengths of the sense and antisense strands are preferably any length from 18 nucleotides to the full length of the open reading frame (ORF) of the target gene, more preferably 10 to 100 nucleotides, further preferably 15 to 30 nucleotides.

In the case of using a double-stranded polynucleotide in which sense and antisense strands of polynucleotides containing alternately bound DNAs and 2'-OMeRNAs are bound by Watson-Crick base pairing between different types of nucleic acids (WO2010/001909) as the double-stranded polynucleotide having an RNA interference effect, the chain length of the sense strand is preferably 18 to 21 nucleotides, more preferably 18 or 19 nucleotides. The chain length of the antisense strand is preferably 19 to 21 nucleotides, more preferably 21 nucleotides. This polynucleotide does not have to be a double-stranded structure as a whole and also includes those partially overhanging at the 5'- and/or 3'-ends. The overhanging end has 1 to 5 nucleotides, preferably 1 to 3 nucleotides, more preferably 2 nucleotides. Most preferred examples of the polynucleotide include a polynucleotide having a structure where the 3'-end of the antisense strand polynucleotide overhangs by 2 nucleotides (overhang structure), and having 18 base pairs.

3-4-1. Polynucleotide Containing Alternately Bound DNAs and 2'-OMeRNAs

One example of the nucleic acid contained in the nucleic acid lipid particle of the present invention can include a double-stranded polynucleotide in which sense and antisense strands of polynucleotides containing alternately bound DNAs and 2'-OMeRNAs are bound by Watson-Crick base pairing between different types of nucleic acids.

Specific examples of such a double-stranded polynucleotide include a double-stranded polynucleotide constituted by a sense strand CT-169 described in Example 51 of WO2010/001909: HO-$G^p$-$C^{m1p}$-$A^p$-$C^{m1p}$-$A^p$-$A^{m1p}$-$G^p$-

A$^{m1p}$-A$^p$-U$^{m1p}$-G$^p$-G$^{m1p}$-A$^p$-U$^{m1p}$-C$^p$-A$^{m1p}$-C$^p$-A$^{m1t}$-H (SEQ ID NO: 1 of the Sequence Listing) and
an antisense strand CT-157 described in Example 45 thereof:
HO—P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 2 of the Sequence Listing); and
a double-stranded polynucleotide constituted by
a sense strand CT-103 described in Example 20 of WO2010/001909:
HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1p}$-A$^t$-H (SEQ ID NO: 3 of the Sequence Listing) and
an antisense strand CT-157 described in Example 45 thereof:
HO—P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 2 of the Sequence Listing).

3-4-2. Modified Double-Stranded Polynucleotide

In the case of using a nucleic acid having an RNA interference effect as the nucleic acid contained in the nucleic acid lipid particle, another example thereof can include a nucleic acid modified at the end of its polynucleotide as long as the nucleic acid has the RNA interference effect. Examples thereof can include a double-stranded polynucleotide derived from a double-stranded polynucleotide having an RNA interference effect (e.g., siRNA, AtuRNAi, or a double-stranded polynucleotide in which sense and antisense strands of polynucleotides containing alternately bound DNAs and 2'-OMeRNAs are bound by Watson-Crick base pairing between different types of nucleic acids (see e.g., WO2010/001909)), and 5'-modified with aryl phosphate at the phosphate group of the 5'-end of its antisense strand (see e.g., WO2010/052715).

Specific examples of such a modified double-stranded polynucleotide include a modified double-stranded polynucleotide constituted by
a sense strand CT-169 described in Example 1 of WO2010/052715:
HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1t}$-H (SEQ ID NO: 1 of the Sequence Listing) and
an antisense strand having any one sequence selected from the following (1) to (3):

(1) an antisense strand CT-292 described in Example 17 thereof:
X—P(=O)(OH)-O-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 4 of the Sequence Listing) wherein
X is represented by the following formula:

[Formula 37]

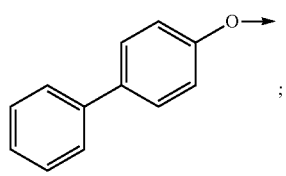
;

(2) an antisense strand CT-315 described in Example 26 thereof:
X—P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 5 of the Sequence Listing) wherein
X is represented by the following formula:

[Formula 38]

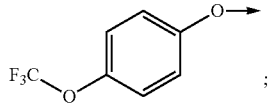
;

(3) an antisense strand CT-387 described in Example 83 thereof:
X—P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 6 of the Sequence Listing) wherein
X is represented by the following formula:

[Formula 39]

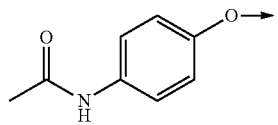

3-4-3. Modified Single-Stranded Polynucleotide

The nucleic acid contained in the nucleic acid lipid particle also includes a polynucleotide that has a sense strand polynucleotide against the target gene and an antisense strand polynucleotide having a nucleotide sequence complementary to the sense strand polynucleotide and has a single-stranded structure where the 5'-end of the antisense strand polynucleotide and the 3'-end of the sense strand polynucleotide are bound to each other through a phosphodiester structure formed via a linker as long as the polynucleotide has an RNA interference effect (see e.g., WO2012/074038).

Specific examples of such a compound can include:
a polynucleotide CT-454 described in Example 12 of WO2012/074038:
HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1p}$-X-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 7 (sense strand region) and SEQ ID NO: 8 (antisense strand region) of the Sequence Listing);
a polynucleotide HS-005 described in Example 28 thereof:
HO-C$^p$-G$^{m1p}$-A$^p$-G$^{m1p}$-A$^p$-C$^{m1p}$-A$^p$-C$^{m1p}$-A$^p$-U$^{m1p}$-G$^p$-G$^{m1p}$-G$^p$-U$^{m1p}$-G$^p$-C$^{m1p}$-T$^p$-A$^{m1p}$-X-P(=O)(OH)—O-U$^{m1p}$-T$^p$-A$^{m1p}$-G$^p$-C$^{m1p}$-A$^p$-C$^{m1p}$-C$^p$-C$^{m1p}$-A$^p$-U$^{m1p}$-G$^p$-U$^{m1p}$-G$^p$-U$^{m1p}$-C$^p$-U$^{m1p}$-C$^p$-G$^{m1p}$-T$^p$-U$^{m1t}$-H (SEQ ID NO: 9 (sense strand region) and SEQ ID NO: 10 (antisense strand region) of the Sequence Listing);
a polynucleotide HS-006 described in Example 29 thereof:
HO—C$^p$-A$^{m1p}$-G$^p$-A$^{m1p}$-C$^p$-A$^{m1p}$-C$^p$-A$^{m1p}$-T$^p$-G$^{m1p}$-G$^p$-G$^{m1p}$-T$^p$-G$^{m1p}$-C$^p$-U$^{m1p}$-A$^p$-U$^{m1p}$-X-P(=O)(OH)—O-U$^{m1p}$-A$^p$-U$^{m1p}$-A$^p$-G$^{m1p}$-C$^p$-A$^{m1p}$-C$^p$-C$^{m1p}$-C$^p$-A$^{m1p}$-T$^p$-G$^{m1p}$-T$^p$-G$^{m1p}$-T$^p$-C$^{m1p}$-T$^p$-G$^{m1p}$-T$^p$-U$^{m1t}$-H (SEQ ID NO: 11 (sense strand region) and SEQ ID NO: 12 (antisense strand region) of the Sequence Listing);
a polynucleotide HS-005s described in Example 30 thereof:
HO-C$^p$-G$^{m1p}$-A$^p$-G$^{m1p}$-A$^p$-C$^{m1p}$-A$^p$-C$^{m1p}$-A$^p$-U$^{m1p}$-G$^p$-G$^{m1p}$-G$^p$-U$^{m1p}$-G$^p$-C$^{m1p}$-T$^p$-A$^{m1p}$-X-P(=O)(OH)—O-U$^{m1p}$-T$^p$-A$^{m1p}$-G$^p$-C$^{m1p}$-A$^p$-C$^{m1p}$-C$^p$-C$^{m1p}$-A$^p$-U$^{m1p}$-G$^p$-U$^{m1p}$-C$^p$-U$^{m1p}$-C$^p$-G$^{m1p}$-T$^{ps}$-U$^{m1t}$-H (SEQ ID NO: 13 (sense strand region) and SEQ ID NO: 14 (antisense strand region) of the Sequence Listing); and a polynucleotide HS-006s described in Example 31 thereof:
HO—C$^p$-A$^{m1p}$-G$^p$-A$^{m1p}$-C$^p$-A$^{m1p}$-C$^p$-A$^{m1p}$-T$^p$-G$^{m1p}$-G$^p$-G$^{m1p}$-T$^p$-G$^{m1p}$-C$^p$-U$^{m1p}$-A$^p$-U$^{m1p}$-X-P(=O)(OH)—O—U$^{m1p}$-A$^p$-U$^{m1p}$-A$^p$-G$^{m1p}$-C$^p$-A$^{m1p}$-C$^p$-C$^{m1p}$-C$^p$-A$^{m1p}$-T$^p$-G$^{m1p}$-T$^p$-G$^{m1p}$-T$^p$-C$^{m1p}$-T$^p$-G$^{m1p}$-T$^{ps}$-U$^{m1t}$-H
(SEQ ID NO: 15 (sense strand region) and SEQ ID NO: 16 (antisense strand region) of the Sequence Listing), wherein X is represented by the following formula:

[Formula 40]

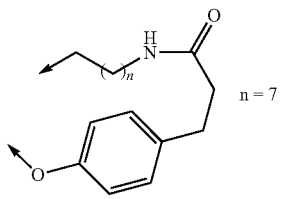

n = 7

The terminal methylene group of X binds to the 3'-end of the sense strand polynucleotide to form a phosphodiester bond, and the oxygen atom bonded to the phenyl group binds to the 5'-end of the antisense strand polynucleotide to form a phosphodiester bond.

3-4-3. Single-Stranded RNA

The nucleic acid contained in the nucleic acid lipid particle can be any single-stranded RNA without particular limitations and also includes mRNA that is translated into a protein. In order to improve translation efficiency, its sequence can also contain a cap structure (e.g., m7GpppG) or an internal ribosome entry site (IRES) at the 5'-end and/or a poly-A tail at the 3'-end. Further, the 3' and/or 5' untranslated region can contain a sequence that contributes to the stabilization of a protein, or a sequence that promotes translation.

The single-stranded RNA can be produced by in vitro transcription reaction from a DNA having a desired nucleotide sequence. Enzymes, buffer solutions, and a nucleoside-5'-triphosphate mixture (adenosine-5'-triphosphate (ATP), guanosine-5'-triphosphate (GTP), cytidine-5'-triphosphate (CTP), and uridine-5'-triphosphate (UTP)) necessary for the in vitro transcription are commercially available (AmpliScribe T7 High Yield Transcription Kit (Epicentre), mMESSAGE mMACHINE T7 Ultra Kit (Life Technologies, Inc.), etc.). The DNA used for producing the single-stranded RNA is a cloned DNA, and, for example, a plasmid DNA or a DNA fragment is used.

In order to improve stability and further obtain an mRNA having reduced immunogenicity, a modified nucleotide may be introduced into the mRNA by using a modified nucleoside-5'-triphosphate together with an unmodified nucleoside-5'-triphosphate in the in vitro transcription reaction (Kormann, M. (2011) Nature Biotechnology 29, 154-157.). Examples of the modified uridine-5'-triphosphate used can include 2-thiouridine-5'-triphosphate, 4-thiouridine-5'-triphosphate, 4'-thiouridine-5'-triphosphate, and pseudouridine-5'-triphosphate. Examples of the modified cytidine-5'-triphosphate used can include 5-methylcytidine-5'-triphosphate and 4-thiocytidine-5'-triphosphate. The modified uridine-5'-triphosphate and the modified cytidine-5'-triphosphate may be used at the same time as the modified nucleoside-5'-triphosphates.

The ratio between the unmodified uridine-5'-triphosphate and the modified uridine-5'-triphosphate is preferably 50 to 95% of the unmodified uridine-5'-triphosphate and 5 to 50% of the modified uridine-5'-triphosphate, more preferably 70 to 95% of the unmodified uridine-5'-triphosphate and 5 to 30% of the modified uridine-5'-triphosphate. The ratio between the unmodified cytidine-5'-triphosphate and the modified cytidine-5'-triphosphate is preferably 50 to 95% of the unmodified cytidine-5'-triphosphate and 5 to 50% of the modified cytidine-5'-triphosphate, more preferably 70 to 95% of the unmodified cytidine-5'-triphosphate and 5 to 30% of the modified cytidine-5'-triphosphate.

The single-stranded RNA containing the modified nucleotide (or modified nucleoside) obtained by the in vitro transcription reaction using the modified nucleoside-5'-triphosphate can be completely hydrolyzed with nuclease (if necessary, which can also be dephosphorylated with phosphatase) and analyzed using, for example, thin-layer chromatography (TLC) or high-performance liquid chromatography (HPLC) to determine the contents of the modified nucleotide and an unmodified nucleotide (or the contents of the modified nucleoside and an unmodified nucleoside).

The ratio between the unmodified uridine and the modified uridine is preferably 50 to 95% of the unmodified uridine and 5 to 50% of the modified uridine, more preferably 70 to 95% of the unmodified uridine and 5 to 30% of the modified uridine. The ratio between the unmodified cytidine and the modified cytidine is preferably 50 to 95% of the unmodified cytidine and 5 to 50% of the modified cytidine, more preferably 70 to 95% of the unmodified cytidine and 5 to 30% of the modified cytidine.

The single-stranded RNA is used for treating a disease or supplying a beneficiary protein. The single-stranded RNA is delivered to an organ responsible for the disease through the nucleic acid lipid particle of the present invention and further transported into the cytoplasm. When the single-stranded RNA encodes a protein, the single-stranded RNA is translated into the protein in the cytoplasm so that this protein brings about the curing of the disease.

A target of the treatment of the disease may be the absence of a protein due to gene mutation or a decreased supply of the protein. Even if the protein is present, the mutation of its gene causes mutation in the protein, and this variant protein may have functions weaker than those of the natural protein in some cases. For such deletion or deficiency of the protein, a single-stranded RNA encoding the protein can be used to bring about the curing of the disease. Examples of the disease that can be cured using the single-stranded RNA can include a disease caused by a genetic defect (genetic disease), and a disease caused by the absence of a protein in the body due to organ failure.

Examples of the disease caused by a genetic defect (genetic disease) (gene name is indicated within the parentheses) can include glycogen storage disease type Ia (glucose-6-phosphatase), glycogen storage disease type Ib (glucose-6-phosphate translocase), glycogen storage disease type III (amylo-1,6-glucosidase), glycogen storage disease type IV (amylo-1,4-1,6 transglucosylase), glycogen storage disease type VI (liver phosphorylase), glycogen storage disease type IX, glycogen storage disease type VIII (liver phosphorylase kinase), a1-antitrypsin deficiency (a1-antitrypsin), congenital hemochromatosis, hepcidin deficiency (hepcidin), hemophilia A and B (coagulation factors VIII and IX, respectively), congenital anticoagulant deficiency (protein C, inactivator of coagulation factors Va and VIIIa), thrombotic thrombocytopenic purpura (ADAMTS13), congenital amegakaryocytic thrombocytopenia, and thrombopoietin deficiency (thrombopoietin). Examples of the disease caused by the absence of a protein in the body due to organ failure can include erythropoietin (EPO) growth hormone (somatotropin or hGH).

3-5. Method for Producing Nucleic Acid Lipid Particle

The method for producing the nucleic acid lipid particle of the present invention is not particularly limited as long as the nucleic acid lipid particle can be produced by the method. The nucleic acid lipid particle can be produced, for example, by a method such as a thin film method, a reverse-phase evaporation method, an ethanol injection method, an ether injection method, a dehydration-rehydration method, a detergent dialysis method, a hydration method, or a freezing-thawing method. More specifically, the nucleic acid lipid particle can be produced by the ethanol injection method described below.

Hydrophobic materials such as the cationic lipid, the amphipathic lipid, and the lipid reducing aggregation during lipid particle formation are dissolved in 50 to 90% ethanol. On the other hand, hydrophilic materials such as the nucleic acid are dissolved in a buffer solution of pH 3 to 6.

The solution of the lipids in ethanol and the aqueous solution of the nucleic acid are mixed at a volume ratio of 1:20 to 1:1 to form a lipid particle and to form a nucleic acid lipid particle through the electrostatic interaction between the negatively charged nucleic acid and the positively charged cationic lipid. As a result, a crude dispersion of the nucleic acid lipid particle is obtained.

In another aspect, the solution of the lipids in ethanol is mixed with a buffer solution free from the nucleic acid to form a lipid particle. Then, the lipid particle may be mixed with the aqueous solution of the nucleic acid to form a nucleic acid lipid particle.

Subsequently, ethanol and free nucleic acids contained in the obtained crude dispersion of the nucleic acid lipid particle are removed by a method such as ultrafiltration or dialysis to obtain a stable nucleic acid lipid particle.

Examples of such a nucleic acid lipid particle can include a nucleic acid lipid particle comprising the constituents at any molar ratio selected from the group consisting of the following (a) to (g):

(a) amphipathic lipid:sterol:cationic lipid:lipid reducing aggregation during lipid particle formation=10:48:40:2, (b) amphipathic lipid:sterol:cationic lipid:lipid reducing aggregation during lipid particle formation=10:38:50:2, (c) amphipathic lipid:sterol:cationic lipid:lipid reducing aggregation during lipid particle formation=10:33:55:2, (d) amphipathic lipid:sterol:cationic lipid:lipid reducing aggregation during lipid particle formation=10:28:60:2, (e) amphipathic lipid:sterol:cationic lipid:lipid reducing aggregation during lipid particle formation=15:33:50:2, (f) amphipathic lipid:sterol:cationic lipid:lipid reducing aggregation during lipid particle formation=10:48.5:40:1.5, and (g) amphipathic lipid:sterol:cationic lipid:lipid reducing aggregation during lipid particle formation=10:47.5:40:2.5.

The ratio (N/P) of the number of molecules of the cationic lipid (N) to the number of phosphorus atoms derived from the nucleic acid (P) in the nucleic acid lipid particle is preferably approximately 2.0 to 15.0, more preferably approximately 2.0 to 12.0, further preferably, 2.0 to 9.0, still further preferably 3.0 to 9.0. The lower limit of the N/P ratio is preferably 2.0, more preferably 2.5, further preferably 3.0, and the upper limit thereof is preferably 15.0, more preferably 12.0, further preferably 9.0.

4. Pharmaceutical Composition Containing Nucleic Acid Lipid Particle

The nucleic acid lipid particle of the present invention can be used in a pharmaceutical product as long as the nucleic acid lipid particle has an RNA interference effect and/or a gene inhibitory effect on a target gene.

The pharmaceutical product is not particularly limited as long as the pharmaceutical product is for the treatment or prevention of a disease derived from the expression of a target gene. Preferred examples thereof include pharmaceutical products for treating or preventing central nervous system disease (e.g., Alzheimer's disease, dementia, and eating disorders), inflammatory disease (e.g., allergy, rheumatism, osteoarthritis, and lupus erythematosus), cardiovascular disease (e.g., hypertension, cardiomegaly, angina pectoris, arteriosclerosis, and hypercholesterolemia), cancer (e.g., non-small cell lung cancer, ovarian cancer, prostatic cancer, gastric cancer, bladder cancer, breast cancer, uterine cervix cancer, colon cancer, rectal cancer, liver cancer, kidney cancer, pancreatic cancer, and malignant melanoma), respiratory disease (e.g., pneumonia, bronchitis, asthma, chronic obstructive pulmonary disease, and lung fibrosis), diabetes mellitus, diabetic retinopathy, diabetic nephropathy, anemia (e.g., anemia associated with chronic disease, iron-refractory iron deficiency anemia, and anemia of cancer), age-related macular degeneration, immunological disease (e.g., Crohn's disease, atopic dermatitis, autoimmune disease, immunodeficiency, and leukemia), liver/gallbladder disease (e.g., non-alcoholic steatohepatitis, liver cirrhosis, hepatitis, liver failure, cholestasis, and calculus), gastrointestinal disease (e.g., ulcer, enteritis, and malabsorption), infection, adiposity, and fibrosis (e.g., lung fibrosis, liver fibrosis, renal fibrosis, and myelofibrosis). The pharmaceutical product is more preferably for the treatment or prevention of cancer (e.g., non-small cell lung cancer, ovarian cancer, prostatic cancer, gastric cancer, bladder cancer, breast cancer, uterine cervix cancer, colon cancer, rectal cancer, liver cancer, kidney cancer, pancreatic cancer, and malignant melanoma), respiratory disease (e.g., pneumonia, bronchitis, asthma, chronic obstructive pulmonary disease, and lung fibrosis), and/or liver/gallbladder disease (e.g., non-alcoholic steatohepatitis, liver cirrhosis, hepatitis, liver failure, cholestasis, and calculus). The pharmaceutical product is further preferably for the treatment or prevention of cancer (colon cancer, rectal cancer, and liver cancer), anemia (e.g., anemia associated with chronic disease, iron-refractory iron deficiency anemia, and anemia of cancer), liver disease (non-alcoholic steatohepatitis, liver cirrhosis, and hepatitis), gallbladder disease (cholestasis), and fibrosis (lung fibrosis, liver fibrosis, and renal fibrosis).

The nucleic acid lipid particle of the present invention can be used in a pharmaceutical product as long as the single-stranded RNA is used for treating a disease or supplying a beneficiary protein. Examples of this case are shown in the paragraph 3-4-3.

The nucleic acid lipid particle of the present invention can be administered either alone or in a mixture with a physiologically acceptable carrier selected according to an administration route and a standard pharmaceutical practice.

In general, standard saline is used as a pharmaceutically acceptable carrier.

Other preferred carriers include, for example, water, buffered water, 0.4% salt solutions, and 0.3% glycine and also include albumins, lipoproteins, and glycoproteins such as globulins in order to enhance stability.

The pharmaceutical carriers are generally added after particle formation. Thus, after the particle formation, the particle can be diluted in a pharmaceutically acceptable carrier such as standard saline.

The particle in a pharmaceutical formulation can have a very wide concentration range. Specifically, the concentration is less than approximately 0.05%, usually approximately 2 to 5%, or from at least approximately 2 to 5% to approximately 10 to 30%, of the weight, and is selected mainly from the volume, viscosity, or the like of a liquid according to a selected specific administration mode. For example, the concentration may be elevated such that a load of the liquid associated with treatment may be decreased. This is particularly desirable for patients with atherosclerosis-related congestive heart failure or severe hypertension. Alternatively, a particle constituted by an irritating lipid can be diluted to a low concentration, which can reduce inflammation at an administration site.

Typically, the concentration of the nucleic acid in the nucleic acid lipid particle is approximately 1 to 20%, more preferably approximately 3 to 10%.

The pharmaceutical composition of the present invention may be sterilized by a usual well-known sterilization technique. An aqueous solution can be packaged for use or can be filtered and freeze-dried under aseptic conditions. The freeze-dried preparation is combined with an aseptic aqueous solution before administration. The composition can contain pharmaceutically acceptable auxiliaries necessary for approaching a physiological state, for example, a pH adjustor and a buffering agent (e.g., sodium acetate, sodium lactate, sodium chloride, potassium chloride, and calcium chloride) and an osmotic regulator.

In addition, the particle suspension may contain a lipid-protecting agent that protects lipids from free radicals and lipid peroxidation damage during storage. A lipophilic free radical quencher such as alpha tocopherol and a water-soluble ion-specific chelating agent such as ferrioxamine are preferred.

Other examples of the use of the nucleic acid lipid particle include, but are not limited to, gels, oils, and emulsions. The nucleic acid lipid particle can also be incorporated into a wide range of local dosage forms. For example, the suspension containing the nucleic acid lipid particle can be formulated and administered as a local cream, paste, ointment, gel, lotion, or the like.

The nucleic acid lipid particle of the present invention also provides a method for transferring a nucleic acid (e.g., plasmid or siRNA) into a cell. The method is carried out in vitro or in vivo by first forming the particle as described above and then contacting the particle with a cell for a time long enough to deliver the nucleic acid into the cell.

The nucleic acid lipid particle of the present invention can be adsorbed to almost every type of cell with which the nucleic acid lipid particle is mixed or contacted. Once the nucleic acid lipid particle is adsorbed thereto, the particle can achieve any of the following events: the particle is endocytosed by the cell moiety; the cell membrane is replaced with the lipid; and the particle is fused with the cell. The delivery or uptake of the nucleic acid moiety of the particle takes place through any one of these routes. Particularly, when the fusion occurs, the particle membrane is incorporated into the cell membrane so that the contents in the particle are combined with the intracellular fluid.

The nucleic acid lipid particle of the present invention is useful for the treatment or prevention of every sign, disease, or symptom involved in or responding to the expression level of a target gene in cells or tissues. The disease to be treated or prevented is not particularly limited as long as it is a disease derived from the expression of a target gene. The disease is preferably cancer, anemia, liver disease, gallbladder disease, fibrosis, or genetic disease. The nucleic acid lipid particle of the present invention can be administered to a mammal (preferably a human) in need thereof.

The present invention provides a method for inhibiting or down-regulating the expression of a target gene in a cell or a tissue. When the target gene is non-coding RNA that is not translated into a protein, the present invention also provides a method for inhibiting or down-regulating the expression of the non-coding RNA and further up-regulating or, in some cases, down-regulating the expression of a gene involved in the non-coding RNA.

EXAMPLES

Hereinafter, the present invention will be described more specifically with reference to Examples, Reference Examples, and Test Examples. However, the present invention is not intended to be limited to them. In the Examples below, procedures of genetic engineering were performed by the methods described in "Molecular Cloning" [Sambrook, J., Fritsch, E. F. and Maniatis, T., published in 1989 by Cold Spring Harbor Laboratory Press] or according to the instructions of the commercially available reagents or kits used, unless otherwise specified.

Reference Example 1

4-Nitrophenyl(6Z,9Z,28Z,31Z)-heptatriaconta-6,9,28,31-tetraen-19-yl Carbonate

To a solution of diisopropylethylamine (0.50 g, 3.8 mmol) and 4-dimethylaminopyridine (0.12 g, 0.95 mmol) in dichloromethane (61 mL), (6Z,9Z,28Z,31Z)-heptatriaconta-6,9,28,31-tetraen-19-ol (0.50 g, 0.95 mmol) described in Examples 1 and 7 of WO2010042877 and 4-nitrophenyl chloroformate (0.38 g, 1.9 mmol) were added, and the mixture was reacted at room temperature for 5 hours. Volatile matter was removed under reduced pressure, and a solid formed by the addition of ethyl acetate was filtered off. The solvent in the obtained solution was distilled off under reduced pressure, and the residue was then subjected to silica gel column chromatography to obtain the compound of interest (0.61 g, 93%).

$^1$H-NMR (500 MHz, CDCl$_3$) δ: 0.89 (6H, t, J=6.8 Hz), 1.21-1.44 (36H, m), 1.59-1.73 (4H, m), 2.00-2.09 (8H, m), 2.77 (4H, t, J=6.8 Hz), 4.77-4.85 (1H, m), 5.28-5.42 (8H, m), 7.38 (2H, d, J=9.3 Hz), 8.28 (2H, d, J=9.3 Hz).

Reference Example 2

2-(Dimethylamino)ethyl(6Z,9Z,28Z,31Z)-heptatriaconta-6,9,28,31-tetraen-19-yl Carbonate To a solution of 4-nitrophenyl(6Z,9Z,28Z,31Z)-heptatriaconta-6,9,28,31-tetraen-19-yl carbonate (0.20 g, 0.29 mmol) obtained in Reference Example 1, 2-dimethylaminoethanol (0.26 g, 2.9 mmol), and diisopropylethylamine (0.15 g, 1.2 mmol) in dichloromethane (10 mL), 4-dimethylaminopyridine (0.14 g, 1.2 mmol) was added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (100 mg, 54%). This compound is a compound described in a table of WO2010/054405.

$^1$H-NMR (500 MHz, CDCl$_3$) δ: 0.89 (6H, t, J=6.8 Hz), 1.20-1.40 (36H, m), 1.45-1.65 (4H, m), 1.96-2.08 (8H, m), 2.28 (6H, s), 2.60 (2H, t, J=5.9 Hz), 2.77 (4H, t, J=6.8 Hz), 4.21 (2H, t, J=5.9 Hz), 4.64-4.71, 1H, m), 5.27-5.42 (8H, m).
MS (ESI+) m/z 644 [M+H]$^+$
HRMS (ESI+) m/z 644.6012 (3.0 mDa).

Example 1

3-(Dimethylamino)propyl(6Z,9Z,28Z,31Z)-heptatriaconta-6,9,28,31-tetraen-19-yl Carbonate (Exemplary Compound 1-467)

To a solution of 4-nitrophenyl(6Z,9Z,28Z,31Z)-heptatriaconta-6,9,28,31-tetraen-19-yl carbonate(0.20 g, 0.29 mmol) obtained in Reference Example 1, 3-dimethylamino-1-propanol (0.30 g, 2.9 mmol), and diisopropylethylamine (0.15 g, 1.2 mmol) in dichloromethane (10 mL), 4-dimethylaminopyridine (0.14 g, 1.2 mmol) was added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (100 mg, 53%).
$^1$H-NMR (500 MHz, CDCl$_3$) δ: 0.89 (6H, t, J=6.8 Hz), 1.20-1.40 (36H, m), 1.45-1.65 (4H, m), 1.84 (2H, tt, J=6.3, 7.3 Hz), 1.95-2.10 (8H, m), 2.22 (6H, s), 2.36 (2H, t, J=7.3 Hz), 2.77 (4H, t, J=6.8 Hz), 4.18 (2H, t, J=6.3 Hz), 4.63-4.73, 1H, m), 5.27-5.43 (8H, m).
MS (ESI+) m/z 658 [M+H]$^+$
HRMS (ESI+) m/z 658.6164 (2.6 mDa).

Reference Example 3

(6Z,9Z,26Z,29Z)-Pentatriaconta-6,9,26,29-tetraen-18-one

To a solution of methyl linoleate (30.0 g, 101 mmol) in xylene (55 mL), a suspension of sodium hydride (5.05 g, 63%, 132 mmol) washed in advance with hexane in xylene (10 mL) was added over 10 minutes, and the mixture was then reacted at 150° C. for 5 hours. The reaction mixture was cooled to room temperature, then treated with water, and subjected to extraction with a hexane-ethyl acetate mixed solution. The obtained organic layer was dried over anhydrous magnesium sulfate, and the solvent was distilled off under reduced pressure to obtain an oil. To this oil, tetrahydrofuran (413 mL) and a 5 N aqueous sodium hydroxide solution (102 mL) were added, and the mixture was reacted at 100° C. for 5.5 hours. The reaction mixture was cooled to room temperature, then treated with water, and subjected to extraction with a hexane-ethyl acetate mixed solution. The obtained organic layer was dried over anhydrous magnesium sulfate. The solvent was distilled off under reduced pressure, and the residue was then subjected to silica gel column chromatography to obtain the compound of interest as a colorless liquid (23.0 g, 91%).
$^1$H-NMR (400 MHz, CDCl$_3$) δ: 0.89 (6H, t, J=6.6 Hz), 1.24-1.40 (28H, m), 1.51-1.60 (4H, m), 2.01-2.09 (8H, m), 2.38 (4H, t, J=7.4 Hz), 2.77 (4H, t, J=6.6 Hz), 5.29-5.43 (8H, m).

Reference Example 4

(6Z,9Z,26Z,29Z)-Pentatriaconta-6,9,26,29-tetraen-18-ol

To a solution of (6Z,9Z,26Z,29Z)-pentatriaconta-6,9,26,29-tetraen-18-one (23.0 g, 46.1 mmol) obtained in Reference Example 3 in methanol (187 mL) and tetrahydrofuran (187 mL), sodium borohydride (1.74 g, 46.1 mmol) was added, and the mixture was then reacted at room temperature for 80 minutes. After treatment with a saturated aqueous solution of ammonium chloride, the reaction mixture was subjected to extraction with a hexane-ethyl acetate mixed solution, and the obtained organic layer was dried over anhydrous magnesium sulfate. The solvent was distilled off under reduced pressure, and the residue was then subjected to silica gel column chromatography to obtain the compound of interest as a colorless liquid (22.2 g, 96%).
$^1$H-NMR (400 MHz, CDCl$_3$) δ: 0.89 (6H, t, J=7.0 Hz), 1.24-1.48 (36H, m), 2.01-2.09 (8H, m), 2.77 (4H, t, J=6.3 Hz), 3.55-3.62 (1H, m), 5.29-5.43 (8H, m).

Reference Example 5

4-Nitrophenyl(6Z,9Z,26Z,29Z)-pentatriaconta-6,9,26,29-tetraen-18-yl Carbonate

To a solution of diisopropylethylamine (0.20 g, 1.5 mmol) and 4-dimethylaminopyridine (0.05 g, 0.38 mmol) in dichloromethane (25 mL), (6Z,9Z,26Z,29Z)-pentatriaconta-6,9,26,29-tetraen-18-ol (0.19 g, 0.38 mmol) obtained in Reference Example 4 and 4-nitrophenyl chloroformate (0.15 g, 0.77 mmol) were added, and the mixture was reacted overnight at room temperature. Volatile matter was removed under reduced pressure, and a solid formed by the addition of hexane was filtered off. The solvent in the obtained solution was distilled off under reduced pressure, and the residue was then subjected to silica gel column chromatography to obtain the compound of interest (0.12 g, 47%).

Example 2

3-(Dimethylamino)propyl(6Z,9Z,26Z,29Z)-pentatriaconta-6,9,26,29-tetraen-18-yl Carbonate (Exemplary Compound 1-118)

To a solution of 4-nitrophenyl(6Z,9Z,26Z,29Z)-pentatriaconta-6,9,26,29-tetraen-18-yl carbonate (0.03 g, 0.05 mmol) obtained in Reference Example 5, 3-dimethylamino-1-propanol (0.05 g, 0.5 mmol), and diisopropylethylamine (0.03 g, 0.2 mmol) in dichloromethane (6 mL), 4-dimethylaminopyridine (0.02 g, 0.2 mmol) was added, and the mixture was reacted at room temperature for 4 days. 3-Dimethylamino-1-propanol (0.1 g, 1 mmol) was further added thereto, and the mixture was reacted for additional 2 days. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (10 mg, 31%).
$^1$H-NMR (400 MHz, CDCl$_3$) δ: 0.89 (6H, t, J=6.6 Hz), 1.22-1.42 (34H, m), 1.48-1.65 (4H, m), 1.85 (2H, tt, J=6.6, 7.4 Hz), 1.98-2.10 (8H, m), 2.22 (6H, s), 2.36 (2H, t, J=7.4 Hz), 2.77 (4H, t, J=6.6 Hz), 4.18 (2H, t, 6.6 Hz), 4.64-4.73 (1H, m), 5.37-5.43 (8H, m).
MS (ESI+) m/z 630 [M+H]$^+$
HRMS (ESI+) m/z 630.5839 (1.4 mDa).

Example 3

4-(Dimethylamino)butyl(6Z,9Z,26Z,29Z)-pentatriaconta-6,9,26,29-tetraen-18-yl Carbonate (Exemplary Compound 1-129)

To a solution of 4-nitrophenyl(6Z,9Z,26Z,29Z)-pentatriaconta-6,9,26,29-tetraen-18-yl carbonate (0.12 g, 0.18 mmol) obtained in Reference Example 5, 4-dimethylamino-1-butanol (0.22 g, 1.8 mmol), and diisopropylethylamine (0.10 g, 0.72 mmol) in dichloromethane (10 mL), 4-dimethylaminopyridine (0.09 g, 0.72 mmol) was added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (30 mg, 26%).

$^1$H-NMR (400 MHz, CDCl$_3$) δ: 0.89 (6H, t, J=6.6 Hz), 1.21-1.42 (34H, m), 1.47-1.64 (6H, m), 1.71 (2H, tt, J=6.6, 7.4 Hz), 1.99-2.09 (8H, m), 2.21 (6H, s), 2.27 (2H, t, J=7.4 Hz), 2.77 (4H, t, J=6.6 Hz), 4.14 (2H, t, J=6.6 Hz), 4.63-4.72 (1H, m), 5.28-5.43 (8H, m).

MS (ESI+) m/z 644 [M+H]$^+$
HRMS (ESI+) m/z 644.6008 (2.6 mDa).

Reference Example 6

(9Z,26Z)-Pentatriaconta-9,26-dien-18-one

To a solution of methyl oleate (10.0 g, 33.4 mmol) in xylene (18 mL), a suspension of sodium hydride (1.65 g, 63%, 43.4 mmol) washed in advance with hexane in xylene (3 mL) was added over 5 minutes, and the mixture was then reacted at 150° C. for 5 hours. The reaction mixture was cooled to room temperature, then treated with water, and subjected to extraction with a hexane-ethyl acetate mixed solution. The obtained organic layer was dried over anhydrous magnesium sulfate, and the solvent was distilled off under reduced pressure to obtain an oil. To this oil, tetrahydrofuran (135 mL) and a 5 N aqueous sodium hydroxide solution (33 mL) were added, and the mixture was reacted at 100° C. for 5.5 hours. The reaction mixture was cooled to room temperature, then treated with water, and subjected to extraction with a hexane-ethyl acetate mixed solution. The obtained organic layer was dried over anhydrous magnesium sulfate, and the solvent was distilled off under reduced pressure, followed by the formation of a solid with an acetone-hexane solvent. After removal of the solid by filtration, the solvent was distilled off from the resulting solution under reduced pressure, and the residue was then subjected to silica gel column chromatography to obtain the compound of interest as a colorless liquid (7.50 g, 89%).

$^1$H-NMR (500 MHz, CDCl$_3$) δ: 0.89 (6H, t, J=6.8 Hz), 1.21-1.36 (40H, m), 1.52-1.60 (4H, m), 1.97-2.04 (8H, m), 2.38 (4H, t, J=7.6 Hz), 5.30-5.39 (4H, m).

Reference Example 7

(9Z,26Z)-Pentatriaconta-9,26-dien-18-ol

To a solution of (9Z,26Z)-pentatriaconta-9,26-dien-18-one (5.0 g, 9.9 mmol) obtained in Reference Example 6 in methanol (40 mL) and tetrahydrofuran (40 mL), sodium borohydride (0.38 g, 9.9 mmol) was added, and the mixture was then reacted at room temperature for 80 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (4.5 g, 90%).

$^1$H-NMR (500 MHz, CDCl$_3$) δ: 0.89 (6H, t, J=6.6 Hz), 1.21-1.37 (48H, m), 1.37-1.49 (4H, m), 1.97-2.06 (8H, m), 3.55-3.62 (1H, m), 5.31-5.40 (4H, m).

Example 4

3-Dimethylaminopropyl(9Z,26Z)-pentatriaconta-9,26-dien-18-yl Carbonate (Exemplary Compound 1-50)

To a solution of (9Z,26Z)-pentatriaconta-9,26-dien-18-ol (0.25 g, 0.50 mmol) obtained in Reference Example 7 and pyridine (0.25 g, 3.1 mmol) in toluene (5.0 mL), a solution of triphosgene (0.10 g, 0.34 mmol) in toluene (0.74 mL) was added over 2 minutes. After stirring at room temperature for 100 minutes, 3-dimethylamino-1-propanol (0.54 g, 5.2 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (296 mg, 94%).

$^1$H-NMR (500 MHz, CDCl$_3$) δ: 0.86-0.91 (6H, m), 1.22-1.36 (44H, m), 1.50-1.59 (4H, m), 1.84 (2H, tt, J=6.8, 7.3 Hz), 1.97-2.04 (8H, m), 2.22 (6H, s), 2.36 (2H, t, J=7.3 Hz), 4.18 (2H, t, J=6.8 Hz), 4.65-4.72 (1H, m), 5.33-5.37 (4H, m).

MS (ESI+) m/z 634 [M+H]$^+$
HRMS (ESI+) m/z 634.6169 (3.1 mDa).

Reference Example 8

(3Z,6Z,9Z,26Z,29Z,32Z)-Pentatriaconta-3,6,9,26,29,32-hexaen-18-one

To a solution of methyl α-linolenate (10.0 g, 33.4 mmol) in xylene (18 mL), a suspension of sodium hydride (1.65 g, 63%, 43.4 mmol) washed in advance with hexane in xylene (3 mL) was added over 5 minutes, and the mixture was then reacted at 150° C. for 5 hours. The reaction mixture was cooled to room temperature, then treated with water, and subjected to extraction with a hexane-ethyl acetate mixed solution. The obtained organic layer was dried over anhydrous magnesium sulfate, and the solvent was distilled off under reduced pressure to obtain an oil. To this oil, tetrahydrofuran (135 mL) and a 5 N aqueous sodium hydroxide solution (33 mL) were added, and the mixture was reacted at 100° C. for 5.5 hours. The reaction mixture was cooled to room temperature, then treated with water, and subjected to extraction with a hexane-ethyl acetate mixed solution. The obtained organic layer was dried over anhydrous magnesium sulfate, and the solvent was distilled off under reduced pressure, followed by the formation of a solid with an acetone-hexane solvent. After removal of the solid by filtration, the solvent was distilled off from the resulting solution under reduced pressure, and the residue was then subjected to silica gel column chromatography to obtain the compound of interest as a colorless liquid (6.10 g, 74%).

¹H-NMR (500 MHz, CDCl₃) δ: 0.98 (6H, t, J=7.6 Hz), 1.22-1.40 (16H, m), 1.52-1.60 (4H, m), 2.00-2.19 (8H, m), 2.39 (4H, t, J=7.6 Hz), 2.74-2.83 (8H, m), 5.28-5.43 (12H, m).

Reference Example 9

(3Z,6Z,9Z,26Z,29Z,32Z)-Pentatriaconta-3,6,9,26,29, 32-hexaen-18-ol

To a solution of (3Z,6Z,9Z,26Z,29Z,32Z)-pentatriaconta-3,6,9,26,29,32-hexaen-18-one (5.0 g, 10.1 mmol) obtained in Reference Example 8 in methanol (41 mL) and tetrahydrofuran (41 mL), sodium borohydride (0.38 g, 10 mmol) was added, and the mixture was then reacted at room temperature for 80 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (4.0 g, 79%).

¹H-NMR (500 MHz, CDCl₃) δ: 0.98 (6H, t, J=7.6 Hz), 1.24-1.48 (24H, m), 2.00-2.20 (8H, m), 2.75-2.84 (8H, m), 3.55-3.61 (1H, m), 5.29-5.43 (12H, m).

Example 5

3-Dimethylaminopropyl(3Z,6Z,9Z,26Z,29Z,32Z)-pentatriaconta-3,6,9,26,29,32-hexaen-18-yl Carbonate (Exemplary Compound 1-176)

To a solution of (3Z,6Z,9Z,26Z,29Z,32Z)-pentatriaconta-3,6,9,26,29,32-hexaen-18-ol (0.25 g, 0.50 mmol) obtained in Reference Example 9 and pyridine (0.25 g, 3.1 mmol) in toluene (5.0 mL), a solution of triphosgene (0.10 g, 0.34 mmol) in toluene (0.75 mL) was added over 2 minutes. After stirring at room temperature for 100 minutes, 3-dimethylamino-1-propanol (0.55 g, 5.3 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (274 mg, 87%, isomeric mixture).

¹H-NMR (500 MHz, CDCl₃) δ: 0.98 (6H, t, J=7.6 Hz), 1.24-1.39 (20H, m), 1.49-1.62 (4H, m), 1.85 (2H, tt, J=6.6, 7.6 Hz), 2.00-2.19 (8H, m), 2.22, (6H, s), 2.36 (2H, t, J=7.6 Hz), 2.74-2.84 (8H, m), 4.17 (2H, t, J=6.6 Hz), 4.65-4.71 (1H, m), 5.28-5.44 (12H, m).

MS (ESI+) m/z 626 [M+H]⁺

HRMS (ESI+) m/z 626.5512 (−0.5 mDa).

Reference Example 10

(6Z,9Z,12Z,23Z,26Z,29Z)-Pentatriaconta-6,9,12,23, 26,29-hexaen-18-one

To a solution of methyl γ-linolenate (5.00 g, 17.1 mmol) in xylene (9 mL), a suspension of sodium hydride (0.85 g, 63%, 22.2 mmol) washed in advance with hexane in xylene (1.5 mL) was added over 5 minutes, and the mixture was then reacted at 150° C. for 5 hours. The reaction mixture was cooled to room temperature, then treated with water, and subjected to extraction with a hexane-ethyl acetate mixed solution. The obtained organic layer was dried over anhydrous magnesium sulfate, and the solvent was distilled off under reduced pressure to obtain an oil. To this oil, tetrahydrofuran (69 mL) and a 5 N aqueous sodium hydroxide solution (17 mL) were added, and the mixture was reacted at 100° C. for 5.5 hours. The reaction mixture was cooled to room temperature, then treated with water, and subjected to extraction with a hexane-ethyl acetate mixed solution. The obtained organic layer was dried over anhydrous magnesium sulfate, and the solvent was distilled off under reduced pressure, followed by the formation of a solid with an acetone-hexane solvent. After removal of the solid by filtration, the solvent was distilled off from the resulting solution under reduced pressure, and the residue was then subjected to silica gel column chromatography to obtain the compound of interest as a colorless liquid (3.80 g, 90%).

¹H-NMR (500 MHz, CDCl₃) δ: 0.86-0.91 (6H, m), 1.23-1.42 (16H, m), 1.55-1.63 (4H, m), 1.98-2.20 (8H, m), 2.39 (4H, t, J=7.6 Hz), 2.78-2.83 (8H, m), 5.25-5.44 (12H, m).

Reference Example 11

(6Z,9Z,12Z,23Z,26Z,29Z)-Pentatriaconta-6,9,12,23, 26,29-hexaen-18-ol

To a solution of (6Z,9Z,12Z,23Z,26Z,29Z)-pentatriaconta-6,9,12,23,26,29-hexaen-18-one (3.0 g, 6.1 mmol) obtained in Reference Example 10 in methanol (25 mL) and tetrahydrofuran (25 mL), sodium borohydride (0.23 g, 6.1 mmol) was added, and the mixture was then reacted at room temperature for 80 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (2.1 g, 70%).

¹H-NMR (500 MHz, CDCl₃) δ: 0.86-0.91 (6H, m), 1.24-1.50 (24H, m), 1.99-2.21 (8H, m), 2.78-2.84 (8H, m), 3.55-3.62 (1H, m), 5.28-5.44 (12H, m).

Example 6

3-Dimethylaminopropyl(6Z,9Z,12Z,23Z,26Z,29Z)-pentatriaconta-6,9,12,23,26,29-hexaen-18-yl Carbonate (Exemplary Compound 1-152)

To a solution of (6Z,9Z,12Z,23Z,26Z,29Z)-pentatriaconta-6,9,12,23,26,29-hexaen-18-ol (0.25 g, 0.50 mmol) obtained in Reference Example 11 and pyridine (0.25 g, 3.1 mmol) in toluene (5.0 mL), a solution of triphosgene (0.10 g, 0.34 mmol) in toluene (0.75 mL) was added over 2 minutes. After stirring at room temperature for 100 minutes, 3-dimethylamino-1-propanol (0.55 g, 5.3 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (240 mg, 76%).

$^1$H-NMR (500 MHz, CDCl$_3$) δ: 0.86-0.91 (6H, m), 1.22-1.42 (20H, m), 1.51-1.63 (4H, m), 1.85 (2H, tt, J=6.6, 7.3 Hz), 1.99-2.19 (8H, m), 2.22 (6H, s), 2.36 (2H, t, J=7.3 Hz), 2.78-2.83 (8H, m), 4.17 (2H, t, J=6.6 Hz), 4.65-4.72 (1H, m), 5.30-5.45 (12H, m).

MS (ESI+) m/z 626 [M+H]$^+$

HRMS (ESI+) m/z 626.5515 (0.3 mDa).

Reference Example 12

Dimethyl di-(9Z,12Z)-octadeca-9,12-dien-1-ylpropanedioate

To a solution of dimethyl malonate (13.5 g, 102 mmol) in toluene (500 mL), a suspension of sodium hydride (5.17 g, 63%, 136 mmol) washed in advance with hexane in toluene (6 mL) was added over 5 minutes. After stirring at 80° C. for 30 minutes, (9Z,12Z)-octadeca-9,12-dien-1-yl methanesulfonate (compound described in Example 1 of WO2009/132131, 23.4 g, 67.9 mmol) was added thereto, and the mixture was stirred at 100° C. for 4 hours and stirred at 120° C. for 2 hours. After treatment with a 1 N aqueous hydrochloric acid solution, the reaction mixture was subjected to extraction, and the obtained organic layer was dried over anhydrous magnesium sulfate. The solvent was distilled off under reduced pressure, and the residue was then subjected to silica gel column chromatography to obtain the compound of interest as a colorless liquid (9.71 g).

$^1$H-NMR (400 MHz, CDCl$_3$) δ: 0.90 (6H, t, J=7.0 Hz), 1.07-1.16 (4H, m), 1.21-1.40 (32H, m), 1.82-1.89 (4H, m), 2.01-2.08 (8H, m), 2.77 (4H, t, J=6.6 Hz), 3.71 (6H, s), 5.29-5.43 (8H, m).

A by-product dimethyl (9Z,12Z)-octadeca-9,12-dien-1-ylpropanedioate was also obtained as a colorless liquid (8.50 g).

$^1$H-NMR (400 MHz, CDCl$_3$) δ: 0.85 (3H, t, J=7.0 Hz), 1.21-1.37 (18H, m), 1.81-1.90 (2H, m), 1.96-2.05 (4H, m), 2.74 (2H, t, J=6.6 Hz), 3.32 (1H, t, J=7.4 Hz), 3.70 (6H, s), 5.25-5.39 (4H, m).

Reference Example 13

Methyl (11Z,14Z)-2-[(9Z,12Z)-octadeca-9,12-dien-1-yl]icosa-11-dienoate

To a solution of dimethyl di-(9Z,12Z)-octadeca-9,12-dien-1-ylpropanedioate (5.00 g, 7.95 mmol) obtained in Reference Example 12 and water (2.15 g, 119 mmol) in dimethyl sulfoxide (39.5 mL), lithium chloride (1.01 g, 23.9 mmol) was added. After stirring at 150° C. for 5 hours, water (2.15 g, 119 mmol) and lithium chloride (1.01 g, 23.9 mmol) were added. The mixture was reacted at 160° C. for 5 hours and cooled to room temperature. After water treatment to terminate the reaction, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (3.00 g, 66%).

$^1$H-NMR (400 MHz, CDCl$_3$) δ: 0.89 (6H, t, J=7.0 Hz), 1.20-1.47 (38H, m), 1.55-1.64 (2H, m), 2.01-2.09 (8H, m), 2.28-2.37 (1H, m), 2.77 (4H, t, J=6.6 Hz), 3.67 (3H, s), 5.29-5.46 (8H, m).

Reference Example 14

(11Z,14Z)-2-[(9Z,12Z)-Octadeca-9,12-dien-1-yl]icosa-11,14-dien-1-ol

To a solution of methyl (11Z,14Z)-2-[(9Z,12Z)-octadeca-9,12-dien-1-yl]icosa-11-dienoate (3.00 g, 5.25 mmol) obtained in Reference Example 13 in tetrahydrofuran (40 mL), lithium aluminum hydride (0.400 g, 10.5 mmol) was added, and the mixture was stirred at room temperature for 1 hour. The reaction mixture was treated with water (0.4 mL), a 15% aqueous sodium hydroxide solution (0.4 mL), and water (1.2 mL) and subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (1.00 g, 35%).

$^1$H-NMR (400 MHz, CDCl$_3$) δ: 0.89 (6H, t, J=7.0 Hz), 1.24-1.44 (38H, m), 1.97-2.09 (9H, m), 2.78 (4H, t, J=6.6 Hz), 4.15 (2H, t, J=6.3 Hz), 5.29-5.43 (8H, m).

Example 7

3-(Dimethylamino)propyl(11Z,14Z)-2-[(9Z,12Z)-octadeca-9,12-dien-1-yl]icosa-11,14-dien-1-yl Carbonate (Exemplary Compound 1-477)

A solution of (11Z,14Z)-2-[(9Z,12Z)-octadeca-9,12-dien-1-yl]icosa-11,14-dien-1-ol (0.15 g, 0.28 mmol) obtained in Reference Example 14 and pyridine (0.14 g, 1.8 mmol) in toluene (0.6 mL) was cooled to 0° C. in an ice bath, and a solution of triphosgene (0.06 g, 0.19 mmol) in toluene (0.24 mL) was added thereto over 2 minutes. After stirring at 0° C. for 2 hours, the reaction mixture was heated to 10° C., stirred for 30 minutes, and cooled to 0° C. again. 3-Dimethylamino 1-propanol (0.30 g, 2.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (130 mg, 70%).

$^1$H-NMR (400 MHz, CDCl$_3$) δ: 0.85-0.92 (6H, m), 1.21-1.40 (40H, m), 1.62-1.69 (1H, m), 1.85 (2H, tt, J=6.6, 7.4 Hz), 2.01-2.09 (8H, m), 2.22 (6H, s), 2.36 (2H, t, J=7.4 Hz), 2.78 (4H, t, J=6.6 Hz), 4.03 (2H, d, J=5.9 Hz), 4.18 (2H, t, J=6.6 Hz), 5.29-5.43 (8H, m).

MS (ESI+) m/z 672 [M+H]$^+$

HRMS (ESI+) m/z 672.6309 (1.4 mDa).

Reference Example 15

(9Z,12Z)—N-Methoxy-N-methyloctadeca-9,12-dienamide

To a solution of linoleic acid (10.0 g, 35.7 mmol) and N,O-dimethylhydroxylamine hydrochloride (6.56 g, 71.3 mmol) in dichloromethane (250 mL), 1-hydroxybenzimidazole hydrate (10.9 g, 71.3 mmol), triethylamine (7.22 g, 71.3 mmol), and 1-ethyl-3-(3'-dimethylaminopropyl)carbodiimide hydrochloride (13.7 g, 71.3 mmol) were added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (11.4 g, 99%).

$^1$H-NMR (400 MHz, CDCl$_3$) δ: 0.89 (3H, t, J=7.0 Hz), 1.24-1.40 (14H, m), 1.63 (2H, quint, J=7.4 Hz), 2.00-2.09 (4H, m), 2.41 (2H, t, J=7.4 Hz), 2.77 (2H, t, J=6.6 Hz), 3.18 (3H, s), 3.68 (3H, s), 5.29-5.43 (4H, m).

Reference Example 16

(19Z,22Z)-Octacosa-19,22-dien-11-one

A solution of (9Z,12Z)—N-methoxy-N-methyloctadeca-9,12-dienamide (11.4 g, 35.2 mmol) obtained in Reference Example 15 in tetrahydrofuran (157 mL) was cooled to 15° C. in a water bath. A solution of 1 N n-decyl magnesium bromide in tetrahydrofuran (52.9 mL, 52.9 mmol) was added dropwise thereto over 20 minutes, and the mixture was then reacted overnight at room temperature. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (14.3 g, 99%).

$^1$H-NMR (400 MHz, CDCl$_3$) δ: 0.89 (3H, t, J=7.0 Hz), 0.90 (3H, t, J=7.0 Hz), 1.20-1.40 (28H, m), 1.50-1.60 (4H, m), 2.00-2.09 (4H, m), 2.38 (4H, t, J=7.4 Hz), 2.77 (2H, t, J=6.6 Hz), 5.28-5.42 (4H, m).

Reference Example 17

(19Z,22Z)-Octacosa-19,22-dien-11-ol

To a solution of (19Z,22Z)-octacosa-19,22-dien-11-one (14.3 g, 35.2 mmol) obtained in Reference Example 16 in methanol (106 mL) and tetrahydrofuran (106 mL), sodium borohydride (1.33 g, 35.2 mmol) was added, and the mixture was then reacted at room temperature for 70 minutes. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (13.5 g, 95%).

$^1$H-NMR (400 MHz, CDCl$_3$) δ: 0.89 (3H, t, J=7.0 Hz), 0.90 (3H, t, J=7.0 Hz), 1.23-1.47 (40H, m), 2.01-2.09 (4H, m), 2.77 (2H, t, J=6.6 Hz), 3.54-3.62 (1H, m), 5.29-5.42 (4H, m).

Example 8

3-Dimethylaminopropyl(9Z,12Z)-octacosa-19,22-dien-11-yl Carbonate (Exemplary Compound 1-72)

A solution of (19Z,22Z)-octacosa-19,22-dien-11-ol (0.15 g, 0.37 mmol) obtained in Reference Example 17 and pyridine (0.18 g, 2.3 mmol) in toluene (0.8 mL) was cooled to 0° C. in an ice bath, and a solution of triphosgene (0.07 g, 0.25 mmol) in toluene (0.31 mL) was added thereto over 2 minutes. After stirring at 0° C. for 1 hour, the reaction mixture was heated to 10° C., stirred for 20 minutes, and cooled to 0° C. again. 3-Dimethylamino 1-propanol (0.40 g, 3.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (100 mg, 51%).

$^1$H-NMR (500 MHz, CDCl$_3$) δ: 0.85-0.92 (6H, m), 1.22-1.39 (32H, m), 1.49-1.62 (4H, m), 1.85 (2H, tt, J=6.6, 7.6 Hz), 2.01-2.08 (4H, m), 2.22 (6H, s), 2.36 (2H, t, J=7.6 Hz), 2.77 (2H, t, J=6.6 Hz), 4.18 (2H, t, J=6.6 Hz), 4.65-4.72 (1H, m), 5.29-5.42 (4H, m).

MS (ESI+) m/z 536 [M+H]$^+$

HRMS (ESI+) m/z 536.5038 (−0.5 mDa).

Example 9

(1-Methylpiperidin-3-yl)methyl(9Z,12Z)-octacosa-19,22-dien-11-yl Carbonate (Exemplary Compound 2-72)

A solution of (19Z,22Z)-octacosa-19,22-dien-11-ol (0.26 g, 0.64 mmol) obtained in Reference Example 17 and pyridine (0.32 g, 4.0 mmol) in toluene (7.4 mL) was cooled to 0° C. in an ice bath, and a solution of triphosgene (0.13 g, 0.44 mmol) in toluene (0.9 mL) was added thereto over 2 minutes. After stirring at 0° C. for 20 minutes, the reaction mixture was heated to room temperature, stirred for 1 hour, and cooled to 0° C. again. (1-Methyl-3-piperidyl)methanol (0.87 g, 6.7 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (360 mg, 55%).

$^1$H-NMR (500 MHz, CDCl$_3$) δ: 0.85-0.91 (6H, m), 1.21-1.39 (32H, m), 1.49-1.76 (9H, m), 1.86-1.92 (1H, m), 1.96-2.07 (5H, m), 2.26 (3H, s), 2.74 (1H, d, J=10.5 Hz), 2.77 (2H, t, J=6.8 Hz), 2.85 (1H, d, J=10.5 Hz), 3.94 (1H, dt, J=3.2, 7.3 Hz), 4.06 (1H, ddd, J=3.2, 5.9, 10.7 Hz), 4.65-4.71 (1H, m), 5.29-5.42 (4H, m).

MS (ESI+) m/z 562 [M+H]$^+$

HRMS (ESI+) m/z 562.5196 (−0.3 mDa).

Example 10

1-Methylpiperidin-4-yl(9Z,12Z)-octacosa-19,22-dien-11-yl Carbonate (Exemplary Compound 2-66)

A solution of (19Z,22Z)-octacosa-19,22-dien-11-ol (0.300 g, 0.738 mmol) obtained in Reference Example 17 and pyridine (0.368 g, 4.65 mmol) in toluene (7.4 mL) was cooled to 0° C. in an ice bath, and a solution of triphosgene (0.151 g, 0.509 mmol) in toluene (1.1 mL) was added thereto over 2 minutes. After stirring at 0° C. for 20 minutes, the reaction mixture was heated to room temperature, stirred for 1 hour, and cooled to 0° C. again. 4-Hydroxy-1-methylpiperidine (0.892 g, 7.75 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (249 mg, 62%).

$^1$H-NMR (400 MHz, CDCl$_3$) δ: 0.85-0.91 (6H, m), 1.20-1.40 (32H, m), 1.49-1.62 (4H, m), 1.73-1.84 (2H, m), 1.92-2.01 (2H, m), 2.01-2.08 (4H, m), 2.16-2.25 (2H, m), 2.28 (3H, s), 2.65-2.73 (2H, m), 2.77 (2H, t, J=6.6 Hz), 4.57-4.66 (1H, m), 4.64-4.73 (1H, m), 5.28-5.43 (4H, m).

MS (ESI+) m/z 548 [M+H]$^+$

HRMS (ESI+) m/z 548.5042 (−0.1 mDa).

Example 11

(1-Methylpyrrolidin-3-yl)methyl(9Z,12Z)-octacosa-19,22-dien-11-yl Carbonate (Exemplary Compound 2-71)

A solution of (19Z,22Z)-octacosa-19,22-dien-11-ol (0.300 g, 0.738 mmol) obtained in Reference Example 17 and pyridine (0.368 g, 4.65 mmol) in toluene (7.4 mL) was cooled to 0° C. in an ice bath, and a solution of triphosgene (0.151 g, 0.509 mmol) in toluene (1.1 mL) was added thereto over 2 minutes. After stirring at 0° C. for 20 minutes, the reaction mixture was heated to room temperature, stirred for 1 hour, and cooled to 0° C. again. (1-Methylpyrrolidin-3-yl)methanol (0.892 g, 7.75 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (234 mg, 58%).

$^1$H-NMR (400 MHz, CDCl$_3$) δ: 0.85-0.91 (6H, m), 1.20-1.40 (32H, m), 1.45-1.64 (5H, m), 1.95-2.07 (5H, m), 2.30 (1H, dd, J=5.5, 9.4 Hz), 2.34 (3H, s), 2.51 (2H, t, J=7.0 Hz), 2.23-2.62 (1H, m), 2.65 (1H, dd, J=7.8, 9.0 Hz), 2.77 (2H, t, J=6.3 Hz), 4.03 (1H, ddd, J=2.0, 7.8, 9.8 Hz), 4.07 (1H, ddd, J=2.0, 7.0, 10.6 Hz), 4.68 (1H, tt, J=5.5, 7.0 Hz), 5.29-5.43 (4H, m).

MS (ESI+) m/z 548 [M+H]$^+$

HRMS (ESI+) m/z 548.5050 (0.7 mDa).

Example 12

1-Methylpyrrolidin-3-yl(9Z,12Z)-octacosa-19,22-dien-11-yl Carbonate (Exemplary Compound 2-64)

A solution of (19Z,22Z)-octacosa-19,22-dien-11-ol (0.150 g, 0.369 mmol) obtained in Reference Example 17 and pyridine (0.184 g, 2.32 mmol) in toluene (3.7 mL) was cooled to 0° C. in an ice bath, and a solution of triphosgene (0.0755 g, 0.254 mmol) in toluene (0.55 mL) was added thereto over 2 minutes. After stirring at 0° C. for 20 minutes, the reaction mixture was heated to room temperature, stirred for 1 hour, and cooled to 0° C. again. 1-Methyl-3-pyrrolidinol (0.392 g, 3.87 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (99.9 mg, 50%).

$^1$H-NMR (400 MHz, CDCl$_3$) δ: 0.88 (3H, t, J=7.0 Hz), 0.89 (3H, t, J=7.0 Hz), 1.22-1.40 (32H, m), 1.47-1.60 (4H, m), 1.92 (1H, dddd, J=2.7, 6.3, 7.4, 13.7 Hz), 2.01-2.09 (4H, m), 2.28 (1H, dddd, J=6.3, 7.4, 7.8, 13.7 Hz), 2.36 (3H, s), 2.41 (1H, ddd, J=6.3, 7.8, 9.0 Hz), 2.67 (1H, dd, J=2.7, 10.9 Hz), 2.73 (1H, ddd, J=6.3, 7.4, 9.0 Hz), 2.77 (2H, t, J=6.6 Hz), 2.82 (1H, dd, J=5.9, 10.9 Hz), 4.67 (1H, tt, J=5.5, 7.0 Hz), 5.08 (1H, ddt, J=5.9, 7.8, 2.7 Hz), 5.28-5.43 (4H, m).

MS (ESI+) m/z 534 [M+H]$^+$

HRMS (ESI+) m/z 534.4891 (0.5 mDa).

Example 13

2-(1-Methylpyrrolidin-2-yl)ethyl(9Z,12Z)-octacosa-19,22-dien-11-yl Carbonate (Exemplary Compound 2-75)

A solution of (19Z,22Z)-octacosa-19,22-dien-11-ol (0.200 g, 0.492 mmol) obtained in Reference Example 17 and pyridine (0.245 g, 3.10 mmol) in toluene (5 mL) was cooled to 0° C. in an ice bath, and a solution of triphosgene (0.101 g, 0.339 mmol) in toluene (0.74 mL) was added thereto over 2 minutes. After stirring at 0° C. for 15 minutes, the reaction mixture was heated to room temperature, stirred for 1 hour, and cooled to 0° C. again. 1-Methyl-2-pyrrolidinemethanol (0.667 g, 5.16 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (98.5 mg, 36%).

$^1$H-NMR (400 MHz, CDCl$_3$) δ: 0.88 (3H, t, J=7.0 Hz), 0.89 (3H, t, J=7.0 Hz), 1.22-1.40 (32H, m), 1.44-1.85 (8H, m), 1.92-2.18 (8H, m), 2.32 (3H, s), 2.77 (2H, t, J=6.6 Hz), 3.06 (1H, ddd, J=2.3, 8.2, 8.6 Hz), 4.11-4.26 (2H, m), 4.65-4.72 (1H, m), 5.29-5.43 (4H, m).

MS (ESI+) m/z 562 [M+H]$^+$

HRMS (ESI+) m/z 562.5203 (0.4 mDa).

Example 14

(1-Methylpiperidin-4-yl)methyl(9Z,12Z)-octacosa-19,22-dien-11-yl Carbonate (Exemplary Compound 2-73)

A solution of (19Z,22Z)-octacosa-19,22-dien-11-ol (0.200 g, 0.492 mmol) obtained in Reference Example 17 and pyridine (0.245 g, 3.10 mmol) in toluene (5 mL) was cooled to 0° C. in an ice bath, and a solution of triphosgene (0.101 g, 0.339 mmol) in toluene (0.74 mL) was added thereto over 2 minutes. After stirring at 0° C. for 15 minutes, the reaction mixture was heated to room temperature, stirred for 1 hour, and cooled to 0° C. again. 4-Hydroxymethyl-1-methylpiperidine (0.667 g, 5.16 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (21.7 mg, 8%).

¹H-NMR (400 MHz, CDCl₃) δ: 0.88 (3H, t, J=7.0 Hz), 0.90 (3H, t, J=7.0 Hz), 1.23-1.39 (28H, m), 1.49-1.61 (6H, m), 1.63-1.71 (1H, m), 1.74 (2H, d, J=14.1 Hz), 1.91 (2H, t, J=11.7 Hz), 2.00-2.03 (4H, m), 2.27 (3H, s), 2.77 (2H, t, J=6.6 Hz), 2.86 (2H, d, J=11.7 Hz), 3.98 (2H, d, J=6.6 Hz), 4.64-4.71 (1H, m), 5.29-5.43 (4H, m).
MS (ESI+) m/z 562 [M+H]⁺
HRMS (ESI+) m/z 562.5204 (0.5 mDa).

Reference Example 18

(21Z,24Z)-Triaconta-21,24-dien-13-ol

To a solution of (9Z,12Z)—N-methoxy-N-methyloctacosa-9,12-dienamide (0.50 g, 1.5 mmol) obtained in Reference Example 15 in tetrahydrofuran (6.9 mL), a solution of 1 N n-dodecyl magnesium bromide in diethyl ether (4.6 mL, 4.6 mmol) was added dropwise over 3 minutes, and the mixture was then reacted at room temperature for 6 hours. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain a mixture containing a presumed intermediate ketone (0.93 g). To a solution of this ketone mixture in methanol (4.6 mL) and tetrahydrofuran (4.6 mL), sodium borohydride (0.06 g, 1.5 mmol) was added, and the mixture was then reacted at room temperature for 3 hours. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure to obtain the compound of interest as a colorless liquid (0.59 g, 89%).
¹H-NMR (500 MHz, CDCl₃) δ: 0.88 (3H, t, J=6.8 Hz), 0.90 (3H, t, J=6.8 Hz), 1.22-1.48 (44H, m), 2.02-2.08 (4H, m), 2.77 (2H, t, J=6.8 Hz), 3.55-3.62 (1H, m), 5.30-5.42 (4H, m).

Example 15

3-(Dimethylamino)propyl(21Z,24Z)-triaconta-21,24-dien-13-yl Carbonate (Exemplary Compound 1-112)

A solution of (21Z,24Z)-triaconta-21,24-dien-13-ol (0.15 g, 0.35 mmol) obtained in Reference Example 18 and pyridine (0.17 g, 2.2 mmol) in toluene (3.4 mL) was cooled to 0° C. in an ice bath, and a solution of triphosgene (0.07 g, 0.24 mmol) in toluene (0.5 mL) was added thereto over 1 minute. After stirring at 0° C. for 2 hours, 3-dimethylamino 1-propanol (0.37 g, 3.6 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (177 mg, 91%).
¹H-NMR (500 MHz, CDCl₃) δ: 0.85-0.92 (6H, m), 1.21-1.40 (36H, m), 1.49-1.63 (4H, m), 1.84 (2H, tt, J=6.6, 7.6 Hz), 2.01-2.08 (4H, m), 2.22 (6H, s), 2.36 (2H, t, J=7.6 Hz), 2.78 (2H, t, J=6.6 Hz), 4.18 (2H, t, J=6.6 Hz), 4.65-4.72 (1H, m), 5.29-5.42 (4H, m).

MS (ESI+) m/z 564 [M+H]⁺
HRMS (ESI+) m/z 564.5359 (0.3 mDa).

Reference Example 19

(19Z,22Z)-Octacosa-19,22-dien-3-yn-11-one

To a solution of (9Z,12Z)—N-methoxy-N-methyl-octacosa-9,12-dienamide (1.00 g, 3.09 mmol) obtained in Reference Example 15 in tetrahydrofuran (6.2 mL), a solution of 0.5 N (decyn-7-ynyl)magnesium chloride in tetrahydrofuran (12.4 mL, 6.20 mmol) was added dropwise over 3 minutes, and the mixture was then reacted at room temperature for 6 hours. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (1.03 g, 83%).
¹H-NMR (500 MHz, CDCl₃) δ: 0.89 (3H, t, J=7.1 Hz), 1.11 (3H, t, J=7.3 Hz), 1.23-1.61 (24H, m), 2.01-2.08 (4H, m), 2.11-2.19 (4H, m), 2.36-2.41 (4H, m), 2.77 (2H, t, J=6.8 Hz), 5.29-5.42 (4H, m).

Reference Example 20

(19Z,22Z)-Octacosa-19,22-dien-3-yn-11-ol

To a solution of (19Z,22Z)-octacosa-19,22-dien-3-yn-11-one (1.0 g, 2.56 mmol) obtained in Reference Example 19 in methanol (7.7 mL) and tetrahydrofuran (7.7 mL), sodium borohydride (0.097 g, 2.6 mmol) was added, and the mixture was then reacted at room temperature for 3 hours. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.78 g, 75%).
¹H-NMR (500 MHz, CDCl₃) δ: 0.89 (3H, t, J=7.1 Hz), 1.11 (3H, t, J=7.3 Hz), 1.24-1.52 (28H, m), 2.02-2.08 (4H, m), 2.11-2.19 (4H, m), 2.77 (2H, t, J=6.8 Hz), 3.55-3.62 (1H, m), 5.30-5.42 (4H, m).

Example 16

3-(Dimethylamino)propyl(19Z,22Z)-octacosa-19,22-dien-3-yn-11-yl Carbonate (Exemplary Compound 1-99)

A solution of (19Z,22Z)-octacosa-19,22-dien-3-yn-11-ol (0.15 g, 0.37 mmol) obtained in Reference Example 20 and pyridine (0.19 g, 2.4 mmol) in toluene (3.7 mL) was cooled to 0° C. in an ice bath, and a solution of triphosgene (0.076 g, 0.26 mmol) in toluene (0.5 mL) was added thereto over 1 minute. After stirring at 0° C. for 2 hours, 3-dimethylamino 1-propanol (0.40 g, 3.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (183 mg, 93%).

$^1$H-NMR (500 MHz, CDCl$_3$) δ: 0.89 (3H, t, J=6.6 Hz), 1.11 (3H, t, J=7.3 Hz), 1.23-1.64 (28H, m), 1.85 (2H, tt, J=6.6, 7.3 Hz), 2.01-2.08 (4H, m), 2.10-2.19 (4H, m), 2.22 (6H, s), 2.36 (2H, t, J=7.3 Hz), 2.77 (2H, t, J=6.6 Hz), 4.18 (2H, t, J=6.6 Hz), 4.64-4.71 (1H, m), 5.29-5.42 (4H, m).

MS (ESI+) m/z 532 [M+H]$^+$

HRMS (ESI+) m/z 532.4739 (0.9 mDa).

Reference Example 21

(3Z,19Z,22Z)-Octacosa-3,19,22-trien-11-ol

To nickel(II) acetate tetrahydrate (0.24 g, 0.97 mmol), ethanol (12 mL) was added under the hydrogen gas atmosphere, and a solution of sodium borohydride (0.037 g, 0.97 mmol) in ethanol (6 mL) was added. After stirring at room temperature for 15 minutes, ethylenediamine (0.23 g, 3.9 mmol) was added, and the mixture was further stirred for 15 minutes. Subsequently, a solution of (19Z,22Z)-octacosa-19,22-dien-3-yn-11-ol (0.39 g, 0.97 mmol) obtained in Reference Example 20 in ethanol (6 mL) was added thereto over 1 minute, and the mixture was stirred at room temperature for 5.5 hours under the hydrogen atmosphere. The reaction mixture was diluted with a 20% solution of ethyl acetate in hexane and subjected to silica gel column chromatography to obtain the compound of interest as a colorless liquid (0.37 g, 95%).

$^1$H-NMR (500 MHz, CDCl$_3$) δ: 0.89 (3H, t, J=7.1 Hz), 0.95 (3H, t, J=7.3 Hz), 1.23-1.48 (28H, m), 1.99-2.08 (8H, m), 2.77 (2H, t, J=6.8 Hz), 3.55-3.61 (1H, m), 5.29-5.42 (6H, m).

Example 17

3-(Dimethylamino)propyl(3Z,19Z,22Z)-octacosa-3,19,22-trien-11-yl Carbonate (Exemplary Compound 1-87)

A solution of (3Z,19Z,22Z)-octacosa-3,19,22-trien-11-ol (0.15 g, 0.37 mmol) obtained in Reference Example 21 and pyridine (0.19 g, 2.4 mmol) in toluene (3.7 mL) was cooled to 0° C. in an ice bath, and a solution of triphosgene (0.075 g, 0.26 mmol) in toluene (0.5 mL) was added thereto over 1 minute. After stirring at 0° C. for 2 hours, 3-dimethylamino 1-propanol (0.40 g, 3.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (136 mg, 69%).

$^1$H-NMR (500 MHz, CDCl$_3$) δ: 0.89 (3H, t, J=6.6 Hz), 0.95 (3H, t, J=7.6 Hz), 1.22-1.40 (24H, m), 1.49-1.64 (4H, m), 1.84 (2H, tt, J=6.6, 7.3 Hz), 1.97-2.08 (8H, m), 2.22 (6H, s), 2.36 (2H, t, J=7.3 Hz), 2.77 (2H, t, J=6.6 Hz), 4.17 (2H, J=6.6 Hz), 4.65-4.71 (1H, m), 5.27-5.43 (6H, m).

MS (ESI+) m/z 534 [M+H]$^+$

HRMS (ESI+) m/z 534.4891 (0.5 mDa).

Example 18

4-(Dimethylamino)butyl(11Z,14Z)-2-[(9Z,12Z)-octadeca-9,12-dien-1-yl]icosa-11,14-dien-1-yl Carbonate (Exemplary Compound 1-478)

A solution of (11Z,14Z)-2-[(9Z,12Z)-octadeca-9,12-dien-1-yl]icosa-11,14-dien-1-ol (0.15 g, 0.28 mmol) obtained in Reference Example 14 and pyridine (0.14 g, 1.8 mmol) in toluene (0.6 mL) was cooled to 0° C. in an ice bath, and a solution of triphosgene (0.06 g, 0.19 mmol) in toluene (0.24 mL) was added thereto over 2 minutes. After stirring at 0° C. for 2 hours, the reaction mixture was heated to 10° C., stirred for 30 minutes, and cooled to 0° C. again. 4-Dimethylamino 1-butanol (0.35 g, 2.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (80 mg, 42%).

$^1$H-NMR (400 MHz, CDCl$_3$) δ: 0.86-0.92 (6H, m), 1.20-1.40 (40H, m), 1.50-1.59 (2H, m), 1.63-1.74 (3H, m), 2.01-2.09 (8H, m), 2.21 (6H, s), 2.28 (2H, t, J=7.4 Hz), 2.78 (4H, t, J=6.6 Hz), 4.02 (2H, d, J=5.9 Hz), 4.14 (2H, t, J=6.6 Hz), 5.29-5.43 (8H, m).

MS (ESI+) m/z 686 [M+H]$^+$

HRMS (ESI+) m/z 686.6461 (1.0 mDa).

Reference Example 22

Octacosan-11-ol

To a solution of octadecanal (0.62 g) in tetrahydrofuran (2.3 mL), a solution of 1 N n-decyl magnesium bromide in diethyl ether (4.6 mL, 4.6 mmol) was added, and the mixture was reacted at room temperature for 20 minutes. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a white waxy solid (0.34 g, 36%).

Example 19

3-(Dimethylamino)propyloctacosan-11-yl Carbonate (Exemplary Compound 1-8)

A solution of octacosan-11-ol (0.11 g, 0.27 mmol) obtained in Reference Example 22 and pyridine (0.13 g, 1.7 mmol) in toluene (2.7 mL) was cooled to 0° C. in an ice bath, and a solution of triphosgene (0.055 g, 0.18 mmol) in toluene (0.40 mL) was added thereto over 1 minute. After stirring at 0° C. for 15 minutes, the reaction mixture was heated to room temperature, stirred for 1 hour, and cooled to 0° C. again. 3-Dimethylamino-1-propanol (0.29 g, 2.8 mmol) was added thereto, and the mixture was reacted overnight at room temperature. After treatment with a saturated aqueous solution of sodium bicarbonate, the reaction mixture was subjected to extraction with hexane, and the obtained organic layer was dried off under reduced pressure, and the residue was then subjected to silica gel column chromatography to obtain the compound of interest as a colorless liquid (114 mg, 79%).

$^1$H-NMR (400 MHz, CDCl$_3$) δ: 0.85-0.91 (6H, m), 1.22-1.35 (46H, m), 1.48-1.64 (4H, m), 1.84 (2H, tt, J=6.6, 7.4 Hz), 2.22 (6H, s), 2.36 (2H, t, J=7.4 Hz), 4.17 (2H, t, J=6.6 Hz), 4.64-4.72 (1H, m).

MS (ESI+) m/z 540 [M+H]$^+$
HRMS (ESI+) m/z 540.5344 (−1.2 mDa).

Reference Example 23

(Z)—N-Methoxy-N-methyloctadec-9-enamide

To a solution of oleic acid (10.3 g, 36.3 mmol) and N,O-dimethylhydroxylamine hydrochloride (7.08 g, 72.6 mmol) in dichloromethane (250 mL), 1-hydroxybenzimidazole hydrate (11.1 g, 72.6 mmol), triethylamine (7.34 g, 72.6 mmol), and 1-ethyl-3-(3'-dimethylaminopropyl)carbodiimide hydrochloride (13.9 g, 72.6 mmol) were added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (12.1 g, 99%).

$^1$H-NMR (500 MHz, CDCl$_3$) δ: 0.88 (3H, t, J=7.1 Hz), 1.22-1.37 (20H, m), 1.63 (2H, quint, J=7.3 Hz), 1.97-2.04 (4H, m), 2.41 (2H, t, J=7.3 Hz), 3.18 (3H, s), 3.68 (3H, s), 5.31-5.38 (2H, m).

Reference Example 24

(Z)-Octacos-19-en-11-one

To a solution of (Z)—N-methoxy-N-methyloctadec-9-enamide (0.50 g, 1.5 mmol) obtained in Reference Example 23 in tetrahydrofuran (7.7 mL), a solution of 1 N n-decyl magnesium bromide in tetrahydrofuran (3.1 mL, 3.1 mmol) was added, and the mixture was then reacted at room temperature for 1 hour and subsequently at 60° C. for 30 minutes. After treatment with a saturated aqueous solution of ammonium chloride, volatile matter was removed under reduced pressure. The residue was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.59 g, 93%).

$^1$H-NMR (500 MHz, CDCl$_3$) δ: 0.85-0.90 (6H, m), 1.20-1.36 (34H, m), 1.52-1.60 (4H, m), 1.98-2.04 (4H, m), 2.38 (4H, t, J=7.3 Hz), 5.32-5.38 (2H, m).

Reference Example 25

(Z)-Octacos-19-en-11-ol

To a solution of (Z)-octacosa-19-en-11-one (0.59 g, 1.4 mmol) obtained in Reference Example 24 in methanol (4.3 mL) and tetrahydrofuran (4.3 mL), sodium borohydride (0.054 g, 1.4 mmol) was added, and the mixture was then reacted at room temperature for 60 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (0.45 g, 77%).

Example 20

3-(Dimethylamino)propyl(19Z)-octacos-19-en-11-yl Carbonate (Exemplary Compound 1-16)

A solution of (Z)-octacosa-19-en-11-ol (0.45 g, 1.1 mmol) obtained in Reference Example 25 and pyridine (0.55 g, 6.9 mmol) in toluene (11 mL) was cooled to 0° C. in an ice bath, and a solution of triphosgene (0.23 g, 6.9 mmol) in toluene (1.7 mL) was added thereto over 2 minutes. After stirring at 0° C. for 30 minutes, the reaction mixture was heated to room temperature, stirred for 1 hour, and cooled to 0° C. again. 3-Dimethylamino-1-propanol (1.2 g, 12 mmol) was added thereto, and the mixture was reacted at room temperature for 3 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (530 mg, 89%).

$^1$H-NMR (500 MHz, CDCl$_3$) δ: 0.88 (6H, t, J=6.8 Hz), 1.21-1.37 (38H, m), 1.49-1.62 (4H, m), 1.84 (2H, tt, J=6.6, 7.6 Hz), 1.97-2.04 (4H, m), 2.22 (6H, s), 2.36 (2H, t, J=7.6 Hz), 4.18 (2H, t, J=6.6 Hz), 4.65-4.71 (1H, m), 5.32-5.37 (2H, m).

MS (ESI+) m/z 538 [M+H]$^+$
HRMS (ESI+) m/z 538.5193 (−0.6 mDa).

Reference Example 26

Octadeca-9,12,15-triyn-1-ol

To a solution of 9-decyn-1-ol (5.15 g, 33.4 mmol) and 1-bromoocta-2,5-diyne (known compound, 6.18 g, 33.4 mmol) in N,N-dimethylformamide (66 mL), sodium iodide (5.56 g, 37.1 mmol), potassium carbonate (10.2 g, 74.1 mmol), and copper(I) iodide (7.06 g, 37.1 mmol) were added in this order, and the mixture was reacted overnight at room temperature. Insoluble matter was removed through celite. After treatment with a saturated aqueous solution of sodium bicarbonate, the reaction mixture was subjected to extraction with a hexane-ethyl acetate mixed solvent, and the obtained organic layer was dried over anhydrous magnesium sulfate. The solvent was distilled off under reduced pressure, and the residue was then subjected to silica gel column chromatography to obtain the compound of interest as a colorless liquid (8.40, 97%).

$^1$H-NMR (500 MHz, CDCl$_3$): 0.12 (3H, t, J=7.6 Hz), 1.24-1.42 (10H, m), 1.48 (2H, tt, J=7.1, 7.6 Hz), 1.57 (2H, tt, J=6.6, 7.1 Hz), 2.12-2.21 (4H, m), 3.14 (2H, s), 3.14 (2H, s), 3.64 (2H, t, J=6.6 Hz).

Reference Example 27

Octadeca-9,12,15-triynoic Acid

To a solution of octadeca-9,12,15-triyn-1-ol (8.40 g, 32.5 mmol) obtained in Reference Example 26 and triethylamine (16.4 g, 163 mmol) in dimethyl sulfoxide (97 mL), sulfur trioxide-pyridine (12.9 g, 81.3 mmol) was added, and the mixture was reacted at room temperature for 3 hours. After water treatment to terminate the reaction, the reaction mixture was subjected to extraction with hexane, and the obtained organic layer was dried over anhydrous magnesium sulfate. The solvent was distilled off under reduced pressure, and the obtained brown liquid was dissolved in tert-butyl alcohol (130 mL) and 2-methyl-2-butene (18 mL). To the solution, a solution of sodium dihydrogen phosphate dihydrate (11.2 g, 71.5 mmol) and sodium chlorite (6.47 g, 71.5 mmol) in water (130 mL) was added dropwise over 5 minutes, and the mixture was then reacted at room temperature for 50 minutes. The reaction mixture was diluted with water and subjected to extraction with a hexane-ethyl acetate mixed solvent, and the obtained organic layer was dried over anhydrous magnesium sulfate. The solvent was distilled off under reduced pressure, and the residue was then subjected to silica gel column chromatography to obtain the compound of interest as a yellow solid (6.13 g, 69%).

$^1$H-NMR (500 MHz, CDCl$_3$) δ: 1.12 (3H, t, J=7.6 Hz), 1.27-1.41 (6H, m), 1.48 (2H, tt, J=7.1, 7.3 Hz), 1.64 (2H, tt, J=7.1, 7.6 Hz), 2.12-2.20 (4H, m), 2.35 (2H, t, J=7.6 Hz), 3.14 (4H, s).

Reference Example 28

N-Methoxy-N-methyloctadeca-9,12,15-triynamide

To a solution of octadeca-9,12,15-triynoic acid (5.13 g, 18.8 mmol) obtained in Reference Example 27 and N,O-dimethylhydroxylamine hydrochloride (3.67 g, 37.7 mmol) in dichloromethane (132 mL), 1-hydroxybenzimidazole hydrate (5.77 g, 37.7 mmol), triethylamine (3.81 g, 37.7 mmol), and 1-ethyl-3-(3'-dimethylaminopropyl)carbodiimide hydrochloride (7.22 g, 37.7 mmol) were added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (4.00 g, 67%).

$^1$H-NMR (500 MHz, CDCl$_3$) δ: 1.12 (3H, t, J=7.6 Hz), 1.29-1.41 (6H, m), 1.48 (2H, tt, J=7.1, 7.3 Hz), 1.63 (2H, quint, J=7.3 Hz), 2.11-2.20 (4H, m), 2.41 (2H, t, J=7.3 Hz), 3.14 (4H, s), 3.18 (3H, s), 3.68 (3H, s).

Reference Example 29

Octacosa-19,22,25-triyn-11-one

To a solution of N-methoxy-N-methyloctadec-9,12,15-triynamide (1.00 g, 3.17 mmol) obtained in Reference Example 28 in tetrahydrofuran (15 mL), a solution of 1 N n-decyl magnesium bromide in tetrahydrofuran (6.34 mL, 6.34 mmol) was added, and the mixture was then reacted at room temperature for 1 hour and subsequently at 60° C. for 30 minutes. After treatment with a saturated aqueous solution of ammonium chloride, volatile matter was removed under reduced pressure. The residue was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.40 g, 32%).

$^1$H-NMR (500 MHz, CDCl$_3$) δ: 0.88 (3H, t, J=7.1 Hz), 1.12 (3H, t, J=7.6 Hz), 1.20-1.39 (20H, m), 1.47 (2H, tt, J=7.1, 7.3 Hz), 1.51-1.59 (4H, m), 2.12-2.20 (4H, m), 2.38 (4H, t, J=7.6 Hz), 3.14 (4H, s).

Reference Example 30

Octacosa-19,22,25-triyn-11-ol

To a solution of octacosa-19,22,25-triyn-11-one (0.40 g, 1.0 mmol) obtained in Reference Example 29 in methanol (3.0 mL) and tetrahydrofuran (3.0 mL), sodium borohydride (0.038 g, 1.0 mmol) was added, and the mixture was then reacted at room temperature for 60 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (0.25 g, 62%).

$^1$H-NMR (500 MHz, CDCl$_3$) δ: 0.88 (3H, t, J=7.1 Hz), 1.12 (3H, t, J=7.6 Hz), 1.21-1.52 (30H, m), 2.12-2.20 (4H, m), 3.14 (2H, s), 3.14 (2H, s), 3.55-3.60 (1H, m).

Reference Example 31

3-(Dimethylamino)propyloctacosa-19,22,25-triyn-11-yl Carbonate

A solution of octacosa-19,22,25-triyn-11-ol (0.25 g, 0.63 mmol) obtained in Reference Example 30 and pyridine (0.31 g, 4.0 mmol) in toluene (6.2 mL) was cooled to 0° C. in an ice bath, and a solution of triphosgene (0.13 g, 0.43 mmol) in toluene (0.9 mL) was added thereto over 2 minutes. After stirring at 0° C. for 20 minutes, the reaction mixture was heated to room temperature, stirred for 1 hour, and cooled to 0° C. again. 3-Dimethylamino-1-propanol (0.68 g, 6.6 mmol) was added thereto, and the mixture was reacted at room temperature for 2.5 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.22 g, 66%).

$^1$H-NMR (500 MHz, CDCl$_3$) δ: 0.88 (3H, t, J=7.1 Hz), 1.12 (3H, t, J=7.6 Hz), 1.20-1.60 (30H, m), 1.84 (2H, tt, J=6.6, 7.6 Hz), 2.11-2.20 (4H, m), 2.22 (6H, s), 2.36 (2H, t, J=7.6 Hz), 3.14 (4H, s), 4.18 (2H, t, J=6.6 Hz), 4.65-4.71 (1H, m).

Example 21

3-(Dimethylamino)propyl(19Z,22Z,25Z)-octacosa-19,22,25-trien-11-yl Carbonate (Exemplary Compound 1-164)

To nickel(II) acetate tetrahydrate (0.104 g, 0.417 mmol), ethanol (5.0 mL) was added under the hydrogen gas atmosphere, and a solution of sodium borohydride (0.015 g, 0.417 mmol) in ethanol (2.5 mL) was added. After stirring at room temperature for 15 minutes, ethylenediamine (0.100 g, 1.67 mmol) was added, and the mixture was further stirred for 15 minutes. Subsequently, a solution of 3-(dimethylamino)propyloctacosa-19,22,25-triyn-11-yl carbonate (0.220 g, 0.417 mmol) obtained in Reference Example 31 in ethanol (2.5 mL) was added thereto over 1 minute, and the mixture was reacted overnight at room temperature under the hydrogen atmosphere. The reaction mixture was diluted with a hexane solution and subjected to silica gel column chromatography to obtain the compound of interest as a colorless liquid.

$^1$H-NMR (500 MHz, CDCl$_3$) δ: 0.88 (3H, t, J=6.8 Hz), 0.98 (3H, t, J=7.6 Hz), 1.20-1.39 (26H, m), 1.49-1.62 (4H, m), 1.84 (2H, tt, J=6.6, 7.3 Hz), 1.99-2.11 (4H, m), 2.22 (6H, s), 2.36 (2H, t, J=7.3 Hz), 2.78-2.83 (4H, m), 4.18 (2H, t, J=6.6 Hz), 4.65-4.71 (1H, m), 5.28-5.43 (6H, m).
MS (ESI+) m/z 534 [M+H]+
HRMS (ESI+) m/z 534.4885 (−0.1 mDa).

Reference Example 32

Methyl (9Z,12R)-12-{[tert-butyl(dimethyl)silyl]oxy}octadec-9-enoate

To a solution of methyl ricinolate (16.7 g, 53.4 mmol) and imidazole (7.28 g, 107 mmol) in N,N-dimethylformamide (53.4 mL), tert-butyl(dimethyl)silane chloride (12.1 g, 80.2 mmol) was added over 2 minutes, and the mixture was then reacted overnight at room temperature. After treatment with water, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (23.2 g, 99%).
$^1$H-NMR (500 MHz, CDCl$_3$) δ: 0.03-0.06 (6H, m), 0.86-0.90 (12H, m), 1.22-1.45 (18H, m), 1.62 (2H, tt, J=6.8, 7.6 Hz), 2.01 (2H, q, J=6.6 Hz), 2.18 (2H, t, J=5.9 Hz), 2.30 (2H, t, J=7.6 Hz), 3.65 (1H, quint, J=5.9 Hz), 3.67 (3H, s), 5.33-5.45 (2H, m).

Reference Example 33

(5R,7Z,24Z,27R)-5,27-Dihexyl-2,2,3,3,29,29,30,30-octamethyl-4,28-dioxa-3,29-disilahentriaconta-7,24-dien-16-one To a solution of methyl (9Z,12R)-12-{[tert-butyl(dimethyl)silyl]oxy}octadec-9-enoate (12 g, 28.1 mmol) obtained in Reference Example 32 in xylene (15 mL), a suspension of sodium hydride (1.37 g, 64%, 36.6 mmol) washed in advance with hexane in xylene (5 mL) was added over 5 minute, and the mixture was then reacted at 150° C. for 5.5 hours. The reaction mixture was cooled to room temperature, then treated with water, and subjected to extraction with hexane. The obtained organic layer was dried over anhydrous magnesium sulfate, and the solvent was distilled off under reduced pressure to obtain an oil. To this oil, tetrahydrofuran (120 mL) and a 5 N aqueous sodium hydroxide solution (28 mL) were added, and the mixture was reacted at 90° C. for 5.5 hours. The reaction mixture was cooled to room temperature, then treated with water, and subjected to extraction with hexane. The obtained organic layer was dried over anhydrous magnesium sulfate. The solvent was distilled off under reduced pressure, and the residue was then subjected to silica gel column chromatography to obtain the compound of interest as a colorless liquid (7.24 g, 67%).
$^1$H-NMR (500 MHz, CDCl$_3$) δ: 0.03-0.06 (12H, m), 0.86-0.90 (24H, m), 1.21-1.45 (36H, m), 1.51-1.59 (4H, m), 2.01 (4H, q, J=6.6 Hz), 2.18 (4H, t, J=5.9 Hz), 2.38 (4H, t, J=7.6 Hz), 3.65 (2H, quint, J=5.9 Hz), 5.32-5.46 (4H, m).

Reference Example 34

(5R,7Z,24Z,27R)-5,27-Dihexyl-2,2,3,3,29,29,30,30-octamethyl-4,28-dioxa-3,29-disilahentriaconta-7,24-dien-16-ol To a solution of (5R,7Z,24Z,27R)-5,27-dihexyl-2,2,3,3,29,29,30,30-octamethyl-4,28-dioxa-3,29-disilahentriaconta-7,24-dien-16-one (5.5 g, 7.2 mmol) obtained in Reference Example 33 in methanol (22 mL) and tetrahydrofuran (22 mL), sodium borohydride (0.27 g, 7.2 mmol) was added over 2 minutes, and the mixture was then reacted at room temperature for 3 hours. After treatment with a saturated aqueous solution of ammonium chloride, volatile matter was removed under reduced pressure. The residue was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (5.0 g, 91%).
$^1$H-NMR (500 MHz, CDCl$_3$) δ: 0.03-0.05 (12H, m), 0.86-0.90 (24H, m), 1.22-1.47 (44H, m), 2.01 (4H, q, J=6.6 Hz), 2.18 (4H, t, J=5.9 Hz), 3.55-3.61 (1H, m), 3.65 (2H, quint, J=5.9 Hz), 5.34-5.46 (4H, m).

Reference Example 35

3-(Dimethylamino)propyl(5R,7Z,24Z,27R)-5,27-dihexyl-2,2,3,3,29,29,30,30-octamethyl-4,28-dioxa-3,29-disilahentriaconta-7,24-dien-16-yl carbonate To a solution of (5R,7Z,24Z,27R)-5,27-dihexyl-2,2,3,3,29,29,30,30-octamethyl-4,28-dioxa-3,29-disilahentriaconta-7,24-dien-16-ol (1.00 g, 1.31 mmol) obtained in Reference Example 34 and pyridine (0.651 g, 8.23 mmol) in toluene (13.1 mL), a solution of triphosgene (0.268 g, 0.690 mmol) in toluene (1.96 mL) was added over 1 minute. After stirring at room temperature for 2 hours, 3-dimethylamino-1-propanol (1.42 g, 13.7 mmol) was added thereto, and the mixture was reacted at room temperature for 3 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (1.15 g, 98%).
$^1$H-NMR (500 MHz, CDCl$_3$) δ: 0.03-0.05 (12H, m), 0.88 (6H, t, J=6.8 Hz), 0.89 (18H, s), 1.21-1.46 (40H, m), 1.49-1.62 (4H, m), 1.84 (2H, tt, J=6.8, 7.3 Hz), 2.01 (4H, q, J=6.6 Hz), 2.18 (4H, t, J=5.9 Hz), 2.22 (2H, t, J=7.3 Hz), 3.65 (2H, quint, J=5.9 Hz), 4.17 (2H, t, J=6.8 Hz), 4.65-4.71 (1H, m), 5.33-5.46 (4H, m).

Example 22

3-(Dimethylamino)propyl(7R,9Z,26Z,29R)-7,29-dihydroxypentatriaconta-9,26-dien-18-yl Carbonate (Exemplary Compound 1-308)

To 3-(dimethylamino)propyl(5R,7Z,24Z,27R)-5,27-dihexyl-2,2,3,3,29,29,30,30-octamethyl-4,28-dioxa-3,29-disilahentriaconta-7,24-dien-16-yl carbonate (1.15 g, 1.29 mmol) obtained in Reference Example 35, a solution of 1 N tetra-n-butylammonium fluoride in tetrahydrofuran (19.3 mL, 19.3 mmol) was added, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.56 g, 65%).

¹H-NMR (500 MHz, CDCl₃) δ: 0.88 (6H, t, J=6.8 Hz), 1.23-1.38 (36H, m), 1.40-1.50 (4H, m), 1.50-1.62 (4H, m), 1.84 (2H, tt, J=6.8, 7.3 Hz), 2.04 (4H, q, J=7.1 Hz), 2.21 (4H, t, J=7.1 Hz), 2.22 (6H, s), 2.36 (2H, t, J=7.3 Hz), 3.57-3.64 (2H, m), 4.17 (2H, t, J=6.8 Hz), 4.65-4.71 (1H, m), 5.37-5.44 (1H, m), 5.54-5.58 (1H, m).

Example 23

(7R,9Z,26Z,29R)-18-({[3-(Dimethylamino)propoxy]carbonyl}oxy)pentatriaconta-9,26-diene-7,29-diyl Diacetate (Exemplary Compound 1-233)

To a solution of 3-(dimethylamino)propyl(7R,9Z,26Z,29R)-7,29-dihydroxypentatriaconta-9,26-dien-18-yl carbonate (0.15 g, 0.23 mmol) obtained in Example 22 and pyridine (0.36 g, 4.5 mmol) in dichloromethane (4.5 mL), acetic acid chloride (0.18 g, 2.3 mmol) was added, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (155 mg, 92%).

¹H-NMR (500 MHz, CDCl₃) δ: 0.85-0.91 (6H, m), 1.22-1.38 (40H, m), 1.49-1.63 (8H, m), 1.85 (2H, tt, J=6.6, 7.3 Hz), 1.98-2.05 (10H, m), 2.22 (6H, s), 2.24-2.33 (4H, m), 2.36 (2H, t, J=7.3 Hz), 4.18 (2H, t, J=6.6 Hz), 4.65-4.71 (1H, m), 4.87 (2H, quint, J=6.3 Hz), 5.29-5.36 (2H, m), 5.44-5.50 (2H, m).

MS (ESI+) m/z 750 [M+H]⁺
HRMS (ESI+) m/z 750.6247 (−0.1 mDa).

Example 24

(7R,9Z,26Z,29R)-7,29-Dihexyl-2,5-dioxo-1,6-dioxacyclononacosa-9,26-dien-18-yl 3-(dimethylamino)propyl Carbonate (Exemplary Compound 1-319)

To a solution of 3-(dimethylamino)propyl(7R,9Z,26Z,29R)-7,29-dihydroxypentatriaconta-9,26-dien-18-yl carbonate (1.19 g, 1.72 mmol) obtained in Example 22 and pyridine (1.13 g, 14.3 mmol) in dichloromethane (40 mL), a solution of succinic acid chloride (0.186 g, 1.20 mmol) in dichloromethane (13 mL) was added dropwise over 1.5 hours, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (20 mg, 1%).

¹H-NMR (500 MHz, CDCl₃) δ: 0.88 (6H, t, J=6.6 Hz), 1.21-1.39 (40H, m), 1.51-1.63 (8H, m), 1.84 (2H, tt, J=6.6, 7.3 Hz), 1.98-2.07 (4H, m), 2.22 (6H, s), 2.28 (2H, t, J=7.1 Hz), 2.32 (2H, t, J=7.3 Hz), 2.36 (2H, t, J=7.6 Hz), 2.60 (4H, s), 4.17 (2H, t, J=6.6 Hz), 4.68 (1H, quint, J=6.1 Hz), 4.86-4.92 (2H, m), 5.29-5.36 (2H, m), 5.43-5.50 (2H, m).

MS (ESI+) m/z 748 [M+H]⁺
HRMS (ESI+) m/z 748.6091 (0.0 mDa).

Reference Example 36

(11Z,14Z)—N-Methoxy-N-methylicosa-11,14-dienamide

To a solution of (11Z,14Z)-icosa-11,14-dienoate (compound 3 described in Chem. Lett. 1998, 2, 175, 4.45 g, 14.4 mmol) and N,O-dimethylhydroxylamine hydrochloride (2.87 g, 28.9 mmol) in dichloromethane (71 mL), 1-hydroxybenzimidazole hydrate (3.90 g, 28.9 mmol), triethylamine (2.95 g, 28.9 mmol), and 1-ethyl-3-(3'-dimethylaminopropyl)carbodiimide hydrochloride (5.53 g, 28.9 mmol) were added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (5.00 g, 99%).

¹H-NMR (400 MHz, CDCl₃) δ: 0.89 (3H, t, J=7.0 Hz), 1.24-1.40 (18H, m), 1.62 (2H, quint, J=7.4 Hz), 2.02-2.07 (4H, m), 2.41 (2H, t, J=7.4 Hz), 2.77 (2H, t, J=6.6 Hz), 3.18 (3H, s), 3.68 (3H, s), 5.29-5.43 (4H, m).

Reference Example 37

(21Z,24Z)-Triaconta-21,24-dien-11-ol

To a solution of (11Z,14Z)—N-methoxy-N-methylicosa-11,14-dienamide (0.50 g, 1.4 mmol) obtained in Reference Example 36 in tetrahydrofuran (6.3 mL), a solution of 1 N n-decyl magnesium bromide in diethyl ether (4.3 mL, 4.3 mmol) was added dropwise over 3 minutes, and the mixture was then reacted at room temperature for 1.5 hours. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography. To a solution of the obtained oil in methanol (5.4 mL) and tetrahydrofuran (5.4 mL), sodium borohydride (0.05 g, 1.3 mmol) was added, and the mixture was then reacted at room temperature for 30 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure to obtain a mixture containing the compound of interest.

Example 25

3-(Dimethylamino)propyl(21Z,24Z)-triaconta-21,24-dien-11-yl Carbonate (Exemplary Compound 1-444)

To a solution of (21Z,24Z)-triaconta-21,24-dien-11-ol (0.15 g, 0.35 mmol) obtained in Reference Example 37 and pyridine (0.17 g, 2.18 mmol) in toluene (0.7 mL), a solution of triphosgene (0.07 g, 0.25 mmol) in toluene (0.29 mL) was added over 2 minutes. After stirring at room temperature for 2 hours, 3-dimethylamino 1-propanol (0.37 g, 3.6 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (100 mg, 51%).

$^1$H-NMR (500 MHz, CDCl$_3$) δ: 0.85-0.92 (6H, m), 1.21-1.40 (36H, m), 1.49-1.61 (4H, m), 1.85 (2H, tt, J=6.6, 7.6 Hz), 2.01-2.08 (4H, m), 2.22 (6H, s), 2.36 (2H, t, J=7.6 Hz), 2.77 (2H, t, J=6.6 Hz), 4.18 (2H, t, J=6.6 Hz), 4.65-4.72 (1H, m), 5.29-5.42 (4H, m).

MS (ESI+) m/z 564 [M+H]$^+$
HRMS (ESI+) m/z 564.5352 (−0.4 mDa).

Example 26

(19Z,22Z)-Octacosa-19,22-dien-11-yl 3-(pyrrolidin-1-yl)propyl Carbonate (Exemplary Compound 1-77)

A solution of (19Z,22Z)-octacosa-19,22-dien-11-ol (0.200 g, 0.492 mmol) obtained in Reference Example 17 and pyridine (0.245 g, 3.10 mmol) in toluene (4.9 mL) was cooled to 0° C. in an ice bath, and a solution of triphosgene (0.101 g, 0.339 mmol) in toluene (0.74 mL) was added thereto over 1 minute. After stirring at 0° C. for 15 minutes, the reaction mixture was heated to room temperature, stirred for 1 hour, and cooled to 0° C. again. 3-(Pyrrolidin-1-yl) propan-1-ol (0.667 g, 5.16 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (127 mg, 46%).

$^1$H-NMR (400 MHz, CDCl$_3$) δ: 0.88 (3H, t, J=6.7 Hz), 0.89 (3H, t, J=6.7 Hz), 1.20-1.40 (32H, m), 1.48-1.64 (4H, m), 1.74-1.81 (4H, m), 1.90 (2H, tt, J=6.7, 7.4 Hz), 2.01-2.09 (4H, m), 2.45-2.54 (4H, m), 2.53 (2H, t, J=7.4 Hz), 2.77 (2H, t, J=6.7 Hz), 4.19 (2H, t, J=6.7 Hz), 4.70 (1H, tt, J=5.5, 7.0 Hz), 5.28-5.43 (4H, m).

MS (ESI+) m/z 562 [M+H]$^+$
HRMS (ESI+) m/z 562.5203 (0.4 mDa).

Reference Example 38

(19Z,22R)-22-{[tert-Butyl(dimethyl)silyl] oxy}octacos-19-en-11-one

To a solution of methyl (9Z,12R)-12-{[tert-butyl(dimethyl)silyl]oxy}octadec-9-enoate (2.00 g, 4.69 mmol) obtained in Reference Example 32 and methyl undecanoate (2.82 g, 14.1 mmol) in xylene (20 mL), a suspension of sodium hydride (0.879 g, 64%, 23.4 mmol) washed in advance with hexane in xylene (8 mL) was added over 5 minutes, and the mixture was then reacted at 150° C. for 6.5 hours. The reaction mixture was cooled to room temperature, then treated with water, and subjected to extraction with hexane-ethyl acetate. The obtained organic layer was dried over anhydrous magnesium sulfate, and the solvent was distilled off under reduced pressure to obtain an oil. To this oil, tetrahydrofuran (94 mL) and a 5 N aqueous sodium hydroxide solution (23 mL) were added, and the mixture was reacted at 90° C. for 5 hours. The reaction mixture was cooled to room temperature, then treated with water, and subjected to extraction with hexane. The obtained organic layer was dried over anhydrous magnesium sulfate. The solvent was distilled off under reduced pressure, and the residue was then subjected to silica gel column chromatography to obtain a liquid containing the compound of interest (3.41 g, containing impurities).

$^1$H-NMR (400 MHz, CDCl$_3$) δ: 0.03-0.05 (6H, m), 0.85-0.91 (15H, m), 1.21-1.44 (36H, m), 1.50-1.60 (4H, m), 1.97-2.04 (2H, m), 2.18 (2H, t, J=6.3 Hz), 2.38 (4H, t, J=7.4 Hz), 3.61-3.68 (1H, m), 5.33-5.46 (2H, m).

Reference Example 39

(19Z,22R)-22-{[tert-Butyl(dimethyl)silyl] oxy}octacos-19-en-11-ol

To a solution of the mixture containing (19Z,22R)-22-{[tert-butyl(dimethyl)silyl]oxy}octacos-19-en-11-one (3.41 g)) obtained in Reference Example 38 in methanol (24 mL) and tetrahydrofuran (24 mL), sodium borohydride (0.30 g, 8.0 mmol) was added over 2 minutes, and the mixture was then reacted at room temperature for 1.5 hours. After treatment with a saturated aqueous solution of ammonium chloride, volatile matter was removed under reduced pressure. The residue was subjected to extraction with hexane, and the obtained organic layer was dried over anhydrous magnesium sulfate. The solvent was distilled off under reduced pressure, and the residue was then subjected to silica gel column chromatography to obtain a liquid containing the compound of interest (3.54 g, containing impurities).

Reference Example 40

(19Z,22R)-22-{[tert-Butyl(dimethyl)silyl] oxy}octacos-19-en-11-yl 3-(dimethylamino)propyl Carbonate A solution of the mixture containing (19Z,22R)-22-{[tert-butyl(dimethyl)silyl]oxy}octacos-19-en-11-ol (3.54 g) obtained in Reference Example 39 and pyridine (4.00 g, 50.6 mmol) in toluene (78.8 mL) was cooled to 0° C. in an ice bath, and a solution of triphosgene (1.62 g, 5.45 mmol) in toluene (11.8 mL) was added thereto over 2 minutes. After stirring at 0° C. for 30 minutes, the reaction mixture was heated to room temperature, stirred for 1 hour, and cooled to 0° C. again. 3-Dimethylamino-1-propanol (8.81 g, 85.4 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain a liquid containing the compound of interest (2.58 g, containing impurities).

$^1$H-NMR (400 MHz, CDCl$_3$) δ: 0.03-0.06 (6H, m), 0.85-0.91 (15H, m), 1.23-1.64 (40H, m), 1.84 (2H, tt, J=6.7, 7.4 Hz), 1.97-2.04 (2H, m), 2.15-2.20 (2H, m), 2.22 (6H, s), 2.36 (2H, t, J=7.4 Hz), 3.61-3.68 (1H, m), 4.17 (2H, t, J=6.7 Hz), 4.69 (1H, tt, J=5.5, 7.0 Hz), 5.32-5.46 (2H, m).

Example 27

3-(Dimethylamino)propyl(19Z,22R)-22-hydroxyoctacos-19-en-11-yl Carbonate (Exemplary Compound 1-298)

To the mixture containing (19Z,22R)-22-{[tert-butyl(dimethyl)silyl]oxy}octacos-19-en-11-yl 3-(dimethylamino)

propyl carbonate (2.58 g,) obtained in Reference Example 40, a solution of 1 N tetra-n-butylammonium fluoride in tetrahydrofuran (23.2 mL, 23.2 mmol) was added, and the mixture was reacted overnight at room temperature. After water treatment to terminate the reaction, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.500 g).

$^1$H-NMR (400 MHz, CDCl$_3$) δ: 0.88 (3H, t, J=6.7 Hz), 0.89 (3H, t, J=6.7 Hz), 1.20-1.38 (28H, m), 1.40-1.62 (8H, m), 1.84 (2H, tt, J=6.7, 7.4 Hz), 2.01-2.08 (2H, m), 2.18-2.23 (2H, m), 2.22 (6H, s), 2.36 (2H, t, J=7.4 Hz), 3.61 (1H, tt, J=5.3, 5.9 Hz), 4.18 (2H, t, J=6.7 Hz), 4.69 (1H, tt, J=5.5, 6.3 Hz), 5.36-5.45 (1H, m), 5.52-5.60 (1H, m).

MS (ESI+) m/z 554 [M+H]$^+$

HRMS (ESI+) m/z 554.5146 (−0.2 mDa).

Example 28

(7R,9Z)-18-({[3-(Dimethylamino)propyloxy]carbonyl}oxy)octacos-9-en-7-yl Acetate (Exemplary Compound 1-212)

To a solution of 3-(dimethylamino)propyl(19Z,22R)-22-hydroxyoctacos-19-en-11-yl carbonate (0.20 g, 0.36 mmol) obtained in Example 27 and pyridine (0.57 g, 7.2 mmol) in dichloromethane (7.2 mL), acetyl chloride (0.28 g, 3.6 mmol) was added, and the mixture was reacted at room temperature for 3 hours. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (42 mg, 20%).

$^1$H-NMR (400 MHz, CDCl$_3$) δ: 0.89 (3H, t, J=6.7 Hz), 0.89 (3H, t, J=6.7 Hz), 1.20-1.37 (32H, m), 1.48-1.61 (4H, m), 1.85 (2H, tt, J=6.7, 7.4 Hz), 1.97-2.02 (2H, m), 2.03 (3H, s), 2.22 (6H, s), 2.28 (2H, dd, J=6.3, 7.0 Hz), 2.36 (2H, t, J=7.4 Hz), 4.18 (2H, t, J=6.7 Hz), 4.69 (1H, tt, J=5.5, 6.3 Hz), 4.87 (1H, quint, J=6.3 Hz), 5.32 (1H, dtt, J=11.0, 1.6, 7.0 Hz), 5.47 (dtt, J=11.0, 1.6, 7.0 Hz).

MS (ESI+) m/z 596 [M+H]$^+$

HRMS (ESI+) m/z 596.5269 (1.5 mDa).

Reference Example 41

1,15-Bis[2-({2-[(2-ethylcyclopropyl)methyl]cyclopropyl}methyl)cyclopropyl]pentadecan-8-one To a solution of methyl 8-[2-({2-[(2-ethylcyclopropyl)methyl]cyclopropyl}methyl)cyclopropyl]octanoate (intermediate of compound 6 described in Bioorg. Med. Chem. Lett. 2003, 13, 1037, 1.50 g, 4.48 mmol) in xylene (6.0 mL), a suspension of sodium hydride (0.219 g, 64%, 5.83 mmol) washed in advance with hexane in xylene (0.7 mL) was added over 2 minutes, and the mixture was then reacted at 150° C. for 5 hours. The reaction mixture was cooled to room temperature, then treated with water, and subjected to extraction with hexane. The obtained organic layer was dried over anhydrous magnesium sulfate, and the solvent was distilled off under reduced pressure to obtain an oil. To this oil, tetrahydrofuran (22.4 mL) and a 5 N aqueous sodium hydroxide solution (5.4 mL) were added, and the mixture was reacted at 90° C. for 5 hours. The reaction mixture was cooled to room temperature, then treated with water, and subjected to extraction with a hexane-ethyl acetate mixed solution. The obtained organic layer was dried over anhydrous magnesium sulfate. The solvent was distilled off under reduced pressure, and the residue was then subjected to silica gel column chromatography to obtain the compound of interest as a colorless liquid (0.294 g, 23%).

$^1$H-NMR (400 MHz, CDCl$_3$) δ: (−0.32)-(−0.17) (6H, m), 0.57-1.61 (60H, m), 2.38 (4H, t, J=7.4 Hz).

Reference Example 42

1,15-Bis[2-({2-[(2-ethylcyclopropyl)methyl]cyclopropyl}methyl)cyclopropyl]pentadecan-8-ol To a solution of 1,15-bis[2-({2-[(2-ethylcyclopropyl)methyl]cyclopropyl}methyl)cyclopropyl]pentadecan-8-one (0.29 g, 0.51 mmol) obtained in Reference Example 41 in methanol (1.5 mL) and tetrahydrofuran (1.5 mL), sodium borohydride (0.019 g, 0.51 mmol) was added, and the mixture was then reacted at room temperature for 90 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (0.23 g, 78%).

$^1$H-NMR (400 MHz, CDCl$_3$) δ: (−0.32)-(−0.16) (6H, m), 0.57-1.60 (64H, m), 3.54-3.63 (1H, m).

Example 29

1,15-Bis[2-({2-[(2-ethylcyclopropyl)methyl]cyclopropyl}methyl)cyclopropyl]pentadecan-8-yl 3-dimethylaminopropyl Carbonate (Exemplary Compound 1-200)

A solution of 1,15-bis[2-({2-[(2-ethylcyclopropyl)methyl]cyclopropyl}methyl)cyclopropyl]pentadecan-8-ol (0.13 g, 0.22 mmol) obtained in Reference Example 42 and pyridine (0.11 g, 1.4 mmol) in toluene (2.2 mL) was cooled to 0° C. in an ice bath, and a solution of triphosgene (0.046 g, 0.15 mmol) in toluene (0.34 mL) was added thereto over 2 minutes. The resulting solution was stirred at 0° C. for 20 minutes, then heated to room temperature, stirred for 40 minutes, and cooled to 0° C. again. 3-Dimethylamino-1-propanol (0.24 g, 2.4 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (150 mg, 94%).

$^1$H-NMR (400 MHz, CDCl$_3$) δ: (−0.32)-(−0.16) (6H, m), 0.56-1.66 (64H, m), 1.84 (2H, tt, J=6.7, 7.4 Hz), 2.22 (6H, s), 2.36 (2H, t, J=7.4 Hz), 4.17 (2H, t, J=6.7 Hz), 4.70 (1H, tt, J=5.5, 7.0 Hz).

MS (ESI+) m/z 710 [M+H]$^+$

HRMS (ESI+) m/z 710.6463 (1.2 mDa).

Reference Example 43

8-[2-({2-[(2-Ethylcyclopropyl)methyl] cyclopropyl}methyl)cyclopropyl]-N-methoxy-N-methyloctanamide To a solution of methyl κ-[2-({2-[(2-ethylcyclopropyl) methyl]cyclopropyl}methyl)cyclopropyl]octanoate (compound 6 described in Bioorg. Med. Chem. Lett. 2003, 13, 1037, 3.00 g, 9.36 mmol) and N,O-dimethylhydroxylamine hydrochloride (1.83 g, 18.7 mmol) in dichloromethane (65.5 mL), 1-hydroxybenzimidazole hydrate (2.87 g, 18.7 mmol), triethylamine (1.89 g, 18.7 mmol), and 1-ethyl-3-(3'-dimethylaminopropyl)carbodiimide hydrochloride (3.59 g, 18.7 mmol) were added, and the mixture was reacted overnight at room temperature. After water treatment to terminate the reaction, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (3.08 g, 91%).

$^1$H-NMR (400 MHz, CDCl$_3$) δ: (−0.32)-(−0.17) (3H, m), 0.57-1.56 (28H, m), 1.57-1.67 (2H, m), 2.41 (2H, t, J=7.4 Hz), 3.18 (3H, s), 3.68 (3H, s).

Reference Example 44

1-[2-({2-[(2-Ethylcyclopropyl)methyl] cyclopropyl}methyl)cyclopropyl]octadecan-8-one A solution of 8-[2-({2-[(2-ethylcyclopropyl)methyl] cyclopropyl}methyl)cyclopropyl]-N-methoxy-N-methyloctanamide (2.00 g, 5.50 mmol) obtained in Reference Example 43 in tetrahydrofuran (24.5 mL) was cooled to 15° C. in a water bath. A solution of 1 N n-decyl magnesium bromide in tetrahydrofuran (8.25 mL, 8.25 mmol) was added dropwise thereto over 15 minutes, and the mixture was then reacted overnight at room temperature. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (1.56 g, 64%).

$^1$H-NMR (400 MHz, CDCl$_3$) δ: (−0.32)-(−0.17) (3H, m), 0.57-1.62 (49H, m), 2.38 (4H, t, J=7.4 Hz).

Reference Example 45

1-[2-({2-[(2-Ethylcyclopropyl)methyl] cyclopropyl}methyl)cyclopropyl]octadecan-8-ol To a solution of 1-[2-({2-[(2-ethylcyclopropyl)methyl] cyclopropyl}methyl)cyclopropyl]octadecan-8-one (1.56 g, 3.51 mmol) obtained in Reference Example 44 in methanol (10.5 mL) and tetrahydrofuran (10.5 mL), sodium borohydride (0.133 g, 3.51 mmol) was added, and the mixture was then reacted at room temperature for 90 minutes. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (1.50 g, 96%).

$^1$H-NMR (400 MHz, CDCl$_3$) δ: (−0.32)-(−0.17) (3H, m), 0.57-1.56 (53H, m), 3.54-3.62 (1H, m).

Example 30

3-Dimethylaminopropyl 1-[2-({2-[(2-ethylcyclopropyl)methyl]cyclopropyl}methyl)cyclopropyl]octadecan-8-yl Carbonate (Exemplary Compound 1-188)

A solution of 1-[2-({2-[(2-ethylcyclopropyl)methyl] cyclopropyl}methyl)cyclopropyl]octadecan-8-ol (0.25 g, 0.56 mmol) obtained in Reference Example 45 and pyridine (0.28 g, 3.5 mmol) in toluene (5.6 mL) was cooled to 0° C. in an ice bath, and a solution of triphosgene (0.12 g, 0.39 mmol) in toluene (0.84 mL) was added thereto over 2 minutes. The resulting solution was stirred at 0° C. for 20 minutes, then heated to room temperature, stirred for 40 minutes, and cooled to 0° C. again. 3-Dimethylamino-1-propanol (0.61 g, 5.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (155 mg, 48%).

$^1$H-NMR (400 MHz, CDCl$_3$) δ: (−0.32)-(−0.16) (3H, m), 0.57-1.65 (53H, m), 1.84 (2H, tt, J=6.7, 7.4 Hz), 2.22 (6H, s), 2.36 (2H, t, J=7.4 Hz), 4.18 (2H, t, J=6.7 Hz), 4.67 (1H, tt, J=5.5, 7.0 Hz).

MS (ESI+) m/z 576 [M+H]$^+$

HRMS (ESI+) m/z 576.5367 (1.1 mDa).

(Example 31) Preparation of Double-Stranded Polynucleotide-Encapsulated Nucleic Acid Lipid Particle A lipid solution having a total lipid concentration of 25 mM in 90% ethanol with distearoylphosphatidylcholine (1,2-distearoyl-sn-glycero-3-phosphocholine: hereinafter, referred to as DSPC, NOF CORPORATION), cholesterol (hereinafter, referred to as Chol, Sigma-Aldrich, Inc.), the compound described in Example 1, 2, 3, or 8 (hereinafter, referred to as LP), and N-[methoxy poly(ethylene glycol) 2000]carbamoyl]-1,2-dimyristyloxypropyl-3-amine (hereinafter, referred to as PEG-C-DMA) were prepared at a molar ratio of DSPC:Chol:LP:PEG-C-DMA=20:48:30:2.

A polynucleotide CT-157:

HO—P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 2 of the Sequence Listing) (polynucleotide containing a sequence complementary to nucleotide positions 3139-3157 of the human β-catenin gene (GenBank accession No. NM-001904.3)) and a polynucleotide CT-169:

HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1t}$-H (SEQ ID NO: 1 of the Sequence Listing) (containing a sequence of nucleotide positions 3139-3156 of the human β-catenin gene (GenBank accession No. NM-001904.3)) described in Examples 45 and 51 of International Publication No. WO 2010/001909 were synthesized using a DNA synthesizer, placed in an amount of 300 pmol/tube, and dried under reduced pressure. 30 μL of an siRNA suspension buffer (Qiagen N.V.) was added thereto, and the mixture was heated at 65° C. for 1 minute and then left at room temperature for 5 minutes for annealing to obtain a 10 µM double-stranded polynucleotide solution. Then, the concentration of the solution was adjusted to 1 mg/mL with a citrate buffer solution (20 mM citrate buffer, pH 4.0) to obtain a double-stranded polynucleotide solution. The lipid solution and the double-stranded polynucleotide solution were heated to 37° C. and mixed (100 µL each). Subsequently, 200 µL of a citrate buffer solution (20 mM citrate buffer, 300 mM NaCl, pH 6.0) was added thereto, and the mixture was incubated at 37° C. for 30 minutes to obtain a nucleic acid lipid particle dispersion. The nucleic acid lipid particle dispersion was dialyzed against approximately 100 mL of a phosphate buffer solution (pH 7.4) for 12 to 18 hours (Float-A-Lyzer G2, MWCO: 100 kD, Spectra/Por) for the removal of ethanol and the removal of unencapsulated double-stranded polynucleotides by neutralization to obtain a purified dispersion of an siRNA-encapsulated nucleic acid lipid particle containing the compound described in Example 1, 2, 3, or 8. The control samples used were the compound described in Reference Example 2 and compound 1 described in WO2012/054365.

(Example 32) Characterization of Double-Stranded Polynucleotide-Encapsulated Nucleic Acid Lipid Particle The nucleic acid lipid particle-containing dispersion prepared in Example 31 was characterized. Each characterization method will be described.

(1) Average Particle Size

The particle size of the liposome was measured using Zeta Potential/Particle Sizer NICOMP™ 380ZLS (Particle Sizing Systems, LLC). In the tables, the average particle size is indicated by a volume-average particle size, and the numeric value following ±represents a deviation.

(2) Rate of Encapsulation of Double-Stranded Polynucleotide

The rate of encapsulation of the double-stranded polynucleotide was measured using Quant-iT RiboGreen RNA Assay kit (Invitrogen Corp.) according to the attached document.

Specifically, the double-stranded polynucleotide in the nucleic acid lipid particle dispersion was quantified in the presence and absence of a 0.015% Triton X-100 detergent, and the rate of encapsulation was calculated according to the following expression:

{[Amount of the double-stranded polynucleotide in the presence of the detergent]−[Amount of the double-stranded polynucleotide in the absence of the detergent]}/[Amount of the double-stranded polynucleotide in the presence of the detergent]}×100(%)

(3) Ratio of Double-Stranded Polynucleotide to Lipid

The nucleic acid lipid particle dispersion was mixed with acetonitrile and chloroform at a ratio of 1:1:1 and centrifuged at 15,000 rpm for 2 minutes. Then, the aqueous layer obtained as an upper layer was recovered, followed by the extraction of the double-stranded polynucleotide. The amount of the double-stranded polynucleotide in the sample was measured by ion-exchange chromatography (system: Agilent 1100 series, column: TSKgel DEAE-2SW (2.6×150 mm) (Tosoh Corp), buffer A: 20% acetonitrile, buffer B: 20% acetonitrile and 1.6 M ammonium formate, gradient (B %): 30-55% (0-20 min), flow rate: 1 mL/min, temperature: 40° C., detection: 260 nm).

The amount of the phospholipid in the nucleic acid lipid particle dispersion was measured using Phospholipid C-Test Wako (Wako Pure Chemical Industries Ltd.) according to the attached document. Specifically, the phospholipid in the sample was quantified in the presence of a 1% Triton X-100 detergent.

The amounts of cholesterol and LP in the nucleic acid lipid particle dispersion were measured by reverse-phase chromatography (system: Agilent 1100 series, column: Chromolith Performance RP-18 endcapped 100-3 monolithic HPLC-column (Merck), buffer A: 0.01% trifluoroacetic acid, buffer B: 0.01% trifluoroacetic acid and methanol, gradient (B %): 87-92% (0-10 min), flow rate: 2 mL/min, temperature: 50° C., detection: 205 nm).

The total amount of lipids was calculated from the amount of the phospholipid and the compositional ratio of lipid components constituting the liposome, and the ratio of the polynucleotide to the lipid was calculated from the aforementioned amount of the polynucleotide and the total amount of lipids according to the following expression:

[Double-stranded polynucleotide concentration]/[Total lipid concentration] (wt/wt)

The results are shown in Table 3.

TABLE 3

| LP name | Rate of polynucleotide encapsulation (%) | Ratio of polynucleotide to lipid siRNA/lipid (wt/wt) | Average particle size (nm) |
|---|---|---|---|
| Reference Example 2 | 89.0 | 0.104 | 139 ± 50 |
| Example 1 | 94.3 | 0.109 | 183 ± 41 |
| Example 2 | 96.3 | 0.099 | 215 ± 70 |
| Example 3 | 98.6 | 0.099 | 187 ± 31 |

The total amount of lipids was calculated from the amount of the phospholipid, the amount of cholesterol, and the amount of LP, and the compositional ratio of lipid components constituting the liposome, and the ratio of the polynucleotide to the lipid was calculated from the aforementioned amount of the polynucleotide and the total amount of lipids according to the following expression:

[Double-stranded polynucleotide concentration]/[Total lipid concentration] (wt/wt)

The results are shown in Table 4.

TABLE 4

| LP name | Rate of polynucleotide encapsulation (%) | Ratio of polynucleotide to lipid siRNA/lipid (wt/wt) | Average particle size (nm) |
|---|---|---|---|
| Compound 1 | 93.0 | 0.075 | 138 ± 24 |
| Example 8 | 96.4 | 0.072 | 157 ± 46 |

These results showed that the double-stranded polynucleotide was encapsulated in the lipid particle, and this nucleic acid lipid particle had an average particle size of approximately 100 nm to approximately 300 nm.

Test Example 1

As described below, the strength of human β-catenin gene expression inhibitory activity was compared among nucleic acid lipid particles each prepared using a novel lipid.

(1) Transfection

The concentration of a human colorectal cancer SW480 cell line (derived from human colorectal adenocarcinoma) was adjusted to 50,000 cells/mL in an RPMI1640 medium (manufactured by Invitrogen Corp.) containing 10% fetal bovine serum (culture medium). Then, the resulting culture solution was inoculated at 100 μL/well to a 96-well flat-bottomed plate (manufactured by Corning Inc./Falcon) and cultured at 37° C. for 1 day under 5.0% $CO_2$. The nucleic acid lipid particle dispersion prepared in Example 31 was diluted with a culture medium to prepare dilution series having final double-stranded polynucleotide concentrations of 30, 3.0, 0.3, and 0.03 nM in the medium. Then, each dilution was added to the cells after removal of the culture supernatant, and the culture was further continued for 3 days. This operation was performed at N=3 for each concentration.

(2) Real-Time PCR

A lysate and cDNA for real-time PCR measurement were prepared from the transfected cells using TaqMan® Fast-Cells-to-Ct kit (Life Technologies, Inc./Ambion) according to the instruction manual. In the lysate preparation, Lysis Solution supplemented with DNase I was used. The probes for real-time PCR used were TaqMan® Gene Expression Assays (CTNNB1, FAM probe) (Hs00355045_m1, manufactured by Applied Biosystems, Inc.) for the human β-catenin gene and a human GAPDH gene probe as an internal standard (VIC probe, Hs99999905_m1, manufactured by Applied Biosystems, Inc.). 5 μL of TaqMan® Fast Advanced Master Mix, 2 μL of RNase-Free Water, 0.5 μL of each gene probe, and 2 μL of the prepared cDNA solution were added per well of a 384-well PCR plate (manufactured by Applied Biosystems, Inc.) to bring the total amount to 10 μL, which was then loaded in ViiA™ 7 Real-time PCR system (manufactured by Applied Biosystems, Inc.) and subjected to PCR under conditions given below. The real-time PCR was carried out at N=4 for the cDNA prepared from the lysate.

PCR initial activation: 95° C. for 20 seconds
PCR: 95° C. for 1 second
62° C. for 20 seconds
This PCR cycle was repetitively performed 40 times.

(3) Real-Time PCR Analysis

The quantitative analysis was conducted by the ΔΔCt method. A value (ΔΔCt) was determined by subtracting ΔCt of an untreated cell (=NC) from the difference in Ct value (ΔCt) between human β-catenin and human GAPDH of each transfectant, and a relative value (RQ) to NC was calculated according to the following expression:

$$RQ = 2^{-\Delta\Delta Ct}$$

When RQ=1 was defined as 0% rate of inhibition and RQ=0 was defined as theoretical 100% rate of inhibition, the $IC_{50}$ value of the nucleic acid lipid particle was calculated using GraphPad PRISM (GraphPad Software Inc.). As a result, as shown in Table 5, the nucleic acid lipid particle containing the compound of Example 1, 2, or 3 exhibited strong inhibitory activity against β-catenin gene expression, as compared with the nucleic acid lipid particle containing the lipid of Reference Example 2 used as a control. These results demonstrated that the compounds of Examples 1, 2, and 3 are novel lipids useful for preparing nucleic acid lipid particles that exhibit strong activity.

TABLE 5

| | β-catenin gene expression inhibitory activity IC50 (nM) |
|---|---|
| Reference Example 2 | >30 |
| Example 1 | 3.5 |

TABLE 5-continued

| | β-catenin gene expression inhibitory activity IC50 (nM) |
|---|---|
| Example 2 | 6.8 |
| Example 3 | 0.44 |

Test Example 2

As described below, the strength of human β-catenin gene expression inhibitory activity was compared among nucleic acid lipid particles each prepared using a novel lipid.

(1) Transfection

The concentration of a human liver cancer HepG2 cell line (derived from human liver cancer) was adjusted to 50000 cells/mL in a DMEM medium (manufactured by Invitrogen Corp.) containing 10% fetal bovine serum (culture medium). Then, the resulting culture solution was inoculated at 100 μL/well to a 96-well flat-bottomed plate (manufactured by Corning Inc./Falcon) and cultured at 37° C. for 1 day under 5.0% $CO_2$. The nucleic acid lipid particle-containing dispersion prepared in Example 31 was diluted with a culture medium to prepare dilution series having final double-stranded polynucleotide concentrations of 30, 3, 0.3, and 0.03 nM in the medium. Then, each dilution was added to the cells after removal of the culture supernatant, and the culture was further continued for 3 days. This operation was performed at N=3 for each concentration.

(2) Real-time PCR

A lysate and cDNA for real-time PCR measurement were prepared from the transfected cells using TaqMan® Fast-Cells-to-Ct kit (Life Technologies, Inc./Ambion) according to the instruction manual. In the lysate preparation, Lysis Solution supplemented with DNase I was used. The probes for real-time PCR used were TaqMan® Gene Expression Assays (CTNNB1, FAM probe) (Hs00355045_m1, manufactured by Applied Biosystems, Inc.) for the human β-catenin gene and a human GAPDH gene probe as an internal standard (VIC probe, Hs99999905_m1, manufactured by Applied Biosystems, Inc.). 5 μL of TaqMan® Fast Advanced Master Mix, 2 μL of RNase-Free Water, 0.5 μL of each gene probe, and 2 μL of the prepared cDNA solution were added per well of a 384-well PCR plate (manufactured by Applied Biosystems, Inc.) to bring the total amount to 10 μL, which was then loaded in ViiA™ 7 Real-time PCR system (manufactured by Applied Biosystems, Inc.) and subjected to PCR under conditions given below. The real-time PCR was carried out at N=4 for the cDNA prepared from the lysate.

PCR initial activation: 95° C. for 20 seconds
PCR: 95° C. for 1 second
62° C. for 20 seconds
This PCR cycle was repetitively performed 40 times.

(3) Real-Time PCR Analysis

The quantitative analysis was conducted by the ΔΔCt method. A value (ΔΔCt) was determined by subtracting ΔCt of an untreated cell (=NC) from the difference in Ct value (ΔCt) between human β-catenin and human GAPDH of each transfectant, and a relative value (RQ) to NC was calculated according to the following expression:

$$RQ = 2^{-\Delta\Delta Ct}$$

When RQ=1 was defined as 0% rate of inhibition and RQ=0 was defined as theoretical 100% rate of inhibition, the $IC_{50}$ value of the nucleic acid lipid particle was calculated using GraphPad PRISM (GraphPad Software Inc.). As a result, as shown in Table 6, the nucleic acid lipid particle containing the compound of Example 1, 2, or 3 exhibited strong inhibitory activity against β-catenin gene expression, as compared with the nucleic acid lipid particle containing the lipid of Reference Example 2 used as a control. These results demonstrated that the compounds of Examples 1, 2, and 3 are novel lipids useful for preparing nucleic acid lipid particles that exhibit strong activity.

TABLE 6

| | β-catenin gene expression inhibitory activity IC50 (nM) |
|---|---|
| Reference Example 2 | >30 |
| Example 1 | 0.38 |
| Example 2 | 0.47 |
| Example 3 | 0.35 |

Test Example 3

As described below, the strength of human β-catenin gene expression inhibitory activity was compared among nucleic acid lipid particles each prepared using a novel lipid.
(1) Transfection The concentration of a human colorectal cancer SW480 cell line (derived from human colorectal adenocarcinoma) was adjusted to 50000 cells/mL in a RPMI1640 medium (manufactured by Invitrogen Corp.) containing 10% fetal bovine serum (culture medium). Then, the resulting culture solution was inoculated at 100 μL/well to a 96-well flat-bottomed plate (manufactured by Corning Inc./Falcon) and cultured at 37° C. for 1 day under 5.0% $CO_2$. The nucleic acid lipid particle-containing dispersion prepared in Example 31 was diluted with a culture medium to prepare dilution series having final double-stranded polynucleotide concentrations of 30, 3, 0.3, and 0.03 nM in the medium. Then, each dilution was added to the cells after removal of the culture supernatant, and the culture was further continued for 4 hours. This operation was performed at N=3 for each concentration.
(2) Real-time PCR A lysate and cDNA for real-time PCR measurement were prepared from the transfected cells using TaqMan® Fast-Cells-to-Ct kit (Life Technologies, Inc./Ambion) according to the instruction manual. In the lysate preparation, Lysis Solution supplemented with DNase I was used. The probes for real-time PCR used were TaqMan® Gene Expression Assays (CTNNB1, FAM probe) (Hs00355045_m1, manufactured by Applied Biosystems, Inc.) for the human β-catenin gene and a human GAPDH gene probe as an internal standard (VIC probe, Hs99999905_m1, manufactured by Applied Biosystems, Inc.). 5 μL of TaqMan® Fast Advanced Master Mix, 2 μL of RNase-Free Water, 0.5 μL of each gene probe, and 2 μL of the prepared cDNA solution were added per well of a 384-well PCR plate (manufactured by Applied Biosystems, Inc.) to bring the total amount to 10 μL, which was then loaded in ViiA™ 7 Real-time PCR system (manufactured by Applied Biosystems, Inc.) and subjected to PCR under conditions given below. The real-time PCR was carried out at N=4 for the cDNA prepared from the lysate.
  PCR initial activation: 95° C. for 20 seconds
  PCR: 95° C. for 1 second
  62° C. for 20 seconds
This PCR cycle was repetitively performed 40 times.

(3) Real-Time PCR Analysis

The quantitative analysis was conducted by the ΔΔCt method. A value (ΔΔCt) was determined by subtracting ΔCt of an untreated cell (=NC) from the difference in Ct value (ΔCt) between human β-catenin and human GAPDH of each transfectant, and a relative value (RQ) to NC was calculated according to the following expression:

$$RQ = 2^{-\Delta\Delta Ct}$$

When RQ=1 was defined as 0% rate of inhibition and RQ=0 was defined as theoretical 100% rate of inhibition, the $IC_{50}$ value of the nucleic acid lipid particle was calculated using GraphPad PRISM (GraphPad Software Inc.). As a result, as shown in Table 7, the nucleic acid lipid particle containing the compound of Example 8 exhibited strong inhibitory activity against β-catenin gene expression, as compared with the nucleic acid lipid particle containing the lipid compound 1 used as a control. These results demonstrated that the compound of Example 8 is a novel lipid useful for preparing nucleic acid lipid particles that exhibit strong activity.

TABLE 7

| | β-catenin gene expression inhibitory activity IC50 (nM) |
|---|---|
| Compound 1 | >30 |
| Example 8 | 8.3 |

Test Example 4

As described below, the strength of human β-catenin gene expression inhibitory activity was compared among nucleic acid lipid particles each prepared using a novel lipid.
(1) Transfection The concentration of a human uterine cervix cancer Hela cell line (derived from human uterine cervix cancer) was adjusted to 50000 cells/mL in a DMEM medium (manufactured by Invitrogen Corp.) containing 10% fetal bovine serum (culture medium). Then, the resulting culture solution was inoculated at 100 μL/well to a 96-well flat-bottomed plate (manufactured by Corning Inc./Falcon) and cultured at 37° C. for 1 day under 5.0% $CO_2$. The nucleic acid lipid particle-containing dispersion prepared in Example 31 was diluted with a culture medium to prepare dilution series having final double-stranded polynucleotide concentrations of 30, 3, 0.3, and 0.03 nM in the medium. Then, each dilution was added to the cells after removal of the culture supernatant, and the culture was further continued for 4 hours. This operation was performed at N=3 for each concentration.
(2) Real-Time PCR A lysate and cDNA for real-time PCR measurement were prepared from the transfected cells using TaqMan® Fast-Cells-to-Ct kit (Life Technologies, Inc./Ambion) according to the instruction manual. In the lysate preparation, Lysis Solution supplemented with DNase I was used. The probes for real-time PCR used were TaqMan® Gene Expression Assays (CTNNB1, FAM probe) (Hs00355045_m1, manufactured by Applied Biosystems, Inc.) for the human β-catenin gene and a human GAPDH gene probe as an internal standard (VIC probe, Hs99999905_m1, manufactured by Applied Biosystems, Inc.). L of TaqMan® Fast Advanced Master Mix, 2 μL of RNase-Free Water, 0.5 μL of each gene probe, and 2 μL of the prepared cDNA solution were added per well of a 384-well PCR plate (manufactured by Applied Biosystems, Inc.) to bring the total amount to 10 μL, which was then loaded in ViiA™ 7 Real-time PCR system (manufactured by Applied Biosystems, Inc.) and subjected to PCR under conditions given below. The real-time PCR was carried out at N=4 for the cDNA prepared from the lysate.

PCR initial activation: 95° C. for 20 seconds
PCR: 95° C. for 1 second
62° C. for 20 seconds
This PCR cycle was repetitively performed 40 times.

(3) Real-Time PCR Analysis

The quantitative analysis was conducted by the ΔΔCt method. A value (ΔΔCt) was determined by subtracting ΔCt of an untreated cell (=NC) from the difference in Ct value (ΔCt) between human β-catenin and human GAPDH of each transfectant, and a relative value (RQ) to NC was calculated according to the following expression:

$$RQ = 2^{-\Delta\Delta Ct}$$

When RQ=1 was defined as 0% rate of inhibition and RQ=0 was defined as theoretical 100% rate of inhibition, the $IC_{50}$ value of the nucleic acid lipid particle was calculated using GraphPad PRISM (GraphPad Software Inc.). As a result, as shown in Table 8, the nucleic acid lipid particle containing the compound of Example 8 exhibited strong inhibitory activity against β-catenin gene expression, as compared with the nucleic acid lipid particle containing the lipid compound 1 used as a control. These results demonstrated that the compound of Example 8 is a novel lipid useful for preparing nucleic acid lipid particles that exhibit strong activity.

TABLE 8

|  | β-catenin gene expression inhibitory activity IC50 (nM) |
| --- | --- |
| Compound 1 | 20 |
| Example 8 | 2.2 |

(Test Example 5) Measurement of Cell Growth Inhibitory Activity of Compound of Example Against Hep3B Cell (Human Liver Cancer Cell)

The medium used is MEM (manufactured by Invitrogen Corp.) (containing 10% fetal bovine serum (manufactured by HyClone Laboratories, Inc.), 1 mM sodium pyruvate (manufactured by Invitrogen Corp.), and 1× non-essential amino acids (manufactured by Invitrogen Corp.)). Human liver cancer cell line Hep3B cells having a given density are placed (150 μL/well) in a 96-well plate and subsequently cultured at 37° C. for 24 hours under 5% $CO_2$. The nucleic acid lipid particle-containing dispersion prepared in Example 31 is further added at final concentrations of 0.01, 0.03, 0.1, 0.3, 1, and 3 μM to each well, and the cells are subsequently cultured for 72 hours (3 days). After the culture for 72 hours (3 days), the cell growth inhibitory activity of the compound of each Example is measured using MTT assay. Specifically, 20 μL of a MTT solution (5 mg/mL in phosphate-buffered saline (PBS)) is further added to each well, and the cells are cultured at 37° C. for 4 hours under 5% $CO_2$. After removal of the culture supernatant, DMSO (150 μL) is further added to each well, followed by shaking for 5 minutes. The absorbance (540 nm) from the plate is measured using a plate reader (SpectraMax Plus[384], manufactured by Molecular Devices Corporation). The relative ratio between the number of live cells in the compound administration group and the number of live cells in an untreated cell group is determined. Then, the $IC_{50}$ concentration at which of the growth of cells is inhibited by 50% is calculated.

(Test Example 6) In Vivo Antitumor Test of Compound of Example

After acclimatization and raising of each nude mouse for 1 week, 1×10[7] cultured human Hep3B cells are subcutaneously transplanted to the lateral region of the nude mouse. Approximately 2 weeks after the tumor transplantation, the mice are grouped with the tumor volume as an index, and the nucleic acid lipid particle-containing dispersion prepared in Example 31 is intravenously administered (administered at a dose such as 1 or 3 mg/kg) twice or three times a week to the tail of each mouse. PBS is administered to a control group. The tumor size is measured, and changes in tumor volume are observed.

In the case of verifying an in vivo knockdown effect, on the day after the administration, a tumor mass is collected from the cancer-bearing mouse, and a nucleic acid is extracted using QIAzol Lysis Reagent (manufactured by Qiagen N.V.) and chloroform. Then, total RNA is purified using RNeasy mini kit (manufactured by Qiagen N.V.) according to the attached protocol. This is used to quantify the mRNA of the target molecule by Taqman PCR.

(Example 33) Preparation of Double-Stranded Polynucleotide-Encapsulated Nucleic Acid Lipid Particle A lipid solution having a total lipid concentration of 26.8 mM in ethanol with distearoylphosphatidylcholine (1,2-distearoyl-sn-glycero-3-phosphocholine: hereinafter, referred to as DSPC, NOF CORPORATION), cholesterol (hereinafter, referred to as Chol, Sigma-Aldrich, Inc.), the compound described in Example 8 (hereinafter, referred to as LP), and N-[methoxy poly(ethylene glycol)2000]carbamoyl]-1,2-dimyristyloxypropyl-3-amine (hereinafter, referred to as PEG-C-DMA) were prepared at a molar ratio described in Table 9.

The concentration of a double-stranded polynucleotide described in Nature Biotechnology (2008) 26, 561-569 (siFVII: siRNA against mouse Factor VII) was adjusted to 1 mg/mL with a citrate buffer solution (10 mM citrate buffer, pH 4.0) containing 30% ethanol to obtain a double-stranded polynucleotide solution.

The lipid solution, the double-stranded polynucleotide solution, and a citrate buffer solution (20 mM citrate buffer, pH 4.0) were heated to 37° C. The lipid solution was added dropwise to the citrate buffer solution (20 mM citrate buffer, pH 4.0) and mixed therewith such that the volume ratio between the lipid solution and the citrate buffer solution was 3:7 to obtain a crude liposome dispersion. Subsequently, the crude liposome dispersion was added dropwise to the double-stranded polynucleotide solution and mixed therewith such that the ratio (N/P) of LP-derived nitrogen atoms (N) to double-stranded polynucleotide-derived phosphorus atoms (P) was 3. The mixture was incubated at 37° C. for 30 minutes to obtain a nucleic acid lipid particle dispersion. The nucleic acid lipid particle dispersion was dialyzed against approximately 100 mL of a phosphate buffer solution (pH 7.4) for 12 to 18 hours (Float-A-Lyzer G2, MWCO: 100 kD, Spectra/Por) for the removal of ethanol and the removal of unencapsulated double-stranded polynucleotides by neutralization to obtain a purified dispersion of a nucleic acid lipid particle containing the double-stranded polynucleotide and the lipid described in Table 9.

TABLE 9

|  | DSPC | Chol | LP | PEG-C-DMA |
|---|---|---|---|---|
| Particle 1 | 10 | 68 | 20 | 2 |
| Particle 2 | 10 | 58 | 30 | 2 |
| Particle 3 | 10 | 48 | 40 | 2 |
| Particle 4 | 10 | 43 | 45 | 2 |
| Particle 5 | 10 | 38 | 50 | 2 |
| Particle 6 | 10 | 33 | 55 | 2 |
| Particle 7 | 10 | 28 | 60 | 2 |
| Particle 8 | 10 | 18 | 70 | 2 |
| Particle 9 | 55 | 33 | 10 | 2 |
| Particle 10 | 45 | 33 | 20 | 2 |
| Particle 11 | 35 | 33 | 30 | 2 |
| Particle 12 | 25 | 33 | 40 | 2 |
| Particle 13 | 20 | 33 | 45 | 2 |
| Particle 14 | 15 | 33 | 50 | 2 |
| Particle 15 | 10 | 33 | 55 | 2 |
| Particle 16 | 5 | 33 | 60 | 2 |
| Particle 17 | 0 | 33 | 65 | 2 |
| Particle 18 | 10 | 49.5 | 40 | 0.5 |
| Particle 19 | 10 | 49 | 40 | 1 |
| Particle 20 | 10 | 48.5 | 40 | 1.5 |
| Particle 21 | 10 | 48 | 40 | 2 |
| Particle 22 | 10 | 47.5 | 40 | 2.5 |
| Particle 23 | 10 | 47 | 40 | 3 |
| Particle 24 | 10 | 46.5 | 40 | 3.5 |
| Particle 25 | 10 | 46 | 40 | 4 |
| Particle 26 | 10 | 45 | 40 | 5 |
| Particle 27 | 10 | 40 | 40 | 10 |

(Example 34) Characterization of Double-Stranded Polynucleotide-Encapsulated Nucleic Acid Lipid Particle The nucleic acid lipid particle dispersion prepared in Example 33 was characterized. The characterization was conducted by the methods described in Example 32, and the rate of polynucleotide encapsulation in the nucleic acid lipid particle described in Example 33, the weight ratio of the polynucleotide to the lipid, and the average particle size are shown in Tables 10, 11, and 12.

TABLE 10

|  | Lipid composition* | Rate of encapsulation (%) | siRNA/lipid (wt/wt)** | Particle size (nm) |
|---|---|---|---|---|
| Particle 1 | 10/68/20/2 | 96 | 0.044 | 133 ± 23 |
| Particle 2 | 10/58/30/2 | 98 | 0.061 | 153 ± 46 |
| Particle 3 | 10/48/40/2 | 98 | 0.083 | 127 ± 20 |
| Particle 4 | 10/43/45/2 | 98 | 0.084 | 143 ± 41 |
| Particle 5 | 10/38/50/2 | 98 | 0.094 | 133 ± 27 |
| Particle 6 | 10/33/55/2 | 94 | 0.115 | 137 ± 10 |
| Particle 7 | 10/28/60/2 | 81 | 0.117 | 184 ± 39 |
| Particle 8 | 10/18/70/2 | 50 | 0.127 | 162 ± 31 |

*Lipid composition: DSPC/Chol/LP/PEG-C-DMA (molar ratio)
**siRNA/lipid (wt/wt): weight ratio of polynucleotide to lipid

TABLE 11

|  | Lipid composition * | Rate of encapsulation (%) | siRNA/lipid (wt/wt) ** | Particle size (nm) |
|---|---|---|---|---|
| Particle 9 | 55/33/10/2 | 93 | 0.014 | 193 ± 42 |
| Particle 10 | 45/33/20/2 | 93 | 0.022 | 206 ± 77 |
| Particle 11 | 35/33/30/2 | 90 | 0.055 | 203 ± 73 |
| Particle 12 | 25/33/40/2 | 93 | 0.084 | 177 ± 59 |
| Particle 13 | 20/33/45/2 | 92 | 0.093 | 109 ± 22 |
| Particle 14 | 15/33/50/2 | 92 | 0.073 | 111 ± 20 |
| Particle 15 | 10/33/55/2 | 95 | 0.111 | 119 ± 13 |
| Particle 16 | 5/33/60/2 | 95 | 0.136 | 135 ± 15 |
| Particle 17 | 0/33/65/2 | 91 | 0.160 | 124 ± 25 |

* Lipid composition: DSPC/Chol/LP/PEG-C-DMA (molar ratio)
** siRNA/lipid (wt/wt): weight ratio of polynucleotide to lipid

TABLE 12

|  | Lipid composition * | Rate of encapsulation (%) | siRNA/lipid (wt/wt) ** | Particle size (nm) |
|---|---|---|---|---|
| Particle 18 | 10/49.5/40/0.5 | 97 | 0.096 | 349 ± 222 |
| Particle 19 | 10/49/40/1 | 96 | 0.091 | 206 ± 54 |
| Particle 20 | 10/48.5/40/1.5 | 97 | 0.098 | 140 ± 54 |
| Particle 21 | 10/48/40/2 | 98 | 0.091 | 109 ± 36 |
| Particle 22 | 10/47.5/40/2.5 | 99 | 0.090 | 140 ± 19 |
| Particle 23 | 10/47/40/3 | 98 | 0.089 | 152 ± 27 |
| Particle 24 | 10/46.5/40/3.5 | 98 | 0.084 | 131 ± 52 |
| Particle 25 | 10/46/40/4 | 98 | 0.086 | 156 ± 66 |
| Particle 26 | 10/45/40/5 | 94 | 0.083 | 79 ± 27 |
| Particle 27 | 10/40/40/10 | 91 | 0.055 | 83 ± 47 |

* Lipid composition: DSPC/Chol/LP/PEG-C-DMA (molar ratio)
** siRNA/lipid (wt/wt): weight ratio of polynucleotide to lipid These results showed that the double-stranded polynucleotide was encapsulated in the lipid particle, and this nucleic acid lipid particle had an average particle size of approximately 80 nm to approximately 300 nm.

(Test Example 7) Factor VII (FVII) Protein Measurement

The Factor VII protein was measured according to a method described in Nature Biotechnology (2010) 28, 172-176. $C_{57}BL6/J$ mice (male, 9 weeks old) were randomly grouped (n=4). The nucleic acid lipid particle dispersion prepared in Example 33 was intravenously injected at a dose of 0.3 mg/kg to the tail of each mouse. One day after the administration, approximately 50 µL of blood was collected from the tail vein, and plasma was obtained. The amount of the Factor VII protein in the obtained plasma was measured using Biophen FVII assay kit (manufactured by Aniara Corp.) according to the attached protocol.

When the amount of FVII of respective plasma samples collected in equal amounts from individuals in a PBS administration group was defined as 100%, the relative ratio (%) of the amount of FVII in a plasma sample of each individual was used as a measurement value (A). An average value (B) was determined from the respective measurement values of the individuals in the PBS administration group. The relative ratio of the measurement value (A) of each individual was determined from the expression: A/B×100 (%). The average value of the relative ratios in the administration group of each nucleic acid lipid particle is shown in Tables 13, 14, and 15. As a result, as shown in Tables 13, 14, and 15, particles 1 to 8, particles 12 to 17, particles 20 to 24, particle 26, and particle 27 as the nucleic acid lipid particles prepared in Example 33 exhibited strong FVII inhibitory activity. These results demonstrated that a nucleic acid lipid particle having lipid composition as found in particles 1 to 8, particles 12 to 17, particles 20 to 24, particle 26, and particle 27 is useful as a nucleic acid lipid particle capable of inhibiting gene expression.

TABLE 13

|  | Relative amount of FVII (%) |
|---|---|
| PBS | 100 |
| Particle 1 | 36 |
| Particle 2 | <10 |
| Particle 3 | <10 |
| Particle 4 | 20 |
| Particle 5 | <10 |
| Particle 6 | <10 |
| Particle 7 | <10 |
| Particle 8 | <10 |

TABLE 14

|  | Relative amount of FVII (%) |
|---|---|
| PBS | 100 |
| Particle 10 | No activity |
| Particle 11 | No activity |
| Particle 12 | 79 |
| Particle 13 | 22 |
| Particle 14 | <10 |
| Particle 15 | 26 |
| Particle 16 | <10 |
| Particle 17 | <10 |

TABLE 15

|  | Relative amount of FVII (%) |
|---|---|
| PBS | 100 |
| Particle 18 | No activity |
| Particle 19 | No activity |
| Particle 20 | <10 |
| Particle 21 | <10 |
| Particle 22 | <10 |
| Particle 23 | <10 |
| Particle 24 | 27 |
| Particle 26 | 28 |
| Particle 27 | 49 |

Reference Example 46

3-Bromopropyl(9Z,12Z)-octacosa-19,22-dien-11-yl Carbonate

A solution of (19Z,22Z)-octacosa-19,22-dien-11-ol (0.55 g, 1.4 mmol) obtained in Reference Example 17 and pyridine (0.67 g, 8.5 mmol) in toluene (14 mL) was cooled to 0° C. in an ice bath, and a solution of triphosgene (0.28 g, 0.93 mmol) in toluene (2.0 mL) was added thereto over 2 minutes. After stirring at 0° C. for 15 minutes, the reaction mixture was heated to room temperature, stirred at for 1 hour, and cooled to 0° C. again. 3-Bromo-1-propanol (2.0 g, 14 mmol) was added thereto, and the mixture was reacted overnight at room temperature. After treatment with a saturated aqueous solution of sodium bicarbonate, the reaction mixture was subjected to extraction with ethyl acetate-hexane, and the obtained organic layer was dried over anhydrous magnesium sulfate. The solvent was distilled off under reduced pressure, and the residue was then subjected to silica gel column chromatography to obtain the compound of interest as a colorless liquid (0.32 g, 41%).

$^1$H-NMR (400 MHz, CDCl$_3$) δ: 0.85-0.91 (6H, m), 1.21-1.40 (32H, m), 1.52-1.61 (4H, m), 2.01-2.09 (4H, m), 2.23 (2H, quint, J=6.3 Hz), 2.77 (2H, t, J=6.6 Hz), 3.49 (2H, t, J=6.3 Hz), 4.27 (2H, t, J=6.3 Hz), 4.66-4.73 (1H, m), 5.29-5.44 (4H, m).

Example 35

3-(Azetidin-1-yl)propyl(9Z,12Z)-octacosa-19,22-dien-11-yl Carbonate (Exemplary Compound 1-76)

To a solution of 3-bromopropyl(9Z,12Z)-octacosa-19,22-dien-11-yl carbonate (0.16 g, 0.28 mmol) obtained in Reference Example 46 in tetrahydrofuran (8.0 mL), azetidine (0.40 g, 7.0 mmol) was added, and the mixture was reacted at 120° C. for 50 minutes under microwave irradiation. After treatment with a saturated aqueous solution of sodium bicarbonate, the reaction mixture was subjected to extraction with ethyl acetate-hexane, and the obtained organic layer was dried over anhydrous magnesium sulfate. The solvent was distilled off under reduced pressure, and the residue was then subjected to silica gel column chromatography to obtain the compound of interest as a colorless liquid (119 mg, 77%).

$^1$H-NMR (400 MHz, CDCl$_3$) δ: 0.85-0.92 (6H, m), 1.21-1.40 (32H, m), 1.47-1.61 (4H, m), 1.71 (2H, tt, J=6.6, 7.4 Hz), 2.01-2.10 (m, 6H), 2.46 (2H, t, J=7.4 Hz), 2.77 (2H, t, J=6.6 Hz), 3.16 (4H, t, J=6.6 Hz), 4.15 (2H, t, J=6.6 Hz), 4.64-4.71 (1H, m), 5.28-5.42 (4H, m).

MS (ESI+) m/z 548 [M+H]$^+$

HRMS (ESI+) m/z 548.5044 (0.1 mDa).

Example 36

(1-Methylpiperidin-3-yl)methyl(6Z,9Z,26Z,29Z)-pentatriaconta-6,9,26,29-tetraen-18-yl Carbonate (Exemplary Compound 2-102)

A solution of (6Z,9Z,26Z,29Z)-pentatriaconta-6,9,26,29-tetraen-18-ol (0.22 g, 0.44 mmol) obtained in Reference Example 4 and pyridine (0.22 g, 2.8 mmol) in toluene (4.4 mL) was cooled to 0° C. in an ice bath, and a solution of triphosgene (0.090 g, 0.30 mmol) in toluene (0.66 mL) was added thereto over 2 minutes. After stirring at 0° C. for 15 minutes, the reaction mixture was heated to room temperature, stirred for 1 hour, and cooled to 0° C. again. (1-Methyl-3-piperidyl)methanol (0.60 g, 4.6 mmol) was added thereto, and the mixture was reacted overnight at room temperature. After treatment with a saturated aqueous solution of sodium bicarbonate, the reaction mixture was subjected to extraction with ethyl acetate-hexane, and the obtained organic layer was dried over anhydrous magnesium sulfate. The solvent was distilled off under reduced pressure, and the residue was then subjected to silica gel column chromatography to obtain the compound of interest as a colorless liquid (201 mg, 70%).

$^1$H-NMR (400 MHz, CDCl$_3$) δ: 0.89 (6H, m), 0.92-1.04 (1H, m), 1.21-1.40 (36H, m), 1.48-1.78 (8H, m), 1.85-1.94 (1H, m), 1.96-2.10 (9H, m), 2.26 (3H, s), 2.77 (4H, t, J=6.6 Hz), 2.72-2.90 (2H, m), 3.94 (1H, dd, J=7.4, 10.6 Hz), 4.05 (1H, dd, J=5.5, 10.6 Hz), 4.64-4.72 (1H, m), 5.28-5.42 (8H, m).

MS (ESI+) m/z 656 [M+H]$^+$

HRMS (ESI+) m/z 656.5981 (−0.1 mDa).

Example 37

3-(Dimethylamino)propyl(19Z,22R)-22-(tetrahydro-2H-pyran-2-yloxy)octacos-19-en-11-yl Carbonate (Exemplary Compound 1-334)

To a solution of 3-(dimethylamino)propyl(19Z,22R)-22-hydroxyoctacos-19-en-11-yl carbonate (0.21 g, 0.38 mmol) obtained in Example 27 and p-toluenesulfonic acid monohydrate (0.079 g, 0.42 mmol) in dichloromethane (3.8 mL), 3,4-dihydro-2H-pyran (0.16 g, 1.9 mmol) was added, and the mixture was reacted at room temperature for 3 hours. After treatment with a saturated aqueous solution of sodium bicarbonate, the reaction mixture was subjected to extraction, and the obtained organic layer was dried over anhydrous magnesium sulfate. The solvent was distilled off under reduced pressure, and the residue was then subjected to silica gel column chromatography to obtain the compound of interest as a colorless liquid (210 mg, 87%).

$^1$H-NMR (400 MHz, CDCl$_3$) δ: 0.85-0.91 (6H, m), 1.22-1.85 (48H, m), 1.84 (2H, tt, J=6.7, 7.4 Hz), 1.98-2.06 (2H, m), 2.22 (6H, s), 2.36 (2H, t, J=7.4 Hz), 3.44-3.52 (1H, m), 3.57-3.72 (1H, m), 3.87-3.97 (1H, m), 4.18 (2H, t, J=6.7 Hz), 4.64-4.75 (2H, m), 5.32-5.50 (2H, m).

MS (ESI+) m/z 638 [M+H]$^+$

HRMS (ESI+) m/z 638.5723 (1.6 mDa).

Reference Example 47

(19Z,22R)-22-Hydroxyoctacos-19-en-11-one

To (19Z,22R)-22-{[tert-butyl(dimethyl)silyl]oxy}octacos-19-en-li-one (2.0 g, 3.7 mmol) obtained in Reference Example 38, a 1 M solution of tetra-n-butylammonium fluoride in tetrahydrofuran was added, and the mixture was reacted at room temperature for 5 hours. After water treatment to terminate the reaction, the reaction mixture was subjected to extraction with hexane, and the obtained organic layer was subjected to silica gel column chromatography to obtain a liquid containing the compound of interest (0.66 g). The product was used directly in the next reaction without being further purified.

Reference Example 48

(7R,9Z)-18-Hydroxyoctacos-9-en-7-yl acetate

To a solution of the mixture containing (19Z,22R)-22-hydroxyoctacos-19-en-11-one (0.33 g) obtained in Reference Example 47 and pyridine (1.1 g, 14 mmol) in dichloromethane (7.1 mL), acetyl chloride (0.56 g, 7.1 mmol) was added dropwise over 1 minute, and the mixture was reacted at room temperature for 1 hour. After water treatment to terminate the reaction, extraction was carried out, and volatile matter was removed under reduced pressure to obtain a liquid mixture. This mixture was dissolved in tetrahydrofuran (2.1 mL) and methanol (2.1 mL). To the solution, sodium borohydride (0.054 g, 1.4 mmol) was added, and the mixture was reacted at room temperature for 1 hour. After treatment with a saturated aqueous solution of ammonium chloride, the reaction mixture was subjected to extraction with ethyl acetate, and the obtained organic layer was subjected to silica gel column chromatography to obtain a liquid containing the compound of interest (0.33 g). The product was used directly in the next reaction without being further purified.

Example 38

(7R,9Z)-18-({[(1-Methylpiperidin-3-yl)methoxy]carbonyl}oxy)octacos-9-en-7-yl Acetate (Exemplary Compound 2-132)

A solution of the mixture containing (7R,9Z)-18-hydroxyoctacos-9-en-7-yl acetate (0.33 g) obtained in Reference Example 48 and pyridine (0.35 g, 4.5 mmol) in toluene (7.1 mL) was cooled to 0° C. in an ice bath, and a solution of triphosgene (0.14 g, 0.49 mmol) in toluene (1.1 mL) was added thereto over 1 minute. After stirring at 0° C. for 10 minutes, the reaction mixture was heated to room temperature, stirred for 30 minutes, and cooled to 0° C. again. (1-Methyl-3-piperidyl)methanol (0.96 g, 7.4 mmol) was added thereto, and the mixture was reacted at room temperature for 90 minutes. After treatment with a saturated aqueous solution of sodium bicarbonate, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (110 mg).

$^1$H-NMR (400 MHz, CDCl$_3$) δ: 0.86-0.91 (6H, m), 0.93-1.05 (1H, m), 1.17-1.38 (36H, m), 1.48-1.78 (8H, m), 1.85-1.94 (1H, m), 1.96-2.07 (6H, m), 2.24-2.34 (5H, m), 2.74 (1H, d, J=10.5 Hz), 2.86 (1H, d, J=10.5 Hz), 3.95 (1H, ddd, J=2.7, 7.4, 10.2 Hz), 4.06 (1H, ddd, J=2.7, 5.9, 10.2 Hz), 4.64-4.71 (1H, m), 4.87 (1H, quint, J=6.3 Hz), 5.27-5.37 (1H, m), 5.43-5.51 (1H, m).

MS (ESI+) m/z 622 [M+H]$^+$

HRMS (ESI+) m/z 622.5438 (2.8 mDa).

Reference Example 49

(7R,9Z)-18-Hydroxyoctacos-9-en-7-yl Caproate

To a solution of the mixture containing (19Z,22R)-22-hydroxyoctacos-19-en-11-one (0.30 g) obtained in Reference Example 47 and pyridine (1.1 g, 14 mmol) in dichloromethane (7.1 mL), caproic anhydride (0.76 g, 3.5 mmol) was added dropwise over 1 minute, then 4-(dimethylamino)pyridine (0.01 g) was added, and the mixture was reacted at room temperature for 90 minutes. After treatment with a saturated aqueous solution of sodium bicarbonate, extraction was carried out, and volatile matter was removed under reduced pressure to obtain a liquid mixture. This mixture was dissolved in tetrahydrofuran (2.1 mL) and methanol (2.1 mL). To the solution, sodium borohydride (0.054 g, 1.4 mmol) was added, and the mixture was reacted at room temperature for 4 hours. After treatment with a saturated aqueous solution of ammonium chloride, the reaction mixture was subjected to extraction with ethyl acetate, and the obtained organic layer was subjected to silica gel column chromatography to obtain a liquid containing the compound of interest (0.17 g). The product was used directly in the next reaction without being further purified.

Example 39

(7R,9Z)-18-({[3-(Dimethylamino)propyloxy]carbonyl}oxy)octacos-9-en-7-yl Caproate (Exemplary Compound 1-255)

A solution of the mixture containing (7R,9Z)-18-hydroxyoctacos-9-en-7-yl caproate (0.17 g) obtained in Reference Example 49 and pyridine (0.16 g, 2.0 mmol) in toluene (3.3 mL) was cooled to 0° C. in an ice bath, and a solution of triphosgene (0.067 g, 0.22 mmol) in toluene (0.49 mL) was added thereto over 1 minute. After stirring at 0° C. for 15 minutes, the reaction mixture was heated to room temperature, stirred for 45 minutes, and cooled to 0° C. again. 3-Dimethylamino-1-propanol (0.35 g, 3.4 mmol) was added thereto, and the mixture was reacted overnight at room temperature. After treatment with a saturated aqueous solution of sodium bicarbonate, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (150 mg).

$^1$H-NMR (400 MHz, CDCl$_3$) δ: 0.84-0.92 (9H, m), 1.20-1.38 (40H, m), 1.48-1.66 (8H, m), 1.84 (2H, tt, J=6.6, 7.4 Hz), 1.97-2.04 (2H, m), 2.22 (6H, s), 2.27 (2H, t, J=7.4 Hz), 2.36 (2H, t, J=7.4 Hz), 4.18 (2H, t, J=6.6 Hz), 4.64-4.72 (1H, m), 4.88 (1H, quint, J=6.3 Hz), 5.27-5.37 (1H, m), 5.42-5.51 (1H, m).

MS (ESI+) m/z 652 [M+H]$^+$

HRMS (ESI+) m/z 652.5892 (1.2 mDa).

Example 40

3-(Dimethylamino)propyl(19Z,22R)-22-(tetrahydrofuran-2-yloxy)octacos-19-en-11-yl Carbonate (Exemplary Compound 1-377)

To a solution of 3-(dimethylamino)propyl(19Z,22R)-22-hydroxyoctacos-19-en-11-yl carbonate (0.055 g, 0.099 mmol) obtained in Example 27 and p-toluenesulfonic acid hydrate (0.026 g, 0.14 mmol) in dichloromethane (1.3 mL), 2,3-dihydrofuran (0.044 g, 0.63 mmol) was added, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (33 mg, 53%).

$^1$H-NMR (400 MHz, CDCl$_3$) δ: 0.82-0.88 (6H, m), 1.20-1.62 (48H, m), 1.74-2.05 (8H, m), 2.21 (6H, s), 2.33 (2H, t, J=7.4 Hz), 3.51-4.05 (3H, m), 4.15 (2H, t, J=6.7 Hz), 4.62-4.70 (1H, m), 5.28-5.46 (3H, m).

MS (ESI+) m/z 624 [M+H]$^+$

HRMS (ESI+) m/z 624.5574 (0.7 mDa).

Example 41

(7R,9Z,26Z,29R)-18-({[3-(Dimethylamino)propoxy]carbonyl}oxy)pentatriaconta-9,26-diene-7,29-diyl Dipropionate To a solution of 3-(dimethylamino)propyl(7R,9Z,26Z,29R)-7,29-dihydroxypentatriaconta-9,26-dien-18-yl carbonate (0.35 g, 0.53 mmol) obtained in Example 22 and pyridine (0.83 g, 10.5 mmol) in dichloromethane (5.3 mL), propionic acid chloride (0.49 g, 5.3 mmol) was added, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (260 mg, 64%).

$^1$H-NMR (400 MHz, CDCl$_3$) δ: 0.84-0.91 (6H, m), 1.13 (6H, t, J=7.4 Hz), 1.22-1.39 (36H, m), 1.48-1.61 (8H, m), 1.84 (2H, tt, J=6.6, 7.4 Hz), 2.01 (4H, dd, J=6.6, 7.0 Hz), 2.22 (6H, s), 2.30 (4H, q, J=7.4 Hz), 2.28-2.33 (4H, m), 2.36 (2H, t, J=7.4 Hz), 4.18 (2H, t, J=6.6 Hz), 4.64-4.72 (1H, m), 4.88 (2H, tt, J=5.9, 6.6 Hz), 5.33 (2H, ttd, J=1.2, 7.0, 10.9 Hz), 5.46 (2H, ttd, J=1.2, 7.0, 10.9 Hz).

MS (ESI+) m/z 778 [M+H]$^+$

HRMS (ESI+) m/z 778.6555 (−0.6 mDa).

Reference Example 50

(9Z,12R)-Octadec-9-ene-1,12-diol

To a solution of lithium aluminum hydride (3.87 g, 102 mmol) in tetrahydrofuran (235 mL), methyl (9Z,12R)-12-hydroxyoctadec-9-enoate (31.1 g, 78.4 mmol, compound known by the literature (J. Org. Chem., 2001, 66, 22, 7487-7495)) was added dropwise over 50 minutes, and the mixture was reacted at room temperature for 1.5 hours. After treatment with water (4 mL), ethyl acetate was added thereto, and solid components were filtered off. The solvent was distilled off under reduced pressure, and the residue was then subjected to silica gel column chromatography to obtain the compound of interest as a colorless liquid (17.9 g, 62%).

$^1$H-NMR (400 MHz, CDCl$_3$) δ: 0.88 (3H, t, J=6.6 Hz), 1.21-1.87 (22H, m), 1.98-2.07 (2H, m), 2.20-2.40 (2H, m), 3.44-3.52 (1H, m), 3.58-3.71 (3H, m), 3.87-3.97 (1H, m), 4.64-4.74 (1H, m), 5.33-5.49 (2H, m).

Reference Example 51

(9Z,12R)-12-Hydroxyoctadec-9-en-1-yl Methanesulfonate

A solution of (9Z,12R)-octadec-9-ene-1,12-diol (17.9 g, 48.6 mmol) obtained in Reference Example 50 and triethylamine (5.90 g, 58.3 mmol) in dichloromethane (122 mL) was cooled to 0° C. Methanesulfonyl chloride (6.68 g, 58.3 mmol) was added dropwise thereto over 5 minutes, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure to obtain a yellow liquid containing the compound of interest.

Reference Example 52

(7R,9Z)-18-Bromooctadec-9-en-7-ol

To a solution of the liquid containing (9Z,12R)-12-hydroxyoctadec-9-en-1-yl methanesulfonate (21.6 g, 48.4 mmol, theoretical amount) obtained in Reference Example 51 in diethyl ether (145 mL), a magnesium bromide-diethyl ether complex (31.2 g, 121 mmol) was added, and the mixture was reacted overnight at room temperature. After treatment with ice water, the reaction mixture was subjected to extraction with diethyl ether, and the obtained organic layer was dried over anhydrous magnesium sulfate. The solvent was distilled off under reduced pressure, and the residue was then dissolved in ethanol (100 mL). To the solution, a 2 N aqueous hydrochloric acid solution (80 mL) was added, and the mixture was stirred overnight at room temperature. Volatile matter was distilled off under reduced pressure. The residue was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (14.1 g, 84%).

Reference Example 53

2-{[(7R,9Z)-18-Bromooctadec-9-en-7-yl]oxy}tetrahydro-2H-pyran

To a solution of (7R,9Z)-18-bromooctadec-9-en-7-ol (14.1 g, 40.6 mmol) obtained in Reference Example 52 and p-toluenesulfonic acid hydrate (0.154 g, 0.81 mmol) in dichloromethane (81.2 mL), 3,4-dihydro-2H-pyran (6.83 g, 81.2 mmol) was added, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (15.1 g, 86%).

Reference Example 54

(7R,9Z,28Z,31R)-7,31-Bis(tetrahydro-2H-pyran-2-yloxy)heptatriaconta-9,28-dien-19-ol Dried magnesium (shavings, 0.42 g, 17.4 mmol) was dipped in tetrahydrofuran (3.0 mL). 1,2-Dibromoethane (3 drops) was added thereto, and the mixture was vigorously stirred. After the solution turned black-gray, a solution of 2-{[(7R,9Z)-18-bromooctadec-9-en-7-yl]oxy}tetrahydro-2H-pyran (5.00 g, 11.6 mmol) obtained in Reference Example 53 in tetrahydrofuran (8.5 mL) was added thereto over 1 hour, and the mixture was stirred at room temperature for 3 hours. To this solution, ethyl formate (0.47 g, 5.79 mmol) was added, and the mixture was reacted overnight at room temperature. After water treatment to terminate the reaction, the reaction mixture was subjected to extraction with hexane, and the obtained organic layer was dried over anhydrous magnesium sulfate. The solvent was distilled off under reduced pressure, and the residue was then dissolved in ethanol (25 mL). To the solution, a 5 N aqueous sodium hydroxide solution (5 mL) was added, and the mixture was stirred at room temperature for 1 hour. The reaction mixture was diluted with water and then subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (2.10 g, 50%).

$^1$H-NMR (400 MHz, CDCl$_3$) δ: 0.85-0.91 (6H, m), 1.23-1.62 (52H, m), 1.66-1.89 (4H, m), 1.98-2.07 (4H, m), 2.20-2.41 (4H, m), 3.45-3.52 (2H, m), 3.54-3.71 (3H, m), 3.87-3.98 (2H, m), 4.64-4.75 (2H, m), 5.33-5.50 (4H, m).

Reference Example 55

(7R,9Z,28Z,31R)-7,31-Bis(tetrahydro-2H-pyran-2-yloxy)heptatriaconta-9,28-dien-19-yl 3-(dimethylamino)propyl A solution of (7R,9Z,28Z,31R)-7,31-bis(tetrahydro-2H-pyran-2-yloxy)heptatriaconta-9,28-dien-19-ol (1.00 g, 1.36 mmol) obtained in Reference Example 54 and pyridine (0.68 g, 8.6 mmol) in toluene (13.6 mL) was cooled to 0° C. in an ice bath, and a solution of triphosgene (0.279 g, 0.94 mmol) in toluene (2.05 mL) was added thereto over 2 minutes. After stirring at 0° C. for 15 minutes, the reaction mixture was heated to room temperature, stirred for 1.5 hours, and cooled to 0° C. again. 3-Dimethylamino-1-propanol (1.48 g, 14.3 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (1.00 g, 85%).

$^1$H-NMR (400 MHz, CDCl$_3$) δ: 0.85-0.91 (6H, m), 1.22-1.85 (56H, m), 1.79-1.88 (2H, m), 1.98-2.06 (4H, m), 2.20-2.38 (12H, m), 3.44-3.52 (2H, m), 3.58-3.71 (2H, m), 3.87-3.97 (2H, m), 4.18 (2H, t, J=6.7 Hz), 4.64-4.74 (3H, m), 5.32-5.49 (4H, m).

Reference Example 56

(7R,9Z,28Z,31R)-7,31-Dihydroxyheptatriaconta-9,28-dien-19-yl 3-(dimethylamino)propyl Carbonate To a solution of (7R,9Z,28Z,31R)-7,31-bis(tetrahydro-2H-pyran-2-yloxy)heptatriaconta-9,28-dien-19-yl 3-(dimethylamino)propyl (1.00 g, 1.16 mmol) obtained in Reference Example 55 in ethanol (11.6 mL), a 2 N aqueous hydrochloric acid solution (5.79 mL, 11.6 mmol) was added, and the mixture was reacted at room temperature for 2.5 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.68 g, 84%).

$^1$H-NMR (400 MHz, CDCl$_3$) δ: 0.85-0.91 (6H, m), 1.22-1.61 (48H, m), 1.84 (2H, tt, J=6.6, 7.4 Hz), 2.01-2.08 (4H, m), 2.18-2.24 (10H, m), 2.34 (2H, t, J=7.4 Hz), 3.61 (2H, quint, J=5.9 Hz), 4.18 (2H, t, J=6.6 Hz), 4.64-4.72 (1H, m), 5.36-5.44 (2H, m), 5.52-5.61 (2H, m).

Example 42

(7R,9Z,28Z,31R)-19-({[3-(Dimethylamino)propoxy]carbonyl}oxy)heptatriaconta-9,28-diene-7,31-diyl Diacetate To a solution of (7R,9Z,28Z,31R)-7,31-dihydroxyheptatriaconta-9,28-dien-19-yl 3-(dimethylamino)propyl carbonate (0.68 g, 0.98 mmol) obtained in Reference Example 56 and pyridine (2.3 g, 29 mmol) in dichloromethane (9.8 mL), acetyl chloride (1.2 g, 15 mmol) was added, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (523 mg, 69%).

$^1$H-NMR (400 MHz, CDCl$_3$) δ: 0.85-0.91 (6H, m), 1.20-1.38 (40H, m), 1.48-1.61 (8H, m), 1.85 (2H, tt, J=6.6, 7.4

Hz), 1.98-2.08 (10H, m), 2.22 (6H, s), 2.29 (4H, dt, J=6.3, 6.6 Hz), 2.36 (2H, t, J=7.4 Hz), 4.18 (2H, t, J=6.6 Hz), 4.64-4.72 (1H, m), 4.87 (2H, quint, J=6.3 Hz), 5.36 (1H, ttd, J=1.2, 6.6, 10.9 Hz), 5.47 (1H, ttd, J=1.2, 6.6, 10.9 Hz).

MS (ESI+) m/z 778 [M+H]$^+$
HRMS (ESI+) m/z 778.6557 (−0.4 mDa).

Reference Example 57

(21Z,24R)-24-{[tert-Butyl(dimethyl)silyl]oxy}triacont-21-en-13-one

To a solution of (9Z,12R)-12-{[tert-butyl(dimethyl)silyl]oxy}-N-methoxy-N-methyloctadec-9-enamide (0.80 g, 1.8 mmol) obtained in Reference Example 32 in diethyl ether (8.8 mL), a solution of 1 N n-dodecyl magnesium bromide in diethyl ether (2.6 mL, 2.6 mmol) was added dropwise over 1 minute, and the mixture was then reacted overnight at room temperature. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.55 g, 55%).

Reference Example 58

(21Z,24R)-24-Hydroxytriacont-21-en-13-one

To (21Z,24R)-24-{[tert-butyl(dimethyl)silyl]oxy}triacont-21-en-13-one (0.55 g, 0.97 mmol) obtained in Reference Example 57, a solution of 1 N tetra-n-butylammonium fluoride in tetrahydrofuran (4.9 mL, 4.9 mmol) was added, and the mixture was reacted overnight at room temperature. After treatment with water, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.23 g, 52%).

Reference Example 59

(7R,9Z)-18-Oxotriacont-9-en-7-yl Acetate

To a solution of (21Z,24R)-24-hydroxytriacont-21-en-13-one (0.23 g, 0.51 mmol) obtained in Reference Example 58 and pyridine (0.81 g, 10 mmol) in dichloromethane (5.1 mL), acetyl chloride (0.40 g, 5.1 mmol) was added, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (0.21 g, 84%).

Reference Example 60

(7R,9Z)-18-Hydroxytriacont-9-en-7-yl Acetate

To a solution of (7R,9Z)-18-oxotriacont-9-en-7-yl acetate (0.21 g, 0.43 mmol) obtained in Reference Example 59 in tetrahydrofuran (1.3 mL) and methanol (1.3 mL), sodium borohydride (32 mg, 0.85 mmol) was added, and the mixture was reacted at room temperature for 1 hour. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure to obtain a yellow liquid containing the compound of interest.

Example 43

(7R,9Z)-18-({[3-(Dimethylamino)propoxy]carbonyl}oxy)triacont-9-en-7-yl Acetate

A solution of the liquid containing (7R,9Z)-18-hydroxytriacont-9-en-7-yl acetate (0.21 g, 0.42 mmol, theoretical amount) obtained in Reference Example 60 and pyridine (0.21 g, 2.7 mmol) in toluene (4.2 mL) was cooled to 0° C. in an ice bath, and a solution of triphosgene (0.087 g, 0.29 mmol) in toluene (0.64 mL) was added thereto over 2 minutes. After stirring at 0° C. for 15 minutes, the reaction mixture was heated to room temperature, stirred for 1.5 hours, and cooled to 0° C. again. 3-Dimethylamino-1-propanol (0.46 g, 4.5 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (111 mg, 42%).

$^1$H-NMR (400 MHz, CDCl$_3$) δ: 0.85-0.91 (6H, m), 1.23-1.35 (36H, m), 1.48-1.66 (6H, m), 1.84 (2H, tt, J=6.6, 7.4 Hz), 1.97-2.05 (2H, m), 2.03 (3H, s), 2.22 (3H, s), 2.25-2.32 (2H, m), 2.36 (2H, t, J=7.4 Hz), 4.18 (2H, t, J=6.6 Hz), 4.64-4.72 (1H, m), 4.86 (1H, quint, J=6.3 Hz), 5.28-5.51 (2H, m).

MS (ESI+) m/z 624 [M+H]$^+$
HRMS (ESI+) m/z 624.5566 (−0.1 mDa).

Reference Example 61

(7R,9Z)-18-Oxotriacont-9-en-7-yl Butyrate

To a solution of (19Z,22R)-22-hydroxyoctacos-19-en-11-one (0.34 g, 0.80 mmol) obtained in Reference Example 39 and pyridine (1.3 g, 16 mmol) in dichloromethane (8.0 mL), butyric acid chloride (0.86 g, 8.0 mmol) was added, and the mixture was reacted overnight at room temperature. After treatment with a saturated aqueous solution of sodium bicarbonate, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a colorless liquid (0.40 g, 100%).

Reference Example 62

(7R,9Z)-18-Hydroxyoctacos-9-en-7-yl Butyrate

To a solution of (7R,9Z)-18-oxotriacont-9-en-7-yl butyrate (0.40 g, 0.81 mmol) obtained in Reference Example 61 in tetrahydrofuran (2.4 mL) and methanol (2.4 mL), sodium borohydride (61 mg, 1.6 mmol) was added, and the mixture was reacted at room temperature for 1 hour. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure to obtain a yellow liquid containing the compound of interest.

Example 44

(7R,9Z)-18-({[3-(Dimethylamino)propoxy]carbonyl}oxy)octacos-9-en-7-yl Butyrate

A solution of the liquid containing (7R,9Z)-18-hydroxyoctacos-9-en-7-yl butyrate (0.40 g, 0.81 mmol, theoretical amount) obtained in Reference Example 62 and pyridine (0.40 g, 5.1 mmol) in toluene (8.1 mL) was cooled to 0° C. in an ice bath, and a solution of triphosgene (0.17 g, 0.56 mmol) in toluene (1.2 mL) was added thereto over 2 minutes. After stirring at 0° C. for 15 minutes, the reaction mixture was heated to room temperature, stirred for 1.5 hours, and cooled to 0° C. again. 3-Dimethylamino-1-propanol (0.88 g, 8.5 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (99 mg, 20%).
$^1$H-NMR (400 MHz, CDCl$_3$) δ: 0.85-0.90 (6H, m), 0.94 (3H, t, J=7.4 Hz), 1.21-1.39 (32H, m), 1.47-1.62 (6H, m), 1.65 (2H, sext, J=7.4 Hz), 1.84 (2H, tt, J=6.6, 7.4 Hz), 2.01 (2H, q, J=6.6 Hz), 2.22 (6H, s), 2.23-2.39 (4H, m), 4.18 (2H, t, J=6.6 Hz), 4.64-4.72 (1H, m), 4.89 (2H, quint, J=6.3 Hz), 5.28-5.50 (2H, m).
MS (ESI+) m/z 624 [M+H]$^+$
HRMS (ESI+) m/z 624.5599 (3.2 mDa).

Reference Example 63

Triacontan-11-ol
To a solution of icosanal (0.64 g, 2.2 mmol) in diethyl ether (11 mL), a solution of 1 N n-decyl magnesium bromide in diethyl ether (3.2 mL, 3.2 mmol) was added dropwise over 2 minutes, and the mixture was then reacted overnight at room temperature. After treatment with a 1 N aqueous hydrochloric acid solution, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.37 g, 39%).
$^1$H-NMR (400 MHz, CDCl$_3$) δ: 0.89 (6H, t, J=7.0), 1.20-1.33 (50H, m), 1.36-1.48 (4H, m), 3.54-3.62 (1H, br).

Example 45

3-(Dimethylamino)propyl triacontan-11-yl Carbonate

To a solution of triacontan-11-ol (0.18 g, 0.41 mmol) obtained in Reference Example 63 and pyridine (0.20 g, 2.6 mmol) in toluene (4.1 mL), a solution of triphosgene (0.084 g, 0.28 mmol) in toluene (0.62 mL) was added over 2 minutes. After stirring at room temperature for 1 hour, 3-dimethylamino-1-propanol (0.44 g, 4.3 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (185 mg, 79%).
$^1$H-NMR (400 MHz, CDCl$_3$) δ: 0.84 (6H, t, J=7.0 Hz), 1.16-1.32 (50H, m), 1.44-1.60 (4H, m), 1.82 (2H, tt, J=6.6, 7.4 Hz), 2.19 (6H, s), 2.32 (2H, t, J=7.4 Hz), 4.14 (2H, t, J=6.6 Hz), 4.61-4.68 (1H, m).
MS (ESI+) m/z 568 [M+H]$^+$
HRMS (ESI+) m/z 568.5663 (−0.6 mDa).

Example 46

(1-Methylpiperidin-3-yl)methyl triacontan-11-yl Carbonate

To a solution of triacontan-11-ol (0.18 g, 0.41 mmol) obtained in Reference Example 63 and pyridine (0.20 g, 2.6 mmol) in toluene (4.1 mL), a solution of triphosgene (0.084 g, 0.28 mmol) in toluene (0.62 mL) was added over 2 minutes. After stirring at room temperature for 1 hour, 1-methyl-3-piperidinemethanol (0.56 g, 4.3 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (145 mg, 60%).
$^1$H-NMR (400 MHz, CDCl$_3$) δ: 0.89 (6H, t, J=7.0 Hz), 1.20-1.36 (50H, m), 1.48-1.77 (8H, m), 1.85-1.94 (1H, m), 1.95-2.07 (1H, m), 2.26 (3H, s), 2.75 (1H, d, J=10.9 Hz), 2.86 (1H, d, J=10.9 Hz), 3.94 (1H, dd, J=7.4, 10.9 Hz), 4.06 (1H, dd, J=5.9, 10.9 Hz), 4.64-4.71 (1H, m).
MS (ESI+) m/z 594 [M+H]$^+$
HRMS (ESI+) m/z 594.5827 (0.2 mDa).

Reference Example 64

(6Z,9Z)-18-[2-(Ethenyloxy)ethoxy]octadeca-6,9-diene

To a solution of linoleyl alcohol (3.90 g, 14.6 mmol), tosylvinyl ethylene glycol (4.76 g, 16.1 mmol) and tetrabutylammonium sulfate (1.24 g, 3.66 mmol) in toluene (23.4 mL), a 50% aqueous sodium hydroxide solution (11.5 mL) was added, and the mixture was reacted overnight at room temperature. Tosylvinyl ethylene glycol (2.00 g, 6.76 mmol) was added thereto, and the mixture was reacted at room temperature for 5 days and nights. The reaction mixture was diluted with water and then subjected to extraction with diethyl ether, and the obtained organic layer was dried over anhydrous magnesium sulfate. The solvent was distilled off under reduced pressure, and the residue was then subjected to silica gel column chromatography to obtain the compound of interest as a yellow liquid (2.44, 50%).
$^1$H-NMR (400 MHz, CDCl$_3$) δ: 0.89 (3H, t, J=7.0 Hz), 1.25-1.40 (16H, m), 1.54-1.63 (2H, m), 2.01-2.08 (4H, m), 2.77 (2H, t, J=6.6 Hz), 3.48 (2H, t, J=6.6 Hz), 3.64-3.68 (2H, m), 3.81-3.85 (2H, m), 4.01 (1H, dd, J=2.0, 7.0 Hz), 4.19 (1H, dd, J=2.0, 14.1 Hz), 6.52 (1H, dd, J=7.0, 14.1 Hz).

Reference Example 65

2-[(9Z,12Z)-Octadeca-9,12-dien-1-yloxy]ethanol

To a solution of (6Z,9Z)-18-[2-(ethenyloxy)ethoxy]octadeca-6,9-diene (5.70 g, 17 mmol) obtained in Reference Example 64 in ethanol (34 mL) and tetrahydrofuran (34 mL), a 1 N aqueous hydrochloric acid solution (17 mL, 17 mmol) was added, and the mixture was reacted at room temperature for 1.5 hours. The reaction mixture was diluted with water and then subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (2.00 g, 38%).

$^1$H-NMR (400 MHz, CDCl$_3$) δ: 0.89 (3H, t, J=7.0 Hz), 1.23-1.40 (16H, m), 1.51-1.63 (2H, m), 1.95 (1H, t, J=6.3 Hz), 2.01-2.09 (4H, m), 2.77 (2H, t, J=6.6 Hz), 3.53 (2H, t, J=4.3 Hz), 3.73 (2H, dt, J=6.3, 4.3 Hz), 5.29-5.43 (4H, m).

Reference Example 66

[(9Z,12Z)-Octadeca-9,12-dien-1-yloxy]acetaldehyde

To a solution of 2-[(9Z,12Z)-octadeca-9,12-dien-1-yloxy]ethanol (1.00 g, 3.2 mmol) obtained in Reference Example 65 and triethylamine (1.63 g, 16.1 mmol) in dimethyl sulfoxide (6.4 mL), a sulfur trioxide-pyridine complex (1.54 g, 9.7 mmol) was added, and the mixture was reacted at room temperature for 1.5 hours. The reaction mixture was diluted with water and then subjected to extraction with hexane, and the obtained organic layer was dried over anhydrous magnesium sulfate. The solvent was distilled off under reduced pressure, and the residue was then subjected to silica gel column chromatography to obtain the compound of interest as a yellow liquid (0.57 g, 57%).

$^1$H-NMR (500 MHz, CDCl$_3$) δ: 1.11 (3H, t, J=6.8 Hz), 1.25-1.41 (16H, m), 1.59-1.67 (2H, m), 2.02-2.08 (4H, m), 2.77 (2H, t, J=6.6 Hz), 3.53 (2H, t, J=6.6 Hz), 4.06 (2H, s), 5.30-5.42 (4H, m), 9.74-9.75 (1H, m).

Reference Example 67

(11Z,14Z)-1-[(9Z,12Z)-Octadeca-9,12-dien-1-yloxy]icosa-11,14-dien-2-ol

To a solution of [(9Z,12Z)-octadeca-9,12-dien-1-yloxy]acetaldehyde (1.27 g, 4.1 mmol) obtained in Reference Example 66 in diethyl ether (12.4 mL), 0.5 N linoleyl magnesium bromide (14 mL, 7.0 mmol) was added, and the mixture was reacted at room temperature for 3 hours and subsequently at 60° C. for 3 hours. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a yellow liquid (0.48 g, 21%).

$^1$H-NMR (400 MHz, CDCl$_3$) δ: 0.89 (6H, t, J=7.0 Hz), 1.23-1.46 (34H, m), 1.52-1.61 (4H, m), 2.01-2.08 (8H, m), 2.31 (1H, d, J=3.1 Hz), 2.77 (4H, t, J=6.6 Hz), 3.23 (1H, dd, J=8.2, 9.4 Hz), 3.39-3.51 (3H, m), 3.72-3.81 (1H, m), 5.29-5.43 (8H, m).

Example 47

3-(Dimethylamino)propyl (11Z,14Z)-1-[(9Z,12Z)-octadeca-9,12-dien-1-yloxy]icosa-11,14-dien-2-yl Carbonate A solution of (11Z,14Z)-1-[(9Z,12Z)-octadeca-9,12-dien-1-yloxy]icosa-11,14-dien-2-ol (0.27 g, 0.48 mmol) obtained in Reference Example 67 and pyridine (0.24 g, 3.0 mmol) in toluene (4.8 mL) was cooled to 0° C. in an ice bath, and a solution of triphosgene (0.099 g, 0.33 mmol) in toluene (0.72 mL) was added thereto over 2 minutes. After stirring at 0° C. for 30 minutes, the reaction mixture was heated to room temperature, stirred for 1.5 hours, and cooled to 0° C. again. 3-Dimethylamino-1-propanol (0.52 g, 5.1 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (330 mg, 24%).

$^1$H-NMR (400 MHz, CDCl$_3$) δ: 0.88-0.94 (6H, m), 1.24-1.43 (34H, m), 1.52-1.67 (4H, m), 1.86 (2H, tt, J=6.6, 7.4 Hz), 1.96-2.11 (8H, m), 2.24 (6H, s), 2.38 (2H, t, J=7.4 Hz), 2.79 (4H, t, J=6.6 Hz), 3.38-3.54 (4H, m), 4.21 (2H, t, J=6.6 Hz), 4.82-4.89 (1H, m), 5.31-5.45 (8H, m).

MS (ESI+) m/z 688 [M+H]$^+$

HRMS (ESI+) m/z 688.6269 (2.5 mDa).

Reference Example 68

10-{2-[(2-Pentylcyclopropyl)methyl]cyclopropyl}-1-[(8-{2-[(2-pentylcyclopropyl)methyl]cyclopropyl}octyl)oxy]decan-2-ol To a solution of a solution of 1.1 N diethylzinc in hexane (7.3 mL, 7.7 mmol) in dichloromethane (12 mL) cooled to 0° C., chloroiodomethane (1.7 g, 9.6 mmol) was added over 10 minutes, then a solution of (11Z,14Z)-1-[(9Z,12Z)-octadeca-9,12-dien-1-yloxy]icosa-11,14-dien-2-ol (0.27 g, 0.48 mmol) obtained in Reference Example 67 and chloroiodomethane (1.0 g, 5.7 mmol) in dichloromethane (7.0 mL) was added over 40 minutes, and the mixture was reacted overnight at room temperature. After treatment with a saturated aqueous solution of ammonium chloride, the reaction mixture was subjected to extraction with dichloromethane, and the obtained organic layer was dried over anhydrous magnesium sulfate. The solvent was distilled off under reduced pressure, and the residue was then subjected to silica gel column chromatography to obtain the compound of interest as a yellow liquid (0.29 g, 98%).

$^1$H-NMR (400 MHz, CDCl$_3$) δ: (−0.32)-(−0.24) (4H, m), 0.57-0.84 (12H, m), 0.85-0.92 (6H, m), 0.97-1.62 (50H, m), 2.31 (1H, d, J=3.1 Hz), 3.23 (1H, dd, J=8.2, 9.4 Hz), 3.39-3.52 (3H, m), 3.73-3.80 (1H, m).

Example 48

3-(Dimethylamino)propyl 10-{2-[(2-pentylcyclopropyl)methyl]cyclopropyl}-1-[(8-{2-[(2-pentylcyclopropyl)methyl]cyclopropyl}octyl)oxy]decan-2-yl Carbonate A solution of 10-{2-[(2-pentylcyclopropyl)methyl]cyclopropyl}-1-[(8-{2-[(2-pentylcyclopropyl)methyl]

cyclopropyl}octyl)oxy]decan-2-ol (0.17 g, 0.28 mmol) obtained in Reference Example 68 and pyridine (0.14 g, 1.7 mmol) in toluene (2.8 mL) was cooled to 0° C. in an ice bath, and a solution of triphosgene (0.056 g, 0.19 mmol) in toluene (0.42 mL) was added thereto over 2 minutes. After stirring at 0° C. for 1 hour, the reaction mixture was heated to room temperature, stirred for 1 hour, and cooled to 0° C. again. 3-Dimethylamino-1-propanol (0.30 g, 2.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (135 mg, 66%).

$^1$H-NMR (400 MHz, CDCl$_3$) δ: (−0.34)-(−0.23) (4H, m), 0.57-0.84 (12H, m), 0.86-0.92 (6H, m), 0.97-1.66 (50H, m), 1.84 (2H, tt, J=6.6, 7.4 Hz), 2.22 (6H, s), 2.36 (2H, t, J=7.4 Hz), 3.35-3.53 (4H, m), 4.18 (2H, t, J=6.6 Hz), 4.80-4.87 (1H, m).

MS (ESI+) m/z 744 [M+H]$^+$

HRMS (ESI+) m/z 744.6876 (0.6 mDa).

Reference Example 69

1-[(9Z,12Z)-Octadeca-9,12-dien-1-yloxy]icosan-2-ol

To a solution of [(9Z,12Z)-octadeca-9,12-dien-1-yloxy]acetaldehyde (0.22 g, 0.71 mmol) obtained in Reference Example 66 in tetrahydrofuran (2.9 mL), 0.5 N octadecyl magnesium chloride (3.0 mL, 1.5 mmol) was added, and the mixture was reacted overnight at room temperature. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a yellow liquid (0.13 g, 31%).

$^1$H-NMR (400 MHz, CDCl$_3$) δ: 0.85-0.92 (6H, m), 1.20-1.62 (52H, m), 2.01-2.08 (4H, m), 2.31 (1H, d, J=3.1 Hz), 2.77 (2H, t, J=6.6 Hz), 3.23 (1H, dd, J=8.2, 9.4 Hz), 3.39-3.55 (3H, m), 3.73-3.80 (1H, m), 5.29-5.42 (4H, m).

Example 49

3-(Dimethylaminopropyl) 1-[(9Z,12Z)-octadeca-9,12-dien-1-yloxy]icosan-2-yl Carbonate A solution of 1-[(9Z,12Z)-octadeca-9,12-dien-1-yloxy]icosan-2-ol (0.13 g, 0.22 mmol) obtained in Reference Example 69 and pyridine (0.11 g, 1.4 mmol) in toluene (2.2 mL) was cooled to 0° C. in an ice bath, and a solution of triphosgene (0.045 g, 0.15 mmol) in toluene (0.33 mL) was added thereto over 2 minutes. After stirring at 0° C. for 40 minutes, the reaction mixture was heated to room temperature, stirred for 1 hour, and cooled to 0° C. again. 3-Dimethylamino-1-propanol (0.24 g, 2.3 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (86 mg, 56%).

$^1$H-NMR (400 MHz, CDCl$_3$) δ: 0.85-0.91 (6H, m), 1.22-1.41 (48H, m), 1.50-1.66 (4H, m), 1.84 (2H, tt, J=6.6, 7.4 Hz), 2.01-2.09 (4H, m), 2.22 (6H, s), 2.36 (2H, t, J=7.4 Hz), 2.77 (2H, t, J=6.6 Hz), 3.35-3.53 (4H, m), 4.18 (2H, t, J=6.6 Hz), 4.80-4.86 (1H, m), 5.29-5.42 (4H, m).

MS (ESI+) m/z 692 [M+H]$^+$

HRMS (ESI+) m/z 692.6588 (3.1 mDa).

Reference Example 70

(11Z,14Z)-1-(Octadecyloxy)icosa-11,14-dien-2-ol

To a solution of octadecan-1-yloxyacetaldehyde (0.25 g, 0.80 mmol) in tetrahydrofuran (2.4 mL), 0.5 N linoleyl magnesium bromide (2.4 mL, 1.2 mmol) was added, and the mixture was reacted at room temperature for 4 hours. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a yellow liquid (0.17 g, 38%).

$^1$H-NMR (400 MHz, CDCl$_3$) δ: 0.88-0.94 (6H, m), 1.22-1.70 (52H, m), 2.04-2.11 (4H, m), 2.35 (1H, d, J=3.1 Hz), 2.80 (2H, t, J=6.6 Hz), 3.26 (1H, dd, J=8.2, 9.4 Hz), 3.42-3.58 (3H, m), 3.75-3.83 (1H, m), 5.32-5.45 (4H, m).

Example 50

3-(Dimethylaminopropyl) (11Z,14Z)-1-(octadecyloxy)icosa-11,14-dien-2-yl Carbonate A solution of (11Z,14Z)-1-(octadecyloxy)icosa-11,14-dien-2-ol (0.17 g, 0.30 mmol) obtained in Reference Example 70 and pyridine (0.15 g, 1.9 mmol) in toluene (3.0 mL) was cooled to 0° C. in an ice bath, and a solution of triphosgene (0.062 g, 0.21 mmol) in toluene (0.45 mL) was added thereto over 1 minute. After stirring at 0° C. for 30 minutes, the reaction mixture was heated to room temperature, stirred for 1 hour, and cooled to 0° C. again. 3-Dimethylamino-1-propanol (0.33 g, 3.2 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (53 mg, 25%).

$^1$H-NMR (400 MHz, CDCl$_3$) δ: 0.85-0.92 (6H, m), 1.21-1.40 (48H, m), 1.50-1.65 (4H, m), 1.84 (2H, tt, J=6.6, 7.4 Hz), 2.01-2.09 (4H, m), 2.22 (6H, s), 2.36 (2H, t, J=7.4 Hz), 2.77 (2H, t, J=6.6 Hz), 3.35-3.53 (4H, m), 4.18 (2H, t, J=6.6 Hz), 4.80-4.87 (1H, m), 5.29-5.42 (4H, m).

MS (ESI+) m/z 692 [M+H]+

HRMS (ESI+) m/z 692.6578 (2.1 mDa).

Reference Example 71

(11Z,14R)-1-(Octadecyloxy)-14-(tetrahydro-2H-pyran-2-yloxy)icos-11-en-2-ol

Dried magnesium (shavings, 0.48 g, 19.8 mmol) was dipped in tetrahydrofuran (4.0 mL). 1,2-Dibromoethane (3 drops) was added thereto, and the mixture was vigorously stirred. After the solution turned black-gray, a solution of 2-{[(7R,9Z)-18-bromooctadec-9-en-7-yl]oxy}tetrahydro-2H-pyran (5.70 g, 13.2 mmol) obtained in Reference Example 53 in tetrahydrofuran (18.5 mL) was added thereto over 40 minutes, and the mixture was stirred at room temperature for 3 hours.

A 7.5 mL aliquot of the obtained Grignard reagent solution was added to a solution of octadecan-1-yloxyacetaldehyde (0.78 g, 2.5 mmol) in tetrahydrofuran (7.5 mL), and the mixture was reacted at room temperature for 6 hours. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (0.61 g, 37%).

$^1$H-NMR (400 MHz, CDCl$_3$) δ: 0.89 (6H, t, J=7.0 Hz), 1.20-2.40 (64H, m), 3.23 (1H, dd, J=8.2, 9.4 Hz), 3.39-3.56 (5H, m), 3.58-3.70 (1H, m), 3.73-3.81 (1H, m), 3.87-3.98 (1H, m), 4.64-4.74 (1H, m), 5.34-5.50 (2H, m).

Reference Example 72

3-(Dimethylamino)propyl (11Z,14R)-1-(octadecyloxy)-14-(tetrahydro-2H-pyran-2-yloxy)icos-11-en-2-yl Carbonate A solution of (11Z,14R)-1-(octadecyloxy)-14-(tetrahydro-2H-pyran-2-yloxy)icos-11-en-2-ol (0.61 g, 0.92 mmol) obtained in Reference Example 71 and pyridine (0.46 g, 5.8 mmol) in toluene (9.2 mL) was cooled to 0° C. in an ice bath, and a solution of triphosgene (0.19 g, 0.63 mmol) in toluene (1.4 mL) was added thereto over 1 minute. After stirring at 0° C. for 15 minutes, the reaction mixture was heated to room temperature, stirred for 1 hour, and cooled to 0° C. again. 3-Dimethylamino-1-propanol (0.99 g, 9.6 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.41 g, 56%).

Reference Example 73

3-(Dimethylamino)propyl (11Z,14R)-14-hydroxy-1-(octadecyloxy)icos-11-en-2-yl Carbonate To a solution of 3-(dimethylamino)propyl (11Z,14R)-1-(octadecyloxy)-14-(tetrahydro-2H-pyran-2-yloxy)icos-11-en-2-yl carbonate (0.41 g, 0.52 mmol) obtained in Reference Example 72 in ethanol (5.2 mL), a 2 N aqueous hydrochloric acid solution (2.6 mL, 5.2 mmol) was added, and the mixture was reacted overnight at room temperature. After treatment with a saturated aqueous solution of sodium bicarbonate, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (0.34 g, 92%).

Example 51

(7R,9Z)-19-({[3-(Dimethylamino)propoxy]carbonyl}oxy)-20-(octadecyloxy)icos-9-en-7-yl Acetate To a solution of 3-(dimethylamino)propyl (11Z,14R)-14-hydroxy-1-(octadecyloxy)icos-11-en-2-yl carbonate (0.11 g, 0.16 mmol) obtained in Reference Example 73 and pyridine (0.25 g, 3.1 mmol) in dichloromethane (1.6 mL), acetic acid chloride (0.12 g, 1.6 mmol) was added, and the mixture was reacted at room temperature for 3 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (75 mg, 64%).

$^1$H-NMR (400 MHz, CDCl$_3$) δ: 0.85-0.91 (6H, m), 1.21-1.37 (50H, m), 1.50-1.66 (6H, m), 1.84 (2H, tt, J=6.6, 7.4 Hz), 1.97-2.06 (5H, m), 2.22 (6H, s), 2.25-2.31 (2H, m), 2.36 (2H, t, J=7.4 Hz), 3.35-3.51 (4H, m), 4.18 (2H, t, J=6.6 Hz), 4.79-4.91 (2H, m), 5.28-5.36 (1H, m), 5.43-5.51 (1H, m).

MS (ESI+) m/z 752 [M+H]$^+$

HRMS (ESI+) m/z 752.6775 (3.4 mDa).

Reference Example 74

(11Z,14R)-1-[(9Z,12Z)-Octadeca-9,12-dien-1-yloxy]-14-(tetrahydro-2H-pyran-2-yloxy)icos-11-en-2-ol Dried magnesium (shavings, 0.24 g, 9.7 mmol) was dipped in tetrahydrofuran (3.0 mL). 1,2-Dibromoethane (4 drops) was added thereto, and the mixture was vigorously stirred. After the solution turned black-gray, a solution of 2-{[(7R,9Z)-18-bromooctadec-9-en-7-yl]oxy}tetrahydro-2H-pyran (2.8 g, 6.5 mmol) obtained in Reference Example 53 in tetrahydrofuran (18.5 mL) was added thereto over 40 minutes, and the mixture was stirred overnight at room temperature.

To the obtained Grignard reagent solution, [(9Z,12Z)-octadeca-9,12-dien-1-yloxy]acetaldehyde (2.0 g, 6.5 mmol) obtained in Reference Example 66 was added, and the mixture was reacted at 60° C. for 2 hours. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.27 g, 6%).

$^1$H-NMR (400 MHz, CDCl$_3$) δ: 0.85-0.92 (6H, m), 1.22-2.40 (54H, m), 2.77 (2H, t, J=6.6 Hz), 3.23 (1H, dd, J=8.2, 9.4 Hz), 3.39-3.56 (5H, m), 3.58-3.72 (1H, m), 3.72-3.81 (1H, m), 3.86-3.98 (1H, m), 4.64-4.74 (1H, m), 5.28-5.49 (6H, m).

Reference Example 75

3-(Dimethylamino)propyl (11Z,14R)-1-[(9Z,12Z)-octadeca-9,12-dien-1-yloxy]-14-(tetrahydro-2H-pyran-2-yloxy)icos-11-en-2-yl Carbonate A solution of (11Z,14R)-1-[(9Z,12Z)-octadeca-9,12-dien-1-yloxy]-14-(tetrahydro-2H-pyran-2-yloxy)icos-11-en-2-ol (0.27 g, 0.41 mmol) obtained in Reference Example 74 and pyridine (0.20 g, 2.6 mmol) in toluene (4.1 mL) was cooled to 0° C. in an ice bath, and a solution of triphosgene (0.084 g, 0.28 mmol) in toluene (0.61 mL) was added thereto over 2 minutes. After stirring at 0° C. for 15 minutes, the reaction mixture was heated to room temperature, stirred for 1 hour, and cooled to 0° C. again. 3-Dimethylamino-1-propanol (0.44 g, 4.3 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.16 g, 48%).

$^1$H-NMR (400 MHz, CDCl$_3$) δ: 0.85-0.92 (6H, m), 1.23-1.88 (50H, m), 1.98-2.09 (8H, m), 2.22 (6H, m), 2.36 (2H, t, J=7.4 Hz), 2.77 (2H, t, J=6.6 Hz), 3.35-3.52 (5H, m), 3.59-3.71 (1H, m), 3.87-3.97 (1H, m), 4.18 (2H, t, J=6.6 Hz), 4.63-4.73 (1H, m), 4.80-4.87 (1H, m), 5.29-5.49 (6H, m).

Reference Example 76

3-(Dimethylamino)propyl (11Z,14R)-14-hydroxy-1-[(9Z,12Z)-octadeca-9,12-dien-1-yloxy]icos-11-en-2-yl Carbonate To a solution of 3-(dimethylamino)propyl (11Z,14R)-1-[(9Z,12Z)-octadeca-9,12-dien-1-yloxy]-14-(tetrahydro-2H-pyran-2-yloxy)icos-11-en-2-yl carbonate (0.16 g, 0.20 mmol) obtained in Reference Example 75 in ethanol (0.98 mL), a 2 N aqueous hydrochloric acid solution (0.49 mL, 0.98 mmol) was added, and the mixture was reacted at room temperature for 3 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.08 g, 60%).

Example 52

(7R,9Z)-19-({[3-(Dimethylamino)propoxy]carbonyl}oxy)-20-[(9Z,12Z)-octadeca-9,12-dien-1-yloxy]icos-9-en-7-yl Acetate To a solution of 3-(dimethylamino)propyl (11Z,14R)-14-hydroxy-1-[(9Z,12Z)-octadeca-9,12-dien-1-yloxy]icos-11-en-2-yl carbonate (0.08 g, 0.11 mmol) obtained in Reference Example 76 and pyridine (0.37 g, 4.5 mmol) in dichloromethane (2.3 mL), acetyl chloride (0.18 g, 2.3 mmol) was added, and the mixture was reacted at room temperature for 3 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (53 mg, 63%).

$^1$H-NMR (400 MHz, CDCl$_3$) δ: 0.85-0.92 (6H, m), 1.23-1.40 (36H, m), 1.50-1.64 (6H, m), 1.84 (2H, tt, J=6.6, 7.4 Hz), 1.97-2.09 (9H, m), 2.22 (6H, s), 2.25-2.32 (2H, m), 2.36 (2H, t, J=7.4 Hz), 2.77 (2H, t, J=6.6 Hz), 3.35-3.52 (4H, m), 4.18 (2H, t, J=6.6 Hz), 4.80-4.91 (2H, m), 5.28-5.51 (6H, m).

MS (ESI+) m/z 748 [M+H]$^+$

HRMS (ESI+) m/z 748.6489 (3.4 mDa).

Reference Example 77

2-{[(9Z,12R)-12-(Tetrahydro-2H-pyran-2-yloxy)octadec-9-en-1-yl]oxy}ethanol

To a suspension of sodium hydride (64%, 2.97 g, 79.2 mmol) in N,N-dimethylformamide, ethylene glycol (5.25 g, 84.5 mmol) was added, and the mixture was stirred at 80° C. for 45 minutes. (9Z,12R)-12-Hydroxyoctadec-9-en-1-yl methanesulfonate (11.8 g, 26.4 mmol) obtained in Reference Example 51 was added thereto, and the mixture was reacted at 80° C. for 2 hours. After treatment with water, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (8.36 g, 77%).

$^1$H-NMR (400 MHz, CDCl$_3$) δ: 0.88 (3H, t, J=7.0 Hz), 1.23-1.62 (26H, m), 1.66-1.75 (1H, m), 1.78-1.87 (1H, m), 1.97-2.07 (3H, m), 2.23 (1H, t, J=6.3 Hz), 2.26-2.41 (1H, m), 3.47 (2H, t, J=6.6 Hz), 3.53 (2H, dd, J=3.1, 5.1 Hz), 3.58-3.72 (1H, m), 3.87-3.98 (1H, m), 4.64-4.74 (1H, m), 5.33-5.49 (2H, m).

Reference Example 78

{[(9Z,12R)-12-(Tetrahydro-2H-pyran-2-yloxy)octadec-9-en-1-yl]oxy}acetaldehyde

To a solution of 2-{[(9Z,12R)-12-(tetrahydro-2H-pyran-2-yloxy)octadec-9-en-1-yl]oxy}ethanol (5.36 g, 13.0 mmol) obtained in Reference Example 77 and triethylamine (6.57 g, 65.0 mmol) in dimethyl sulfoxide (26.0 mL), a sulfur trioxide-pyridine complex (5.17 g, 32.5 mmol) was added, and the mixture was reacted at room temperature for 2.5 hours. The reaction mixture was diluted with water and then subjected to extraction with hexane, and the obtained organic layer was dried over anhydrous magnesium sulfate. The solvent was distilled off under reduced pressure, and the residue was then subjected to silica gel column chromatography to obtain the compound of interest as a yellow liquid (3.96 g, 74%).

$^1$H-NMR (400 MHz, CDCl$_3$) δ: 0.88 (3H, t, J=7.0 Hz), 1.23-1.67 (26H, m), 1.66-1.75 (1H, m), 1.78-1.86 (1H, m), 1.98-2.07 (3H, m), 2.20-2.41 (2H, m), 3.44-3.54 (3H, m), 3.55-3.71 (1H, m), 3.87-3.97 (1H, m), 4.06 (2H, s), 4.64-4.74 (1H, m), 5.32-5.49 (2H, m), 9.75 (1H, s).

Reference Example 79

1-{[(9Z,12R)-12-(Tetrahydro-2H-pyran-2-yloxy)octadec-9-en-1-yl]oxy}icosan-2-ol

To a solution of {[(9Z,12R)-12-(tetrahydro-2H-pyran-2-yloxy)octadec-9-en-1-yl]oxy}acetaldehyde (0.40 g, 0.97 mmol) obtained in Reference Example 78 in tetrahydrofuran (2.9 mL), 0.5 N octadecyl magnesium chloride (2.4 mL, 1.2 mmol) was added, and the mixture was reacted overnight at room temperature. After treatment with a saturated aqueous solution of ammonium chloride, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a yellow liquid (0.24 g, 37%).

Reference Example 80

3-(Dimethylamino)propyl 1-{[(9Z,12R)-12-(tetrahydro-2H-pyran-2-yloxy)octadec-9-en-1-yl]oxy}icosan-2-yl Carbonate A solution of 1-{[(9Z,12R)-12-(tetrahydro-2H-pyran-2-yloxy)octadec-9-en-1-yl]oxy}icosan-2-ol (0.24 g, 0.36 mmol) obtained in Reference Example 79 and pyridine (0.18 g, 2.3 mmol) in toluene (3.6 mL) was cooled to 0° C. in an ice bath, and a solution of triphosgene (0.074 g, 0.25 mmol) in toluene (0.54 mL) was added thereto over 1 minute. After stirring at 0° C. for 10 minutes, the reaction mixture was heated to room temperature, stirred for 1 hour, and cooled to 0° C. again. 3-Dimethylamino-1-propanol (0.39 g, 3.8 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.24 g, 84%).
$^1$H-NMR (400 MHz, CDCl$_3$) δ: 0.88 (3H, t, J=7.0 Hz), 1.21-1.75 (60H, m), 1.81-2.40 (8H, m), 2.22 (6H, s), 3.35-3.53 (5H, m), 3.58-3.72 (1H, m), 3.87-3.97 (1H, m), 4.18 (2H, t, J=6.6 Hz), 4.64-4.73 (1H, m), 4.80-4.87 (1H, m), 5.32-5.49 (2H, m).

Reference Example 81

3-(Dimethylamino)propyl 1-{[(9Z,12R)-12-hydroxyoctadec-9-en-1-yl]oxy}icosan-2-yl Carbonate To a solution of 3-(dimethylamino)propyl 1-{[(9Z,12R)-12-(tetrahydro-2H-pyran-2-yloxy)octadec-9-en-1-yl]oxy}icosan-2-yl carbonate (0.24 g, 0.30 mmol) obtained in Reference Example 80 in ethanol (3.0 mL), a 2 N aqueous hydrochloric acid solution (1.5 mL, 3.0 mmol) was added, and the mixture was reacted at room temperature for 2 hours. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.16 g, 76%).
$^1$H-NMR (400 MHz, CDCl$_3$) δ: 0.85-0.91 (6H, m), 1.21-1.65 (54H, m), 1.84 (2H, dd, J=6.6, 7.4 Hz), 2.05 (2H, q, J=6.6 Hz), 2.18-2.24 (2H, m), 2.22 (6H, s), 2.36 (2H, t, J=7.4 Hz), 3.35-3.52 (4H, m), 3.37-3.65 (1H, m), 4.18 (2H, t, J=6.6 Hz), 4.83 (1H, quint, J=5.9 Hz), 5.35-5.44 (1H, m), 5.52-5.61 (1H, m).

Example 53

(20,23R)-2-Methyl-9-octadecyl-7-oxo-6,8,11-trioxa-2-azanonacos-20-en-23-yl Acetate To a solution of 3-(dimethylamino)propyl 1-{[(9Z,12R)-12-hydroxyoctadec-9-en-1-yl]oxy}icosan-2-yl carbonate (0.16 g, 0.23 mmol) obtained in Reference Example 81 and pyridine (0.36 g, 4.6 mmol) in dichloromethane (2.3 mL), acetyl chloride (0.18 g, 2.3 mmol) was added, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (121 mg, 70%).
$^1$H-NMR (400 MHz, CDCl$_3$) δ: 0.85-0.91 (6H, m), 1.22-1.38 (50H, m), 1.49-1.65 (6H, m), 1.84 (2H, tt, J=6.6, 7.4 Hz), 1.97-2.06 (5H, m), 2.22 (6H, s), 2.25-2.32 (2H, m), 2.36 (2H, t, J=7.4 Hz), 3.35-3.53 (4H, m), 4.18 (2H, t, J=6.6 Hz), 4.79-4.91 (2H, m), 5.28-5.36 (1H, m), 5.43-5.51 (1H, m).
MS (ESI+) m/z 752 [M+H]$^+$
HRMS (ESI+) m/z 752.6802 (3.4 mDa).

Reference Example 82

(11Z,14Z)-1-{[(9Z,12R)-12-(Tetrahydro-2H-pyran-2-yloxy)octadec-9-en-1-yl]oxy}icosa-11,14-dien-2-ol To a solution of {[(9Z,12R)-12-(tetrahydro-2H-pyran-2-yloxy)octadec-9-en-1-yl]oxy}acetaldehyde (0.40 g, 0.97 mmol) obtained in Reference Example 78 in tetrahydrofuran (2.9 mL), 0.5 N linoleyl magnesium bromide (2.9 mL, 1.5 mmol) was added, and the mixture was reacted overnight at room temperature. After treatment with a saturated aqueous solution of ammonium chloride, the reaction mixture was subjected to extraction with ethyl acetate, and the obtained organic layer was dried over anhydrous magnesium sulfate. The solvent was distilled off under reduced pressure, and the residue was then subjected to silica gel column chromatography to obtain the compound of interest as a yellow liquid (0.37 g, 57%).
$^1$H-NMR (400 MHz, CDCl$_3$) δ: 0.85-0.92 (6H, m), 1.23-1.87 (48H, m), 1.98-2.40 (9H, m), 2.77 (2H, t, J=6.6 Hz), 3.23 (1H, dd, J=8.2, 9.4 Hz), 3.39-3.52 (4H, m), 3.58-3.71 (1H, m), 3.73-3.80 (1H, m), 3.87-3.97 (1H, m), 4.64-4.74 (1H, m), 5.29-5.49 (6H, m).

Reference Example 83

3-(Dimethylamino)propyl (11Z,14Z)-1-{[(9Z,12R)-12-(tetrahydro-2H-pyran-2-yloxy)octadec-9-en-1-yl]oxy}icosa-11,14-dien-2-yl Carbonate A solution of (11Z,14Z)-1-{[(9Z,12R)-12-(tetrahydro-2H-pyran-2-yloxy)octadec-9-en-1-yl]oxy}icosa-11,14-dien-2-ol (0.37 g, 0.56 mmol) obtained in Reference Example 82 and pyridine (0.28 g, 3.5 mmol) in toluene (5.6 mL) was cooled to 0° C. in an ice bath, and a solution of triphosgene (0.11 g, 0.39 mmol) in toluene (0.84 mL) was added thereto over 1 minute. After stirring at 0° C. for 30 minutes, the reaction mixture was heated to room temperature, stirred for 1 hour, and cooled to 0° C. again. 3-Dimethylamino-1-propanol (0.61 g, 5.9 mmol) was added thereto, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.33 g, 75%).

$^{1}$H-NMR (400 MHz, CDCl$_3$) δ: 0.85-0.92 (6H, m), 1.23-1.75 (48H, m), 1.84 (2H, tt, J=6.6, 7.4 Hz), 1.98-2.40 (8H, m), 2.22 (6H, s), 2.36 (2H, t, J=7.4 Hz), 2.77 (2H, t, J=6.3 Hz), 3.35-3.53 (5H, m), 3.58-3.71 (1H, m), 3.87-3.97 (1H, m), 4.18 (2H, t, J=6.6 Hz), 4.64-4.74 (1H, m), 4.80-4.87 (1H, m), 5.29-5.48 (6H, m).

Reference Example 84

3-(Dimethylamino)propyl (11Z,14Z)-1-{[(9Z,12R)-12-hydroxyoctadec-9-en-1-yl]oxy}icosa-11,14-dien-2-yl Carbonate To a solution of 3-(dimethylamino)propyl (11Z,14Z)-1-{[(9Z,12R)-12-(tetrahydro-2H-pyran-2-yloxy)octadec-9-en-1-yl]oxy}icosa-11,14-dien-2-yl carbonate (0.33 g, 0.42 mmol) obtained in Reference Example 83 in ethanol (4.2 mL), a 2 N aqueous hydrochloric acid solution (2.1 mL, 4.2 mmol) was added, and the mixture was reacted overnight at room temperature. After treatment with a saturated aqueous solution of sodium bicarbonate, the reaction mixture was subjected to extraction with hexane-ethyl acetate, and the obtained organic layer was dried over anhydrous magnesium sulfate. The solvent was distilled off under reduced pressure, and the residue was then subjected to silica gel column chromatography to obtain the compound of interest as a colorless liquid (0.29 g, 98%).

Example 54

(20,23R)-2-Methyl-9-[(9Z,12Z)-octadeca-9,12-dien-1-yl]-7-oxo-6,8,11-trioxa-2-azanonacos-20-en-23-yl Acetate To a solution of 3-(dimethylamino)propyl (11Z,14Z)-1-{[(9Z,12R)-12-hydroxyoctadec-9-en-1-yl]oxy}icosa-11,14-dien-2-yl carbonate (0.51 g, 0.72 mmol) obtained in Reference Example 84 and pyridine (1.1 g, 14 mmol) in dichloromethane (7.2 mL), acetyl chloride (0.57 g, 7.2 mmol) was added, and the mixture was reacted overnight at room temperature. After treatment with a saturated aqueous solution of sodium bicarbonate, the reaction mixture was subjected to extraction with hexane, and the obtained organic layer was dried over anhydrous magnesium sulfate. The solvent was distilled off under reduced pressure, and the residue was then subjected to silica gel column chromatography to obtain the compound of interest as a colorless liquid (0.42 g, 78%).

$^{1}$H-NMR (400 MHz, CDCl$_3$) δ: 0.85-0.92 (6H, m), 1.23-1.40 (36H, m), 1.49-1.65 (6H, m), 1.84 (2H, tt, J=6.6, 7.4 Hz), 1.98-2.08 (9H, m), 2.22 (6H, s), 2.25-2.32 (2H, m), 2.36 (2H, t, J=7.4 Hz), 2.77 (2H, t, J=6.6 Hz), 3.35-3.53 (4H, m), 4.18 (2H, t, J=6.6 Hz), 4.80-4.91 (2H, m), 5.28-5.51 (6H, m).

MS (ESI+) m/z 748 [M+H]$^{+}$

HRMS (ESI+) m/z 748.6476 (2.1 mDa).

(Example 55) Characterization of Double-Stranded Polynucleotide-Encapsulated Nucleic Acid Lipid Particle A dispersion of a nucleic acid lipid particle containing the compound described in Reference Example 2, Example 41, Example 42, or Example 43 was obtained in the same way as in Example 31. The obtained nucleic acid lipid particle-containing dispersion was characterized by the following methods.

(1) Average Particle Size

The particle size of the liposome was measured using Zeta Potential/Particle Sizer NICOMP™ 380ZLS (Particle Sizing Systems, LLC). In the tables, the average particle size is indicated by a volume-average particle size, and the numeric value following ± represents a deviation.

(2) Rate of Encapsulation of Double-Stranded Polynucleotide

The rate of encapsulation of the double-stranded polynucleotide was measured using Quant-iT RiboGreen RNA Assay kit (Invitrogen Corp.) according to the attached document.

Specifically, the double-stranded polynucleotide in the nucleic acid lipid particle dispersion was quantified in the presence and absence of a 0.015% Triton X-100 detergent, and the rate of encapsulation was calculated according to the following expression:

{[Amount of the double-stranded polynucleotide in the presence of the detergent]−[Amount of the double-stranded polynucleotide in the absence of the detergent]}/[Amount of the double-stranded polynucleotide in the presence of the detergent]}×100(%)

(3) Ratio of Double-Stranded Polynucleotide to Lipid

The amount of the double-stranded polynucleotide in a sample from the nucleic acid lipid particle dispersion was measured in the presence of a 5% Triton X-100 detergent by ion-exchange chromatography (system: Agilent 1100 series, column: DNAPac PA200 (4×250 mm) (Thermo Fisher Scientific K.K.), buffer A: 10 mM Tris, 25 mM sodium perchlorate, and 20% ethanol, pH 7.0, buffer B: 10 mM Tris, 250 mM sodium perchlorate, and 20% ethanol, pH 7.0, gradient (B %): 20-70% (0-15 min), flow rate: 0.5 mL/min, temperature: 40° C., detection: 260 nm).

The amount of the phospholipid in the nucleic acid lipid particle dispersion was measured using Phospholipid C-Test Wako (Wako Pure Chemical Industries Ltd.) according to the attached document. Specifically, the phospholipid in the sample was quantified in the presence of a 1% Triton X-100 detergent.

The amounts of cholesterol and LP in the nucleic acid lipid particle dispersion were measured by reverse-phase chromatography (system: Agilent 1100 series, column: Chromolith Performance RP-18 endcapped 100-3 monolithic HPLC-column (Merck), buffer A: 0.01% trifluoroacetic acid, buffer B: 0.01% trifluoroacetic acid and methanol, gradient (B %): 82-92% (0-10 min), flow rate: 2 mL/min, temperature: 50° C., detection: 205 nm).

The total amount of lipids was calculated from the amount of the phospholipid, the amount of cholesterol, and the amount of LP, and the compositional ratio of lipid components constituting the liposome, and the ratio of the polynucleotide to the lipid was calculated from the aforementioned amount of the polynucleotide and the total amount of lipids according to the following expression:

[Double-stranded polynucleotide concentration]/[Total lipid concentration] (wt/wt)

The results are shown in Table 16.

TABLE 16

| LP name | Rate of polynucleotide encapsulation (%) | Ratio of polynucleotide to lipid siRNA/lipid (wt/wt) | Average particle size (nm) |
|---|---|---|---|
| Reference Example 2 | 94 | 0.055 | 165 ± 11 |
| Example 41 | 97 | 0.101 | 158 ± 40 |
| Example 42 | 97 | 0.077 | 188 ± 45 |
| Example 43 | 97 | 0.075 | 174 ± 31 |

These results showed that the double-stranded polynucleotide was encapsulated in the lipid particle, and this nucleic acid lipid particle had an average particle size of approximately 100 nm to approximately 200 nm.

Test Example 8

By the same procedures as in Test Example 3, SW480 cells were treated with 50 nM, 5 nM, 0.5 nM, and 0.05 nM each of nucleic acid lipid particles each prepared using a novel lipid, and the strength of human β-catenin gene expression inhibitory activity was compared among these particles.

As a result, as shown in Table 17, the nucleic acid lipid particle containing the compound of Example 41, 42, or 43 exhibited strong inhibitory activity against β-catenin gene expression, as compared with the nucleic acid lipid particle containing the lipid of Reference Example 2 used as a control. These results demonstrated that the compound of Example 8 is a novel lipid useful for preparing nucleic acid lipid particles that exhibit strong activity.

TABLE 17

| | β-catenin gene expression inhibitory activity IC50 (nM) |
|---|---|
| Reference Example 2 | >50 |
| Example 41 | 2.6 |
| Example 42 | 6.0 |
| Example 43 | 24 |

(Example 56) Characterization of Double-Stranded Polynucleotide-Encapsulated Nucleic Acid Lipid Particle A lipid solution having a total lipid concentration of 26.8 mM in ethanol with distearoylphosphatidylcholine (1,2-distearoyl-sn-glycero-3-phosphocholine: hereinafter, referred to as DSPC, NOF CORPORATION), cholesterol (hereinafter, referred to as Chol, Sigma-Aldrich, Inc.), the compound described in Example 23 or 28 (hereinafter, referred to as LP), and N-[methoxy poly(ethylene glycol) 2000]carbamoyl]-1,2-dimyristyloxypropyl-3-amine (hereinafter, referred to as PEG-C-DMA) were prepared at a molar ratio of DSPC:Chol:LP:PEG-C-DMA=10:48:40:2.

The concentration of a double-stranded polynucleotide described in Nature Biotechnology (2008) 26, 561-569 (siFVII: siRNA against mouse Factor VII) was adjusted to 1 mg/mL with a citrate buffer solution (10 mM citrate buffer, pH 4.0) containing 30% ethanol to obtain a double-stranded polynucleotide solution.

The lipid solution, the double-stranded polynucleotide solution, and a citrate buffer solution (20 mM citrate buffer, pH 4.0) were heated to 37° C. The lipid solution was added dropwise to the citrate buffer solution (20 mM citrate buffer, pH 4.0) and mixed therewith such that the volume ratio between the lipid solution and the citrate buffer solution was 3:7 to obtain a crude liposome dispersion. Subsequently, the crude liposome dispersion was added dropwise to the double-stranded polynucleotide solution and mixed therewith such that the ratio (N/P) of LP-derived nitrogen atoms (N) to double-stranded polynucleotide-derived phosphorus atoms (P) was 3. The mixture was incubated at 37° C. for 30 minutes to obtain a nucleic acid lipid particle dispersion. The nucleic acid lipid particle dispersion was dialyzed against approximately 100 mL of a phosphate buffer solution (pH 7.4) for 12 to 18 hours (Float-A-Lyzer G2, MWCO: 100 kD, Spectra/Por) for the removal of ethanol and the removal of unencapsulated double-stranded polynucleotides by neutralization to obtain a purified dispersion of a nucleic acid lipid particle containing the double-stranded polynucleotide and the compound described in Example 23 or 28.

The obtained nucleic acid lipid particle was characterized by the methods described in Example 55, and the rate of polynucleotide encapsulation in the nucleic acid lipid particle, the weight ratio of the polynucleotide to the lipid, and the average particle size are shown in Table 18.

TABLE 18

| LP name | Rate of polynucleotide encapsulation (%) | Ratio of polynucleotide to lipid siRNA/lipid (wt/wt) | Average particle size (nm) |
|---|---|---|---|
| Example 23 | 99 | 0.076 | 219 ± 49 |
| Example 28 | 97 | 0.083 | 177 ± 36 |

These results showed that the double-stranded polynucleotide was encapsulated in the lipid particle, and this nucleic acid lipid particle had an average particle size of approximately 100 nm to approximately 300 nm.

(Test Example 9) Factor VII (FVII) Protein Measurement

By the same procedures as in Test Example 7, the strength of Factor VII protein expression inhibitory activity was compared among nucleic acid lipid particles each prepared using a novel lipid. The prepared nucleic acid lipid particle dispersion was intravenously injected at a dose of 0.1 mg/kg to the tail of each mouse. One day and 6 days after the administration, approximately 50 μL of blood was collected from the tail vein, and plasma was obtained.

The results obtained 1 day and 6 days after the administration are each shown in Table 19. As a result, the nucleic acid lipid particle containing the compound of Example 23 or 28 exhibited strong FVII inhibitory activity. These results demonstrated that the nucleic acid lipid particle having the compound of Example 23 or 28 is useful as a nucleic acid lipid particle capable of inhibiting gene expression.

TABLE 19

| | Relative amount of FVII (%) | |
|---|---|---|
| | 1 day later | 6 days later |
| PBS | 100 | 100 |
| Example 23 | 21 | 32 |
| Example 28 | 45 | 57 |

(Example 57) Characterization of Double-Stranded Polynucleotide-Encapsulated Nucleic Acid Lipid Particle A lipid solution having a total lipid concentration of 6.5 mM in ethanol with dipalmitoylphosphatidylcholine (1,2-dipalmitoyl-sn-glycero-3-phosphocholine: hereinafter, referred to as DPPC, NOF CORPORATION), cholesterol (hereinafter, referred to as Chol, Sigma-Aldrich, Inc.), the compound described in Example 19, 45, or 54 (hereinafter, referred to as LP), and N-[methoxy poly(ethylene glycol) 2000]carbamoyl]-1,2-distearoyloxypropyl-3-amine (hereinafter, referred to as PEG-C-DSA) were prepared at a molar ratio of DPPC:Chol:LP:PEG-C-DSA=7:33.5:57:2.5.

The concentration of a double-stranded polynucleotide described in Journal Clinical Investigation (2009) 119, 661-673 (PLK1424-2/A: siRNA against mouse PLK1) was adjusted to 1 mg/mL with a citrate buffer solution (10 mM citrate buffer, pH 4.0) containing 30% ethanol to obtain a double-stranded polynucleotide solution.

The lipid solution, the double-stranded polynucleotide solution, and a citrate buffer solution (20 mM citrate buffer, pH 4.0) were heated to 37° C. The lipid solution was added dropwise to the citrate buffer solution (20 mM citrate buffer, pH 4.0) and mixed therewith such that the volume ratio between the lipid solution and the citrate buffer solution was 3:7 to obtain a crude liposome dispersion. Subsequently, the crude liposome dispersion was added dropwise to the double-stranded polynucleotide solution and mixed therewith such that the ratio (N/P) of LP-derived nitrogen atoms (N) to double-stranded polynucleotide-derived phosphorus atoms (P) was 3. The mixture was incubated at 37° C. for 30 minutes to obtain a nucleic acid lipid particle dispersion. The nucleic acid lipid particle dispersion was dialyzed against approximately 100 mL of a phosphate buffer solution (pH 7.4) for 12 to 18 hours (Float-A-Lyzer G2, MWCO: 100 kD, Spectra/Por) for the removal of ethanol and the removal of unencapsulated double-stranded polynucleotides by neutralization to obtain a purified dispersion of a nucleic acid lipid particle containing the double-stranded polynucleotide and the compound described in Example 19, 45, or 54.

The obtained nucleic acid lipid particle was characterized by the methods described in Example 55, and the rate of polynucleotide encapsulation in the nucleic acid lipid particle, the weight ratio of the polynucleotide to the lipid, and the average particle size are shown in Table 20.

TABLE 20

| LP name | Rate of polynucleotide encapsulation (%) | Ratio of polynucleotide to lipid siRNA/lipid (wt/wt) | Average particle size (nm) |
|---|---|---|---|
| Example 19 | 97 | 0.095 | 103 ± 16 |
| Example 45 | 96 | 0.093 | 100 ± 27 |
| Example 54 | 98 | 0.078 | 127 ± 29 |

These results showed that the double-stranded polynucleotide was encapsulated in the lipid particle, and this nucleic acid lipid particle had an average particle size of approximately 50 nm to approximately 150 nm.

Test Example 10

After acclimatization and raising of each nude mouse (CAnN.Cg-Foxn1[nu]/CrlCrlj[Foxn1nu/Foxn1nu]) for 8 days, cultured human Hep3B cells ($1 \times 10^7$ cells/mouse) were subcutaneously transplanted to the right lateral region of the mouse. 19 days after the tumor transplantation, the mice were grouped with the tumor volume as an index, and, on the next day, the nucleic acid lipid particle-containing dispersion prepared in Example 57 was intravenously administered (administered at doses of 1 mg/kg and 3 mg/kg) to the tail of each mouse. PBS was administered to a control group. On the day after the administration of the nucleic acid lipid particle, a tumor mass was collected from the cancer-bearing mouse, and a nucleic acid was extracted using QIAzol Lysis Reagent (manufactured by Qiagen N.V.) and chloroform. Then, total RNA was purified using QIAGNE RNeasy Plus Mini kit (manufactured by Qiagen N.V.) according to the attached protocol.

16 µL of the purified RNA and 4 µL of SuperScript VILO Master mix (Life Technologies, Inc.) were mixed and used in RT reaction under conditions given below.

RT reaction: 25° C. for 10 min
42° C. for 60 min
85° C. for 5 min.

The probes for real-time PCR used were TaqMan® Gene Expression Assays (PLK-1, FAM probe, Hs00153444_m1, manufactured by Applied Biosystems, Inc.) as a human PLK-1 gene probe and TaqMan® Gene Expression Assays (VIC probe, Hs99999905_m1, manufactured by Applied Biosystems, Inc.) as a human GAPDH gene probe as an internal standard. 5 µL of TaqMan® Fast Advanced Master Mix, 2.66 µL of RNase-Free Water, 0.17 µL of each gene probe, and 2 µL of the prepared cDNA solution were added per well of a 384-well PCR plate (manufactured by Applied Biosystems, Inc.) to bring the total amount to 10 µL, which was then loaded in ViiA™ 7 Real-time PCR system (manufactured by Applied Biosystems, Inc.) and subjected to PCR under conditions given below. The real-time PCR was carried out at N=4 for the prepared cDNA.

PCR initial activation: 95° C. for 20 seconds
PCR: 95° C. for 1 second
62° C. for 20 seconds
This PCR cycle was repetitively performed 40 times.

The quantitative analysis was conducted by the ΔΔCt method. A value (ΔΔCt) was determined by subtracting ΔCt of the PBS administration group from the difference in Ct value (ΔCt) between human PLK-1 and human GAPDH in the administration group of each nucleic acid lipid particle, and a relative value (RQ) to the PBS administration group, RQmax, and RQmin were calculated according to the following expressions:

$$RQ = 2^{-\Delta\Delta Ct}$$

$RQ\text{max} = 2^{-95\% \, CI \, of \, \Delta\Delta Ct}$ (95% CI of ΔΔCt: the maximum value of 95% confidence interval of ΔΔCt)

$RQ\text{min} = 2^{-95\% \, CI \, of \, \Delta\Delta Ct}$ (95% CI of ΔΔCt: the minimum value of 95% confidence interval of ΔΔCt)

(CI: Confidence Interval)

The results are shown in FIG. 5. In the diagram, error bars were calculated according to the following expression:

+error bars:$RQ$max–$RQ$,–error bars:$RQ$–$RQ$min)

As a result, as shown in FIG. 5, the nucleic acid lipid particle having the compound of Example 19, 45, or 54 exhibited strong PLK-1 expression inhibitory activity in tumor. These results demonstrated that the nucleic acid lipid particle having the compound of Example 19, 45, or 54 is useful as a nucleic acid lipid particle capable of inhibiting gene expression.

(Example 58) Preparation of mRNA-Encapsulated Nucleic Acid Lipid Particle

Distearoylphosphatidylcholine (1,2-distearoyl-sn-glycero-3-phosphocholine: hereinafter, referred to as DSPC, NOF CORPORATION), cholesterol (hereinafter, referred to as Chol, Sigma-Aldrich, Inc.), the compound described in Example 8 (hereinafter, referred to as LP), and N-[methoxy poly(ethylene glycol)2000]carbamoyl]-1,2-dimyristyloxy-propyl-3-amine (hereinafter, referred to as PEG-C-DMA) were dissolved at a molar ratio of DSPC:Chol:LP:PEG-C-DMA=10:48:40:2 in ethanol to give a total lipid concentration of 10 mM. The obtained lipid solution was added dropwise to a citrate buffer solution (20 mM citrate buffer, pH 4.0) and mixed therewith such that the volume ratio between the lipid solution and the citrate buffer solution was 3:7 to obtain a crude dispersion of a lipid particle.

On the other hand, the concentration of mCherry mRNA (5meC, ψ) (hereinafter, referred to as mCherry mRNA, Catalog No.: L-6113, TriLink BioTechnologies, Inc.) or firefly luciferase mRNA (5meC, ψ) (hereinafter, referred to as FLuc mRNA, Catalog No.: L-6107, TriLink BioTechnologies, Inc.) was adjusted to 0.1 mg/mL with a citrate buffer solution (20 mM citrate buffer, pH 4.0) containing 30% ethanol.

Subsequently, 790 μL of the crude lipid particle dispersion and 350 μL of the mRNA solution were mixed such that the ratio (N/P) of the number of LP molecules (N) to the number of mRNA-derived phosphorus atoms (P) was N/P molar ratio=9.0. The mixture was incubated at 37° C. for 30 minutes to obtain a nucleic acid lipid particle dispersion. The nucleic acid lipid particle dispersion was dialyzed against approximately 100 mL of a phosphate buffer solution (pH 7.4) for 12 to 18 hours (Float-A-Lyzer G2, MWCO: 100 kD, Spectra/Por) for the removal of ethanol to obtain a purified dispersion of an mRNA-encapsulated nucleic acid lipid particle containing the compound described in Example 8.

(Example 59) Characterization of mRNA-Encapsulated Nucleic Acid Lipid Particle

The nucleic acid lipid particle-containing dispersion prepared in Example 58 was characterized. Each characterization method will be described.
(1) Average Particle Size The particle size of the liposome was measured using Zeta Potential/Particle Sizer NICOMP™ 380ZLS (Particle Sizing Systems, LLC). In the tables, the average particle size is indicated by a volume-average particle size, and the numeric value following ±represents a deviation.
(2) Rate of Encapsulation of mRNA The rate of encapsulation of the mRNA was measured using Quant-iT RiboGreen RNA Assay kit (Invitrogen Corp.) according to the attached document.

Specifically, the mRNA in the nucleic acid lipid particle dispersion was quantified in the presence and absence of a 0.015% Triton X-100 detergent, and the rate of encapsulation was calculated according to the following expression:

{[Amount of the mRNA in the presence of the detergent]–[Amount of the mRNA in the absence of the detergent]}/[Amount of the mRNA in the presence of the detergent]}×100(%)

(3) Ratio of mRNA to Lipid

The amount of the phospholipid in the nucleic acid lipid particle dispersion was measured using Phospholipid C-Test Wako (Wako Pure Chemical Industries Ltd.) according to the attached document. Specifically, the phospholipid in the sample was quantified in the presence of a 1% Triton X-100 detergent.

The amounts of cholesterol and LP in the nucleic acid lipid particle dispersion were measured by reverse-phase chromatography (system: Agilent 1100 series, column: Chromolith Performance RP-18 endcapped 100-3 monolithic HPLC-column (Merck), buffer A: 0.01% trifluoroacetic acid, buffer B: 0.01% trifluoroacetic acid and methanol, gradient (B %): 82-92% (0-10 min), flow rate: 2 mL/min, temperature: 50° C., detection: 205 nm).

The total amount of lipids was calculated from the amount of the phospholipid, the amount of cholesterol, and the amount of LP, and the compositional ratio of lipid components constituting the liposome, and the ratio of the mRNA to the lipid was calculated from the "amount of the mRNA in the presence of the detergent" of the preceding paragraph (2) according to the following expression:

[mRNA concentration in the presence of the detergent]/[Total lipid concentration] (wt/wt)

The results are shown in Table 21.

TABLE 21

| mRNA | Rate of encapsulation of mRNA (%) | Ratio of mRNA to lipid mRNA/lipid (wt/wt) | Average particle size (nm) |
|---|---|---|---|
| mCherry | 98 | 0.037 | 151 ± 71 |
| FLuc | 98 | 0.038 | 145 ± 56 |

These results showed that the mRNA was encapsulated in the lipid particle, and this nucleic acid lipid particle had an average particle size of approximately 100 nm to approximately 200 nm.

Test Example 11

As described below, the expression of mCherry was measured using a nucleic acid lipid particle prepared using a novel lipid.
(1) Transfection The concentration of a human hepatocellular carcinoma HuH-7 cell line was adjusted to 10,000 cells/mL in a DMEM medium (manufactured by Invitrogen Corp.) containing 10% fetal bovine serum (culture medium). Then, the resulting culture solution was inoculated at 100 μL/well to a 96-well flat-bottomed plate (manufactured by Corning Inc./Falcon) and cultured at 37° C. for 1 day under 5.0% $CO_2$. The nucleic acid lipid particle dispersion prepared in Example 58 was diluted with a culture medium to prepare dilution series having final mRNA concentrations of 2, 0.4, and 0.08 μg/mL in the medium. Then, each dilution was added to the cells after removal of the culture supernatant, and the culture was further continued. This operation was performed at N=3 for each concentration. A control group was cultured in only a culture medium.

(2) Fluorescent Observation of mCherry

One day after the transfection, the culture medium was removed, and 100 μL of 10 N Mildform (Wako Pure Chemical Industries Ltd.) was added to each well and left at room temperature for 10 minutes in the dark. After washing off of 10 N Mildform with DPBS (Dulbecco's PBS, Life Technologies, Inc.), 50 μL of Hoechst 33342, trihydrochloride, trihydrate (manufactured by Invitrogen Corp.) concentration-adjusted to 20 μg/mL with DPBS was added to each well and left at room temperature for 1 hour in the dark. After replacement with DPBS, the fluorescence was observed using IN Cell Analyzer 6000 (GE Healthcare Japan Corp.). The measurement conditions were as follows: Hoechst; excitation wavelength: 405 nm, detection wavelength: 455 nm/50 nm (filter central wavelength/band width), and mCherry; excitation wavelength: 561 nm, detection wavelength: 605 nm/52 nm (filter central wavelength/band width).

The results are shown in FIG. 6. The upper boxes of this diagram depict images of nuclei stained with Hoechst, and the lower boxes depict images of mCherry. The nucleic acid lipid particle having the compound of Example 8 was found to promote the expression of mCherry. These results demonstrated that the nucleic acid lipid particle containing the compound of Example 8 is useful as a nucleic acid lipid particle capable of promoting the expression of mRNA.

(3) Measurement of Expression Level of Luciferase

Six hours after the transfection, the expression level of luciferase was measured using Luciferase reporter Gene Assay, high sensitivity (manufactured by F. Hoffmann-La Roche, Ltd.) according to the attached document. An average value of relative luminescent units (RLU) at N=3 is shown in Table 22.

TABLE 22

| mRNA concentration (μg/mL) | RLU (1 × $10^5$) |
|---|---|
| 0 | 0 |
| 0.08 | 0.7 |
| 0.4 | 2.7 |
| 2.0 | 3.7 |

As a result, the nucleic acid lipid particle having the compound of Example 8 was found to promote the expression of FLuc. These results demonstrated that the nucleic acid lipid particle containing the compound of Example 8 is useful as a nucleic acid lipid particle capable of promoting the expression of mRNA.

(Example 60) Preparation of Double-Stranded Polynucleotide-Encapsulated Nucleic Acid Lipid Particle Distearoylphosphatidylcholine (1,2-distearoyl-sn-glycero-3-phosphocholine: hereinafter, referred to as DSPC, NOF CORPORATION), cholesterol (hereinafter, referred to as Chol, Sigma-Aldrich, Inc.), the compound described in Example 8 (hereinafter, referred to as LP), and N-[methoxy poly(ethylene glycol)2000]carbamoyl]-1,2-dimyristyloxy-propyl-3-amine (hereinafter, referred to as PEG-C-DMA) were prepared at a molar ratio of DSPC:Chol:LP:PEG-C-DMA=10:48:40:2 into a lipid solution having a total lipid concentration of 26.8 mM in ethanol.

The concentration of a double-stranded polynucleotide described in Nature Biotechnology (2008) 26, 561-569 (siFVII: siRNA against mouse Factor VII) was adjusted to 1 mg/mL with a citrate buffer solution (10 mM citrate buffer, pH 4.0) containing 30% ethanol to obtain a double-stranded polynucleotide solution.

The lipid solution, the double-stranded polynucleotide solution, and a citrate buffer solution (20 mM citrate buffer, pH 4.0) were heated to 37° C. The lipid solution was added dropwise to the citrate buffer solution (20 mM citrate buffer, pH 4.0) and mixed therewith such that the volume ratio between the lipid solution and the citrate buffer solution was 3:7 to obtain a crude liposome dispersion. Subsequently, the crude liposome dispersion was added dropwise to the double-stranded polynucleotide solution and mixed therewith such that the ratio (N/P) of the number of LP molecules (N) to the number of double-stranded polynucleotide-derived phosphorus atoms (P) was a molar ratio described in Table 23. The mixture was incubated at 37° C. for 30 minutes to obtain a nucleic acid lipid particle dispersion. The nucleic acid lipid particle dispersion was dialyzed against approximately 100 mL of a phosphate buffer solution (pH 7.4) for 12 to 18 hours (Float-A-Lyzer G2, MWCO: 100 kD, Spectra/Por) for the removal of ethanol and the removal of unencapsulated double-stranded polynucleotides by neutralization to obtain a purified dispersion of a nucleic acid lipid particle containing the double-stranded polynucleotide and the lipid described in Example 8.

TABLE 23

| | N/P ratio |
|---|---|
| Particle 28 | 2.0 |
| Particle 29 | 2.5 |
| Particle 30 | 3.0 |
| Particle 31 | 3.5 |
| Particle 32 | 4.0 |
| Particle 33 | 4.5 |
| Particle 34 | 5.0 |
| Particle 35 | 6.0 |

(Example 61) Characterization of Double-Stranded Polynucleotide-Encapsulated Nucleic Acid Lipid Particle The nucleic acid lipid particle dispersion prepared in Example 60 was characterized. The characterization was conducted by the methods described in Example 32, and the rate of polynucleotide encapsulation in the nucleic acid lipid particle described in Example 60, the weight ratio of the polynucleotide to the lipid, and the average particle size are shown in Table 24.

TABLE 24

| | N/P ratio * | Rate of encapsulation (%) | siRNA/lipid (wt/wt) ** | Particle size (nm) |
|---|---|---|---|---|
| Particle 28 | 2.0 | 96 | 0.128 | 126 ± 40 |
| Particle 29 | 2.5 | 97 | 0.099 | 134 ± 9 |
| Particle 30 | 3.0 | 97 | 0.085 | 139 ± 50 |
| Particle 31 | 3.5 | 98 | 0.066 | 147 ± 39 |
| Particle 32 | 4.0 | 98 | 0.063 | 142 ± 43 |
| Particle 33 | 4.5 | 98 | 0.057 | 141 ± 23 |

TABLE 24-continued

|  | N/P ratio * | Rate of encapsulation (%) | siRNA/lipid (wt/wt) ** | Particle size (nm) |
|---|---|---|---|---|
| Particle 34 | 5.0 | 99 | 0.051 | 137 ± 26 |
| Particle 35 | 6.0 | 99 | 0.037 | 151 ± 38 |

* N/P ratio: ratio of the number of molecules of LP (N) to the number of phosphorus atoms derived from double-stranded polynucleotide (P)
** siRNA/lipid (wt/wt): weight ratio of polynucleotide to lipid These results showed that the double-stranded polynucleotide was encapsulated in the lipid particle, and this nucleic acid lipid particle had an average particle size of approximately 100 nm to approximately 200 nm.

(Test Example 12) Factor VII (FVII) Protein Measurement

The Factor VII protein was measured according to a method described in Nature Biotechnology (2010) 28, 172-176. C57BL6/J mice (male, 9 weeks old) were randomly grouped (n=4). The nucleic acid lipid particle dispersion prepared in Example 60 was intravenously injected at a dose of 0.3 mg/kg to the tail of each mouse. One day after the administration, approximately 50 μL of blood was collected from the tail vein, and plasma was obtained. The amount of the Factor VII protein in the obtained plasma was measured using Biophen FVII assay kit (manufactured by Aniara Corp.) according to the attached protocol.

When the amount of FVII of respective plasma samples collected in equal amounts from individuals in a PBS administration group was defined as 100%, the relative ratio (%) of the amount of FVII in a plasma sample of each individual was used as a measurement value (A). An average value (B) was determined from the respective measurement values of the individuals in the PBS administration group. The relative ratio of the measurement value (A) of each individual was determined from the expression: A/B×100 (%). The average value of the relative ratios in the administration group of each nucleic acid lipid particle is shown in Table 25. As a result, as shown in Table 25, particles 28 to 35 as the nucleic acid lipid particles prepared in Example 60 exhibited strong FVII inhibitory activity. These results demonstrated that a nucleic acid lipid particle having lipid composition as found in particles 28 to 35 is useful as a nucleic acid lipid particle capable of inhibiting gene expression.

TABLE 25

|  | Relative amount of FVII (%) |
|---|---|
| PBS | 100 |
| Particle 28 | 38 |
| Particle 29 | 11 |
| Particle 30 | <10 |
| Particle 31 | <10 |
| Particle 32 | 31 |
| Particle 33 | <10 |
| Particle 34 | <10 |
| Particle 35 | <10 |

INDUSTRIAL APPLICABILITY

The present invention may provide a novel cationic lipid that forms a lipid particle in combination with an amphipathic lipid, a sterol, and a lipid reducing aggregation during lipid particle formation.

The present invention may also provide a lipid particle comprising the cationic lipid.

The present invention may further provide a nucleic acid lipid particle comprising the lipid particle and further a nucleic acid. The nucleic acid lipid particle of the present invention can be used in a pharmaceutical composition.

Free Text of Sequence Listing
SEQ ID NO: 1: CT-169
SEQ ID NO: 2: CT-157
SEQ ID NO: 3: CT-103
SEQ ID NO: 4: CT-292
SEQ ID NO: 5: CT-315
SEQ ID NO: 6: CT-387
SEQ ID NO: 7: Sense strand region of CT-454
SEQ ID NO: 8: Antisense strand region of CT-454
SEQ ID NO: 9: Sense strand region of HS-005
SEQ ID NO: 10: Antisense strand region of HS-005
SEQ ID NO: 11: Sense strand region of HS-006
SEQ ID NO: 12: Antisense strand region of HS-006
SEQ ID NO: 13: Sense strand region of HS-005s
SEQ ID NO: 14: Antisense strand region of HS-005s
SEQ ID NO: 15: Sense strand region of HS-006s
SEQ ID NO: 16: Antisense strand region of HS-006s

The invention claimed is:

1. A method of inhibiting the expression of a target gene, the method comprising administering a nucleic acid lipid particle to a mammal, the nucleic acid lipid particle comprising:
 a lipid having the formula:

or a pharmacologically acceptable salt thereof, and
a nucleic acid,
 wherein the nucleic acid lipid particle has an RNA interference effect and/or a gene inhibitory effect on the target gene.

2. The method of claim 1, wherein the nucleic acid is selected from the group consisting of a single-stranded DNA, a single-stranded RNA, a single-stranded polynucleotide of a DNA and an RNA mixed with each other, a double-stranded DNA, a double-stranded RNA, a DNA-RNA hybrid polynucleotide, and two polynucleotides of a DNA and an RNA mixed with each other.

3. The method of claim 1, wherein the nucleic acid is a single-stranded or double-stranded polynucleotide having an RNA interference effect.

4. The method of claim 1, wherein the nucleic acid is a single-stranded RNA.

5. The method of claim 1, wherein the ratio of the number of molecules of the cationic lipid to the number of phosphorus atoms derived from the nucleic acid is 2.0 to 9.0.

6. The method of claim 1, wherein the ratio of the number of molecules of the cationic lipid to the number of phosphorus atoms derived from the nucleic acid is 3.0 to 9.0.

7. The method of claim 1, wherein the average particle size is approximately 30 nm to approximately 300 nm.

8. The method of claim 1, wherein the average particle size is approximately 30 nm to approximately 200 nm.

9. The method of claim 1, wherein the average particle size is approximately 30 nm to approximately 100 nm.

10. A method of treating a disease derived from the expression of a target gene, the method comprising administering a nucleic acid lipid particle to a mammal, the nucleic acid lipid particle comprising:

a lipid having the formula:

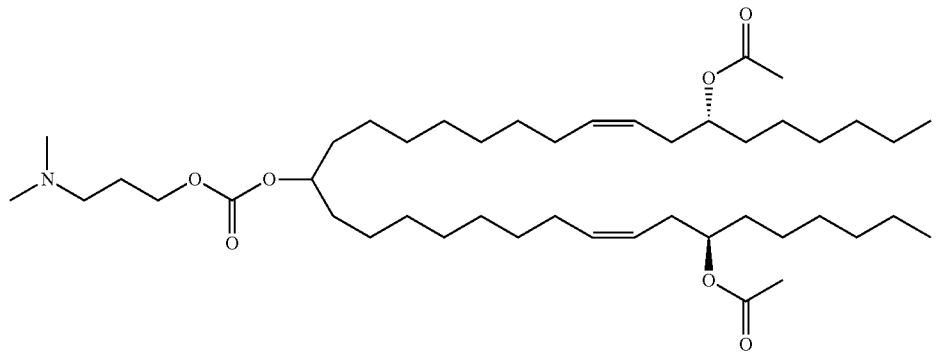 [SMILES: CCCCCC[C@H](C/C=C\CCCCCCCC(CCCCCCC/C=C\C[C@@H](CCCCCC)OC(C)=O)OC(=O)OCCCN(C)C)OC(C)=O]

or a pharmacologically acceptable salt thereof, and a nucleic acid,
  wherein the nucleic acid lipid particle has a gene expression effect on the target gene.

11. The method of claim 10, wherein the gene expression effect is an inhibitory effect.

12. The method of claim 10, wherein the gene expression effect is an RNA interference effect.

13. The method of claim 10, wherein the gene expression effect is promoting the expression of mRNA.

14. The method of claim 10, wherein the target gene is a non-coding RNA and the nucleic acid lipid particle inhibits or down-regulates the expression of the non-coding RNA and up- or down-regulates the expression of a gene involved in the non-coding RNA.

15. The method of claim 10, wherein the nucleic acid is a single-stranded RNA that encodes a protein that is beneficial for the treatment of the disease.

16. The method of claim 15, wherein the disease is caused by a genetic defect or by the absence of a protein in the body.

17. The method of claim 16, wherein the disease is glycogen storage disease type Ia (glucose-6-phosphatase gene), glycogen storage disease type Ib (glucose-6-phosphate translocase gene), glycogen storage disease type III (amylo-1,6-glucosidase gene), glycogen storage disease type IV (amylo-1,4→1,6 transglucosylase gene), glycogen storage disease type VI (liver phosphorylase gene), glycogen storage disease type IX, glycogen storage disease type VIII (liver phosphorylase kinase gene), a1-antitrypsin deficiency (α1-antitrypsin gene), congenital hemochromatosis, hepcidin deficiency (hepcidin gene), hemophilia A (coagulation factor VIII gene), hemophilia B (coagulation factor IX gene), congenital anticoagulant deficiency (protein C gene), thrombotic thrombocytopenic purpura (ADAMTS13 gene), congenital amegakaryocytic thrombocytopenia, thrombopoietin deficiency, erythropoietin deficiency, or growth hormone (somatotropin or hGH) deficiency.

18. The method of claim 10, wherein the disease derived from the expression of a target gene is cancer.

19. The method of claim 10, wherein the disease derived from the expression of a target gene is cancer, liver disease, gallbladder disease, fibrosis, anemia, or genetic disease.

* * * * *

UNITED STATES PATENT AND TRADEMARK OFFICE
CERTIFICATE OF CORRECTION

PATENT NO. : 10,731,159 B2
APPLICATION NO. : 16/692284
DATED : August 4, 2020
INVENTOR(S) : Koizumi et al.

Page 1 of 1

It is certified that error appears in the above-identified patent and that said Letters Patent is hereby corrected as shown below:

In the Claims

In Claim 1, Column 193, Lines 40-61, delete the following formula,

"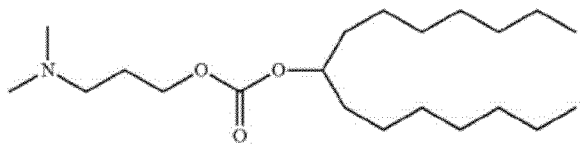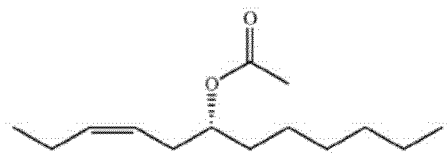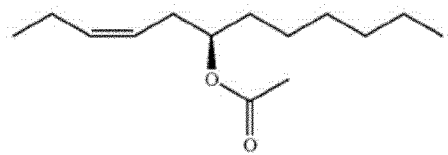" and insert therefor

--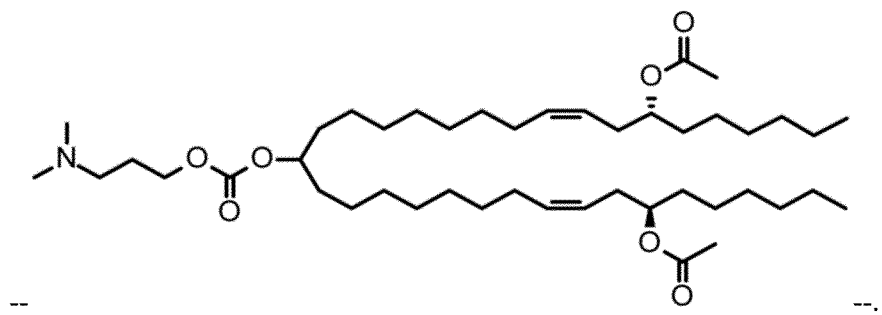--.

In Claim 17, Column 196, Lines 25-26, delete "a1-antitrypsin deficiency (α1-antitrypsin gene)" and insert therefor -- "α1-antitrypsin deficiency (α1-antitrypsin gene)" --.

Signed and Sealed this
Sixth Day of October, 2020

Andrei Iancu
*Director of the United States Patent and Trademark Office*